United States Patent
Beyar et al.

(10) Patent No.: US 10,524,838 B2
(45) Date of Patent: Jan. 7, 2020

(54) COMPOSITE MATERIAL SPINAL IMPLANT

(71) Applicant: Carbofix In Orthopedics LLC, Wilmington, DE (US)

(72) Inventors: Mordechay Beyar, Caesarea (IL); Oren Globerman, Kfar-Shemaryahu (IL)

(73) Assignee: Carbofix In Orthopedics LLC, Wilmington, DE (US)

( * ) Notice: Subject to any disclaimer, the term of this patent is extended or adjusted under 35 U.S.C. 154(b) by 13 days.

(21) Appl. No.: 15/507,768

(22) PCT Filed: Sep. 1, 2015

(86) PCT No.: PCT/IB2015/056635
§ 371 (c)(1),
(2) Date: Mar. 1, 2017

(87) PCT Pub. No.: WO2016/035010
PCT Pub. Date: Mar. 10, 2016

(65) Prior Publication Data
US 2017/0281238 A1    Oct. 5, 2017

Related U.S. Application Data

(63) Continuation-in-part of application No. 14/421,158, filed as application No. PCT/IL2014/050782 on Sep. 1, 2014, now Pat. No. 9,918,746.
(Continued)

(51) Int. Cl.
*A61B 17/70* (2006.01)
*A61B 17/88* (2006.01)
*A61B 17/64* (2006.01)

(52) U.S. Cl.
CPC ...... *A61B 17/7008* (2013.01); *A61B 17/7011* (2013.01); *A61B 17/7032* (2013.01);
(Continued)

(58) Field of Classification Search
CPC ............ A61B 17/7008; A61B 17/7011; A61B 17/7032; A61B 17/7035; A61B 17/7037;
(Continued)

(56) References Cited

U.S. PATENT DOCUMENTS

| 4,796,637 A | 1/1989 | Mascuch et al. |
| 5,586,984 A | 12/1996 | Errico et al. |

(Continued)

FOREIGN PATENT DOCUMENTS

| CN | 101766501 | 7/2010 |
| CN | 102525616 | 7/2012 |

(Continued)

OTHER PUBLICATIONS

Applicant-Initiated Interview Summary dated Sep. 28, 2017 From the US Patent and Trademark Office Re. U.S. Appl. No. 14/421,158. (3 pages).
(Continued)

*Primary Examiner* — Pedro Philogene

(57) ABSTRACT

A pedicle screw implant construct kit, comprising at least one pedicle screw, at least one collar comprising a recess for receiving a rod, the collar configured to be coupled to a head of the pedicle screw, an elongated rod for connecting the collar to one more additional collars to couple between the pedicle screw and one or more additional screws, and a locking ring sized to be positioned over at least a distal portion of the collar to restrain relative movement of the screw head and rod by exerting radial compression force onto the collar. In some embodiments, the components of the kit are comprised of carbon reinforced composite material, optionally with no radiation blocking material. In some exemplary embodiments of the invention, the kit includes two locking rings on a collar, optionally both below the rod.

23 Claims, 67 Drawing Sheets

Related U.S. Application Data

(60) Provisional application No. 62/030,084, filed on Jul. 29, 2014, provisional application No. 61/980,076, filed on Apr. 16, 2014, provisional application No. 61/926,328, filed on Jan. 12, 2014, provisional application No. 61/872,728, filed on Sep. 1, 2013.

(52) U.S. Cl.
CPC ...... *A61B 17/7035* (2013.01); *A61B 17/7037* (2013.01); *A61B 17/7038* (2013.01); *A61B 17/7052* (2013.01); *A61B 17/7076* (2013.01); *A61B 17/7082* (2013.01); *A61B 17/8863* (2013.01); *A61B 17/6475* (2013.01); *A61B 17/7086* (2013.01)

(58) Field of Classification Search
CPC ............ A61B 17/7038; A61B 17/7052; A61B 17/7076; A61B 17/7082; A61B 17/8863; A61B 17/6475; A61B 17/7086
USPC ................... 606/246–279, 911; 411/433
See application file for complete search history.

(56) References Cited

U.S. PATENT DOCUMENTS

| | | | | |
|---|---|---|---|---|
| 5,683,392 | A | * | 11/1997 | Richelsoph ........ A61B 17/7037 606/272 |
| 5,919,044 | A | | 7/1999 | Sicurelli, Jr. et al. |
| 6,022,350 | A | | 2/2000 | Ganem |
| 6,273,888 | B1 | * | 8/2001 | Justis ................. A61B 17/7032 606/272 |
| 7,090,674 | B2 | * | 8/2006 | Doubler ............. A61B 17/7032 606/277 |
| 7,419,714 | B1 | | 9/2008 | Magerl et al. |
| 7,731,736 | B2 | * | 6/2010 | Guenther ........... A61B 17/7037 606/265 |
| 7,988,694 | B2 | | 8/2011 | Barrus et al. |
| 8,162,991 | B2 | * | 4/2012 | Strauss .............. A61B 17/7037 606/269 |
| 8,287,576 | B2 | | 10/2012 | Barrus |
| 8,696,717 | B2 | | 4/2014 | Rock et al. |
| 8,876,874 | B2 | | 11/2014 | Abdou |
| 9,101,427 | B2 | | 8/2015 | Globerman et al. |
| 9,241,739 | B2 | | 1/2016 | Mueller et al. |
| 2004/0158324 | A1 | | 8/2004 | Lange |
| 2004/0172039 | A1 | | 9/2004 | Dye |
| 2004/0260287 | A1 | | 12/2004 | Ferree |
| 2005/0027360 | A1 | | 2/2005 | Webb et al. |
| 2005/0096653 | A1 | | 5/2005 | Doubler et al. |
| 2005/0277927 | A1 | | 12/2005 | Guenther et al. |
| 2006/0149244 | A1 | | 7/2006 | Amrein et al. |
| 2006/0173456 | A1 | | 8/2006 | Hawkes et al. |
| 2007/0016192 | A1 | * | 1/2007 | Woods ............... A61B 17/7032 606/86 A |
| 2007/0156145 | A1 | | 7/2007 | Demakas et al. |
| 2008/0027432 | A1 | | 1/2008 | Strauss et al. |
| 2008/0262548 | A1 | | 10/2008 | Lange et al. |
| 2008/0269810 | A1 | | 10/2008 | Zhang et al. |
| 2009/0005813 | A1 | | 1/2009 | Crall et al. |
| 2009/0036934 | A1 | | 2/2009 | Biedermann et al. |
| 2009/0093819 | A1 | | 4/2009 | Joshi |
| 2009/0105716 | A1 | | 4/2009 | Barrus |
| 2009/0105756 | A1 | | 4/2009 | Richelsoph |
| 2009/0105769 | A1 | | 4/2009 | Rock et al. |
| 2009/0163955 | A1 | * | 6/2009 | Moumene ............ A61B 17/701 606/257 |
| 2009/0182384 | A1 | | 7/2009 | Wilcox et al. |
| 2009/0192384 | A1 | | 7/2009 | Fontius |
| 2010/0042167 | A1 | | 2/2010 | Nebosky et al. |
| 2010/0114180 | A1 | | 5/2010 | Rock et al. |
| 2010/0160967 | A1 | | 6/2010 | Capozzoli |
| 2010/0168800 | A1 | | 7/2010 | Biedermann et al. |
| 2010/0198260 | A1 | | 8/2010 | Gabelberger et al. |
| 2010/0228300 | A1 | | 9/2010 | Armstrong et al. |
| 2010/0241171 | A1 | | 9/2010 | Clement et al. |
| 2011/0022094 | A1 | | 1/2011 | Ritland |
| 2011/0106179 | A1 | | 5/2011 | Prevost et al. |
| 2011/0172718 | A1 | | 7/2011 | Felix et al. |
| 2011/0238119 | A1 | | 9/2011 | Moumene et al. |
| 2011/0265538 | A1 | | 11/2011 | Trieu et al. |
| 2011/0270314 | A1 | | 11/2011 | Mueller et al. |
| 2012/0203288 | A1 | | 8/2012 | Lange et al. |
| 2012/0330361 | A1 | | 12/2012 | Gepstein |
| 2013/0079829 | A1 | | 3/2013 | Globerman et al. |
| 2013/0123861 | A1 | | 5/2013 | Biedermann et al. |
| 2013/0211465 | A1 | | 8/2013 | Savage |
| 2015/0282842 | A1 | | 10/2015 | Beyar et al. |
| 2016/0051288 | A1 | | 2/2016 | Beyar et al. |
| 2016/0074075 | A1 | | 3/2016 | Beyar et al. |

FOREIGN PATENT DOCUMENTS

| | | |
|---|---|---|
| CN | 102525617 | 7/2012 |
| DE | 3711013 | 6/1988 |
| EP | 0799124 | 10/1997 |
| EP | 0923908 | 6/1999 |
| EP | 2198792 | 12/2008 |
| EP | 2198796 | 12/2008 |
| EP | 2047812 | 4/2009 |
| EP | 2153784 | 7/2009 |
| EP | 2705802 | 12/2009 |
| EP | 2462887 | 6/2012 |
| FR | 2956803 | 9/2011 |
| WO | WO 2005/041521 | 5/2005 |
| WO | WO 2007/040750 | 4/2007 |
| WO | WO 2010/078901 | 7/2010 |
| WO | WO 2011/111048 | 9/2011 |
| WO | WO 2012/162550 | 11/2012 |
| WO | WO 2014/016824 | 1/2014 |
| WO | WO 2014/138736 | 9/2014 |
| WO | WO 2015/029042 | 3/2015 |
| WO | WO 2016/035010 | 3/2016 |

OTHER PUBLICATIONS

Official Action dated Sep. 26, 2017 From the US Patent and Trademark Office Re. U.S. Appl. No. 14/951,709. (14 pages).
Office Action dated Aug. 15, 2017 From the State Intellectual Property Office of the People's Republic of China Re. Application No. 201480059442.1 and an English Summary. (14 Pages).
Communication Pursuant to Article 94(3) EPC dated Oct. 5, 2017 From the European Patent Office Re. Application No. 14840679.6. (6 Pages).
Applicant-Initiated Interview Summary dated May 10, 2016 From the US Patent and Trademark Office Re. U.S. Appl. No. 14/620,231.
Communication Relating to the Results of the Partial International Search dated Nov. 25, 2015 From the International Searching Authority Re. Application No. PCT/IB2015/056635.
International Preliminary Report on Patentability dated Feb. 5, 2015 From the International Bureau of WIPO Re. Application No. PCT/IL2013/050581.
International Preliminary Report on Patentability dated Mar. 10, 2016 From the International Bureau of WIPO Re. Application No. PCT/IL2014/050782.
International Preliminary Report on Patentability dated Mar. 16, 2017 From the International Bureau of WIPO Re. Application No. PCT/IB2015/056635. (16 Pages).
International Preliminary Report on Patentability dated Sep. 20, 2012 From the International Bureau of WIPO Re. Application No. PCT/IL2011/000233.
International Search Report and the Written Opinion dated Aug. 5, 2011 From the International Searching Authority Re. Application No. PCT/IL2011/000233.
International Search Report and the Written Opinion dated Dec. 10, 2014 From the International Searching Authority Re. Application No. PCT/IL2014/050782.
International Search Report and the Written Opinion dated Feb. 17, 2016 From the International Searching Authority Re. Application No. PCT/IB2015/056635.

(56) References Cited

OTHER PUBLICATIONS

International Search Report and the Written Opinion dated Oct. 20, 2013 From the International Searching Authority Re. Application No. PCT/IL2013/050581.
Official Action dated Feb. 5, 2016 From the US Patent and Trademark Office Re. U.S. Appl. No. 14/421,158.
Official Action dated Feb. 10, 2016 From the US Patent and Trademark Office Re. U.S. Appl. No. 14/620,231.
Official Action dated Dec. 12, 2013 From the US Patent and Trademark Office Re. U.S. Appl. No. 14/421,158. (10 pages).
Official Action dated Feb. 13, 2017 From the US Patent and Trademark Office Re. U.S. Appl. No. 14/951,709. (13 pages).
Official Action dated Jun. 14, 2016 From the US Patent and Trademark Office Re. U.S. Appl. No. 14/421,158.
Official Action dated Sep. 14, 2016 From the US Patent and Trademark Office Re. U.S. Appl. No. 14/951,709.
Official Action dated Apr. 19, 2017 From the US Patent and Trademark Office Re. U.S. Appl. No. 14/421,158. (10 pages).
Official Action dated Oct. 30, 2015 From the US Patent and Trademark Office Re. U.S. Appl. No. 14/620,231.
Restriction Official Action dated Aug. 19, 2015 From the US Patent and Trademark Office Re. U.S. Appl. No. 14/620,231.
Supplementary European Search Report and the European Search Opinion dated Jan. 2, 2017 From the European Patent Office Re. Application No. 14840679.6. (8 Pages).
Notification of Office Action and Search Report dated Dec. 24, 2018 From the State Intellectual Property Office of the People's Republic of China Re. Application No. 201580058465.5. (10 Pages).
Communication Pursuant to Article 94(3) EPC dated Nov. 16, 2018 From the European Patent Office Re. Application No. 14840679.6. (4 Pages).
Communication Under Rule 164(2)(a) EPC dated Nov. 23, 2018 From the European Patent Office Re. Application No. 15767316.1. (11 Pages).
Notification of Office Action dated Mar. 2, 2018 From the State Intellectual Property Office of the People's Republic of China Re. Application No. 201480059442.1 and Its Translation Into English. (6 Pages).
Translation of Notification of Office Action dated Aug. 15, 2017 From the State Intellectual Property Office of the People's Republic of China Re. Application No. 201480059442.1. (8 Pages).
Communication Pursuant to Rule 164(2)(b) and Article 94(3) EPC dated Feb. 26, 2019 From the European Patent Office Re. Application No. 15767316.1. (15 Pages).
Translation dated Jan. 29, 2019 of Notification of Office Action dated Dec. 24, 2018 From the State Intellectual Property Office of the People's Republic of China Re. Application No. 201580058465.5. (9 Pages).

* cited by examiner

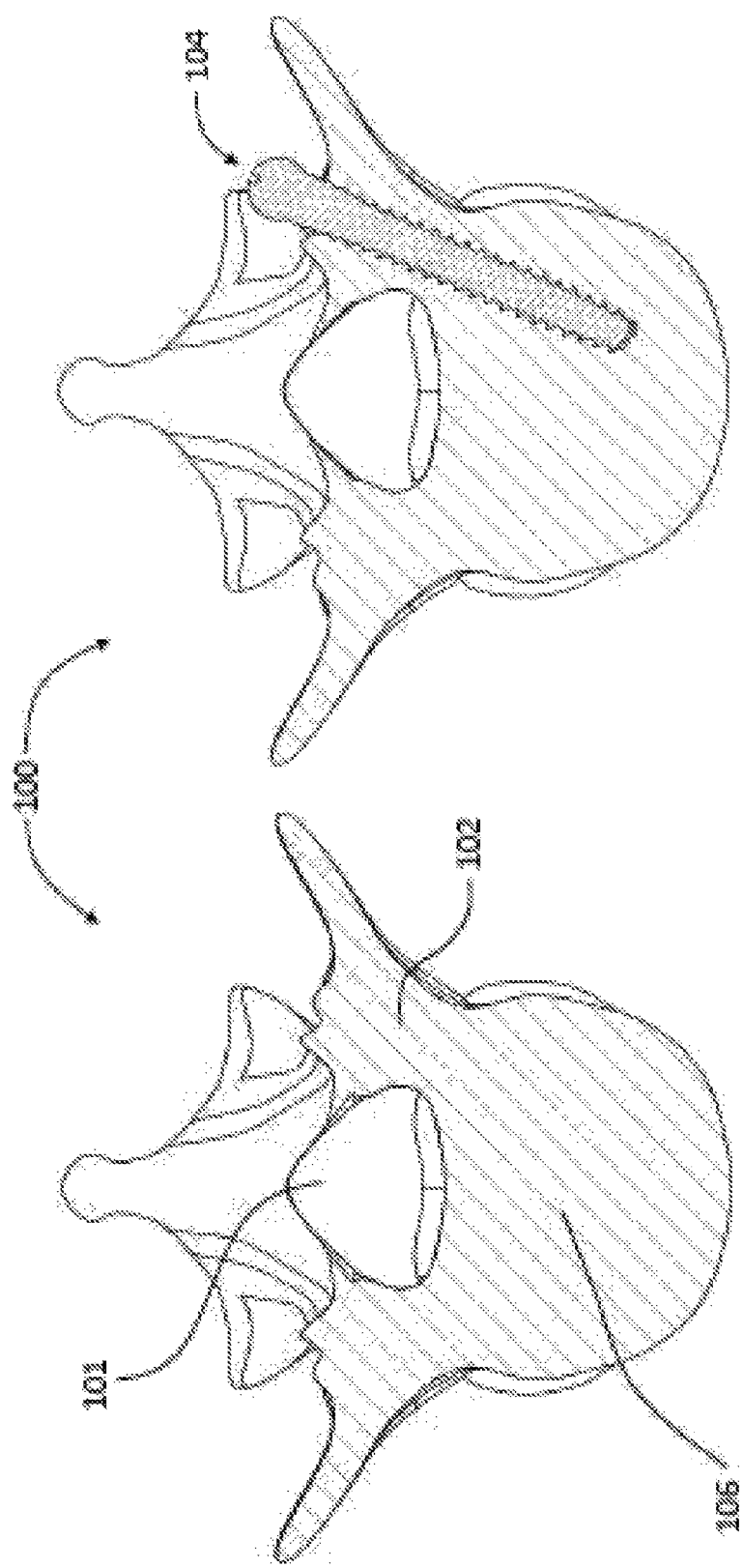

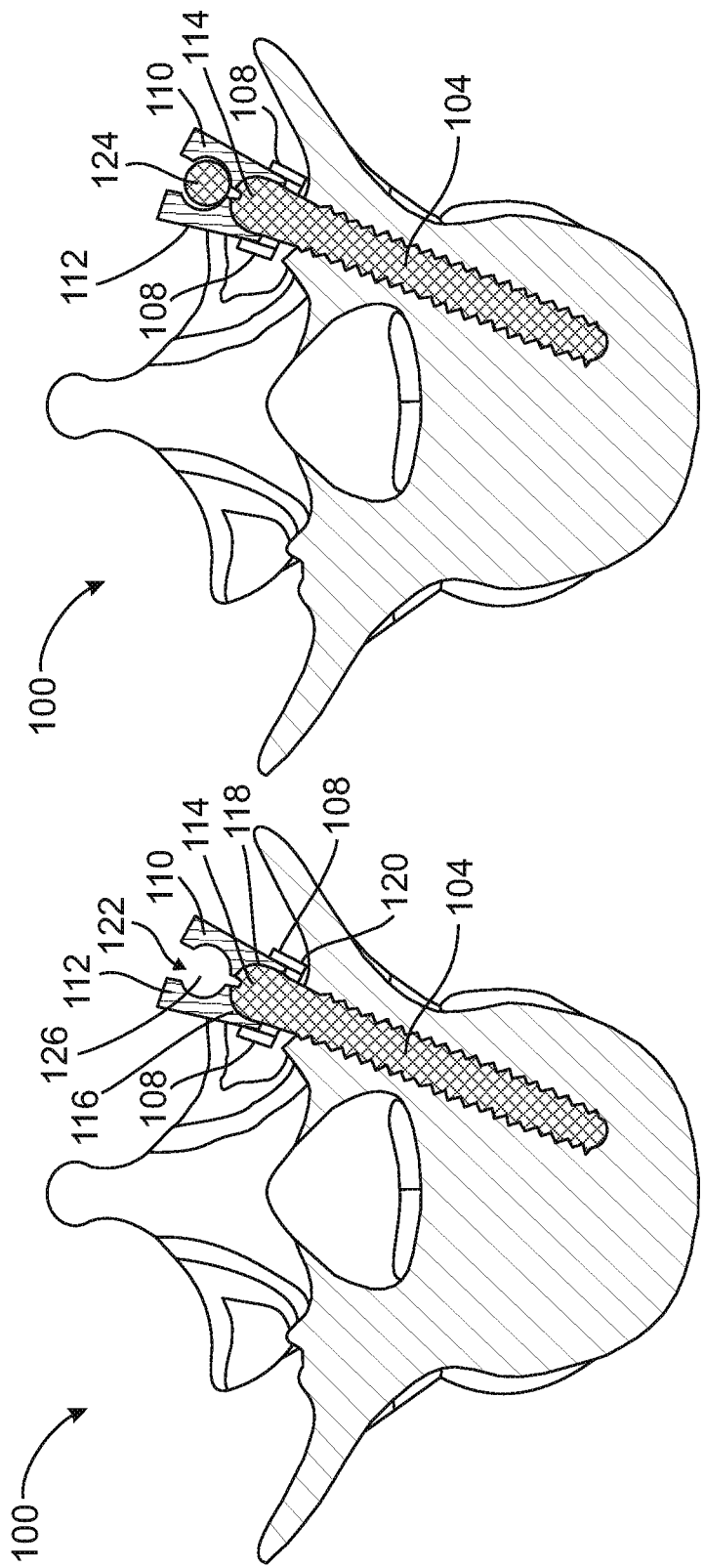

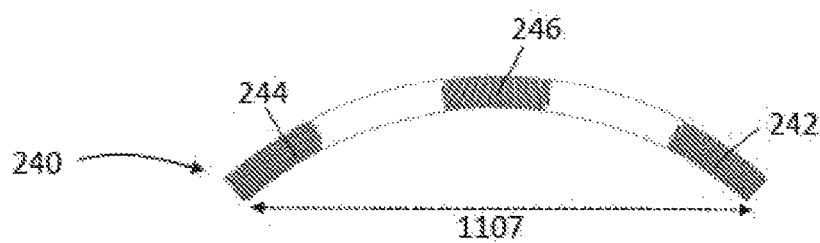
Figure 11D
Figure 11C
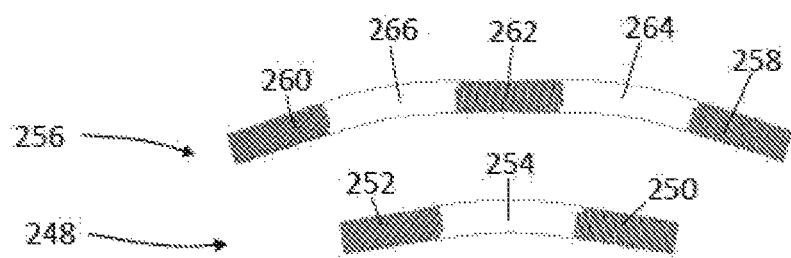
Figure 11F
Figure 11E
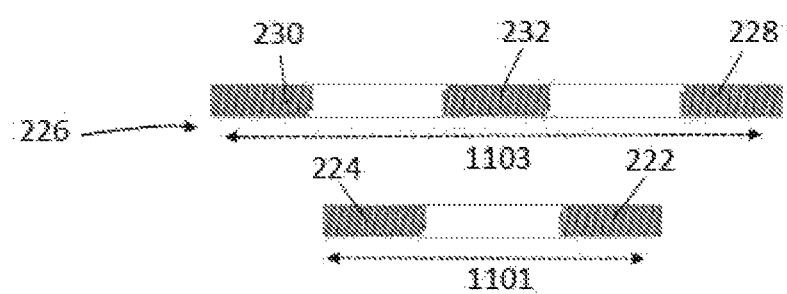
Figure 11B
Figure 11A

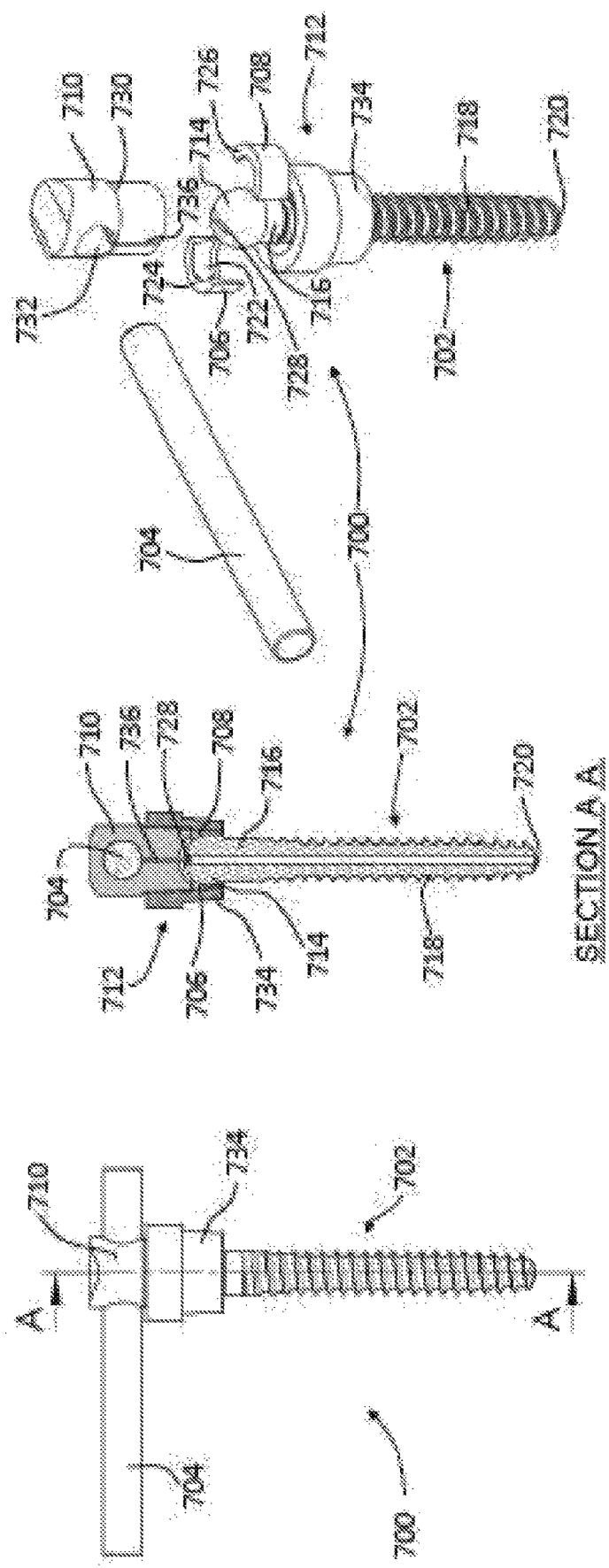

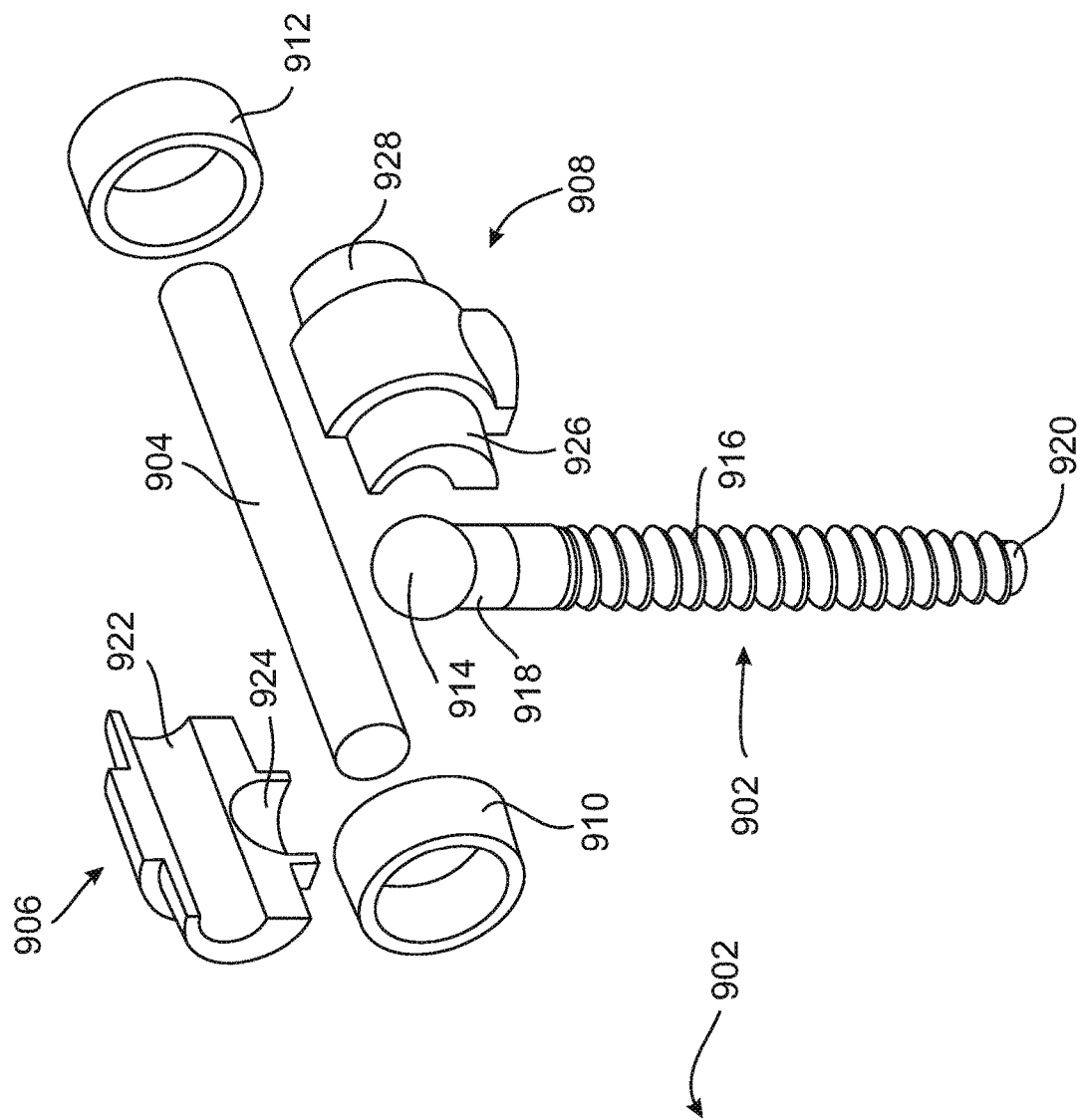
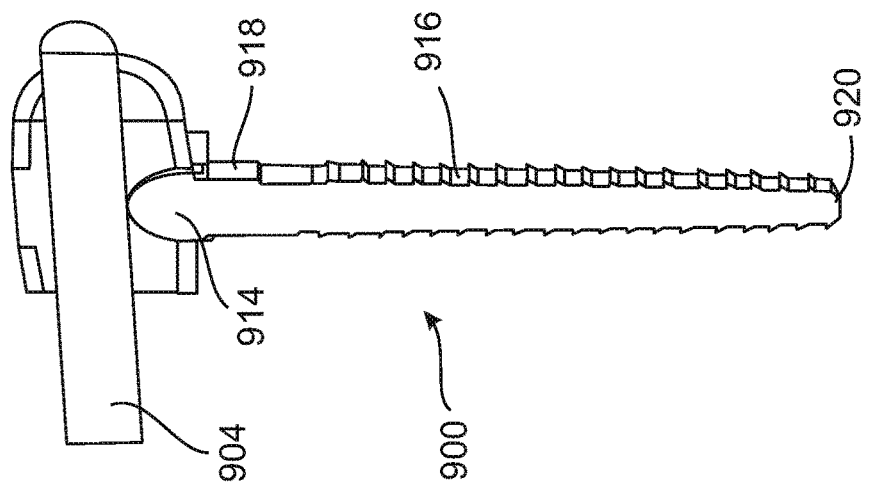
Figure 21B
Figure 21A

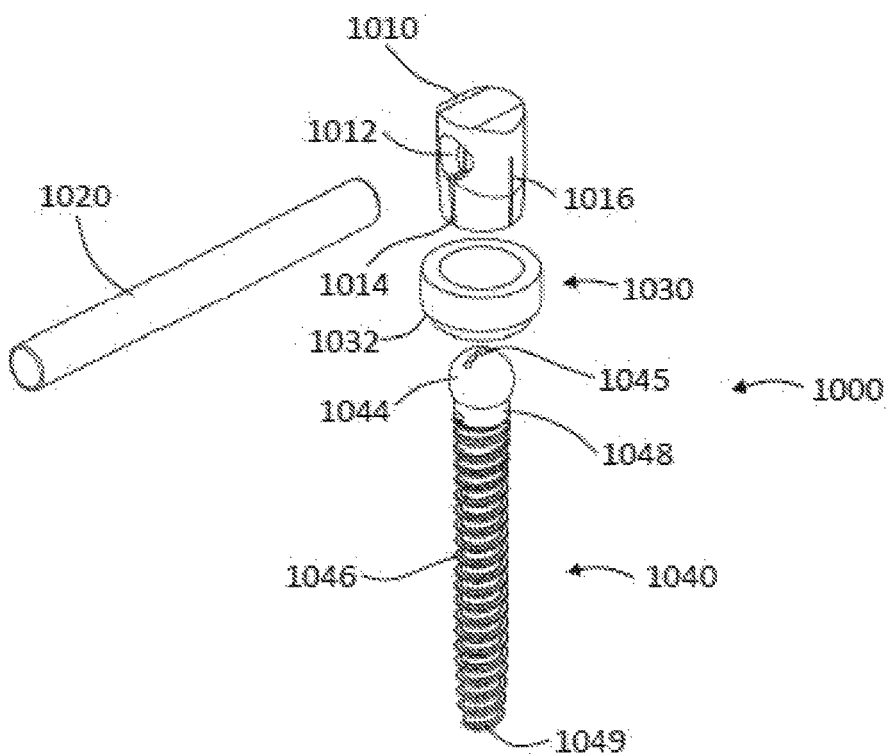
Figure 22A
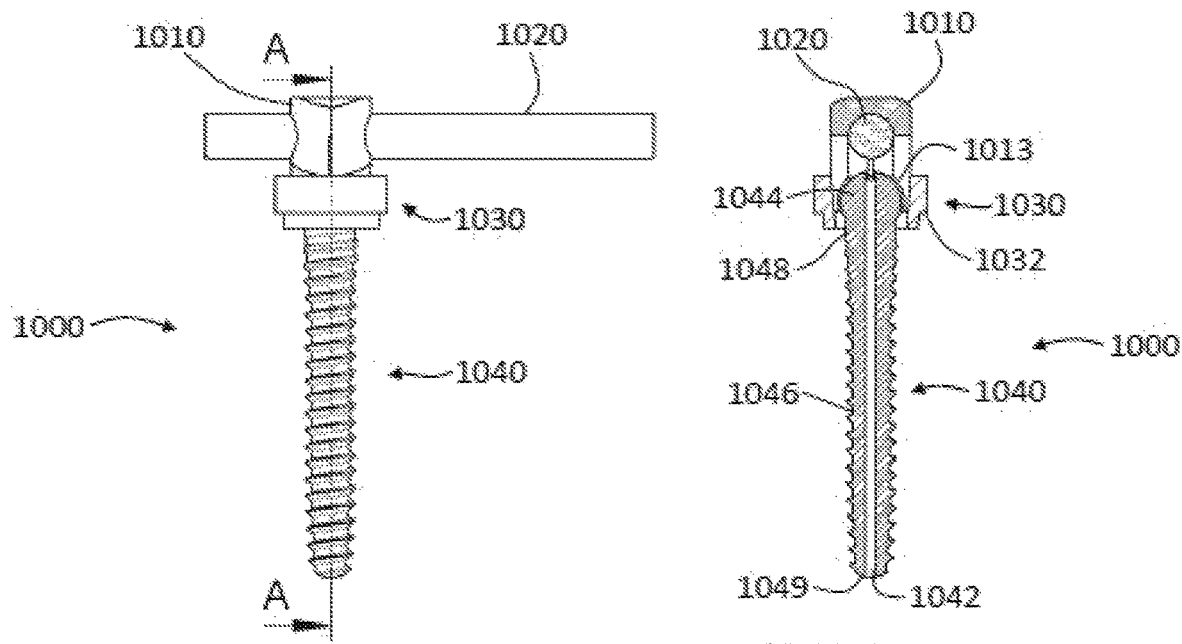
Figure 22B
Figure 22C
SECTION A-A

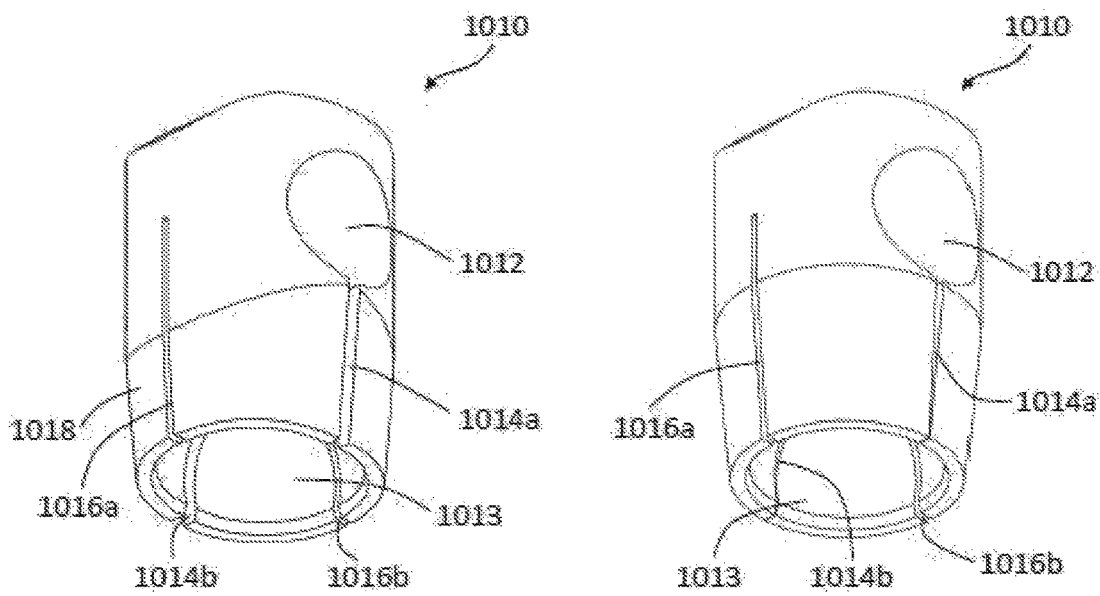
Figure 23A
Figure 23C
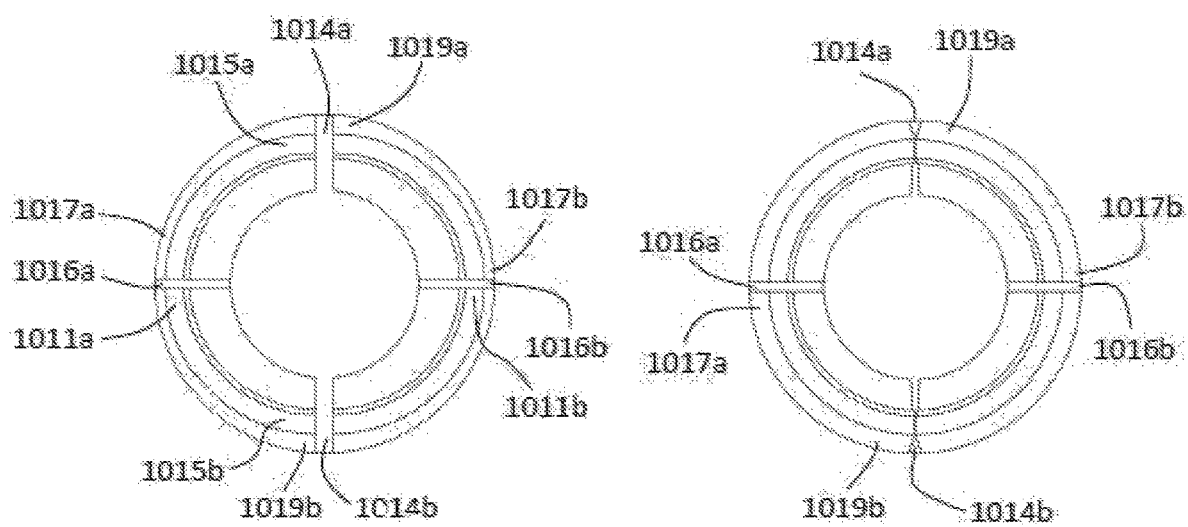
Figure 23B
Figure 23D

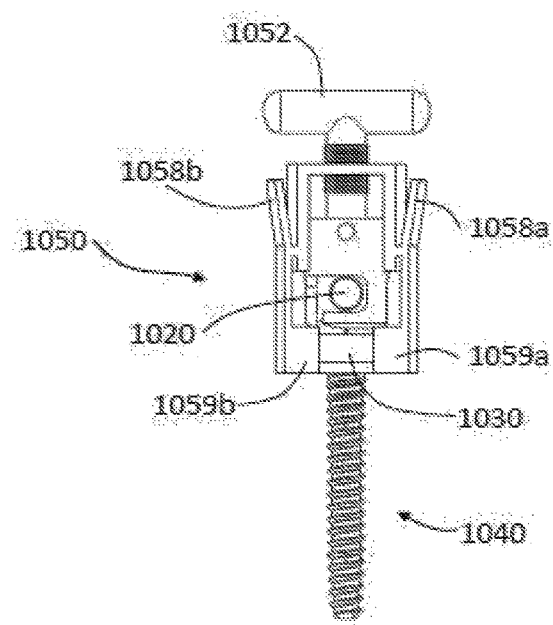
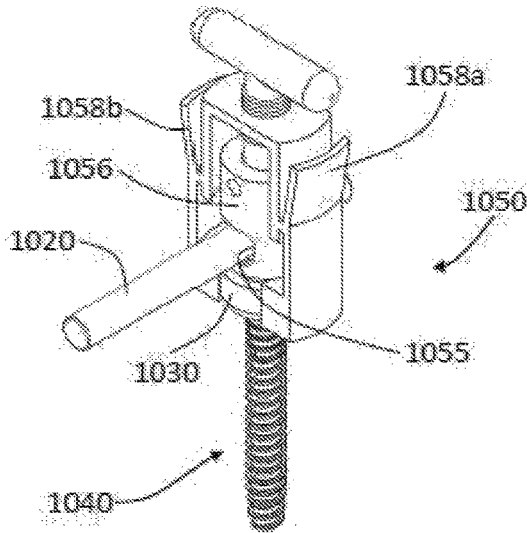
Figure 25B
Figure 25A
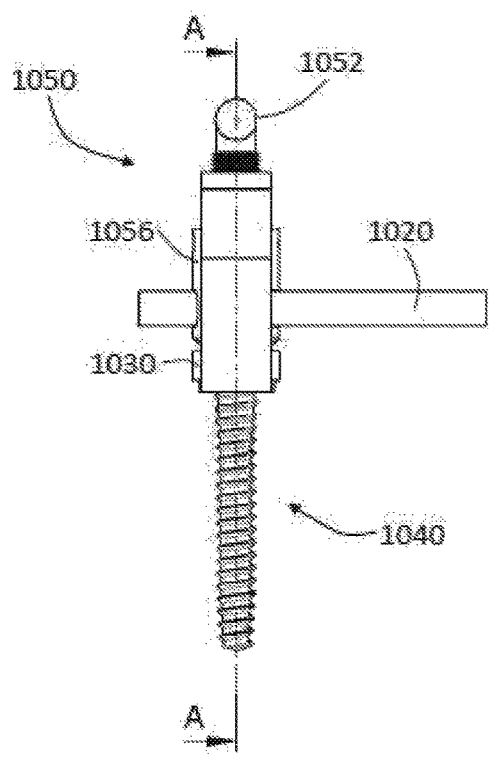
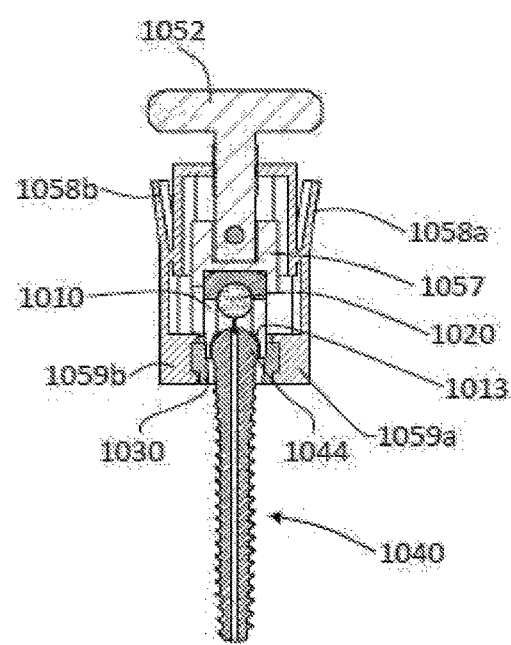
Figure 25C
SECTION A-A
Figure 25D

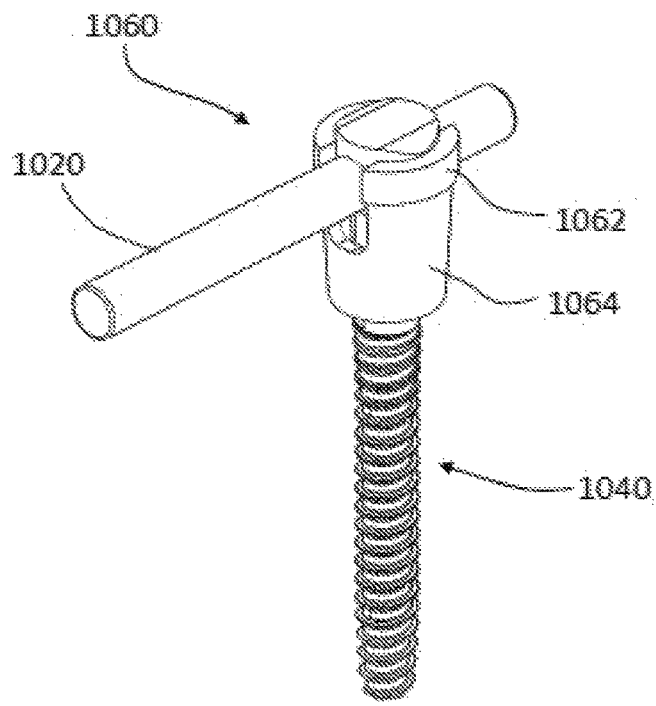
Figure 26A
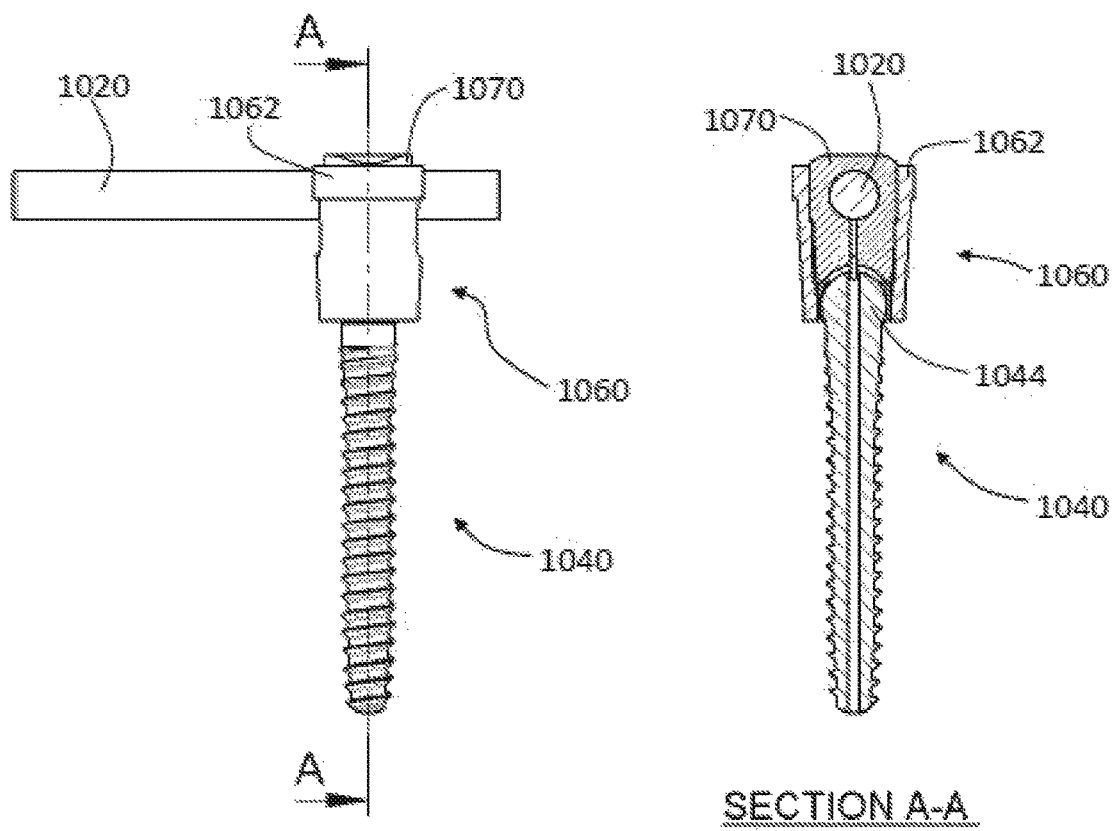
Figure 26B
SECTION A-A
Figure 26C

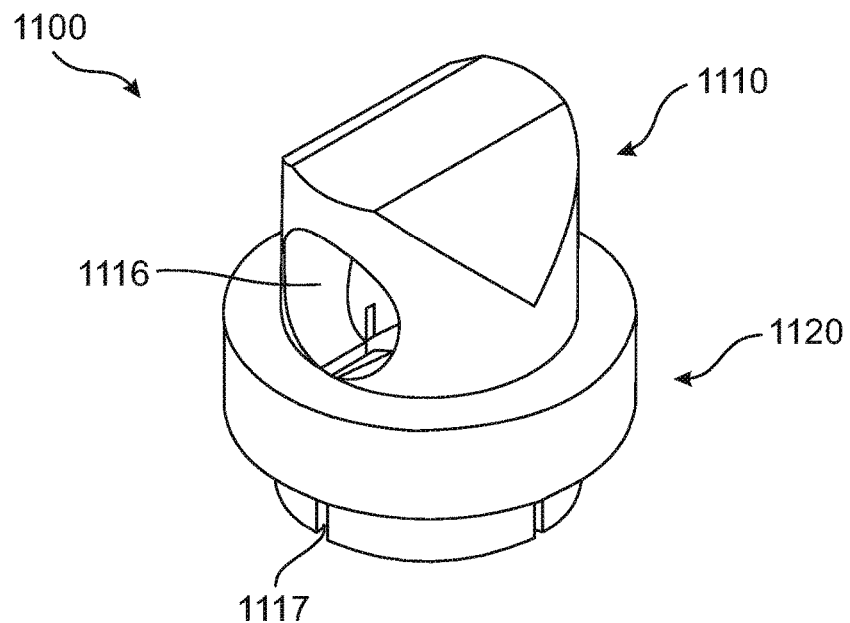
Figure 28A
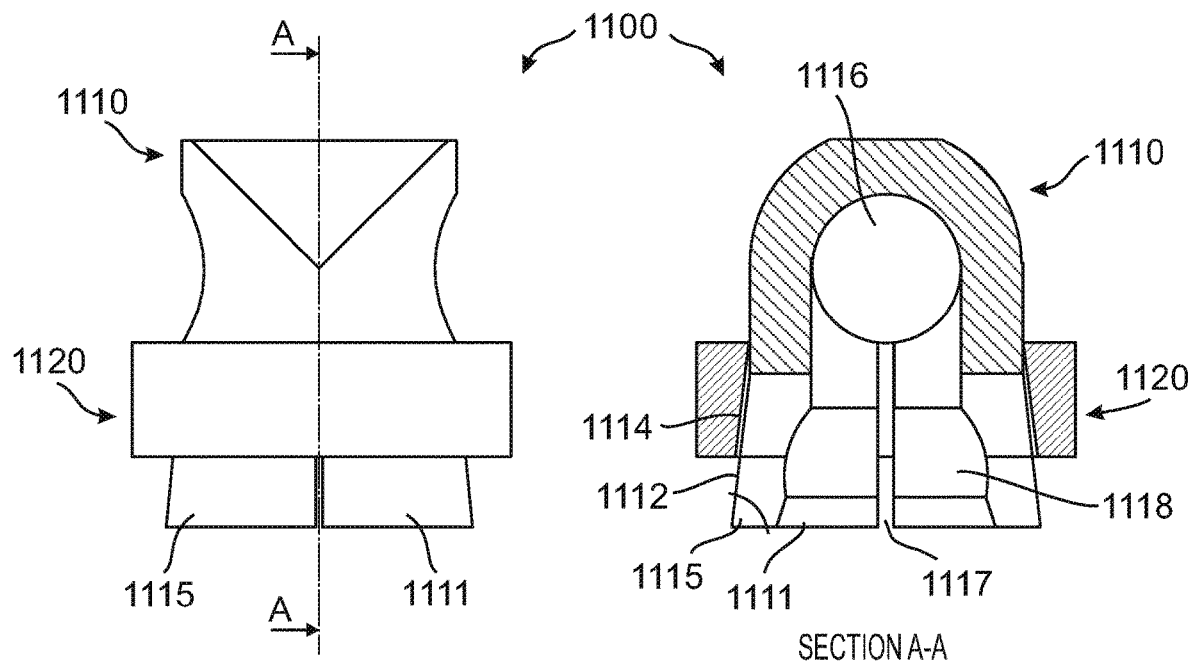
Figure 28B
Figure 28C

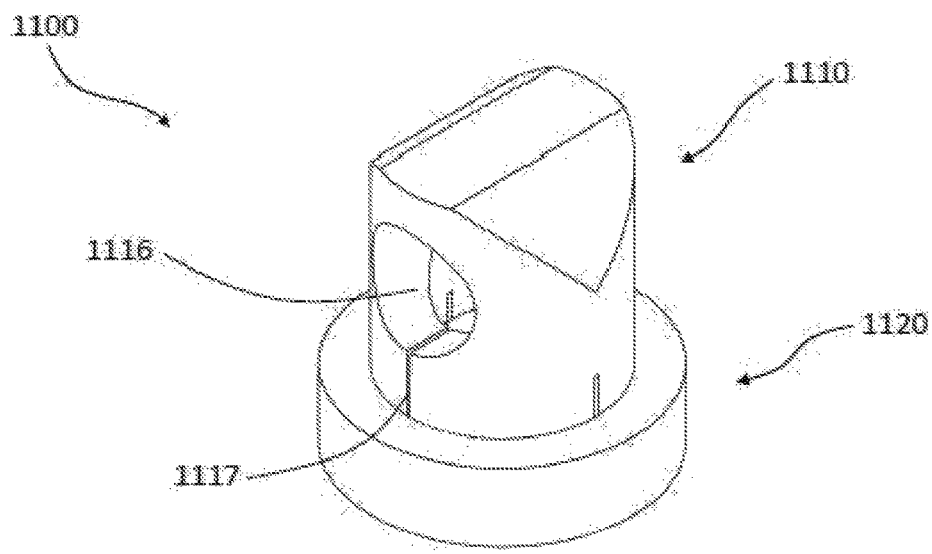
Figure 29A
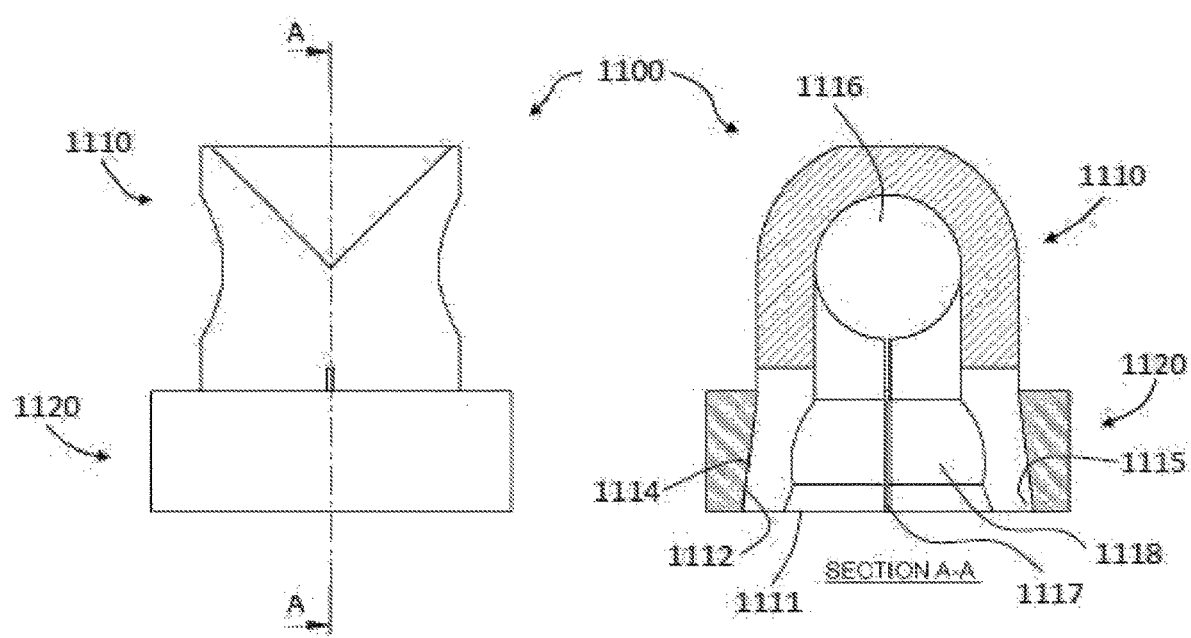
Figure 29B
Figure 29C

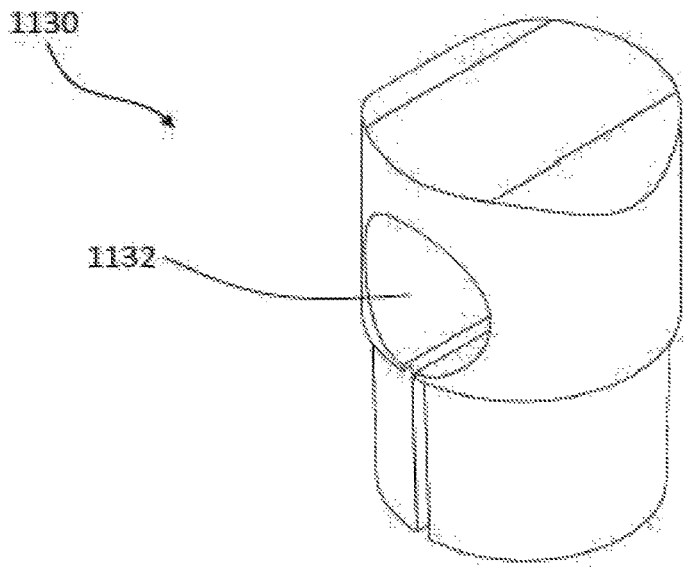
Figure 30A
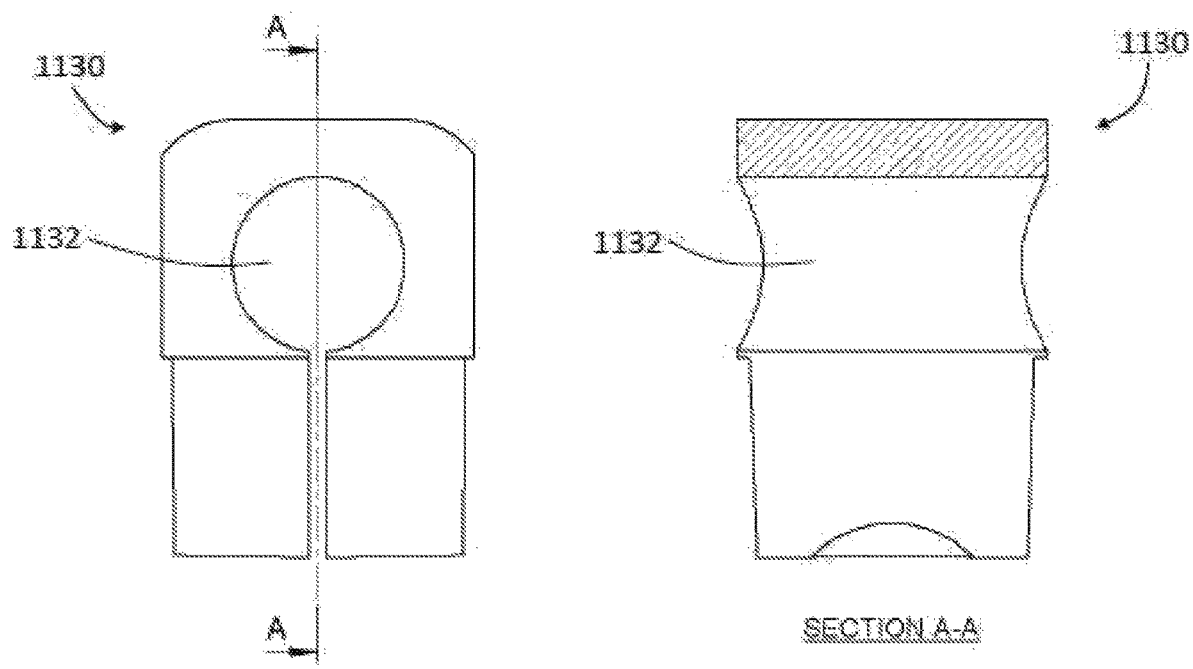
Figure 30B
SECTION A-A
Figure 30C

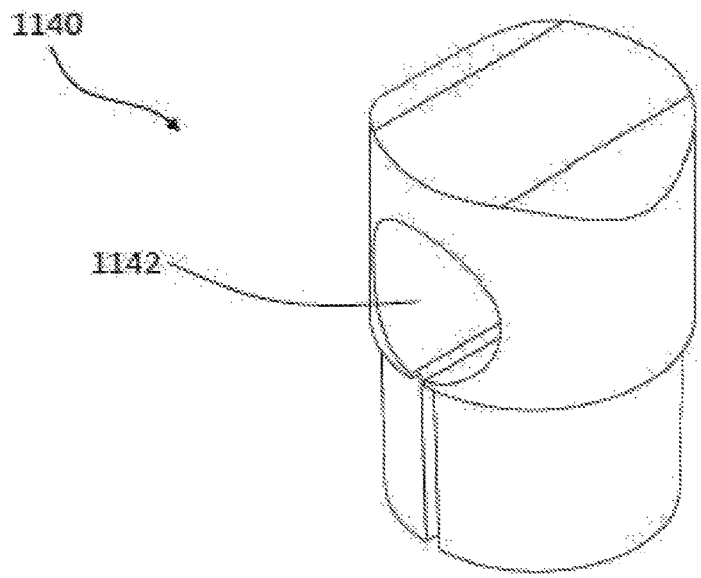
Figure 31A
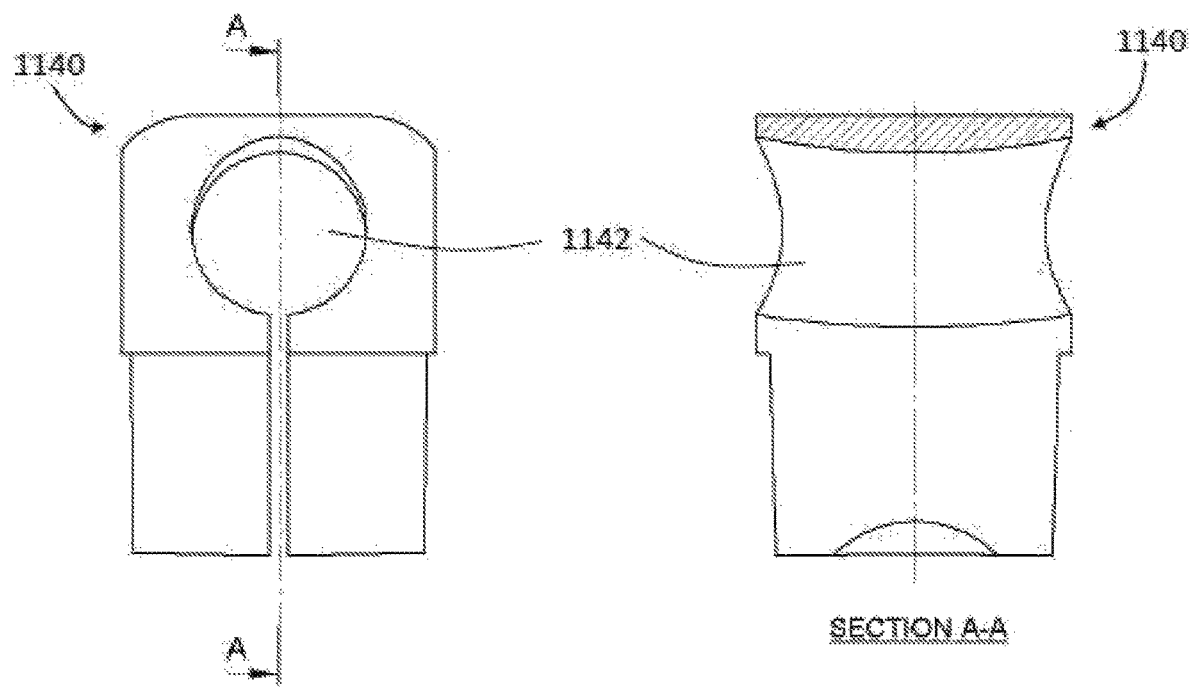
Figure 31B
Figure 31C

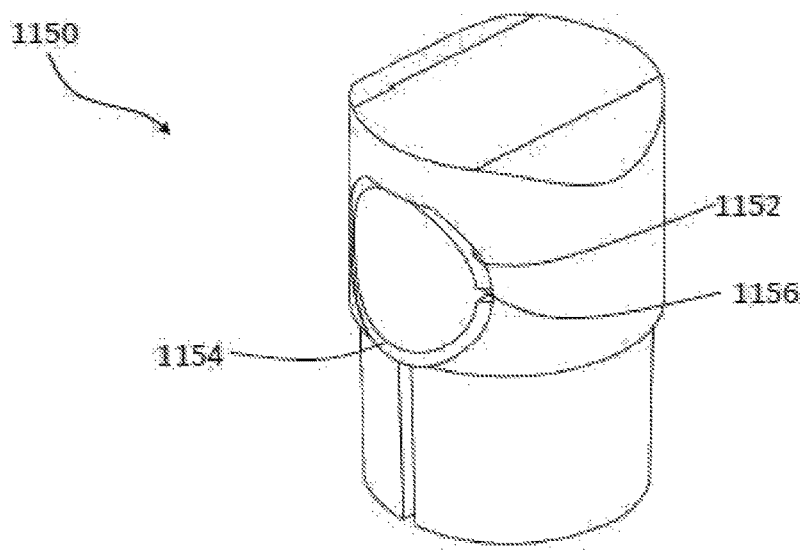
Figure 32A
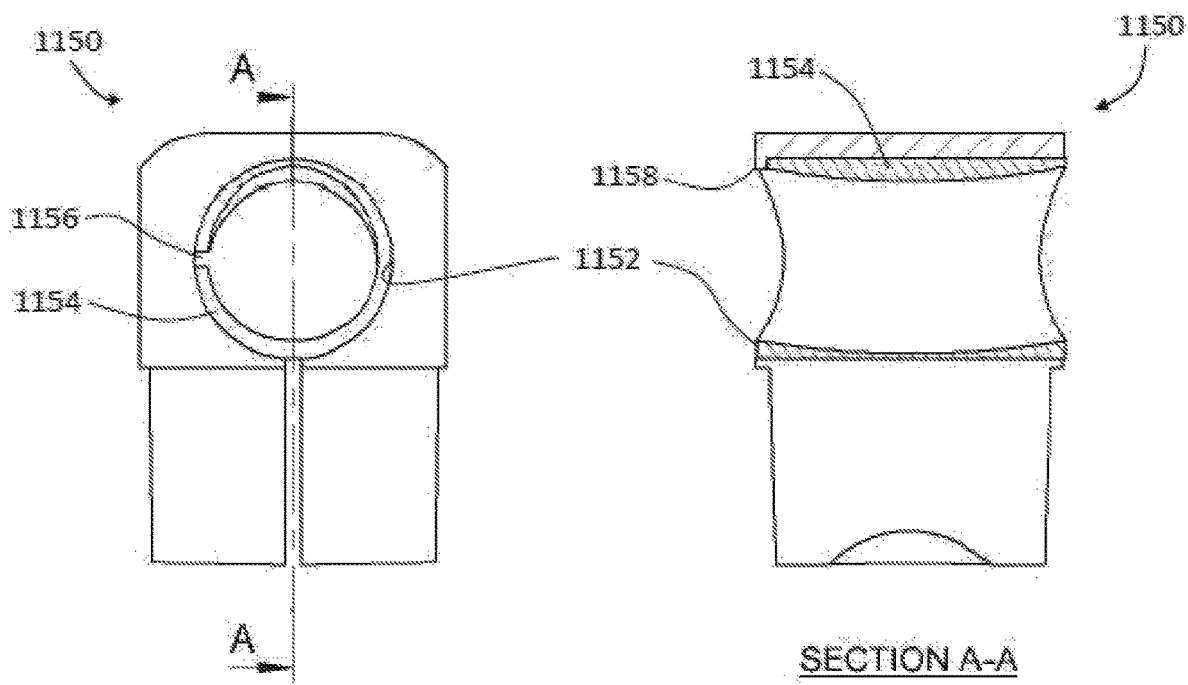
Figure 32B
SECTION A-A
Figure 32C

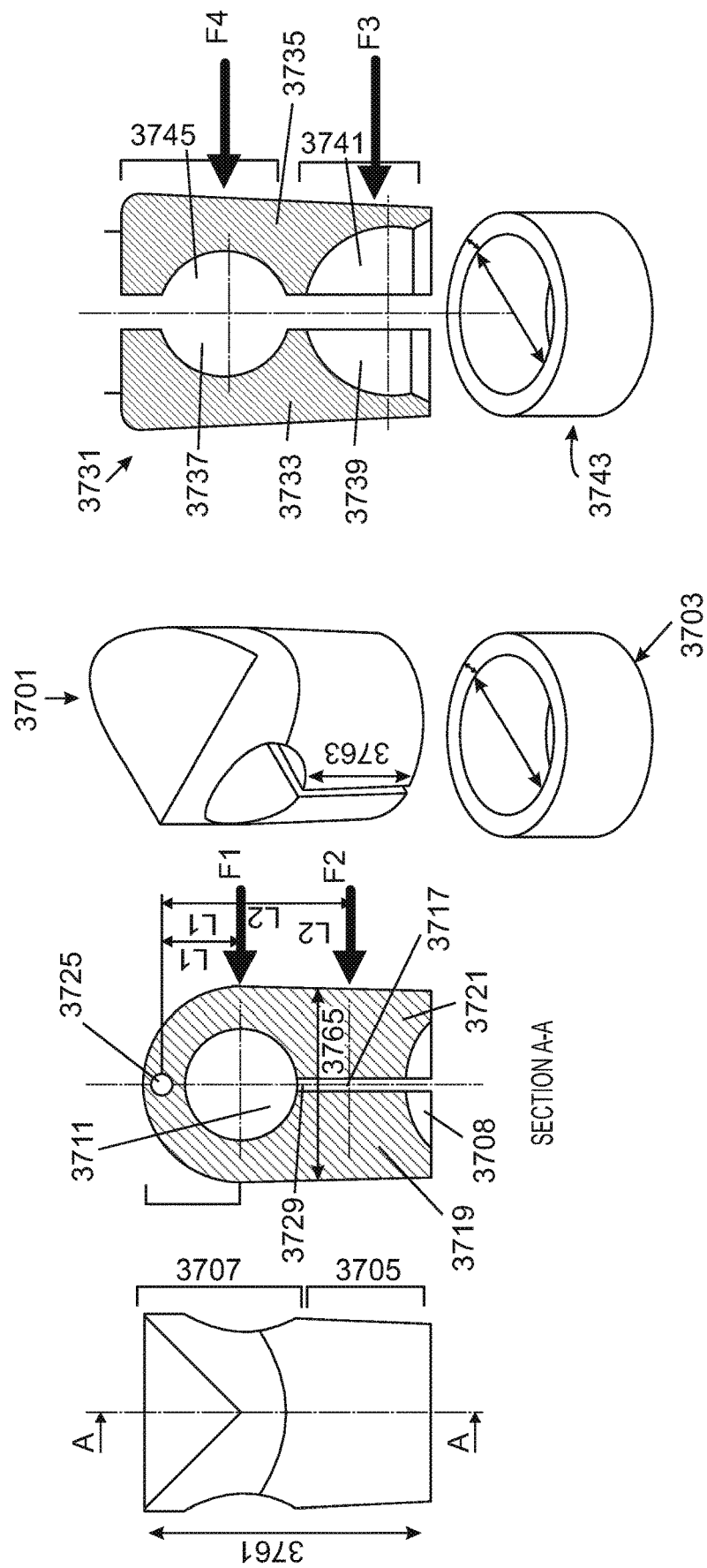

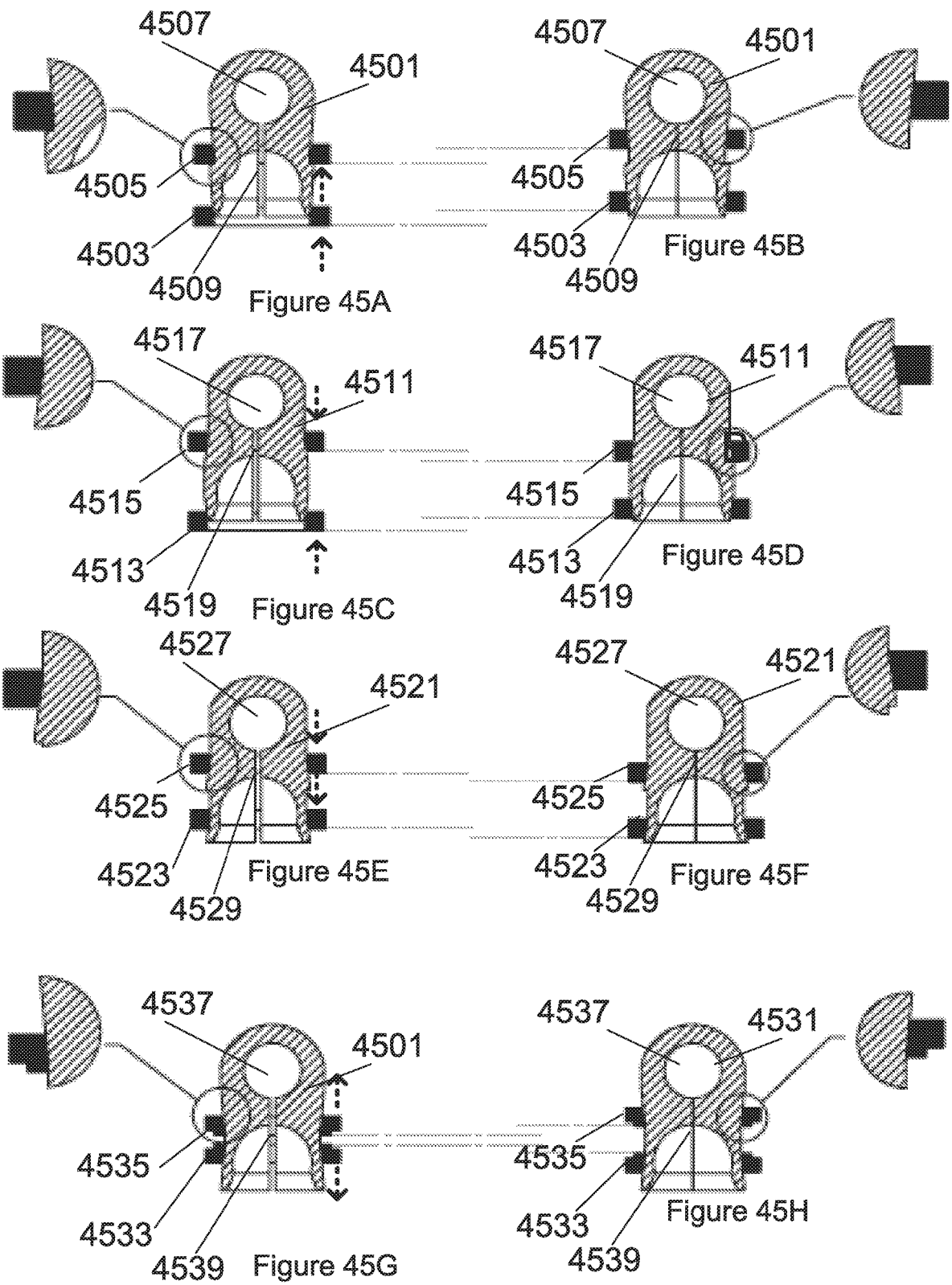

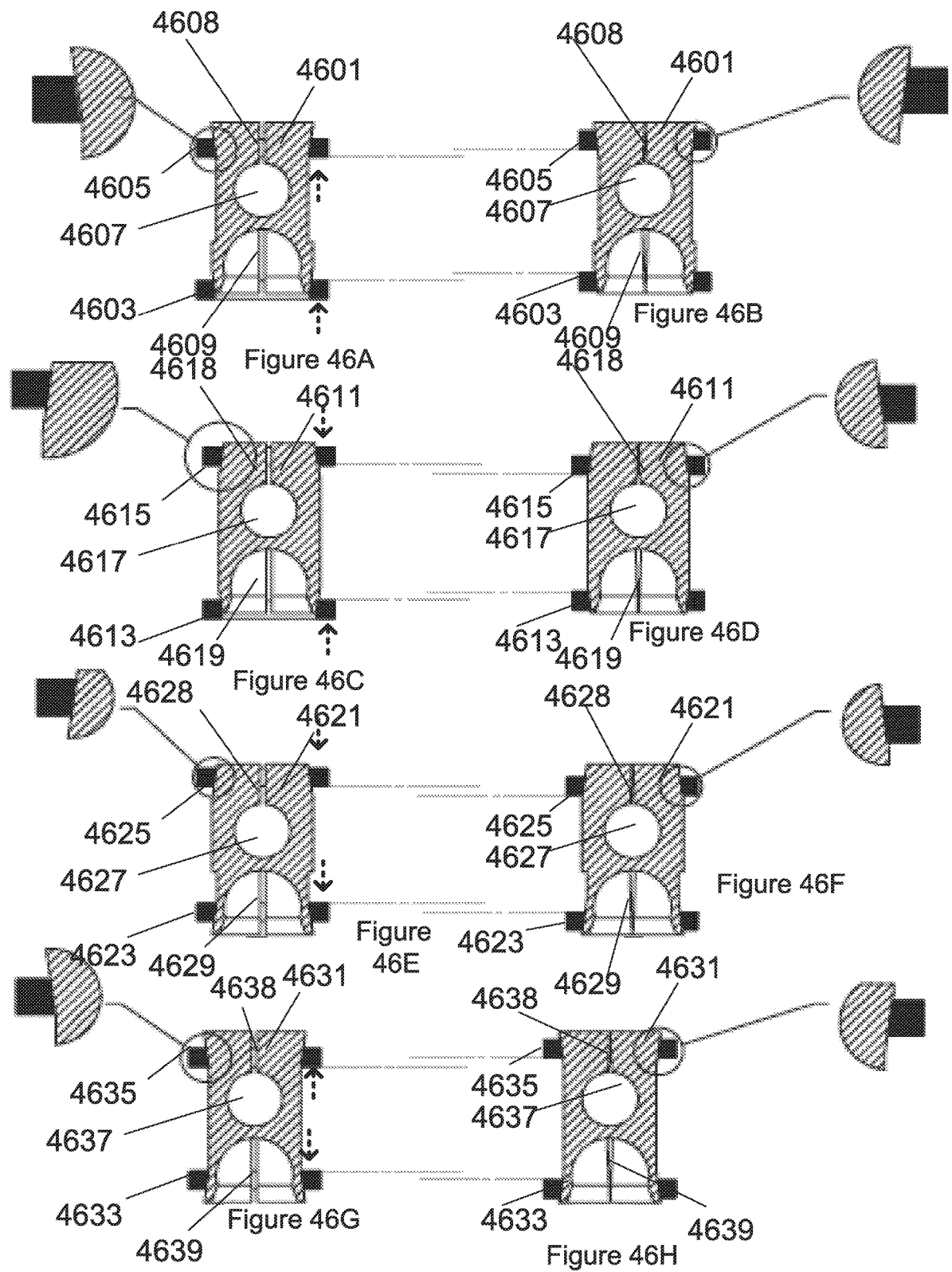

COMPOSITE MATERIAL SPINAL IMPLANT

RELATED APPLICATION/S

This application is a National Phase of PCT Patent Application No. PCT/IB2015/056635 having International filing date of Sep. 1, 2015, which is a Continuation-in-Part (CIP) of U.S. patent application Ser. No. 14/421,158 filed on Feb. 12, 2015, which is a National Phase of PCT Patent Application No. PCT/IL2014/050782 having International filing date of Sep. 1, 2014, which claims the benefit of priority under 35 USC § 119(e) of U.S. Provisional Patent Application Nos. 61/872,728 filed on Sep. 1, 2013, 61/926,328 filed on Jan. 12, 2014, 61/980,076 filed on Apr. 16, 2014, and 62/030,084 filed on Jul. 29, 2014. The contents of the above applications are all incorporated by reference as if fully set forth herein in their entirety.

FIELD OF INVENTION

The present invention in some embodiments thereof, relates to composite material bone implant devices, for example to spinal devices such as pedicle screw constructs, and/or to manufacturing methods for such devices, and/or to surgical instrumentation and procedures used during implantation and removal of the said composite material bone implants.

BACKGROUND OF THE INVENTION

Spinal fusion is a common surgery for the treatment of various spinal pathologies. During a spinal fusion, two or more vertebrae are fused together in order to eliminate abnormal motion caused by various pathologies (e.g., degenerative disc). Supplementary bone tissue, either from the patient or a donor, is used in conjunction with the patient' natural bone growth processes, to fuse the vertebrae.

Improvements in spinal fusion operations were achieved with the introduction of internal fixation devices, which are used as an adjunct to spinal fusion. The fixation device contributes to the stabilization and immobilization of the treated spinal segment, thereby enhancing fusion and reducing pain. One such device is a construct of pedicle screws and rods: two screws are placed into the pedicles of each treated vertebrae, and rods are used to longitudinally connect the screws, using locking elements.

Pedicle screw systems, with or without fusion, are used, for example, for stabilizing broken vertebrae until healing (fracture union), oncologic cases, and treatment of vertebra abnormal curvatures, such as scoliosis and kyphosis. Also, dynamic stabilization method, using pedicle screw system without spinal fusion, is also performed nowadays.

U.S. Pat. No. 5,683,392 to Richelsoph et al. discloses "A locking mechanism for locking a rod to a bone member. The locking mechanism includes a bone fixation member for attachment to the bone member, the bone fixation member having a spherical portion; an inner housing member having a channel for receiving the rod and having a spherical portion for engaging the spherical portion of the bone fixation member; and an outer housing member for locking the inner housing member to the rod and the spherical portion of the bone fixation member."

Normally, the pedicle screw-rod constructs are made of metal, such as titanium and stainless steel. Although metallic implants provide numerous advantages, they also have a few drawbacks. Metals obstruct visualization of the implant and surrounding tissue upon using fluoroscopy, CT and MR imaging. It is noted, that about 20%-30% of the patients continue to suffer following surgery with intra-pedicular implants. As the pedicle screws are located in adjacent to the spinal cord and nerves, such imaging means are highly important for follow-up evaluation, including for identifying screws exact location and determining whether the screws are the cause for pain. This problem also exist in cervical surgeries, where, for example, metal plates and screws are used for stabilizing cervical vertebrae with various pathologies (such as degenerative disc, fracture, tumor, stenosis), normally during fusion surgeries. Also, in oncology cases, evaluation of tumor progress may be limited due to artifacts produced by the metallic implants. Furthermore, metallic implants interfere with radiotherapy given to oncological patients. The relatively large electronic mass and the scattering phenomena reduce the radiation effectiveness and necessitate radiation in higher doses, that further provoke side effects on surrounding tissue.

In addition, metal construction normally provides adequate bending and torsion strength, thus reducing problems associated with implant fracture. However, the rigid metal implant, having different elasticity than that of the bone, may contribute to stress shielding phenomena. Furthermore, metals such as stainless steel may cause biocompatibility problems related to corrosion and sensitization reaction (mainly due to allergy to nickel). In addition, a resistance of metals to fatigue loads may be poorer than a resistance of some composite materials to a similar fatigue load.

Non-metal, composite material, spinal bone implants are currently available on the market, for example cage and vertebral body replacement devices made of carbon-polyetheretherketone (PEEK). Lumbar and/or cervical cages are also produced from PEEK, carbon fiber reinforced polymer or carbon.

Metal pedicle screw systems with rods made of polymer material (e.g., PEEK) are also market available. Yet, those devices provide for lower stiffness compared to metal devices and are used in limited indications. In addition, metal pedicle screw systems with rods or plates made of carbon fiber reinforced polymer (e.g., PEEK or PEKEKK) are also available.

Composite material bone implants, made of, for example, carbon fiber-reinforced PEEK, are also used for other bone applications, such as intramedullary nails and bone plates (CarboFix Orthopedics Ltd.).

SUMMARY OF THE INVENTION

Some embodiments of the present invention are exemplified by the following examples. It is noted that features form examples may be combine and some embodiments of the invention. Also some embodiments of the invention include the features of a plurality of examples selected from any combination of the examples herein.

EXAMPLE 1

A pedicle screw implant construct kit, comprising:
at least one pedicle screw including a head, said screw comprising composite material including reinforcing filaments embedded in a polymer matrix;
at least one unitary collar, said collar comprising composite material including reinforcing filaments embedded in a polymer matrix, said collar including at least one recess defining a cavity shaped and sized for receiving a rod, said collar sized, shaped and configured to be coupled to said head of said pedicle screw;

an elongated rod sized and shaped for connecting said collar to one or more additional collars, thereby coupling between said at least one pedicle screw and one or more additional screws, said rod comprising composite material including reinforcing filaments embedded in a polymer matrix; and at least one locking ring, said ring comprising composite material including reinforcing filaments embedded in a polymer matrix, said ring sized and shaped to be positioned over at least portion of said collar and restrict relative movement of one or both of the screw head and the rod relative to said collar, by exerting radial compression force onto said collar.

EXAMPLE 2

A kit according to example 1, wherein said collar and said ring do not have threading at an interface therebetween.

EXAMPLE 3

A kit according to any of the preceding examples, wherein said kit is less than 1% by weight atoms with an atomic number over 25.

EXAMPLE 4

A kit according to any of the preceding examples, wherein said kit is less than 0.01% by weight atoms with an atomic number over 25.

EXAMPLE 5

A kit according to any of the preceding examples, wherein said kit contains no radio-opaque markers.

EXAMPLE 6

A kit according to any of the preceding examples, wherein said cavity shaped and sized for a receiving a rod has a different cross-section than said rod and/or has no rotationally symmetric offset relative to the rod shape.

EXAMPLE 7

A kit according to example 6, wherein said cavity shaped and sized for a receiving a rod is elongated in a direction radial to a longitudinal axis thereof.

EXAMPLE 8

A kit according to example 7, wherein said elongation is over an entire length of said cavity.

EXAMPLE 9

A kit according to example 7 or example 8, wherein said elongation is different at ends of said cavity from any elongation at a center of said cavity.

EXAMPLE 10

A kit according to any of examples 7-9, wherein said elongation support the engagement by said cavity of both straight rods and rods bent with a radius of curvature of at least 30 mm.

EXAMPLE 11

A kit according to any of examples 7-10, wherein said elongation is vertical with respect to said collar.

EXAMPLE 12

A kit according to any of the preceding examples, wherein said ring is mounted on said collar prior to said ring causing said motion restriction.

EXAMPLE 13

A kit according to example 12, wherein said ring is mounted in a narrowing in an outer profile of said collar, vertically adjacent to a gradual widening in said outer profile and is configured to lock to said widening by friction.

EXAMPLE 14

A kit according to example 13, wherein said ring is mounted vertically adjacent an abrupt widening in said outer profile.

EXAMPLE 15

A kit according to any of examples 12-14, comprising at least two rings, both mounted on said collar without causing said restricting.

EXAMPLE 16

A kit according to any of examples 12-15, wherein said collar is slotted at both a proximal end and a distal end thereof.

EXAMPLE 17

A kit according to any of the preceding examples, comprising two locking rings for said collar and wherein said collar includes two regions for locking of said rings to said collar.

EXAMPLE 18

A kit according to example 17, wherein both said rings are pre-loaded on said collar prior to them causing said restricting.

EXAMPLE 19

A kit according to example 17 or example 18, wherein said collar includes at least one radial extension which prevents sliding off of at least one ring from said collar.

EXAMPLE 20

A kit according to any of examples 17-19, wherein at least one ring is narrower away from said collar than adjacent said collar.

EXAMPLE 21

A kit according to any of examples 17-20, wherein said collar is slotted at both a proximal and at a distal end thereof and each ring is mounted at a vertical position corresponding to a different one of said slots.

EXAMPLE 22

A kit according to any of examples 17-21, wherein said collar is shaped so that locking one ring only restricts the movement of one of said rod and said head of said screw.

EXAMPLE 23

A kit according to any of examples 17-22, wherein said collar is shaped so that locking of the two rings requires movement of the two rings in a same direction.

EXAMPLE 24

A kit according to any of examples 17-22, wherein said collar is shaped so that locking of the two rings requires movement of the two rings in opposite directions.

EXAMPLE 25

A kit according to any of examples 17-24, wherein said two rings are mounted below said rod.

EXAMPLE 26

A kit according to any of the preceding examples, wherein said collar is shaped so that a locking ring can be mounted thereon without said restricting and then locked without extending during a mounting state nor during a locking state more than 1 mm below said collar.

EXAMPLE 27

A kit according to example 26, wherein said collar is shaped so that said ring locks by a distal movement away from said two cavities.

EXAMPLE 28

A method of tightening a collar on a pedicle screw, comprising:
  providing a collar having a composite locking ring mounted thereon;
  adjusting the position and/or orientation relative to the collar of at least one of a rod and a screwhead within the collar;
  moving said locking ring from one configuration on the collar to another configuration on the collar, thereby causing the collar to radially reduce in size and engage said rod and/or said screwhead.

EXAMPLE 29

A method of tightening a collar on a pedicle screw, comprising:
  providing a collar;
  adjusting the position and/or orientation relative to the collar of at least one of a rod and a screwhead within the collar;
  moving at least two locking ring relative to said collar to radially reduce a cavity in said collar, thereby engaging said rod and/or said screwhead.

EXAMPLE 30

A method according to example 29, comprising moving said locking rings in opposite directions along an axis of said collar.

EXAMPLE 31

A method according to example 29 or example 30, comprising moving said locking rings in same directions along an axis of said collar.

EXAMPLE 32

A method according to any of examples 29-31, comprising moving said locking rings at a same time.

EXAMPLE 33

A method according to any of examples 29-32, comprising separately clocking said rod and said screwhead by separately moving said two locking rings.

EXAMPLE 34

A method of selecting kit components for a spinal fixation procedure, comprising:
  determining a desired layout of two rods, including different bending for the two rods, said different bendings including a first bend with a bending radius of between 30 and 60 mm and a second bend with at least a double bending radius; and
  selecting a same collar for both rods, independent of said different bendings.

EXAMPLE 35

A method of providing radiation treatment to a patient, comprising:
  determining that said patient needs radiation treatment near or via a spine thereof;
  selecting an all composite spinal fixation kit which does not interfere with radiation more than aluminum based on said determination;
  implanting said system; and
  providing radiation treatment to the patient.

EXAMPLE 36

A method according to example 35, comprising removing an existing metal-containing spinal fixation component prior to said selecting and after said determining.

EXAMPLE 37

A method according to example 35 or example 36, comprising providing said radiation treatment to said patient with no metal adjacent said spine and associated with said kit.

EXAMPLE 38

A locking collar for use with a rod and a pedicle screw for spinal fixation, comprising:

at least one collar body, said collar comprising composite material including reinforcing filaments embedded in a polymer matrix, said collar including at least one recess defining a cavity shaped and sized for receiving a rod, said collar sized, shaped and configured to be coupled to said head of said pedicle screw; and at least one locking ring, said ring comprising composite material including reinforcing filaments embedded in a polymer matrix, said ring sized and shaped to be positioned over at least portion of said collar and restrict relative movement of one or both of the screw head and rod relative to said collar by exerting radial compression force onto said collar.

EXAMPLE 39

A collar according to example 38, having two locking rings for locking at two different vertical locations on said collar, relative to a spine and/or wherein said collar is flexible enough and said cavity shaped to allow said collar to be advanced along a rod bent in a direction and/or amount which does not match said cavity and/or wherein said collar is slotted and is flexible enough to be transversely mounted on a rod suitable for locking in said cavity using said locking ring.

EXAMPLE 40

A locking collar for use with a rod and a pedicle screw for spinal fixation, comprising:

at least one unitary collar body, said collar comprising composite material including reinforcing filaments embedded in a polymer matrix, said collar including at least one recess defining a cavity shaped and sized for receiving a rod, said collar sized, shaped and configured to be coupled to said head of said pedicle screw; and at least one locking ring, said ring comprising composite material including reinforcing filaments embedded in a polymer matrix, said ring sized and shaped to be positioned over at least portion of said collar and restrict relative movement of one or both of the screw head and rod relative to said collar by exerting radial compression force onto said collar.

EXAMPLE 41

A locking collar according to example 40, comprising at least two locking rings.

EXAMPLE 42

A locking collar according to example 41, wherein said rings are positioned on said collar below said cavity for a rod.

EXAMPLE 43

A locking collar according to any of examples 40-42, wherein said collar and said ring do not have threading at an interface therebetween.

EXAMPLE 44

A pedicle screw implant construct kit, comprising:
at least one pedicle screw including a head, said screw comprising composite material including reinforcing filaments embedded in a polymer matrix;

at least one collar, said collar comprising composite material including reinforcing filaments embedded in a polymer matrix, said collar including at least one recess defining a cavity shaped and sized for receiving a rod, said collar sized, shaped and configured to be coupled to said head of said pedicle screw;

an elongated rod sized and shaped for connecting said collar to one or more additional collars, thereby coupling between said at least one pedicle screw and one or more additional screws, said rod comprising composite material including reinforcing filaments embedded in a polymer matrix; and at least one locking ring, said ring comprising composite material including reinforcing filaments embedded in a polymer matrix, said ring sized and shaped to be positioned over at least portion of said collar and restrict relative movement of one or both of the screw head and the rod relative to said collar, by exerting radial compression force onto said collar.

EXAMPLE 45

A kit according to example 44, wherein said collar and said ring do not have threading at an interface therebetween and/or wherein said kit is less than 1% by weight atoms with an atomic number over 25 and/or wherein said cavity shaped and sized for a receiving a rod has a different cross-section than said rod and/or has no rotationally symmetric offset relative to the rod shape and/or wherein said ring is mounted on said collar prior to said ring causing said motion restriction and/or wherein the kit comprises two locking rings for said collar and wherein said collar includes two regions for locking of said rings to said collar and/or wherein the kit comprises two locking rings for said collar and wherein said collar includes two regions below said rod for locking of said rings to said collar.

EXAMPLE 46

A device for tightening two locking rings on a collar, which collar is shaped and sized for holding a spine rod and a pedicle screw, comprising:

(a) at least one arm including at least one ring-engaging portion;

(b) at least one element adapted to engage said collar or a second ring; and (c) a lever including a handle and coupled to said arm and separately coupled to said element and causing relative movement therebetween.

There is provided in accordance with some embodiments of the invention a pedicle screw implant construct kit, comprising:

at least one pedicle screw including a head, said screw comprising composite material including reinforcing filaments embedded in a polymer matrix;

at least one collar, said collar comprising composite material including reinforcing filaments embedded in a polymer matrix, said collar including at least one recess defining a cavity shaped and sized for receiving a rod, said collar sized, shaped and configured to be coupled to said head of said pedicle screw;

an elongated rod sized and shaped for connecting said collar to one or more additional collars, thereby coupling between said at least one pedicle screw and one or more additional screws, said rod comprising composite material including reinforcing filaments embedded in a polymer matrix; and at least one locking ring, said ring comprising composite material including reinforcing filaments embedded in a polymer matrix, said ring sized and shaped to be positioned over at least portion of said collar and restrict relative movement of the screw head and rod by exerting radial compression force onto said collar.

In some exemplary embodiments of the invention, said collar comprises at least two portions that are movable towards each other in a direction perpendicular to a long axis of said collar. Optionally or alternatively, said collar comprises an integral cap section designed to encircle a part of said rod which faces away from said screw. Optionally or alternatively, said portions of said collar are separated by a slot extending transversely along at least an axial segment of the collar, and wherein said ring is configured to approximate said collar portions, thereby reducing a width of said slot.

In some exemplary embodiments of the invention, said ring comprises a non-threaded internal wall.

In some exemplary embodiments of the invention, said ring has an internal wall which defines a channel, and wherein said channel decreases in diameter in a distal direction. Optionally, a tapering angle of said internal wall is between 1-5 degrees relative to an axis passing through a center of the ring.

In some exemplary embodiments of the invention, said reinforcing filaments are carbon fibers and wherein said polymer matrix is PEEK.

In some exemplary embodiments of the invention, said collar includes at least one recess that defines a generally spherical cavity for coupling to said screw head and wherein said screw head comprises a spherical or nearly-spherical profile, defining a surface area which contacts between 50% and 95% of the inner surface of said spherical recess, thereby leaving spaces between the walls of the recess and the screw head, even when said collar is closed on said screw head.

In some exemplary embodiments of the invention, said collar includes at least one recess that defines a generally spherical cavity for coupling to said screw head and wherein said screw head comprises a generally-spherical profile, wherein a contact surface between said collar recess and said screw head is defined to lie at least 90% in a band around an equator of said screw head when said screw is vertically aligned in said collar and having an angular range of between 20 and 80 degrees and wherein, within said band said collar recess contacts said screw head over between 75% and 95% of said contact surface.

In some exemplary embodiments of the invention, said kit further comprises an embracing structure configured to be positioned over said screw head, said embracing structure comprising at least one adapter, said at least one adapter defining a recess for said screw head, and wherein said locking ring acts as an external housing holding said collar on top of said at least one adapter upon implanting of said collar. Optionally, said at least one adapter comprises a plurality of adaptors that are positionable and cooperate to define a cylindrical or conical external profile.

In some exemplary embodiments of the invention, a distal portion of said collar comprises a second cavity configured to receive at least a portion of said screw head.

In some exemplary embodiments of the invention, a radiolucency level of the reinforced composite material used in all of said kit is high enough to support imaging the treated spine segment in the presence of said construct.

In some exemplary embodiments of the invention, the components have a low enough metal composition to allow imaging with CT or MRI within between 1.5 and 2.5 mm distant from said construct.

In some exemplary embodiments of the invention, the components have a low enough metal composition to not substantially interfere with visualization under CT or MRI imaging.

In some exemplary embodiments of the invention, at least one of said pedicle screw, collar, rod and ring comprise one or more radiopaque markers to enable visualization under imaging.

In some exemplary embodiments of the invention, said radiopaque markers are located along at least one of a long axis of said pedicle screw and a long axis of said rod.

In some exemplary embodiments of the invention, said radiopaque marker is in the form of powder incorporated within said composite material of one or more of said pedicle screw, collar, rod and ring, said powder occupying a content volume of 0.2%-2%. Optionally, said powder comprises gold.

In some exemplary embodiments of the invention, said rod comprises a marker in the form of a tantalum wire extending lengthwise along said rod, wherein said collar comprises a marker in the form of a tantalum pin positioned in a proximal portion of said collar, wherein the ring comprises a tantalum wire marker in the form of a non-closed ring; and wherein said pedicle screw comprises a marker in the form of metal powder embedded within at least a portion of said composite material of said pedicle screw.

In some exemplary embodiments of the invention, an external profile of said ring comprises a portion of larger diameter and a portion of smaller diameter.

In some exemplary embodiments of the invention, an external profile of said ring does not axially vary. Alternatively, said external profile comprises one or more of a generally cylindrical profile, a tapering profile, a conical profile and a stepped profile with at least one abrupt change in diameter.

In some exemplary embodiments of the invention, an external profile of said ring comprises at least one radially directed projection or recess sized for engaging of a tool thereby.

In some exemplary embodiments of the invention, an external profile of said ring comprises a portion of axial extent of at least 50% of a length of said ring which is cylindrical in profile.

In some exemplary embodiments of the invention, an external profile of said collar at a distal portion of said collar includes section which tapers in a distal direction following and due to positioning of said ring at said locking position over said collar.

In some exemplary embodiments of the invention, at least a portion of said pedicle screw is coated by a metal layer having a thickness between 1 μm-100 μm, wherein said metal layer does not substantially interfere with visualization of said screw under CT or MRI imaging.

In some exemplary embodiments of the invention, at least 50% of said reinforcing fibers of said pedicle screw are elongated fibers extending substantially in parallel to a longitudinal axis of said screw.

In some exemplary embodiments of the invention, said reinforced composite material of at least one of the collar, screw head and rod is elastic enough to slightly deform to at least partially fill spaces between said components when said radial compression force is applied by said ring.

In some exemplary embodiments of the invention, said cavity sized and shaped for receiving a rod comprises one of (a) an inner cylindrical profile and (b) an inner curved profile.

In some exemplary embodiments of the invention, said cavity sized and shaped for receiving a rod comprises an insert which modifies a geometry of inner walls of said recess defining said cavity.

There is provided in accordance with some embodiments of the invention a collar sized and shaped for coupling between a rod and a pedicle screw or one or more adapters of the screw, comprising:

a distal end comprising a geometry shaped to engage at least one of (a) a head of said pedicle screw and (b) one or more adapters, if any, mounted on said head of said pedicle screw;

a proximal end;

a portion adjacent said proximal end, said portion defines a cavity shaped and sized to receive at least a portion of a rod, wherein a collar wall defining said cavity extends over at least 60% of a top semicircular arc of a cross section of a rod positioned within said cavity. Optionally, walls of said cavity encircle at least 70% of a circumference of a rod received within said cavity. Optionally or alternatively, said geometry of said distal end of said collar defines a second cavity, shaped and sized to receive at least a portion of said pedicle screw. Optionally or alternatively, said collar comprises a slot separating a distal portion of said collar into at least two sub portions. Optionally, said collar wall defining said cavity extending over said top semicircular arc of the rod is arc shaped, and acts as a bridging load transferring element between first and second sub portions of said collar separated from each other by said slot. Optionally, said collar comprises reinforcing fibers arranged in an upside down U-shape complying with a contour of said collar wall.

In some exemplary embodiments of the invention, a distal portion of said collar comprises one or more slots extending from said distal end of said collar in the proximal direction to allow the collar to compressively fit over a head of a screw.

There is provided in accordance with some embodiments of the invention a method of coupling a composite material pedicle screw to a rod using a collar and a locking ring, comprising:

passing said rod through a first cavity of said collar;

positioning a second cavity of said collar over a head of said screw;

radially compressing at least a portion of said collar to fasten said collar to at least one of said rod and screw, such that at least 5% of the composite material of at least one of said screw head and collar enters recesses between said screw head and walls of said second cavity.

There is provided in accordance with some embodiments of the invention a method of assembling a pedicle screw construct, comprising:

implanting at least one pedicle screw onto which a locking ring is slideably mounted in a pedicle of a vertebra, said ring extending beyond said screw head to receive a collar;

positioning at least one collar over a rod, outside the body;

implanting the rod and collar assembly by positioning said collar above a head of said screw, while said ring acts as an external housing to couple between the screw head and the collar; and fastening said collar over said rod and screw head by elevating said ring to an axial location in which the ring exerts radial compression onto the collar to restrain movement of said screw head and rod relative to each other. Optionally, the method comprises positioning said locking ring at a selected orientation relative to a longitudinal axis of said pedicle screw prior to implanting said rod and collar assembly. Optionally or alternatively, said screw head is embraced by one or more adapters which define a recess for said screw head, and wherein said collar is positioned over a proximal surface of said adapters while said ring acts as external housing holding said collar to said adapters. Optionally or alternatively, elevating said locking ring approximates at least two collar portions that are separated from each other towards each other, said portions defining a cavity for said rod such that said approximating presses said portions against said rod to restrain at least one of axial and rotational movement of said rod in said cavity. Optionally or alternatively, elevating of said locking ring exerts a first force on said collar which approximates lower collar portions and induces a second force which presses said collar against said rod.

There is provided in accordance with some embodiments of the invention a method for reshaping a composite material rod of a pedicle screw construct, comprising:

heating at least a portion of said composite material rod;

applying a force onto the heated portion of said rod to bend said portion relative to a longitudinal axis of the pre-deformed rod, while a cross sectional diameter of said rod portion at a direction substantially perpendicular to a post-deformation longitudinal axis of said rod changes less than 5% relative to a diameter of said rod before deformation.

There is provided in accordance with some embodiments of the invention a device for driving a pedicle screw into a vertebra and for engaging a locking ring positioned over the screw, comprising:

a shaft comprising:

a distal end comprising a recess shaped to receive a head of the pedicle screw while the locking ring is elevated over at least a portion of the screw;

a proximal end engageable or integrally attached to a handle for handling by a physician, said handle configured for firmly connecting said pedicle screw to said device and for rotating said shaft to rotate said distal end for screwing the screw into the pedicle;

an extension extending in a distal direction from said distal end of said shaft, said extension comprising a radially inward protrusion at its distal end, said protrusion shaped and sized to engage a portion of said ring and retract the ring by proximal pulling of said extension. Optionally, said shaft comprises an internal rod axially movable within said shaft, said rod comprising a distal end configured to be pushed in between a set of adapters which embrace the screw head to couple said device to said embraced screw.

There is provided in accordance with some embodiments of the invention a method of restraining relative movement of components of a pedicle screw construct, comprising:

coupling a rod and a pedicle screw using a collar;

radially compressing the collar to restrain movement of said rod relative to said pedicle screw. Optionally, said radially compressing comprises elevating a locking ring over said collar.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7F schematically illustrate the procedure steps for pedicle screw construct implantation, in accordance with some embodiments of the present invention;

FIGS. 11A-11F schematically illustrate several embodiments of a rod component of a polyaxial pedicle screw-rod construct, in accordance with some embodiments of the present invention;

FIGS. 19A-19B schematically illustrate a pedicle screw construct, in accordance with some embodiments of the present invention;

FIGS. 20A-20D schematically illustrate a screwdriver intended for pedicle screw assembly insertion, in accordance with some embodiments of the present invention;

FIGS. 21A-21B schematically illustrate a pedicle screw construct, in accordance with some embodiments of the present invention;

FIGS. 22A-22C schematically illustrate a pedicle screw construct, in accordance with some embodiments of the present invention;

FIGS. 23A-23D schematically illustrate a collar component, in accordance with some embodiments of the present invention;

FIGS. 24A-24B and 25A-25D schematically illustrate an instrument for rod connection to a pedicle screw, in accordance with some embodiments of the present invention;

FIGS. 26A-26C schematically illustrate a locking ring component (as part of a construct), in accordance with some embodiments of the present invention;

FIGS. 28A-28C and 29A-29C schematically illustrate locking ring and collar components, in accordance with some embodiments of the present invention;

FIGS. 30A-30C schematically illustrate a collar component, in accordance with some embodiments of the present invention;

FIGS. 31A-31C schematically illustrate a collar component, in accordance with some embodiments of the present invention;

FIGS. 32A-32C schematically illustrate a collar component, in accordance with some embodiments of the present invention;

FIGS. 37A-37B is a schematic illustration of forces acting on a single-component collar (37A) and a double-component collar (37B), in accordance with some embodiments of the present invention;

FIGS. 45A-45H show, in pairs, various collar based locking mechanisms, in accordance with some exemplary embodiments of the invention which use a closed top collar;

FIGS. 46A-46H show, in pairs, various collar based locking mechanisms, in accordance with some exemplary embodiments of the invention which use an open top collar;

DESCRIPTION OF SPECIFIC EMBODIMENTS OF THE INVENTION

Figure 1:
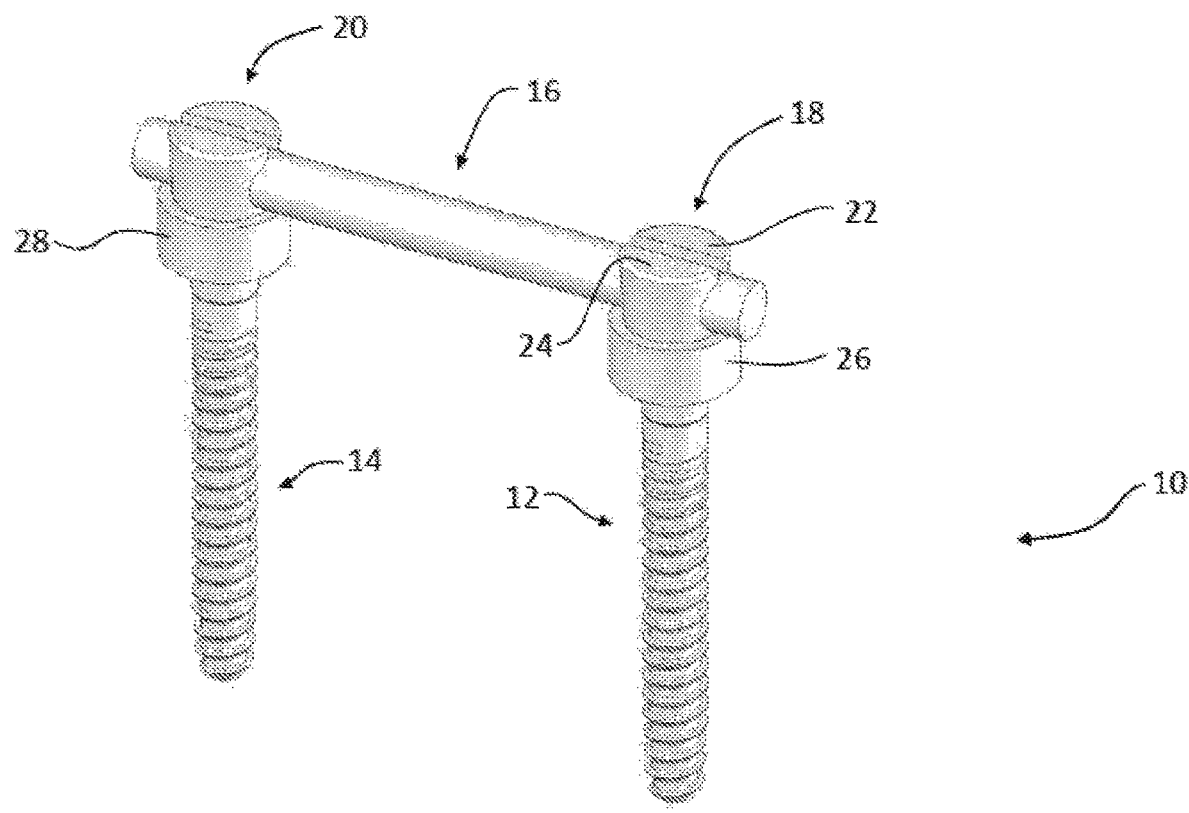
FIG. 1 illustrates a pedicle screw construct, in accordance with some embodiments of the present invention.

The present invention, in some embodiments thereof, relates to composite material bone implant devices; mainly, but not limited to, spinal implants such as a pedicle screw construct, and/or to a kit comprising components of a pedicle screw construct and/or to manufacturing methods for such devices, and/or to tools usable with the construct or components thereof, for example tools used during implantation. More particularly, the invention relates to such devices and methods as applied to implant devices constructed of fiber-reinforced polymer matrices.

Some embodiments of the invention relate to a pedicle screw construct composed of one or more pedicle screws (e.g., two pedicle screws), one or more rods, holding means, such as a collar configured to couple between the rod and the screw, and locking means, for example in the form of a ring configured to fasten the collar over the rod and/or screw. In some embodiments of the invention, the construct is composed of at least four pedicle screws, placed within the pedicles of at least two vertebrae; two rods, connecting said screws along the long axis of the spine; and means to secure the pedicle screws and rods together. In some embodiments, a kit comprising one or more components of the construct is provided, for example including four pedicle screws, two rods, and four locking means, each locking mean including, for example, a collar configured to receive the rod and optionally at least a portion of the screw, and a locking ring positionable over at least a part of the collar. In some embodiments, the kit components are assembled by a physician, before and/or during operation. In some embodiments, components of the construct are assembled externally to the body, for example two or more collars are positioned on the rod prior to insertion into the body. Additionally or alternatively, components are assembled inside the body, for example the collar is positioned over the screw. Additionally or alternatively, in some embodiments, components of the construct such as adapters and/or ring configured on a screw, are assembled during manufacturing.

An aspect of some embodiments of the invention relates to a kit for spinal fusion including a rod and at least two collars to hold the rod, wherein the collars each include a passage therethrough and each have a vertical axis designated to lie generally perpendicular to a spine. In some exemplary embodiments of the invention, the passage is not rotationally symmetric with respect to an axis perpendicular to said vertical axis. In some embodiments, the collar also includes a cavity sized and shaped for holding the head of a pedicle screw.

In some exemplary embodiments of the invention, lack of symmetry is due to the passageway lying at a non-perpendicular angle to and/or laterally offset from, the vertical axis.

In some exemplary embodiments of the invention, the passageway is curved, for example, upwards or downwards (towards the spine) at one or both ends thereof.

In some exemplary embodiments of the invention, the cross-section of the passageway is not circular and/or, if the rod does not have a circular cross-section, otherwise does not match the rod. Optionally, this change in cross-section allows a bent rod to fit and/or pass through the passageway.

In some exemplary embodiments of the invention, the passageway is a composite of two cavities, one is a straight cylindrical cavity and one is add-on moon-shaped channel portions which expand the passageway at one or both ends thereof.

In some exemplary embodiments of the invention, the passageway is in stretched in a vertical direction, for example, having a cross-section of two half circles connected by straight lines.

In some exemplary embodiments of the invention, the passageway includes one or more protrusions therein so as to engage the rod (e.g., by elastic deformation of the rod and/or passageway) when the collar is tightened.

In some exemplary embodiments of the invention, the passageway is designed to grip rods of various configurations, including, for example, straight and curved, for example, over a range of bending radiuses of 30 to 240 mm, for example, one or both of concave and convex (e.g., towards or away from spine) and/or curved in other directions. In some embodiments, a design which supports bending in two or more direction may support only larger bending radiuses.

In some embodiments the passageway includes, two, three or more of the above features.

In some exemplary embodiments of the invention, the dimensions and/or shape of the channel are sized to fit multiple rod diameters, in the range of about 3 to 8 mm, for example, differing by 1-2 mm, for example rods with diameters between 5 and 6 mm. Optionally or alternatively, the design is for a single rod diameter (e.g., 6 mm), but at various bending radiuses and/or directions.

In addition to or alternatively to different rod shapes (e.g., rods with rectangular and/or elliptical cross-section or other polygonal and/or curved cross-section). A potential advantage of using round-cross-section rods and/or rods that are at least near-rotationally symmetric is that the collar can be rotated around the rod, during implantation.

An aspect of some embodiments of the invention relates to a kit for spinal fusion including a rod and at least two collars to hold the rod, wherein the collars each include a passage therethrough and each have a vertical axis designated to lie generally perpendicular to a spine and wherein the passage way is configured to operate with both curved and straight rods. In some exemplary embodiments of the invention, the passageway is configured to rigidly engage rods of same diameter but different layout, for example, straight and curved rods. Optionally or alternatively, the collar and passageway are flexible enough to allow a collar to travel along a bent rod and/or flexible enough to allow transverse mounting on a rod. In some exemplary embodiments of the invention, a collar with a preferred rod bending direction and/or amount is flexible enough to travel along a rod with a different bending amount and/or direction.

An aspect of some embodiments of the invention relates to a locking element for locking a collar to a spine rod and/or a screw head, especially for composite material spinal systems, in which the locking ring is mounted on the collar before threading the rod through the collar. In some exemplary embodiments of the invention, this has the potential advantage of reducing a space between the collar and bone, as there is no need to locate a ring at that location. Optionally or alternatively, this may reduce the risk of locking rings dropping off during surgery and/or may simplify a tightening system, as the ring is already located and held in place by the collar. In some exemplary embodiments of the invention, the collar includes a section with increased outer radius and the ring is vertically moved (e.g., rotated and/or slid) over that area to lock and compress the collar. In some exemplary embodiments of the invention, the ring is pre-mounted on the collar and does not extend past the collar at any time and/or does not extend after tightening thereof. A potential advantage of not extending or of extending less than, for example, 1 mm, 2 mm, 3 mm, is that the ring does not interfere with a screw held by the collar at an angle. The angle of the screw might otherwise be limited by contact against the ring that extends downwards past the collar. Another potential advantage is that a space between the collar and the bone may be needed for fitting the ring and/or a tightening tool thereof.

A potential advantage of reducing the space between the collar and the bone is that the larger the space, the more likely the screw held by the collar and the bone, is to bend. A shorter space may reduce this risk and/or degree of bending.

An aspect of some embodiments of the invention relates to locking a collar by lowering a ring towards a bone to which the collar is coupled. The ring may be previously mounted on the collar or not.

An aspect of some embodiments of the invention relates to locking a collar using two locking rings. Optionally, the collar is in two or more parts so the rings both lock the collar and hold its parts together.

It is a particular feature of some embodiments of the invention that two rings are used on a single part collar. A potential advantage of such use, for example, as described herein, is selective/different locking and/or locking forces on the rod and on the screw-head. Another potential advantage is that less force may be applied, for example, if the rings are moved separately. Optionally, the rig moving device is made lighter due to reduced forces.

A single part, unitary, collar may include splits only in a lower portion thereof and/or in an upper portion thereof. If splits are provided on only one side, the splits optionally cross one cavity to reach or cross the other cavity of the collar (rod/screw cavities). If two splits are provided, there may be an unsplit boundary between the cavities. In some exemplary embodiments of the invention, the top of the collar is unsplit. This may support better interaction with the tissue and/or reduce a risk of a ring migrating away from the device, e.g., by both rings being below the rod.

In some exemplary embodiments of the invention, the rings move in opposite ways for locking, for example, towards each other or away from each other. In some exemplary embodiments of the invention, both rings rather than only one, are on a same side of the rod, for example, the bone side or the side opposite the bone.

An aspect of some embodiments of the invention relates to a collar with two rings where both the rings are below the rod. Optionally, one or both rings are above the screw.

An aspect of some embodiments of the invention relate to simultaneous manipulation of two locking rings on a collar. In some exemplary embodiments of the invention, a device includes a lever, which lever includes two portions suitable for engaging ring, e.g., one for each ring, e.g., depending on the ring/collar design. In use, the lever is manually (or otherwise) moved, thereby moving the ring engaging portions and thereby moving the rings.

In some exemplary embodiments of the invention, the two ring engaging portions are on a same mechanical side of the lever relative to a lever pivot (e.g., when the two rings are to move in a same direction). Optionally, the device includes a rest which rests against a portion of the collar to provide a contra-force to that applied to the rings. Optionally, when a ring reaches its position, the ring-holder disengages from it, for example, by movement of the holder being arcuate and reaching a radial distance from the collar too large to engage the ring, once the ring is in location.

In some exemplary embodiments of the invention, the two ring engaging portions are on mechanically opposite sides of the pivot. This may be useful, for example, for applying most of the forces between the rings, rather than to the collar and bone.

In some exemplary embodiments of the invention, the movement of the rings is not simultaneous. For example, one ring may have higher friction. Optionally or alternatively, the spacing between the two ring engaging portions is different (e.g., 0.5 mm, 1 mm, 2 mm or intermediate or greater or smaller distances) from the spacing between the rings, so one ring is engaged first.

In some exemplary embodiments of the invention, the distance between the pivot and the rings is different, thereby providing different amounts of relative movement and/or different applied forces, for example, as desired.

In some exemplary embodiments of the invention, the length of the portion interconnecting a ring and the pivot is adjustable, for example, using a telescoping arm with inner threading which can be rotated to change the distance. Other length varying mechanisms may be used as well.

An aspect of some embodiments of the invention relates to providing a spinal fusion kit with no metal, for example, less than 2%, 1%, 0.5%, 0.05%, or even substantially 0% by weight and/or volume of metal, for example, free metal, metal alloy and/or metal crystals and/or other material which significantly interacts with radiations (e.g., photon radiation and/or proton and/or other particles, for example, such as used for cancer treatment). A potential advantage of avoiding any metal is reducing interference with radiation therapy, such as proton therapy. It is noted that radiation therapy may be more sensitive to metal (e.g., heating, reflections, blocking, secondary radiation generation) than MRI or CT imaging. Another potential advantage is reducing interference with imaging, which imaging may be used to calculate doses and aiming protocols.

In some exemplary embodiments of the invention, the kit, in implantable portions thereof, contains less than 5%, 1%, 0.5%, 0.05% or substantially 0% by weight of atoms with an atomic number above, for example, 40, 30, 20, 13 and/or 11. In some exemplary embodiments of the invention, the kit is absent any implantable portion of volume of 1 cubic mm having a radio-opacity of more than 200%, 100%, 50% or smaller or intermediate percentages of the radiopacity of aluminum.

In some exemplary embodiments of the invention, the kit contains no implantable portions which cause a streak artifact in CT of more than 15 mm, 10 mm, 5 mm, 1 mm or smaller or intermediate lengths.

In some exemplary embodiments of the invention, the kit contains no implantable portions which have a magnetic susceptibility and/or support eddy currents in an amount which cause image distortion in a 5T MRI spin-echo imaging protocol.

In some exemplary embodiments of the invention, the implantable portion of the kit includes no coloring agent other than carbon and/or organic compounds.

In some exemplary embodiments of the invention, a patient in need of radiation therapy and having metal spinal fixation elements is treated with radiation by first removing the metal elements and replacement thereof by non-metallic components, for example, as described herein, and then irradiating the patient.

Optionally or alternatively, a patient in need of radiation therapy is selected to have non-metallic implants rather than metallic implants.

In some exemplary embodiments of the invention, the implant has no metal, not even for radio-opaque markers. Optionally, radio-opaque tools, for example, a k-wire with radio-opaque markers or wholly radio-opaque, is used for positioning under imaging.

An aspect of some embodiments of the invention relates to locking by rotation of a locking ring. In some exemplary embodiments of the invention, threading is provided on the ring and/or collar, so that rotation causes vertical displacement. Optionally, threads on the ring, for example, metal threads, can self-thread on the collar, when the ring is rotated.

However, it is a particular feature of some embodiments of the invention that no threading is provided in any part of the system and/or in the locking rings or collar. Optionally, this allows the avoidance of use of metal parts.

An aspect of some embodiments of the invention relates to coupling a pedicle screw to a rod using a collar, and restraining movement of the rod by radial compression of said collar. In some embodiments, radial compression is applied by elevating a ring over the collar, approximating portions of the collar towards each other to squeeze the rod in between. In some embodiments, one or more components of the collar such as the ring, collar, screw, and/or rod are formed of a reinforced composite material. Optionally, the composite material is elastic enough to allow for a slight deformation of material during locking of the construct, to obtain a closer fit of the collar over the rod and/or over a head of the screw. In some embodiments, the collar comprises an integrated top portion which encircles the rod, the closed top portion effective to transfer and distribute forces, such as forces applied to a more distal portion of the collar, for example radial compression force applied by the ring.

In an exemplary construction of the construct, the pedicle screws, each comprising a locking ring which was pre-positioned over the screw, are implanted in pedicles of vertebrae, such as adjacent vertebrae. In some embodiments, the ring is moved (e.g., axially elevated and/or rotated and/or tilted and/or otherwise oriented) to a selected axial and/or angular position relative to the implanted screw, for example such that a longitudinal axis passing through a center of the ring is at an angle to a longitudinal axis of the screw, for example an angle between 5-70 degrees, such as 10 degrees, 40 degrees, 60 degrees or intermediate, larger or smaller angles. In some embodiments, outside the patient's body, the two or more collars are positioned over a rod, for example such that the rod passes within cavities of the collars. The externally-assembled rod and collars are then inserted into the body, and the collars are positioned above the heads of the screws, optionally at least partially within the channel defined by the ring. In some embodiments, a collar is configured to receive at least a portion of the screw head and is positioned over the screw head. Optionally, the collar can be tilted relative to the screw to position the collar at an angle to the screw axis, for example an angle between for example an angle between 5-70 degrees, such as 10 degrees, 40 degrees, 60 degrees or intermediate, larger or smaller angles. Additionally or alternatively, an additional structure such as a set of adapters which embrace the screw head are used, and the collar is positioned on top of the adapters while the ring is positioned to act as a housing to hold the screw-adapters assembly together with the collar-rod assembly. In some embodiments, the locking ring is then elevated over each of the collar, applying radially inward force which is effective to fasten the collar over the rod and/or screw head and restrain their movement relative to each other.

An aspect of some embodiments of the invention relates to a pedicle screw construct in which the components are constructed from fiber reinforced composite material, wherein a geometry of the construct acts together with the properties of the fiber reinforced composite material (such as elasticity and load transfer abilities) to restrain relative movement of the components of the construct.

In some embodiments, fastening of composite material construct components to each other results in a slight deformation of the composite material of one or both of the components being restrained. Optionally, the slight deformation causes some of the material to change shape (e.g., by spreading out and/or being pushed out) and enter gaps between the coupled components. For example, during fastening of the collar onto the rod and, in some embodiments, the screw head that are received within the collar, composite material of the collar and/or screw head and/or rod is slightly deformed, optionally as a result of radial compression applied by the elevated ring. In some embodiments, the screw head comprises a nearly spherical but not fully spherical configuration, which results in one or more spaces between the spherical recess of the collar and/or a spherical recess defined by the adapters within which the screw head is received. During locking, material may flow into these spaces. A potential advantage of the material at least partially filling gaps between the collar and the rod and/or the collar and the screw head may include providing a geometric locking between the components, for example in addition to a friction-based locking, restraining movement of the rod and/or screw and enhancing their grip by the collar. Another potential advantage of a composite material rod and collar may include adaptation of the collar, to a certain extent, to a curvature of the rod.

In some embodiments, a fiber arrangement of a construct component is selected to provide the component with one or more mechanical properties, such as elasticity and/or load transfer ability. In some embodiments, the fibers are arranged as one or more carbon PEEK tapes, each tape including a plurality of elongated carbon fibers arranged in parallel. In an example, a collar portion comprising an upside down U-shape (upside down horseshoe shape) comprises a plurality of PEEK tapes arranged in a similar U-shaped contour. Optionally, the upside down U-shaped fibers of the collar may contribute to distributing force applied by the ring over a lower portion of the collar (such as radially inward force) to an upper portion of the collar in which the rod is received, potentially obtaining a stronger hold of the rod by the collar to restrain movement (such as axial and/or rotational movement) of the rod within the collar cavity. In yet another example, a locking ring comprises PEEK tapes wrapped to form a helix, which may increase the resistance of the ring to radially outward forces, for example applied onto the ring by two collar portions which were approximated towards each other by the ring. In another example, elongated components of the construct such as the screw and/or rod comprise of PEEK tapes extending parallel to a longitudinal axis of the screw and/or rod respectively. Longitudinal fibers of the screw, for example, may increase the screw resistance to axial tension load.

Additionally or alternatively, the components such as screw, rod, collar and/or ring include PEEK tapes having elongated carbon fibers arranged in a direction which is at an angle to the directions of the PEEK tapes described herein above, for example a direction perpendicular to a longitudinal axis of the screw, such as along a diameter of the screw.

In some embodiments of the invention, chopped fibers may be used with longitudinal fibers, such as fibers extending substantially along the screw axis. Alternatively, the construct or components of it or portions thereof is comprised of chopped fibers without longitudinally extending fibers.

In an embodiment of the present invention, the volume contents of the reinforcing elements (e.g., carbon fibers (CFR)) within the composite material (e.g., PEEK) is at least 50%, 60%, at least 70%, at least 80%, optionally 55%-65%, or intermediate, larger or smaller ranges. The relatively high content of reinforcing fibers may contribute to the load bearing abilities of the construct.

In some embodiments, the fiber reinforced composite material comprises filaments such as carbon fibers embedded in a polymer matrix, such as, but not limited to, PEEK, polyetherketoneketone (PEKK), and/or other polyketone based polymers.

In some embodiments, the radiolucent composite material construct enables a physician to see through the construct during operation and may facilitate manipulating the spine and/or construct (e.g., with the aid of radiopaque markers incorporated in the composite material) under imaging to obtain a desired alignment of the vertebrae. A potential advantage of the relative transparency of the composite material (for example as compared to metal) may include a clearer visualization of the spine under imaging, allowing a physician to position and/or lock the system in more accurate anatomic location. The radiolucency of the composite material construct may be especially advantageous during follow up, for example when CT imaging is performed, allowing a physician to diagnose a condition of the tissue, a fusing stage of the bones, and/or other parameters which can be clearly viewed due to the transparency of the composite material. In an example, due to a radiolucency of the composite material screw for example, it may be easier to prevent damage to tissue such as nerve tissue during implantation. In another example, a radiolucency of the composite material screw for example, a condition of the treated bone tissue can be easily observed during follow up, such as to assess the healing rate.

Additionally or alternatively to composite material, in some embodiments, one or more components of the pedicle screw construct are made of or comprise of metal, such as titanium. In an example, a thread of the pedicle screw is coated by a thin metal shell. The inventors have observed that since the construct does not comprise or comprises only a small metal content, for example in the form of a screw thread shell having a thickness between 5-20 μm, artifacts in imagining such as MRI and/or CT are reduced or prevented, for example, by 50%, 70%, 90%, 95% or intermediate or greater percentages as compared to artifacts generated in MRI or CT if the construct were formed of pure titanium.

In an exemplary embodiment of the invention, a particular type of artifact which is avoided/reduced in CT and/or MRI imaging, is an artifact which blocks out viewing near the surface of the pedicle screw and/or other parts of the construct. In an exemplary embodiment of the invention, the use of a composite kit allow imaging of hard and/or soft tissue to within 3 mm, 2 mm, 1 mm or intermediate or even smaller distances from the construct, optionally to within a diagnostic quality. For example, tissue in the distances 1-3 or 1-2 mm are imagable when using a composite construct in accordance with some embodiments of the invention, even, for some embodiments, if the construct has metal inserts and/or coating. Optionally, this is used to detect inflammation and/or other pathologies, bone anchoring problems and/or implant malpositioning (e.g., relative to bone, nerves). Optionally or alternatively, the artifacts which are reduces/avoided are streaks (e.g., as in CT) caused by metal artifacts. Optionally, such artifacts are reduced by percentages (e.g., voxels affected in diagnostic quality) to a degree as noted above.

An aspect of some embodiments relates to a pedicle screw construct comprising a composite material locking ring. In some embodiments, the ring is axially movable over at least a portion of the screw and further over at least a portion of the collar configured above the screw. In some embodiments, the ring does not comprise an internal threading. A potential advantage of a non threaded inner wall of the ring may include facilitating pulling the ring over the external surface of the collar. In some embodiments, the collar does not comprise an external threading. In some embodiments, as long as the ring is not internally threaded, or the collar is not externally threaded, the ring can be slidably pulled up over the collar, without the need for rotation to obtain advancement and/or locking. Alternatively, in some embodiments, the ring comprises a thread. In some embodiments, elevation of the ring over the collar fastens the collar over a rod received within it, and/or over a at least a portion of a screw head received within in it, to restrain movement of the rod and screw components relative to the collar and thereby relative to each other. Additionally or alternatively, the ring acts as an external housing which holds a structure that embraces the head of the screw (such as a set of adapters) together with the collar. Additionally or alternatively, the construct comprises one or more rings which are configured to be slid over the rod, such that the ring axis is parallel to that of the rod, to lock an axial position of collar with respect to the rod axis, for example by positioning two rings on both sides of the collar.

In some embodiments, the ring comprises an internal conical profile, comprising a channel which decreases in diameter in a distal direction. By axial elevation of the ring over the collar, the internal tapering profile exerts radial inward force onto the collar and/or onto the structure that embraces the screw head and/or onto the screw head. Optionally, an internal wall of the ring is slanted at a relatively small angle of about 1 degree, 3 degrees, 5 degrees, 7 degrees or intermediate, larger or smaller angles producing the conical configuration. A potential advantage of a relatively small tapering angle of the internal wall of the ring may include reducing a risk of the ring sliding off the collar, as the radial force applied by the ring is translated into only a small axial force (i.e. a force that would cause the ring to slide off) which can be overcome by friction between the surfaces of the components. Another potential advantage of a small tapering angle may include increasing a ratio between the amount of radial compression force applied by the ring onto the collar, and the axial force needed to applied to elevate the ring to a locked position. Decreasing the tapering angle may facilitate pulling the ring axially. Alternatively, in some embodiments, the internal profile of the ring is not tapering, for example cylindrical.

In some embodiments, the composite material ring may be able to provide locking of increased strength using a ring of relatively small wall thickness, for example as compared to a wall thickness of a metal ring which would be adapted to withstand similar amounts of tension. Optionally, the structure of the reinforced composite material (e.g., reinforcing fiber volume, fiber arrangement, and/or other parameters) is selected to be about 0.9-10 times more tear resistant than a metal, such as titanium, having a similar wall thickness.

In some embodiments, the ring is pulled over collar portions that in a non-restrained configuration are separated by a gap extending lengthwise in between the collar portions, and advancement of the ring over the collar brings the collar portions towards each other. The restrained collar portions may apply a counteracting radially outward force on the inner walls of the ring, which prevents the ring from sliding off the collar, for example from sliding in a distal direction.

In some embodiments the internal profile of the ring is tapering, for example conical. In some embodiments, the external profile of the ring is cylindrical, tapering (for example in the distal direction or, alternatively, in the proximal direction), formed with one or more circumferential protrusions or "steps" and/or otherwise shaped. In some embodiments, the protrusions and/or steps can be used for elevating the ring and/or removing the ring, for example by a tool configured to engage the protrusions or steps.

Alternatively, the internal and/or external profiles of the ring are not tapering. In some embodiments, the collar does not comprise a tapering profile. Optionally, in embodiments in which both the internal profile of the ring and the collar are non-tapering, one or both of the components may comprise a different geometry which provides for pulling the ring over the collar. In an example, the geometry comprises squeezable projections or bumps on the internal wall of the ring and/or on the external wall of the collar, which may be forced towards the wall (of the ring or collar respectively) when the ring is elevated over the collar.

An aspect of some embodiments relates to a component of a pedicle screw construct configured for coupling a rod to a pedicle screw, wherein the component is shaped to cover the rod from above. In some embodiments, the component is shaped to encircle at least 60%, at least 80%, at least 95% of a circumference of the rod received within it. In some embodiments, at least 50%, 60%, 80% of the top semicircular arc of the rod is covered by the component. In an exemplary embodiment, the component fully covers the top semicircular arc of the rod (e.g., extending along 100% of the length of the arc).

In some embodiments, the component is in the form of a collar comprising a cavity in which the rod is received. In some embodiments, the component comprises a second lower cavity in which a portion of the screw such as the screw head is received. Alternatively, the collar does not comprise a direct coupling with the screw head, and may instead be attached to a structure that receives the screw head such as a set of adapters. In some embodiments, the collar comprises one or more slots, for example a transverse slot extending from below a cavity in which the rod is received, separating a lower portion of the collar into two sub-portions which can be approximated towards each other. In some embodiments, the top portion of the collar which covers the rod acts as a bridging element between the two sub portions.

In some embodiments the top portion is arched, for example having an upside down U-shape (or horseshoe) configuration.

In some embodiments, when external force is applied onto a lower portion of the collar, such as radially inward force applied by elevation of the locking ring over the lower portion of the collar, walls of the rod cavity at an upper portion of the collar are squeezed against the collar, obtaining a hold of the rod by the collar which is effective to restrain axial and/or rotational movement of the rod within the collar cavity. When referring to a center point of the top portion as a theoretical axis of rotation, a produced moment of the force being applied by the ring onto a lower portion of the collar is determined by the distance of the point onto which force is applied from the center point (i.e. axis of rotation) of the upper collar portion, multiplied by the amount of force. In an example, resulting force that acts on the upper portion of the collar which in turn compresses the rod to obtain a firmer grip by the collar is increased by a ratio of a distance between the center point (i.e. axis of rotation) and the location in which the ring-exerted force acts, divided by a distance between the center point (i.e. axis of rotation) and a substantial center of the rod.

A potential advantage of a collar in which the rod is substantially surrounded by the walls of the cavity of the collar may include reducing axial and/or rotational movement of the rod within the collar. The closed top collar portion that covers the rod may be especially advantageous for the composite material collars described herein, since the composite material is more elastic than, for example, a corresponding metal collar, and covering the rod from above contributes to limiting movement of the rod within the collar cavity.

An aspect of some embodiments relates to a device for driving a pedicle screw into a vertebra and for engaging a locking ring positioned over the screw, such as to enable pulling of the ring over a collar. In some embodiments, the device comprises a shaft having a distal end which is shaped and sized to receive the head of the screw, and/or an embracing structure (such as a set of adaptors) which embraces the head of the screw, and/or a ring which is at least partially elevated over the head of the screw and/or elevated over the adapters. In an example, the distal end defines a lumen which is cylindrical and complies with an external cylindrical profile of the ring. (It is noted that the external profile of the ring may be other than cylindrical, for example a tapering profile such as a conical profile, a profile comprising one more protrusions or steps, and/or other profiles).

In some embodiments, a proximal end of the shaft is coupled to a handle, to enable maneuvering by a user such as a physician. Optionally, after the head of the screw and/or the structures that are coupled to the head of the screw (e.g., the adapters and/or ring) are engaged by the distal end of the device, the shaft of the device is advanced distally and rotated to thread the screw into the pedicle.

In some embodiments, an axial tongue-like extension extends distally from a distal end of the device, to engage at least a portion of the ring. Optionally, the extension comprises a radially inward protrusion at its distal end which can be positioned beneath the distal end of the ring, to enable pulling the ring axially relative to the screw and/or collar, following implantation of the screw into the pedicle, by pulling the device in a proximal direction.

An aspect of some embodiments relates to a pedicle screw head, comprising a nearly-spherical shape. In some embodiments, the nearly spherical screw head defines a volume which fills up between 85-95% of a volume of a spherical recess in which the screw head is received, such as a recess defined in the collar or a recess defined by an embracing element such as a set of adapters. In some embodiments, the remaining volume between the screw head and the walls of the recess is at least partially filled by composite material of the screw head and/or walls which was deformed during fastening of the construct, such as due to radial compression force applied by the ring. A potential advantage of a slightly deformable screw head may include obtaining a closer fit between the screw head and its receiving structure, thereby potentially increasing the coupling strength between the implanted screw and other components of the construct, such as the collar and/or adapters. In some embodiments, the nearly spherical shape of the screw head is comprised of a cuboidal middle section, and two dome like portions configured above and below the cuboidal middle section. In some embodiments, the screw head comprises one or more proximally facing slots, for example a single slot extending across the head of the screw and/or a cross shaped slot in which a distal end of a tool such as a screwdriver comprising a respective line-protrusion or cross shaped protrusion can be received.

An aspect of some embodiments relates to a pedicle screw construct in which the radiolucent composite material implant is marked with a radiopaque material, such as tantalum and/or other radiopaque material, to enable visualization under imaging (e.g., fluoroscopy). In some embodiments, the markers indicate a location and/or orientation of a component, for example relative to other components of the construct and/or relative to the treated spine segment. In some embodiments, a location of the one or more markers of components is selected to indicate an orientation of the components relative to each other and/or relative to the bones, for example a non-closed ring wire marker of the locking ring may be visualized relative to an elongated axial wire marker of the implanted screw, to indicate the planar orientation of the ring relative to the screw axis. In some embodiments, the ring is a closed ring.

Additionally or alternatively, the markers are positioned to indicate edges or ends of the components, for example ends of the rod, and/or a distal end of a screw, such as to avoid damage to tissue, such as nerve tissue. Additionally or alternatively, the markers are positioned to indicate a distance of the components from each other and/or from the bones, for example top surfaces of collars on a rod are marked to indicate a distance between them. A potential advantage of a construct comprising components that are marked with radiopaque markers may include facilitating adjustment of the construct under imaging to obtain a selected alignment of the treated vertebrae and fixate the vertebrae in the selected configuration.

In some embodiments, the marker is provided in the form of a wire. In some embodiments, the marker is in the form of a thin coating. In some embodiments, the marker is in the form of powder incorporated within the composite material. In some embodiments, markers of various shapes and/or sizes (such as shaped as lines, dots, rings, small pins, rods and/or other shapes) may be incorporated in the components of the construct.

In some embodiments, the markers are positioned at locations suitable to indicate a location and/or orientation of the components relative to each other, for example a planar orientation of the ring relative to a longitudinal axis of the screw, a curvature of the rod relative to a longitudinal axis of the collar, and/or other relationships between the components.

In an exemplary embodiment, the rod comprises a marker in the form of an elongated wire extending lengthwise along the rod, for example having a diameter between 0.1-0.2 mm; the collar comprises a marker in the form of a tantalum pin or wire, for example having a diameter of 0.5 mm and a length of 0.5 mm, positioned for example at a proximal portion of the collar (at or adjacent the point referred to as "center point" described herein); the locking ring comprises a tantalum wire marker in the form of a non-closed ring, the wire having a diameter of, for example, 0.1-0.2 mm; the pedicle screw comprising a marker in the form of powder and/or particles, such as gold powder, embedded within the composite material of the screw.

An aspect of some embodiments relates to reshaping a rod component of a pedicle screw construct, optionally intra-operatively. In some embodiments, the rod is reshaped such as by bending or otherwise deforming the rod, for example to obtain a certain alignment and/or distance between the adjacent pedicle screws, thereby defining the relative positioning of the vertebrae in which the screws are implanted. In some embodiments, the relative positioning comprises a selected angle between a longitudinal axis of the pedicle screw and a longitudinal axis of the rod. In some embodiments, the composite material of the rod is bent under heat. Optionally, the rod is bent under heat while force such as compression force is applied to deform the rod to a selected curvature. In some embodiments, the deformation does not affect a cross section profile (e.g., a size and shape of cross sectional area) of the rod. Optionally, reshaping comprises bending at least a portion of the rod relative to a longitudinal axis of the pre-deformed rod.

In some embodiments, a plurality of collars is positioned over the rod, and the rod is curved and/or otherwise deformed to obtain a selected distance and/or orientation between the collars. In some embodiments of the invention, the rod is straight, and may be provided to the user as such. Alternatively, the rod is provided curved, for example curved to an arc shape having a constant radius of curvature, or curved to an S-shape complying with a curvature of the spine. Alternatively, the rod is provided bent or with means, such as a bending tool, to bend it during surgery. In an exemplary embodiment of the invention, a bending tool is used intra-operatively to bend the rod to the desired configuration (e.g., curvature). In some embodiments, the tool is configured to heat the rod while applying force to deform the rod to a desired curvature. In some embodiments, heating is provided one or more by heating elements that are configured to heat a leading element in which the rod is received. In some embodiments, application of force to deform the rod is provided by relative movement of two portions of the tool over the rod.

In some embodiments, components of the construct such as the collar and ring, the collar and screw, the collar and rod, the screw and ring and/or any other combination of components thereof are preassembled together. Optionally, the components are coupled by a loose coupling which allows multiple degrees of freedom, enabling the user such as the physician to select a position (e.g., location and/or alignment) of the components relative to each other. In an example, the ring is pre-assembled over the screw, and is elevated, optionally once a desired fixation configuration of the vertebrae is obtained, over the collar to lock the collar onto the components received within it such as the rod and/or the screw head.

In some embodiments, the collar is comprised of two or more components, for example comprising two halves that complete each other to define a first, upper cavity in which the rod is received, and a second, lower cavity in which the screw head is received. In some embodiments, the collar portions comprise a gap such as a transverse, longitudinally extending gap in between them. In some embodiments, at least the lower portion of the collar comprises an external conical configuration, tapering for example in a distal direction (e.g., towards a tip of the screw). Optionally, when a locking ring is positioned over the collar, such as over a lower portion of the collar, the sub portions are approximated towards each other, engaging the rod and screw head and clamping them in a pliers-like manner. Implantation of this configuration may include placing the rod in the collar from above, such as through an opening defined between the collar halves.

In some embodiments, the collar comprises an external conical profile. In some embodiments, a diameter of the collar decreases in a distal direction, so that the collar tapers distally. In some embodiments, the conical profile prevents the locking ring which is positioned to surround the collar from sliding upwards on the collar. Additionally or alternatively, the collar comprises a step or one or more protrusions extending radially outwards relative to the collar which limit the advancement of the ring in a proximal direction and/or distal direction.

In some embodiments, the composite material implant, or a portion of it, for example one or more components of the pedicle screw construct, is coated with a material suitable to enhance a desired property of the implant and/or implant surface. In an embodiment, the bone implant is coated with a thin layer intended to strengthen and/or to improve the hardness of the implant/surface. For example, a thread of the screw is coated by a metal coating. In an exemplary embodiment of the invention, the implant is coated with a material harder than bone, such as titanium and/or other metal. In an exemplary embodiment of the invention, the thickness of the shell is in the range of a few microns to 100 μm, for example a thickness between 10-20 μm, 40-60 μm, 50-70 μm or intermediate, larger or smaller thicknesses. For example, a threaded portion of a screw and optionally the screw distal tip may be coated with such a thin layer shell. Additionally or alternatively, a proximal end of the screw, for example on the head of the screw, is coated by the thin layer. In an example, one or more proximal surface of the screw which are intended to engage an insertion tool such as a screwdriver are coated by a thin layer of material such as metal. A potential advantage of coating a screw portion which is intended to contact an insertion tool may include increasing a rigidity of the portion and reducing a risk of damage to the screw such as breakage or crumbling of the screw head.

Additionally or alternatively, one or more components of the construct other than the screw, such as the rod of the construct and/or the collar and/or the locking ring are coated by the thin layer. In an example, an inner surface of the ring and/or an external surface of the collar on which the ring is positioned is coated by a thin metal shell. A potential advantage of a metal coating may include reducing chipping and/or other breakage of the composite material.

Such thin shell may include enabling visualization of the implant and/or construct components under imaging means, while not adversely affecting visualization (e.g., create artifacts), for example as further described below.

In an embodiment, the shell coating the implant is formed of a foil. According to experiments conducted by the inventors, the strength and surface properties of a foil made of, for example, titanium (pure titanium (Ti) or titanium alloy such as Ti-6Al-4V), are substantially superior relative to other coating such as titanium/titanium nitride/titanium oxide, produced using a vacuum plasma spray (VPS) technique. The latter are too brittle and do not have the mechanical strength (e.g., in a radial and/or axial direction) of the foil.

In some embodiments, the coating includes a relatively small amount of material (e.g., metallic material), which almost does not affect the implant properties (e.g., the visualized implant dimensions and/or position) under imaging, such as CT or MRI.

In some embodiments, the radiolucent composite material implant is marked with a radiopaque material, such as tantalum and/or other radiopaque material, to enable its visualization under imaging (e.g., fluoroscopy). Optionally, a radiopaque longitudinal thread is incorporated along the long axis of the implant (e.g., screw axis and/or rod axis). Alternatively or additionally, the marker is positioned at one or both ends of the implant, and/or at any location along it. Optionally, the marker has a shape of a thread, dot, ring, pin, and/or other shape. Optionally, the implant comprises more than one marker, having the same or different shape and/or size, for example comprising a plurality of markers of various shapes and/or sizes.

In some embodiments, in case the composite material implant is coated or partly coated with a thin layer of metal, such as titanium, the addition of a radiopaque marker may be redundant, and said layer may also serve to view the implant under imaging means. In some embodiments, powder and/or particles of radiopaque material is incorporated into the implant. In some embodiments, the implant comprises both a thin layer of metal, and incorporated powder. In an embodiment, the powder content is relatively low, for example the volumetric content of the powder ranges between 0.2%-2% of the volume of material from which the component is made of, so that the addition of the radiopaque powder does not compromise the mechanical properties of the implant. In some embodiments, the powder content is relatively low, so that the addition of the radiopaque powder has negligible effect on the metal-induced artifacts during MRI and/or CT scanning. In an exemplary embodiment of the invention, the powder is made of noble metal or other metal, such as gold, platinum, rhenium, tungsten, tantalum, etc., and/or a combination of the materials, and/or from other radiopaque material. In some embodiments, the powder is homogenously distributed along the radiolucent implant. Alternatively, a non-homogeneous distribution of the powder is desired, to position or to concentrate the powder at specific locations (such as implant circumference). This may be important, for example, in situations in which a specific implant component or portion is monitored during radiographic imaging: for instance, powder may be incorporated in the threaded portion of the pedicle screw to visualize the thread and/or distal tip upon screw insertion into the vertebral pedicle and/or at post-operation period, to minimize the risk for neurological compromise or to detect such compromise. In case the implant or part of it is coated, for example with metal (e.g., titanium) coating or polymeric (e.g., PEEK) coating, the powder may be added beneath and/or above said coating. In an embodiment, the powder may comprise particles in the size of nano-particles to particles of a few hundred microns, preferably particles of approximately 1 µm-10 µm, 10-20 µm, 50-100 µm or intermediate, larger or smaller diameters. In an embodiment, the powder is added between the prepreg CFR-PEEK tapes, at desired locations and concentrations, prior to compression molding of the implant. In some embodiments, a size of the metal particles is homogeneous, at least to some extent. Alternatively, the particles comprise various sizes.

According to comparative tests performed by the inventors, the addition of (a) a titanium shell to the threaded portion of a CFR-PEEK screw; and (b) the incorporation of a tantalum wire having a diameter of less than 0.25 mm along said screw, and/or incorporation of a small amount of gold powder to the screw shank and thread (for example occupying 1% of the screw shank and thread volume) results in only very small or similar amount of artifacts under MRI compared to CFR-PEEK screw and reference screw made of nylon. Optionally, the artifacts do not interfere with imaging. Optionally, the metal layer does not substantially interfere with visualization under imaging, for example the amount and/or size of artifacts that appear under imaging is small enough to allow a user such as a physician to implant the screw in a selected anatomical location and/or view the treated bone and/or soft tissue, during operation and/or during follow up. On the contrary, a titanium alloy screw (e.g., a screw formed of titanium alloy) produced a large amount of artifacts. It is noted, that all tested screws had the same dimensions.

In an embodiment, the composite material implant does not comprise metal, or comprises a small amount of metal, so that the implant does not interfere with radiotherapy nor produces backscattering. In an exemplary embodiment, a composite material screw includes a thin layer titanium shell over its threaded portion, and/or a tantalum wire marker along at least part of its long axis (e.g., along the non-coated portion), and/or a radiopaque powder. Due to the small metal amount, the metal amount is insignificant in imaging, and the interference/scattering during radiation is negligible. Comparative tests conducted by the inventors using CT scan and pedicle screws-rod constructs made of different materials, supported this issue.

In some embodiments, a monoaxial or biaxial composite material pedicle screws are provided. In some embodiments, in a monoaxial screw, the screw and the collar and/or ring comprise a similar longitudinal axis. In an alternative embodiment, the composite material pedicle screws are polyaxial. In some embodiments, in a polyaxial screw the ring and/or collar can be positioned relative to the screw such that the longitudinal axis of the ring and/or of the collar is configured at an angle relative to the longitudinal axis of the screw. This may facilitate application of the rods, such as by the collar and/or ring being pivotable with respect to the head of the screw.

In an embodiment, the pedicle screw comprises a threaded stem portion (shank) and a head, optionally spherical or partially spherical. Optionally, the diameter of the threaded portion changes along the stem or at least along part of it, so that the said part (the stem or a portion of it) tapers toward the distal end of the screw. In some embodiments, the tapering stem is configured to compact bone tissue when the screw is driven into the bone. Optionally, an external diameter of thread remains constant along the length of the stem, while a core of the screw tapers distally. Optionally, the pedicle screw is cannulated, to enable its insertion over a guide wire.

In some embodiments, the pedicle screw head comprises one or more proximally facing slots, for example a single slot or a cross shaped slot in which a compatible projection of a screwdriver can be received, to facilitate screwing into the bone.

In an embodiment, the pedicle screw construct comprises restraining means that are placed, optionally during surgery, over the spherical head of the polyaxial screw. In an exemplary embodiment of the invention, said restraining means are composed of more than one component, for example two halves of a collar with internal geometry matching (e.g., by a fitted matching or by a somewhat spaced-out matching) the shape of the screw head and the rod; and a ring, which is placed over said collar, and radially (inward) presses the construct to secure the rod and screw head relative to each other. Optionally, the collar and/or ring slightly taper, so that their diameter is larger posteriorly. Alternatively, the collar and/or ring slightly taper so that their diameter increases in an anterior direction. Optionally, element/s (such as projections or recesses) on the ring engage with complementary elements (such as respective recesses or projections) at the collar, to assure ring is secured in place. Optionally, the elements are positioned to align the ring with respect to the collar.

In an embodiment, the inner walls of the collar that define a cavity in which the rod is received, include a non-smooth surface, for example a textured surface comprising, for example, bumps or protrusions, to further restrain rod axial and/or rotational movement. The non-smooth surface may increase the friction between the rod and the collar, potentially reducing axial and/or rotational movement of the rod within a cavity of the collar. In an example, the internal surface of the collar at the designated socket or cavity for the rod may be threaded. In an embodiment, the rod includes complementary thread/s, for instance at its ends or at additional locations along the rod. Other non-smooth surfaces, such as a rough surface, an array of radial groves, and/or a surface with protrusions, are also within the scope of this invention.

In some embodiments, designs of restraining means, which do not comprise a threaded component such as screw or threaded locking cap, are also within the scope of this invention.

In an embodiment, the collar and/or screw head components are designed to enable additional locking (e.g., a locking of increased strength that can better resist movement of the rod and/or screw), upon radial, inward pressing of the surrounding ring. In an exemplary embodiment of the invention, the collar halves include a slot or an internal recess, for example in proximity to a plane perpendicular to the common plane of the rod and the screw. Optionally, upon elevating the locking ring to its final location, the collar halves and screw head are pressed, e.g., the collar halves are radially and/or axially squeezed towards each other to compress the head, and the spherical head may slightly undergo deformation, so that material of the screw head slightly protrudes into the collar slots/recess. Alternatively or additionally, a nearly-spherical screw head comprises a non-spherical portion, for example comprising a cylindrical portion located in between two opposing substantially dome-shaped portions. In an example, the screw head comprises a recess, for example a cylindrical surface or reduced diameter at part of the area it engages with the collar. In some embodiments, the nearly spherical but not fully spherical shape of the screw head leaves a small space between the round internal wall of the collar and the screw head. Optionally, a volume of the screw head occupies only 80%, 90%, 95% of a volume of a recess defined in the collar and/or within one or more adapters in which the screw head is received. Optionally, a surface of the screw head contacts only 70%, 80%, 90% of a surface of the internal walls of the recess.

While referring to a curvature of the rod, in some embodiments, when the rod comprises an arched configuration, an angle is set between a longitudinal axis of the screw and an axis tangential to the rod. Optionally, the angle ranges between 70-110 degrees, 60-120 degrees, or intermediate, larger or smaller angles.

In some embodiments of the invention, the rod is straight, and may be provided to the user as such. Alternatively, the rod is provided bent or with means, such as a bending tool, to bend it during surgery. In an exemplary embodiment of the invention, a dedicated heating apparatus is used intraoperatively to bend the rod to the desired angle and configuration (e.g. curvature) (or, similarly, to bend during surgery a bone plate to a desired configuration matching the patient anatomy). Optionally, bending of the rod comprises the use of a leading element that covers the rod during bending procedure, and prevents its damage, for example damage to the rod surface. In an exemplary embodiment, such leading element may be comprised of two metal plates, for example made of stainless steel and/or Nitinol, which comprise or are positioned relative to each other to define a recess to accommodate the rod between them. In some embodiments, during the bending process, the plates are also slightly modified under heating. Optionally, the entire bending apparatus is provided sterile. Alternatively, only part of the apparatus (e.g., the leading elements) is provided sterile within dedicated pouches that resist the bending temperature.

In some embodiments, the present invention provides for devices and methods for locking polyaxial pedicle screw construct—made of metal, composite material or combination thereof. In some embodiments, the construct does not include a threaded locking component (e.g., a screw or cap). In an embodiment, securing of the construct components together is achieved using a conical ring that presses the construct, radially inward.

Some embodiments of the present invention refer to methods of implantation of bone implants, including methods and devices for deployment and locking of a pedicle screw construct that comprises, in some embodiments, non-threaded restraining/locking means. In some embodiments, prior to locking the construct components, the locking ring is placed over the screw, surrounding the screw neck. Alternatively, prior to locking the locking ring is placed over the collar in a non-final locking position. In general, a common feature to said methods and devices in some embodiments thereof comprises gripping the ring from beneath (e.g., engaging a distal end or portion of the ring, for example by tool) and/or engaging one or more hook elements configured on the ring that enable pulling the ring, and operating the tool (e.g., advancing the tool proximally) in order to elevate the ring to its final location (e.g., surrounding the screw head).

Alternatively, a locking ring or an additional locking ring may be placed over the implant in downward direction, e.g., by sliding the ring over the collar in a proximal to distal direction, optionally above the rod implant.

In some embodiments, one or more rings having a central longitudinal axis which is similar to the rod axis are used for limiting movement of the collar over the rod (along the rod axis). Optionally, rings are positioned on both sides of the collar (e.g., laterally to the collar).

In some embodiments, one or more devices or tools are used to assist in assembling the screw construct or components thereof. Optionally, operation of such devices may include using a mechanical mechanism, hydraulic mechanism, electronic mechanism, and/or other mechanisms. In an example, a mechanical mechanism comprising a cable, for example a knitted/weaved fibers (made of, for example, UHMWPE Dyneema Purity, by DSM), is used to elevate the ring.

According to an aspect of some embodiments of the invention, dedicated tools are used during the implantation procedure of the pedicle screw construct. Such tools may be for pedicle screw insertion and/or restraining means and/or deployment and/or locking.

Some embodiments of the invention refer to the ability to thread the screw into the bone together with its "tulip" (e.g., a collar and/or restraining means such as a ring) as a single unit, in order to facilitate components assembly during the procedure and reduce operation time. In an embodiment, a pedicle screw such as a polyaxial screw with a spherical head is provided to the user assembled with a collar and/or locking ring, mounted on a designated delivery system, with the ring being located at a primary, non-final locking, position. In an example, the ring is pre-positioned over the screw. In an embodiment, other and/or additional components accompany the polyaxial screw and are provided assembled to the screw and/or mounted on the delivery system, such as a tulip-like component, adaptor/s, additional ring, and/or other components. Optionally, said delivery system serves not only as a screwdriver that allows pedicle screw assembly insertion, but also to lock implant components (screw and rod) at subsequent stage, for example by moving the restraining ring to its final, locked position.

Some embodiments of the invention refer to the ability to connect the rod to the screw with the rod connected to the "tulip" (e.g., a collar a) as a single unit (e.g., by pre-assembling the collars over the rod, the subassembly of the rod and collar may function as a single unit), in order to facilitate components assembly during the procedure and reduce operation time. In an embodiment, the collar and/or restraining means (e.g., a ring defining a central axis corresponding with the rod axis) placed over the rod are connected in a non-locked position, optionally with the help of a holding device. Optionally, such holding device can also be used for initial, non-final locking of a restraining element such as a locking ring over the collar. Additionally or alternatively, the holding device is configured for fastening the restraining element to its final, locked position over the collar.

In some embodiments, more than one tulip is connected to the rod, e.g., the number of tulips connected to the rod complies with the number of screws to be connected to that rod. In an embodiment only the collar(s) are pre-assembled on the rod and the ring is located over the screw.

It is emphasized, that the devices and methods described in this document for the connection and locking of a pedicle screw and a rod may also be used, with the necessary changes, for transverse connection and locking of two implant rods.

Some embodiments of the present invention refer to method of extracting bone implants such as a pedicle screw-rod construct.

In some embodiments, the composite material bone implant is manufactured using compression molding process. According to some embodiments, device is constructed from pre-impregnated (prepreg) tapes of carbon fiber-reinforced PEEK. Optionally, following molding the device is machined to its final design and/or shape.

In an embodiment of the invention, a screw, for example a pedicle screw, is formed from a composite material, such as carbon fiber-reinforced PEEK. In an embodiment, using compression molding, a rod or other elongated form is produced from prepreg tapes of longitudinal reinforcing fibers within a polymer matrix. The rod is then machined, to create the desired configuration and the thread of the screw.

In another embodiment, the screw, including its thread, is manufactured from prepreg tapes of fiber-reinforced polymer using compression molding process. During said process, the material is axially pressed (i.e., parallel to the fibers and device long axis) under heat and pressure in a mold having the screw configuration, so that folds are created in the elongate filaments and the material is forced to gain the shape of the thread at the mold circumference.

In another embodiment of the invention, the screw comprises a longitudinal core of, for example, carbon fiber-reinforced polymer, and further comprises a profile winding, for instance with triangle cross section, that creates the thread around the said core.

Optionally, screw manufacturing is performed by a combination of the methods described herein.

According to some embodiments of the invention, a thin shell covers a portion of a screw, such as the threaded portion of a composite material screw, for example a pedicle screw. In an embodiment, the thin layer coating is a foil, for example a titanium foil. Production of such coated screw may be accomplished in various methods, including:

(1) In some embodiments, a composite material bone screw is manufactured in one or more of the methods described herein (e.g., compression molding using a mold that does not comprise a thread shape, followed by machining to produce the thread; and/or compression molding using a mold that comprises thread shape, using axial compression). Alternatively, a composite material bone screw with an unthreaded stem is constructed using a mold that does not comprise a thread shape and is not machined following molding.

(2) In some embodiments, a foil with a width of a single screw tooth (or more) is used. In some embodiments, the foil is forced (e.g., shaped) to accommodate a "tooth" (or a plurality of teeth, in accordance with its width) shape of similar size and design as that of the screw's tooth, for example using dedicated mandrel and pulley.

(3) In some embodiments, the said foil (e.g., pre shaped foil) is positioned or wound over the thread of a composite material screw and/or over an unthreaded stem portion of a composite material screw (for example as described in the above section (1)), to form a shell (not yet connected to the screw) with the same dimensions and geometry of that of the screw thread. Optionally, the said foil is wound over composite material prepreg tapes of proper size and volume to form a desired screw. In some embodiments, the foil is located over the place (e.g., a selected portion of the volume of prepreg tapes) intended to form the screw thread. Alternatively, the foil is wound over a dedicated device (e.g., a mandrel) with the same dimensions as those of the threaded portion of the screw, and is then laser welded to form a shell of the shape of the screw threaded portion; following, the said shell is threaded over the thread of a composite material screw or over an unthreaded stem portion of a composite material screw (as described in the above section (1)), or over composite material prepreg tapes of proper size and volume to form a desired screw.

(4) In some embodiments, the coated screw (with or without a thread) undergoes compression molding. Optionally, at this stage, the shell is connected to the screw, and in case an unthreaded stem was used, a composite material thread is produced as well, under axial compression.

Additionally and/or alternatively, biocompatible adhesive means, such as implant-grade epoxy or silicone compound, are added, to further assure firm connection of the shell to the screw. Optionally, low energy laser welding of the titanium layer may be performed after compression molding is completed.

In an alternative embodiment, the thin shell of the screw thread is produced in compression molding process, without undergoing previous manipulation. In this embodiment, the shell, for example a foil or thin tube, optionally made of titanium Grade I, II and V, is placed over the stem of composite material unthreaded screw that was constructed using compression molding. The thickness of the foil/tube may be of 4-5 µm, optionally ranging between 1-200 µm, such as 10-50 µm, 2-9 µm, 70-90 µm or intermediate, larger or smaller ranges. In some embodiments, the unthreaded screw and shell are then axially compressed under pressure and heating (e.g., of 400° C. or more) in a mold having the configuration of the threaded screw. The fact that the process is conducted under heating increases the elongation of the shell material, thereby facilitates its "reshaping" to the desired threaded configuration. According to Tan M J, Microstructure evolution of CP titanium during high temperature deformation, *Archive of Materials Science and Engineering*, 2007, Vol. 28, p. 5-11, CP titanium alloy may obtain a maximum elongation of almost 200% under 600° C. or 700° C., depending on strain rate.

In another embodiment, for example in order to provide for a higher elongation of the shell material without compromising the properties of the composite material construct, a foil or a thin tube is placed over an unthreaded stem portion of a screw that acts as a dummy, and may later be disposed of. The disposable screw is made of material that can undergo compression molding in high temperatures (e.g., 600° C. and more) in a mold having a screw configuration. In some embodiments, following compression molding, the core of the coated screw is removed, leaving a threaded thin shell. At this stage the shell is placed over a composite material screw and the coated screw undergoes compression molding in temperature suitable for the composite material. Additionally or alternatively, biocompatible adhesive means, such as implant-grade epoxy or silicone compound, are added, to further assure firm connection of the shell to the screw. Optionally, low energy laser welding of the titanium layer may be performed after compression molding is completed.

In another embodiment, the shell for said coating is made using superplastic forming. In this embodiment, the shell, for example a thin sheet or tube made of titanium alloy (e.g., Ti-6Al-4V), is placed within a mold having the form of the desired threaded configuration. Internal pressure (e.g., using argon) is placed on the sheet or in the tube, against the mold, in a controlled environment (e.g., under vacuum, in an oxygen free environment), and under high temperature (e.g., of the order of 850° C.). At this stage the formed shell is placed over a composite material screw and the coated screw undergoes compression molding under temperature suitable for the composite material. Additionally and/or alternatively, biocompatible adhesive means, such as implant-grade epoxy or silicone compound, are added, to further assure firm connection of the shell to the screw. Optionally, low energy laser welding of the titanium layer may be performed after compression molding is completed.

In an embodiment, the foil comprises a rough and/or textured internal surface, achieved, for example, using sand blasting or chemical techniques, for example to enhance adhesion of the composite material to the foil upon compression molding. In some embodiments of the invention, the pedicle screw construct comprises a highly rigid rod, for example a metal rod, such as a rod made of CP titanium or titanium alloy such as Ti-6Al-4V, and/or a rod made of fiber-reinforced polymer with relatively high fiber volume contents, such as at least 55% CFR-PEEK. In some embodiments, the rigid rod immobilizes movement of the treated spinal segments, fixating the vertebrae relative to each other upon locking the components, for example during operation.

For embodiments in which the construct comprises a metal rod or a partially metallic rod, it is noted that artifacts which may appear during imaging may not substantially interfere with viewing the treated bones and/or tissue, as the rod is positioned a certain distance above (e.g., posteriorly) to the treated segment.

Alternatively, in some embodiments, the construct comprises a less rigid rod, providing for dynamic stabilization of the treated spinal segments. A potential advantage of a less rigid, partially flexible rod may include reducing stress on adjacent discs and facet joints. Another potential advantage of reducing the stress by a less rigid rod may include increased rates of bone growth during fusion.

Is some embodiments, a less rigid rod comprises a polymer such as PEEK, a rod made of CFR-PEEK with a lower volumetric content of fiber (e.g., 30% fibers), a rod with a CFR-PEEK core and PEEK outer shell; a rod with PEEK core and CFR-PEEK shell, a rods of braided CFR-PEEK, and/or other material compositions suitable for providing some flexibility to the rod. Other materials and/or designs for fabrication of semi-rigid rods and/or combination of any of the above mentioned options for manufacturing of such rods are also within the scope of this invention.

It is noted, that the present invention, in some embodiments thereof, also includes combination of the above-described methods for screw and coated screw manufacturing.

It is stressed, that the said coating methods are not limited to screws or to composite materials, but rather are applicable to coating of every material that may be coated in the above described methods.

It is further noted that one or more components of the pedicle screw construct may be used for other applications, for example the pedicle screw may be used as a multi-purpose bone fixation screw.

In some embodiments, the construct or one or more components thereof are used in the treatment of acute and/or chronic instabilities and/or deformities of the spine, including but not limited to degenerative disc disease, spondylolisthesis, fracture, dislocation, spinal stenosis, scoliosis, kyphosis, lordosis, spinal tumor and/or pseudoarthrosis. In some embodiments, the construct or one or more components thereof is used as an adjunct to fusion. In some embodiments, the construct or one or more components thereof is used without vertebral fusion. In some embodiments, the construct or one or more components thereof are used in the treatment of collapsed vertebrae, recessed vertebrae, damaged vertebrae (for example as a result of trauma and/or due to a tumor) and/or other spinal applications.

It is noted that the terms "adjacent vertebrae" and/or "neighboring vertebrae" as disclosed herein may refer to two or more vertebrae being connected to each other by the construct, such as vertebrae in which pedicle screws are implanted, and not necessarily vertebrae which are anatomically adjacent each other. In some embodiments, the terms "adjacent vertebrae" and/or "neighboring vertebrae" refer to vertebrae which are anatomically adjacent each other.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Referring now to FIG. 1, FIG. 1 illustrates an exemplary polyaxial pedicle screw construct 10, comprising two pedicle screws 12, 14; a rod 16; and restraining means including collars 18, 20, and locking rings 26, 28, according to some embodiments of the invention. The components of the construct are made of or comprise of one or more of composite material (such as carbon fiber-reinforced PEEK), metal (such as titanium), other polymeric material, and/or any combination thereof. In some embodiments, in practice, the two screws 12, 14 are normally introduced into two pedicles of adjacent vertebrae (e.g., lumbar or thoracic vertebrae), on the same side, for example on the same side relative to the long axis of the spinal cord. In some embodiments, rod 16 is coupled and optionally locked to the screws 12, 14, using collars 18, 20 and rings 26, 28.

The exemplary collar 18, 20 in the figure is composed of two identical components 22, 24. Alternatively, in some embodiments, a collar comprises more than two components, for example 3, 4, 5 components. In some embodiments, the components are not identical, and are formed with a different shape and/or size. In some embodiments, the collar components complete each other to form a substantially cylindrical configuration. In some embodiments, the components complete each other to form a substantially conical configuration, tapering for example in the distal direction. Additionally or alternatively, a conical configuration is obtained when the components or portions thereof are approximated towards each other, for example by the locking ring 26, 28.

In some embodiments, a similar construct is implanted on the contra-lateral side.

Figure 2:
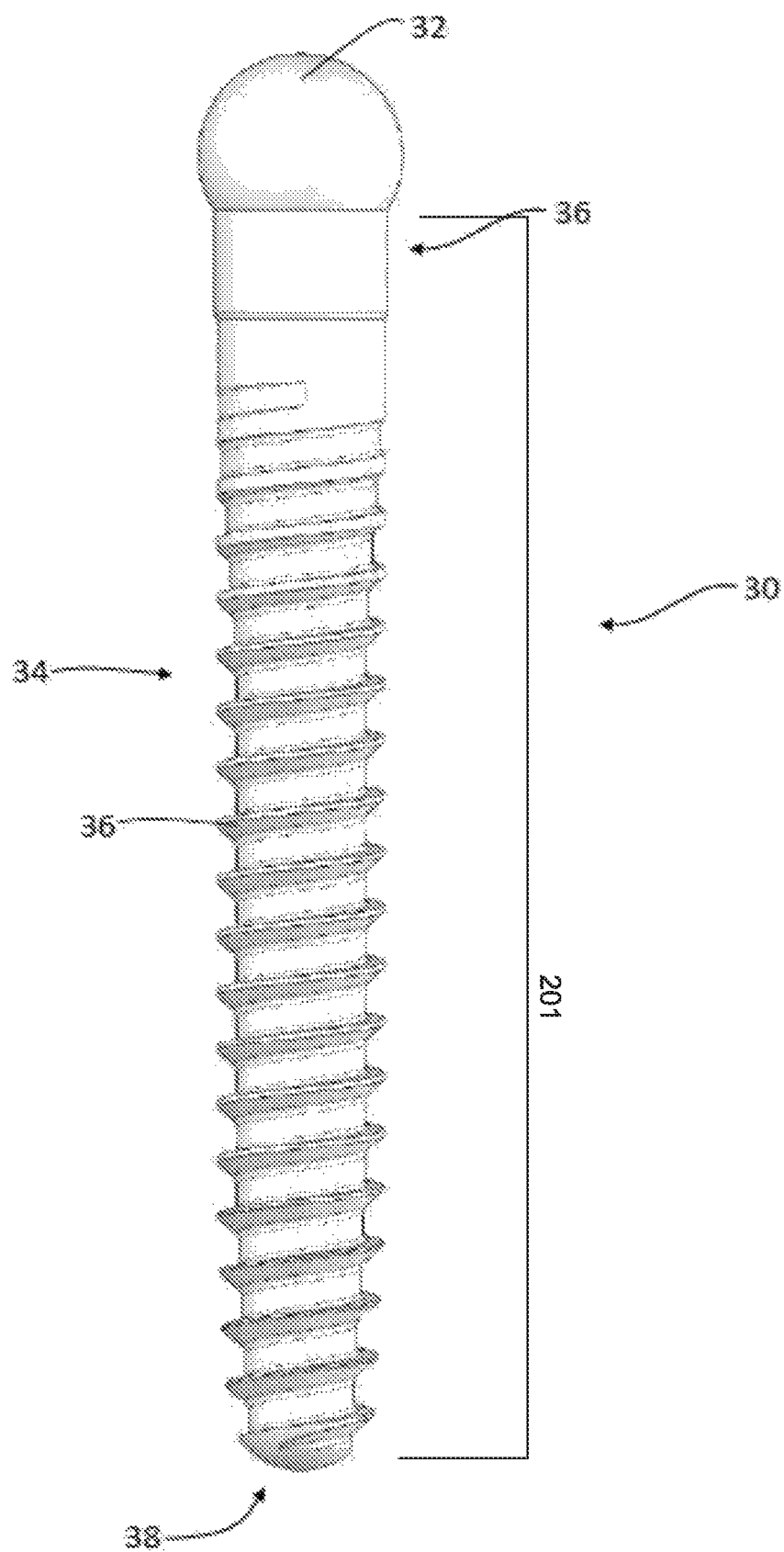
FIG. 2 is perspective view of the pedicle screw of FIG. 1, in accordance with some embodiments of the present invention.

FIG. 2 illustrates a pedicle screw 30 component of a pedicle screw construct (FIG. 1), in accordance with some embodiments of this invention. In some embodiments, screw 30 comprises a spherical (or partially spherical) head 32, configured at a proximal end of the screw. Alternatively, the screw head is shaped in other configurations, for example a hex head, a square head, a button head, and/or any other configuration. In some embodiments, screw 30 comprises a stem 34. Optionally, at least a portion of stem 34 is threaded. In some embodiments, stem 34 extends between a neck 36 of the screw, the neck coupling between head 32 and stem 34, and a distal tip 38 of the screw. In some embodiments, neck 36 is unthreaded. Alternatively, neck 36 is threaded at least in part.

In some embodiments, screw 30 is made of or comprises of one or more of composite material, metals, or a combination thereof.

In some embodiments, screw 30 is positionable relative to the collar in which it is received, for example the screw head is pivotable within the collar cavity before locking of the construct. Optionally, screw 30 extends along a continuation of the long axis of the collar. Alternatively, screw 30 extends at an angle relative to the collar, for example a 10 degree, 20 degree, 50 degree, 60 degree or intermediate, larger smaller angles relative to the collar, to obtain a desired angle of implantation into the pedicle. A potential advantage of a spherical screw head 32 may include placing the screw at a desired angle, for example an angle relative to the collar in which screw is received. Another potential advantage of a spherical, polyaxial screw may include facilitating placing of a rod, (e.g., FIGS. 1; 16A-C), for example by changing the positioning of the collar relative to the screw to facilitate insertion of the rod.

In some embodiments, for example before locking of the construct, the collar is rotatable relative to the screw, for example rotatable and/or otherwise oriented relative to the screw shank 201, which includes stem 34 and/or neck 36. A rotatable collar may provide an advantage in cases in which pedicle screws are used in bones having an, irregular bone anatomy. In such cases, it may be difficult to align the screw head relative to the collar in a configuration which will allow deployment of the rod through the collar, and rotation of the collar relative to the screw may assist.

In some embodiments, screw 30 is cannulated (not shown in the figure), for example to allow screw insertion over a guide wire. In some embodiments, a diameter of the screw shank (e.g., a total diameter of the shank with the thread, or a diameter of the shank without a thread) along various portions of the shank varies. Optionally, the screw shank tapers, or part of it tapers, towards the distal tip 38.

In some embodiments, screw dimensions are similar to those of typical pedicle screws available on the market, for example a screw comprising a diameter (e.g., a diameter of the shank with the thread or a diameter of the shank without the thread) ranging between 4.5-8.0 mm, for example having a larger diameter at a proximal end which decreases towards the distal end, and a length ranging between 30-65 mm (or more) for lordotic vertebrae. Optionally, a screw with smaller dimensions is implanted in smaller vertebrae.

The thread 36 shown in the figure is for illustration only, and may be of different geometry and size.

In some embodiments, screw 30 comprises a radiopaque marker. The marker may be formed in various shapes (e.g., thread, dot, ring, pin, or other shape) and/or various dimensions, may be positioned at various locations of the screw (e.g., at head 32 distal end 38 and/or along shank 201), and may comprise various materials, for example as described herein. Additionally and/or alternatively, a radiopaque powder (or particles) is added to the screw, for example as described herein.

In some embodiments, the screw 30, for example made of composite material, is coated with a thin layer of different material, which potentially improves a desired characteristic of the implant and/or its surface (not shown in the figure), for example strengthening the surface (thereby potentially providing additional strength to the implant), smoothing the surface, and/or otherwise modifying the implant (e.g., the screw). Optionally, the thin shell covers only a portion of the screw 30. In an example, a titanium shell of about 1-100 µm thickness covers the threaded portion of the screw 34. Additionally or alternatively, the thin shell covers the distal end of the screw 38 and/or the neck of the screw 36. It is noted, that such a thin shell also enables visualization of screw circumference upon screw insertion into the bone as well as following the surgery, while not generating substantial artifacts during imaging or interfering with radiotherapy. Embodiments related to shell material, dimensions and production methods were referred to earlier in this document. It should be appreciated that such methods are not limited to pedicle screws, but rather may be also used for the production of other implants, including various bone screws.

Optionally, a composite material screw, that comprises a thin metal shell (e.g., over its threaded portion), also includes a radiopaque marker. For example, a wire of 0.10-0.35 mm diameter, made of tantalum for example, is incorporated along the proximal, non-threaded portion of the screw. Additionally or alternatively, the screw (or a portion thereof, for example the portion that enters the vertebra) and/or the shell comprise radiopaque powder.

Figure 3:
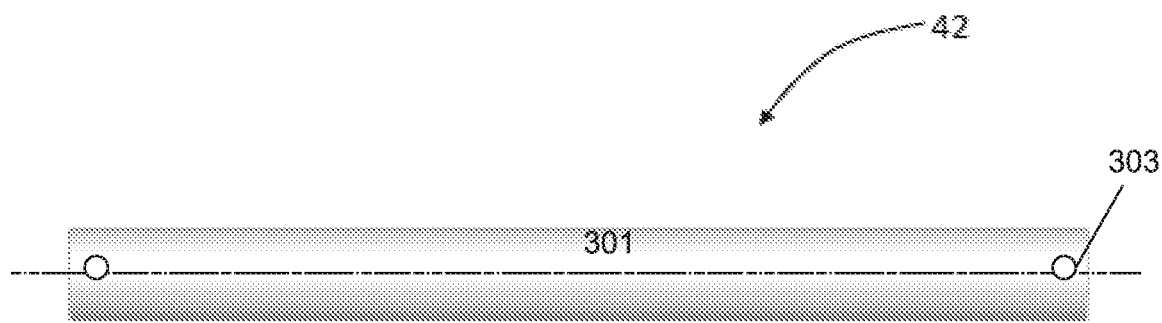
FIG. 3 shows a cross section of the rod of FIG. 1, in accordance with some embodiments of the present invention.

In some embodiments, a diameter of the head of the screw, for example a largest diameter of a nearly-spherical head for example as described herein, ranges between 5-9 mm, such as 6 mm, 7 mm, 8.3 mm, or intermediate, larger or smaller diameters. FIG. 3 illustrates a longitudinal cross section of a rod component 42 of a pedicle screw construct (see FIG. 1), in accordance with some embodiments of this invention. In some embodiments, rod 42 is made of or comprises one or more of composite materials, metals, other polymeric material, or combination thereof. In some embodiments, rod dimensions are similar to those of other rods available on the market, for example a rod of 4.5-6.5 mm diameter and a length of 35-180 mm, or intermediate, longer or shorter lengths for lordotic vertebrae. Optionally, a rod with smaller dimensions is used for smaller vertebrae. Optionally, a rod with larger dimensions is used for a multilevel construct, e.g., one that couples between more than two vertebrae.

In some embodiments, a radiopaque marker is added to the rod 42. Each of the shapes, dimensions, locations and/or materials of markers detailed previously in this document may apply. In an example, rod 42 comprises a tantalum wire of 0.10-0.35 mm diameter, placed along the longitudinal axis 301 of the rod. Additionally or alternatively, other markers such as 303 are incorporated in the rod, for example markers in the form of lines (e.g., lines formed by wires) or points (e.g., points formed by small pins) mounted at the opposite ends of the rod 42. Additionally and/or alternatively, a radiopaque powder (or particles) is added to the rod, as detailed described earlier in this document.

In some embodiments, rod 42 is straight, for example as shown in the figure and may be provided to the user as such. Alternatively, the rod may be provided to the user already bent and/or provided to the user with a dedicated apparatus suitable for bending the rod, optionally during surgery, to a desired curvature.

Figure 16B:
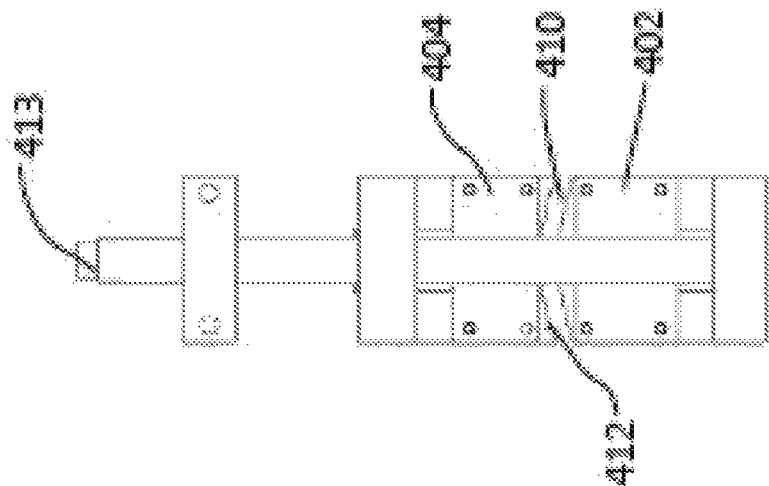
FIGS. 16A-16C schematically illustrate an apparatus for bending an implant intra-operatively, in accordance with some embodiments of the present invention.
Figure 16A:
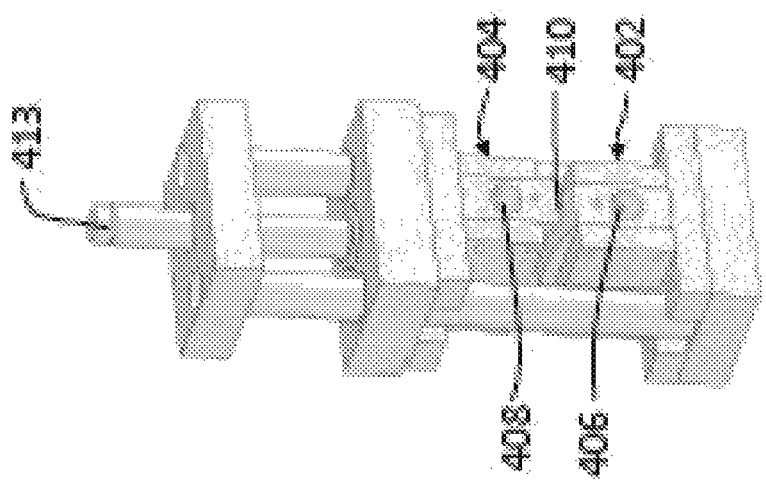
Figure 16C:
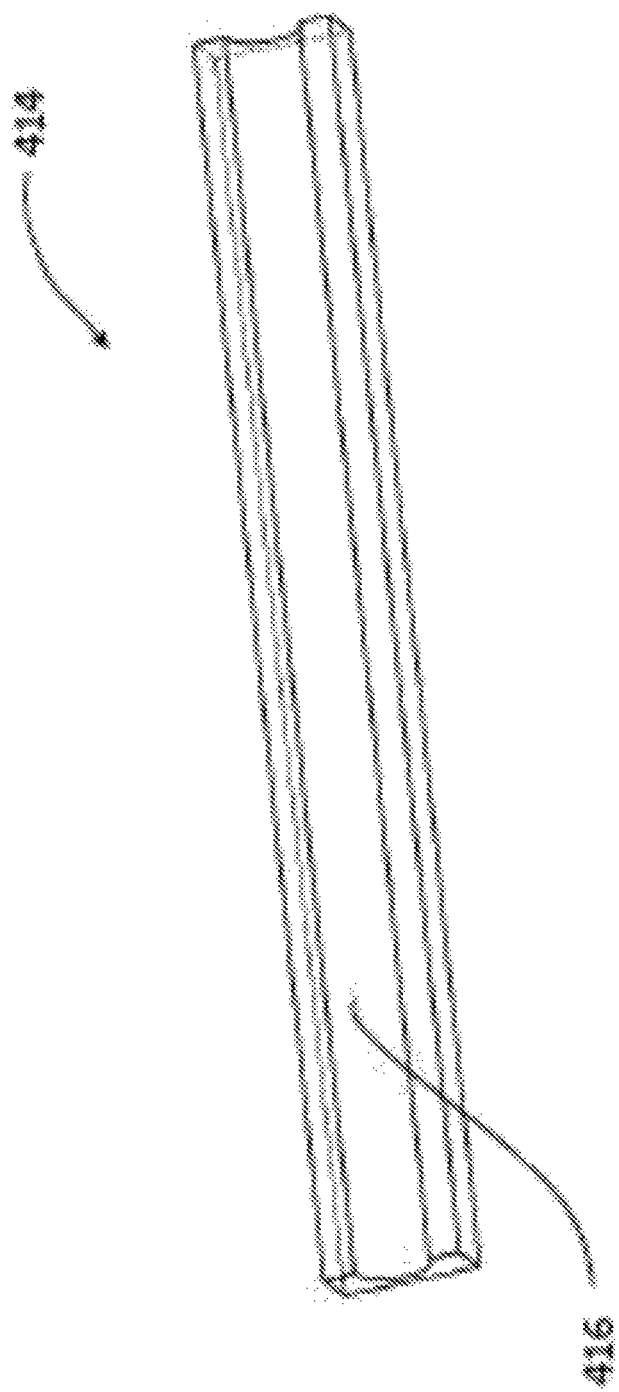

In some embodiments, the rod is deformed by heating, for example as further described below (FIGS. 16A-16C). Additionally or alternatively, the rod is deformed by application of pressure, heat and/or other methods suitable for reshaping the rod.

Figure 4:
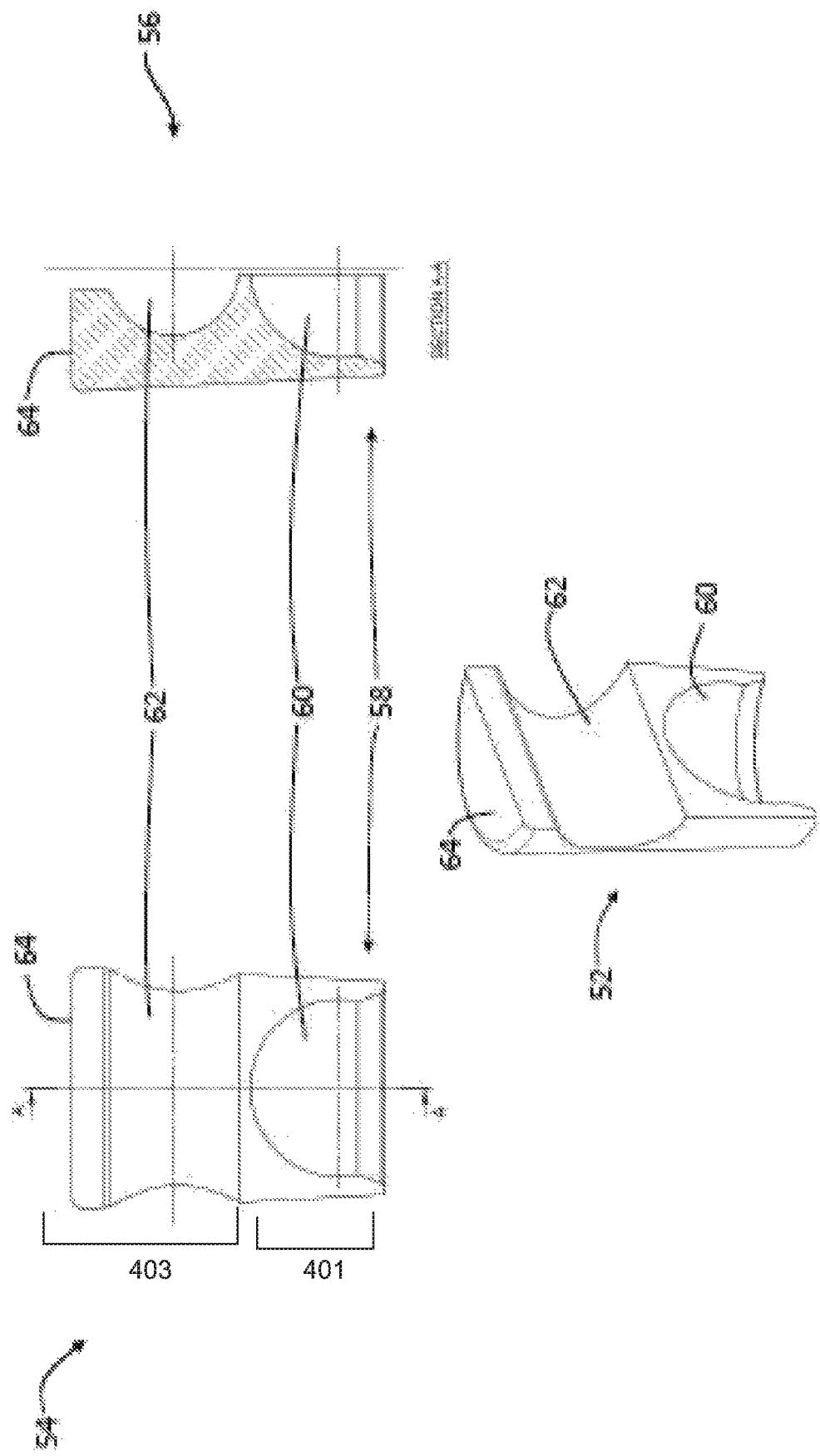
FIG. 4 illustrates a collar component of FIG. 1, in accordance with some embodiments of the present invention.
Figure 5:
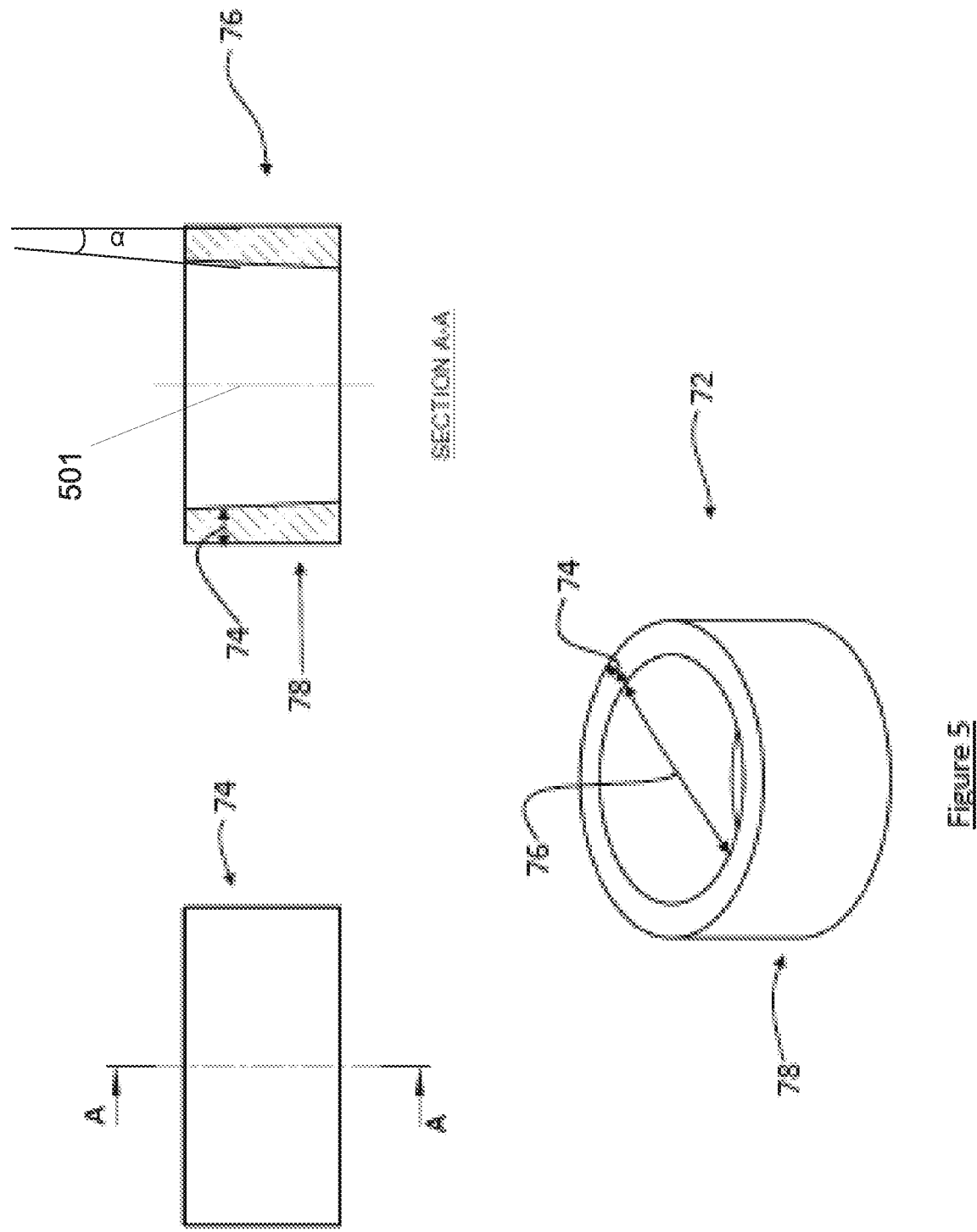
FIG. 5 illustrates a locking ring of FIG. 1, in accordance with some embodiments of the present invention.

In some embodiments, during implantation of a pedicle screw construct, the rod should be secured to the pedicle screws. A thread mechanism for pedicle screw-rod locking (e.g., in the form of a threaded screw or a threaded locking cap) has been shown by prior art. This thread mechanism may be less desired when composite materials are involved. In some embodiments, the components (e.g., screw and rod) are held by the collar due to friction forces. FIGS. 4 and 5 below describe an example of non-threaded locking means, comprising a collar and an external restraining ring.

FIG. 4 illustrates several views of a collar component, in this example showing a component which forms half of the collar (22, 24 in FIG. 1), in accordance with some embodiments of this invention. Perspective view 52, front (internal) view 54, and longitudinal cross section 56, are presented.

In some embodiments, the collar is made of or comprises of one or more of composite material, metals, or a combination thereof. Optionally, the collar comprises a radiopaque marker. In some embodiments, at its lower portion 401, the collar embraces the spherical screw head. In some embodiments, the rod is situated at the collar's upper portion 403.

According to embodiments related to this figure, two identical halves build a collar (e.g., complete each other to form a collar, optionally with a gap in between them). Yet, it is stressed that this invention is not limited to such collar design. For example, a collar of additional components, or alternatively a single-component collar, optionally slotted at its upper (dorsal) portion 403, may be used as well.

Referring to the exemplary 2-component collar presented in FIGS. 1 and 4—the collar comprises a tubular external configuration, with a diameter that tapers towards the lower (anterior) portion 58 of the collar (forming a conical shape). In some embodiments, the internal surface of each collar half comprises a socket 60, optionally rounded, at the lower end portion 401 of the component. In some embodiments, the geometry and dimensions of socket 60 match the screw head, for example matching a spherical screw head. In some embodiments, a cavity 62 at the upper portion 403 of the component is configured to receive the rod by comprising a geometry and/or size that match the rod shape and/or size. In some embodiments, at the upper (posterior) end, the component 52 ends with a straight, optionally smooth surface 64. Optionally, surface 64 is flat. Alternatively, surface 64 is non-flat, for example formed with one or more concavities. In some embodiments, for example as detailed below, during operation the two halves of the collar are placed to surround the pedicle screw head and the rod is inserted into the tubular cavity created by the two halves of the collar.

Figure 10:
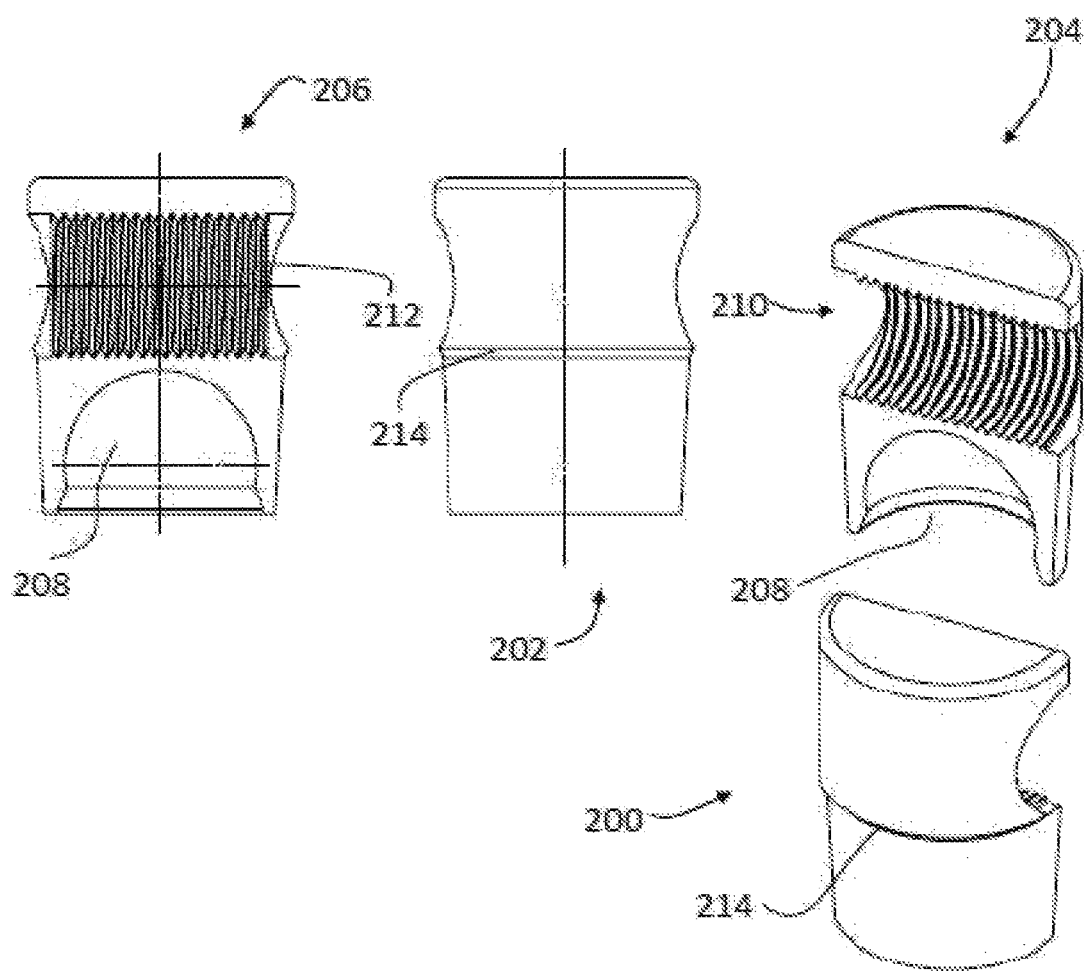
FIG. 10 schematically illustrates several views of a collar component of a polyaxial pedicle screw-rod construct, in accordance with some embodiments of the present invention.

FIG. 10 illustrates another design of the collar component (half), in accordance with some embodiments of this invention. The exterior of a collar half is shown in views 200 and 202. Collar interior is shown in views 204 and 206. In some embodiments, the collar comprises one or more of composite material, metals, or a combination thereof, and may comprise a radiopaque marker. In an example, a tantalum wire of 0.10-0.35 mm diameter is located along the axes (e.g., longitudinal or transverse axes) of the collar half. Optionally, a tantalum pin is positioned at the upper (dorsal) surface of each collar half. Additionally and/or alternatively, a radiopaque powder (or particles) is added to the collar, for example as described earlier in this document. In some embodiments, each collar half comprises, at the lower portion, a round recess 208 comprising geometry and dimensions that is sized according to the spherical screw head to embrace the screw head, for example being slightly smaller than the screw head such that the screw head is slightly deformed to fit within the recess. In some embodiments, at their upper portion, the collar halves define a tubular recess 210, matching the shape and size of the rod. As can be seen for example in 204 and 206, the upper recess 210 in which the rod is received is threaded. In some embodiments, thread 212 matches (e.g., is complementary to) a thread located at the rod (for example as described below in FIGS. 11A-F). Optionally, thread 212 of the collar recess defines an internal (female) thread in which an external (male) thread of the rod is received. In some embodiments, the matching threads provide a geometric lock, for example between the collar and the rod, thereby potentially increasing the gripping strength, for example the axial strength, of the pedicle screw-rod construct. In some embodiments, at its exterior surface 200, 202, the collar half comprises a step 214, so that the diameter of the assembled collar is reduced at its lower portion (where the locking ring is situated) compared to its upper portion. Optionally, step 214 serves as a stop upon elevating the ring, to assure the ring is properly located at its designated place. Additionally or alternatively, the collar half comprises one or more protrusions which extend radially outwards with respect to the collar. Optionally, the one or more protrusions act as a stop for preventing over-advancing of the ring in the proximal direction, for example during assembly of the screw construct. Optionally, the one or more protrusions prevent the ring from sliding relative to the collar.

FIGS. 11A-11F schematically illustrate several configurations of a rod component comprising a thread, complementary to the collar internal thread (e.g., the thread lining the tubular recess of the collar), in accordance with some embodiments of the present invention. FIG. 11A presents a straight rod 220 having a length 1101 suitable for the treatment of a single spinal level (two vertebrae). Optionally, length 1101 ranges between 30-55 mm. In some embodiments, rod 220 comprises, at each end (i.e. a proximal end and a distal end) a thread 222, 224 respectively. Optionally, threads 222, 224 comprise opposite handedness (right-hand thread and left-hand thread). In some embodiments, upon coupling the rod to the screws, using, for example, the collar and locking ring, the rod may be oriented, for example rotated, to bring the treated vertebrae to a desired anatomic distance and/or alignment relative to each other. FIG. 11B presents a straight rod 226 having a length 1103 suitable for the treatment of two spinal levels (three vertebrae). Optionally, length 1103 ranges between 55-95 mm. In some embodiments, rod 226 comprises a thread at each end 228, 230 and an additional thread at the rod center 232.

FIGS. 11C and 11D illustrate two bent rods 234, 240, having lengths 1105 and 1107 respectively, corresponding to a single level and a two-level surgery, respectively. Optionally, length 1105 ranges between 30-55 mm. Optionally, length 1107 ranges between 55-95 mm. In some embodiments, one or more of the threaded portions 236, 238, 242, 244, 246 are also bent to a certain curvature.

In some embodiments, a rod comprises a linear, straight configuration. Alternatively, a rod comprises one or more curvatures and/or bends.

In some embodiments, a rod is provided bent, for example provided to a user such as a physician performing the procedure in a pre-selected configuration. Additionally or alternatively, the rod is bent and/or otherwise deformed and/or reshaped during operation, optionally according to the patient anatomy and needs. In some embodiments, the bending radius of the rods 234, 240 is constant along the entire rod. In some embodiments, the shorter rod 234, which is intended to connect two pedicle screws, includes two threads 236, 238 at its ends (i.e. proximal and distal ends). In some embodiments, the longer rod 240, which is intended to connect three pedicle screws, includes three threads—two threads 242, 244 at its ends (i.e. proximal and distal ends), and an additional thread 246 at its center.

FIGS. 11E and 11F illustrate additional two bent rods 248, 256, having lengths corresponding to a single level- and a two-level surgery, respectively. In some embodiments, a rod is provided bent. Additionally or alternatively, the rod is bent and/or otherwise deformed during operation, according to the patient anatomy and needs.

In some embodiments, the shorter rod 248, which is intended to connect two pedicle screws, includes two threads 250, 252 at its ends. In some embodiments, the longer rod 256, which is intended to connect three pedicle screws, includes three threads—two threads 258, 260 at its ends, and additional thread 262 at its center. In some embodiments, the bending (e.g., curvature) of the rods 248, 256 is not continuous; in this example, the non-threaded portions 254, 264, 266 of the rods are bent, while the threaded portions 250, 252, 258, 260, 262 are relatively straight. Optionally, one or more portions of the rod comprise a different curvature (e.g., a different radius of curvature) with respect to one or more other portions of the rod.

Optionally, other or additional areas and/or segments along the rod are threaded. Optionally, the threaded portion/s are larger than or smaller than the threaded portions shown in the figure. Optionally, the entire rod is threaded. Optionally, the rod is bent in a non-planar curvature, for example having a three dimensional spatial arrangement.

Figure 12:
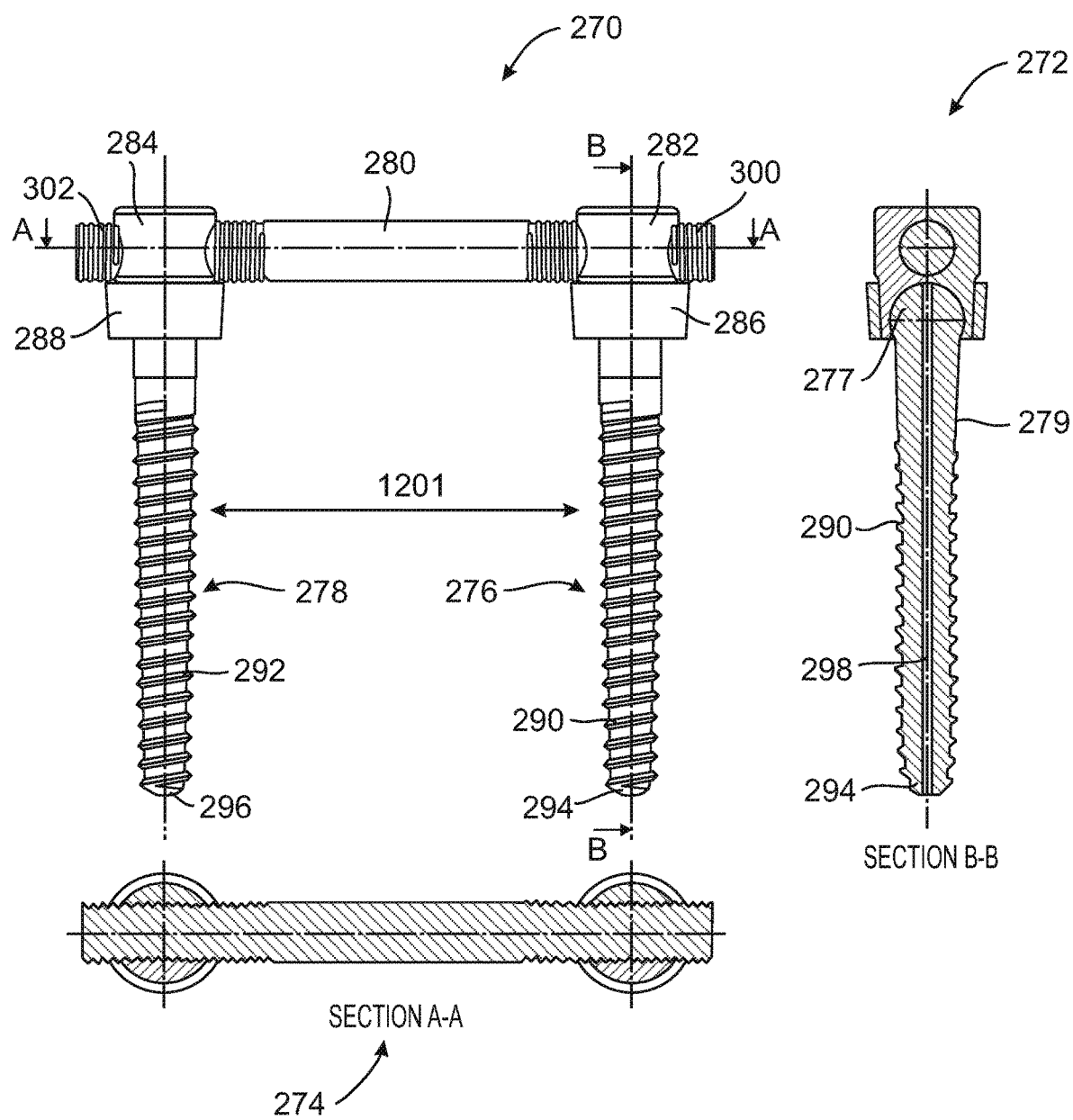
FIG. 12 schematically illustrates a polyaxial pedicle screw-rod construct, in accordance with some embodiments of the present invention.

FIG. 12 illustrates a side view of a pedicle screw construct 270, and two cross section views 272, 274. In some embodiments, construct 270 comprises two pedicle screws 276, 278 and a rod 280, which is secured to the screws 276, 278 using collars 282, 284 and/or locking rings 286, 288. In some embodiments, implant components are made of or comprise of composite material, such as CFR-PEEK. Optionally, the implant comprises one or more radiopaque markers, such as tantalum wires. Optionally, the markers are shaped as pins, dots, and/or other shapes, and are incorporated within and/or mounted to the components (not shown in the figure). In some embodiments, radiopaque powder is incorporated in the components. In the example described earlier in FIG. 2, screw 276 comprises a spherical (or partially spherical) head 277; a threaded stem 290; an unthreaded neck 279, connecting the head 277 to the screw threaded stem 290; and a distal tip 294. In some embodiments, the screw does not comprise a neck portion, and the threaded stem 290 is directly coupled to head 277.

A potential advantage of a spherical, polyaxial screw head 277 may include placing the screw at a desired angle, for example an angle relative to the collar in which screw is received. Another potential advantage of a spherical screw may include the ability to spatially orient the locking ring relative to the screw. In an example, the screw is implanted with the locking ring attached, the ring being held against, for example, adapters encompassing the screw head. Optionally, prior to elevating the ring to a locked position, the ring is tilted for example to be positioned at an angle relative to the longitudinal axis of the screw. Such positioning may facilitate coupling an assembly of the rod and collars (the collars being prepositioned on the rod) over the screw heads.

Optionally, the screw shank tapers, or part of it tapers, towards the distal tip 294.

In some embodiments, screw dimensions are similar to those of typical pedicle screws available on the market, for example a screw comprising a diameter ranging between 4-8.0 mm, and a length ranging between 30-60 mm (or more) for lordotic vertebrae. Optionally, a screw with smaller dimensions is implanted in smaller vertebrae.

The thread shown in the figure is for illustration only, and may be of different geometry and size.

In some embodiments, the threaded portion of the screws 290, 292, and/or the screws distal tips 294, 296, may be coated with a thin layer shell, optionally made of metal (e.g., pure titanium (not shown in the figure)). In some embodiments, as shown for example in cross section 272, screws 276, 278 are cannulated 298, to enable their introduction over a guide wire. In some embodiments, rod ends 300, 302 are threaded (for example with right-hand and left-hand threads, respectively). Optionally, the rod's threads match the collars' internal threads (not shown in the figure). A potential advantage of the complementary threads of the rod and collar may include increasing the axial gripping strength of the construct, e.g., the strength of a coupling between the rod and the collar which prevents the rod from moving (e.g., axially sliding) relative to the collar cavity. Another potential advantage may include enabling manipulation of the construct (e.g., rotating the rod for reducing or increasing the distance 1201 between the two screws, such as by threading or unthreading the threaded portions of the rod into and/or out of the collar cavity).

In some cases, the implant is removed from the body. In some embodiments, removal of the construct may be performed in a conventional manner, for example as performed for other pedicle screw systems. In an embodiment of the invention, an alternative method for removal of pedicle screws-rod construct comprises:

a. Cutting the rod between the screws. Optionally, the rod is divided into two or more portions.

b. Counterclockwise or, in some embodiments, clockwise rotation (optionally manually) of one of the cut rod portions relative to a longitudinal axis of the screw, to screw-out (e.g., unscrew) the pedicle screw from the bone; Optionally, the restrained coupling between the rod and collar and the collar and screw is maintained, allowing for use of the rod as a screwdriver which can unscrew the screw from the bone.

c. Repeating Step b. for the remaining screw, (or remaining screws in an arrangement which comprises more than two pedicle screws).

FIG. 5 illustrates several views 72, 74, 76 of the locking ring component of the pedicle screw construct, in accordance with some embodiments of this invention. In some embodiments, ring 72 is designed (e.g., structured and/or sized) to surround the collar and screw spherical head and to restrain the construct motion by exerting radial inward force.

In some embodiments, ring 72 is made of or comprises one or more of composite material, metals, or a combination thereof. Optionally, ring 72 comprises a radiopaque marker. In an example, a tantalum wire of 0.10-0.35 mm diameter, is located (e.g., incorporated within the material and/or mounted) along the ring perimeter, for example on the outer wall of the ring, inner wall of the ring, or inside the wall of the ring. Additionally and/or alternatively, radiopaque powder (or particles) is added to the ring, for example as described earlier in this document.

In some embodiments, the ring has an internal conical shape. As shown in this example, the width (wall thickness) 74 of the ring is not constant (e.g., smaller at the upper portion), resulting in ring internal diameter 76 that tapers (decreases) towards ring's lower (anterior) end 78. Alternatively (not shown in the figure), the ring wall thickness is constant, and its internal and external diameters taper towards the lower portion in the same rate. Optionally, the ring conical shape has an angle α in the range of 1-10 degrees, for example being the opening angle between the internal and external walls of the ring when measured, for example, from the upper end of the ring to the lower end of the ring. Angle α can be referred to as a tapering angle of the inner walls of the ring relative to a long axis 501 of the ring (i.e. an axis passing through a center of the lumen defined by the ring), for example in embodiments in which an outer wall of the ring is not parallel to the central axis (such as if the outer wall comprises a conical and/or "step" profile). Optionally, for example as hereby described, the ring 72 locks the rod to the screw, to assure construct immobilization, e.g., restrict relative movement of the components such as rod, screw head and/or collar, relative to each other and/or relative to the vertebrae.

It is noted, that results of experiments conducted by the inventors demonstrated that the ring of pedicle screw constructs comprising conical ring and collar of 2-4 degrees (e.g., the tapering angle of the collar and optionally a matching opening angle α between the external and internal walls) did not slip downwards upon application of substantial loads, such as compression load, for example applied onto a proximal end of the collar.

Figure 6:
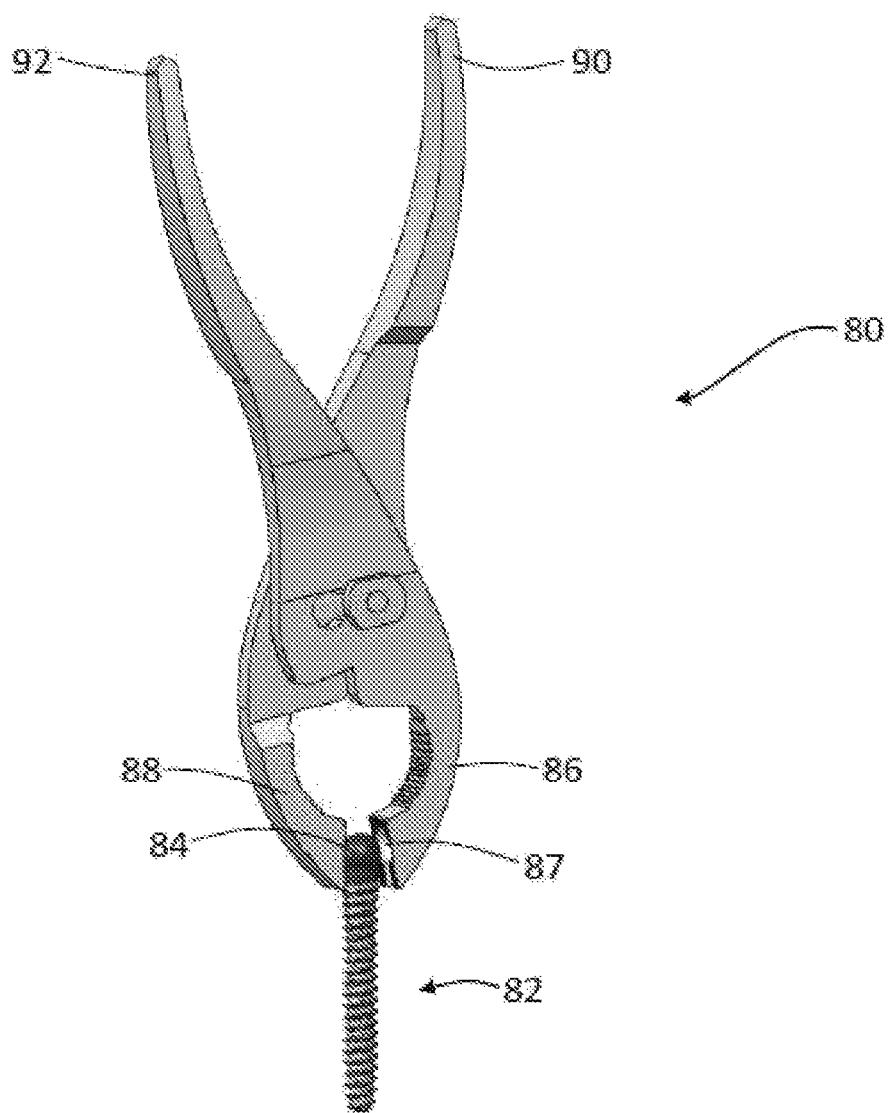
FIG. 6 schematically illustrates an insertion tool for a pedicle screw, in accordance with some embodiments of the present invention.
Figure 7F:
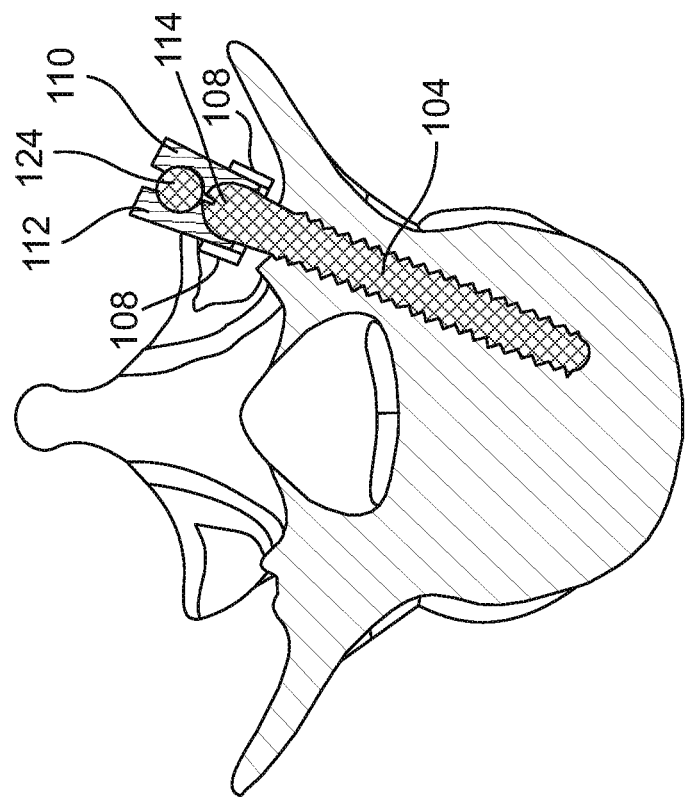
Figure 7E:
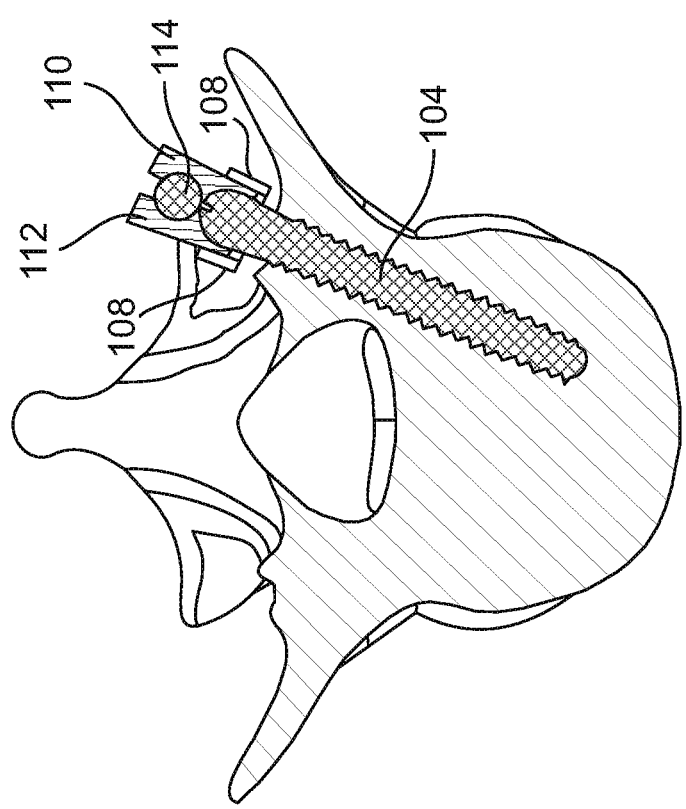

FIG. 6 illustrates a screw insertion tool 80, with accordance with some embodiments of this invention. In some embodiments, the insertion tool 80 is designed to enable the gripping of the screw's spherical head 84 and the insertion (screwing) of the screw 82 into the bone. In some embodiments, insertion tool 80 comprises at its distal end two curved, spoon-like, elements 86, 88 configured to firmly grip the screw head 84. In some embodiments, the distal end of the curved element 86 comprises a recess 87 with a geometry and/or size complementary to that of the screw head 84, to increase the gripping strength of the screw by the tool. In some embodiments, at its proximal end, the insertion tool 80 includes two handles 90, 92. Optionally, handles 90, 92 are operatively coupled to elements 88, 86 respectively. In some embodiments, pressing the handles 90, 92 one against the other (e.g., by approximating the handles towards each other, in a scissor-like motion) results in closure of the curved elements 86, 88 around the screw head to grip the screw. In some embodiments, in order to insert the screw into the bone, the tool is rotated and serves as a screwdriver.

In some embodiments, the screw is self-tapping, for example comprising a cutting edge or flute at distal end of the screw. Optionally, the self tapping screw is inserted into a preformed pilot hole in the bone.

Figure 13:
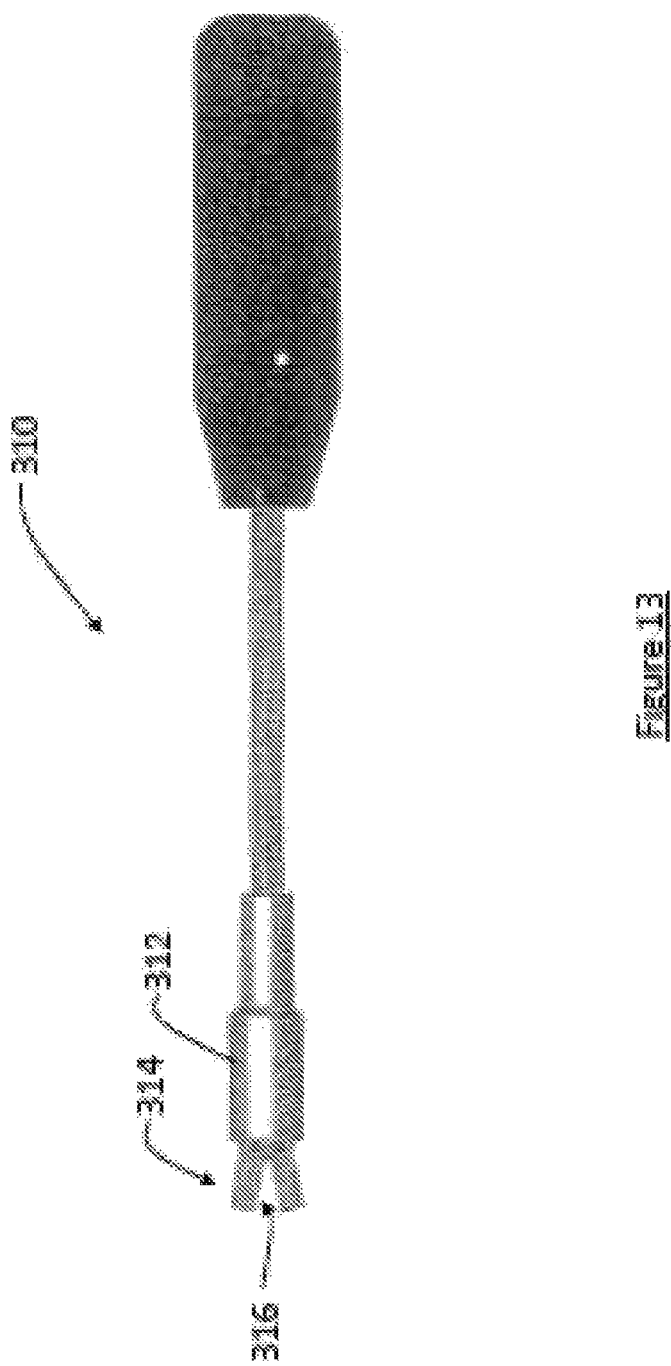
FIG. 13 schematically illustrates an insertion tool for a pedicle screw, in accordance with some embodiments of the present invention.

FIG. 13 illustrates another insertion tool for a pedicle screw, in accordance with some embodiments of the present invention. In some embodiments, insertion tool 310 is cannulated (not shown in the figure), for example to be delivered over a guide wire. In some embodiments, at its distal end, the tool 310 comprises a ring 312 and a pliers-like component 314 with internal spherical socket 316, designed (e.g., shaped and/or sized) to surround the screw's spherical head. Optionally, during operation, the screw head (not shown in the figure) is positioned within the pliers' socket 316, and the ring 312 is manually pushed distally over the pliers 314, to secure the insertion tool 310 to the screw. Optionally, insertion tool 310 comprises a torque limiter (not shown in the figure). Optionally, insertion tool 310 comprises a depth gauge (not shown in the figure), for example for measuring the extent in which the screw has been advanced into the vertebrae.

The following paragraph demonstrates an example of a surgical procedure using the discussed pedicle screw system, in accordance with some embodiments of this invention (see FIGS. 7A-7F).

1. (FIG. 7A) In some embodiments, the treated vertebrae 100 are prepared, for example using common practices. In the figure, the vertebra pedicle 102, vertebral body 106 and spinal cord canal 101 are marked.
2. In some embodiments, a channel is created in the vertebra pedicles 102 and its integrity is verified, for example as commonly performed in such surgeries. Optionally, the channel is created by using an awl and one or more probes, to generate a path through the intrapedicular cancellous bone (not shown in this figure) into the vertebral body.
3. (FIG. 7B) In some embodiments, optionally using a dedicated insertion tool (see, for example, FIGS. 6 and 13), the pedicle screws 104 are introduced via said channels into the vertebral bodies 106.
4. (FIG. 7C) In some embodiments, a dedicated tool (not shown in the figure) is used at this stage, to simultaneously grasp the locking ring 108 and the collar components 110, 112, and to deploy said components in place, e.g., position the collar such that it can be coupled to the screw, for example to the head of the screw, and/or position the collar over the screw. Optionally, the tool enables performing said actions (grasping and deployment) simultaneously for two neighboring screws, for example as further described herein. Optionally, the connecting rod is held and deployed in conjunction with the screws upon their deployment. With the help of this instrument, for example as described below, the locking ring 108 and collar components 110, 112 are positioned in place having the lower portion of the collar positioned over screw head 114. In some embodiments, following rod placement, (e.g., threading or otherwise positioning of the rod within a tubular cavity 126 defined by the collar components), the tool (or optionally a different tool) is used to raise the locking ring 108 to an intermediate location (e.g., an axial position relative to the screw and/or collar and then to a final location, corresponding with provisional locking and final locking, respectively, of the components of the pedicle screw construct.
5. (FIG. 7C) In some embodiments, as explained in more detail hereinbelow, with the help of the said tool, the locking ring 108 and collar components 110, 112 are located over the screw head 114: Optionally, the two halves of the collar 110, 112 are placed around the screw head 114 in a manner that the round socket 116, 118 of each collar half encapsulates almost half of the round screw head, and the ring 108 surrounds the lower part of the collar and screw head 114. At this stage, the lower portion 120 of the ring is located beyond the screw head and collar, for example extending distally past the distal end of the collar, such that only a portion of the length of the ring is fitted around the collar. In some embodiments, a small distance (e.g., gap) 122 exists between the two components (halves) of the collar 110, 112, allowing the subsequent introduction of the rod into its designated place in the collars' upper portion. Optionally, gap 122 is narrower in width than a diameter of tubular cavity 126, to encapsulate or at least partially cover the rod when it is received within the cavity. Optionally, gap 122 is reduced in width when the collar halves are approximated towards each other, for example during locking, enclosing the rod in the cavity.
6. (FIG. 7D) In some embodiments, a rod 124 is introduced into the tubular cavity 126 at the upper portion of two adjacent collars located at the same spinal column side. Optionally, distance 122 is large enough to enable insertion of the rod through the proximal gap between the components of each collar. Additionally or alternatively, the rod is inserted laterally, for example by threading the rod into tubular cavity 126 through a side face of the collar. Optionally, the rod is threaded through a cavity of the first collar, and then through a cavity of the second collar.

7. (FIG. 7E) In some embodiments, optionally using the same tool, the locking ring 108 is slightly raised over the lower portion of the collar, so that the collar halves engage with each other at their anterior (lower) part. Optionally, opposing portions of the interior surfaces of the collar halves contact each other, for example portions configured above the screw head. This provides for a provisional, partial and/or reversible locking of the construct. Optionally, at this stage the collar may still be rotated over the screw, for example axially rotated, and the physician may perform final manipulation on the spine (e.g., increase and/or reduce tension) and adjust the instrumentation accordingly.

8. (FIG. 7F) In some embodiments, when satisfying positioning of the vertebrae and instrumentation is accomplished and optionally verified radiographically, final locking of the components of the pedicle screw construct is performed, by further elevating the ring 108, to its final designation over the collar. Optionally, ring 108 is elevated to a position in which the ring remains under the rod 124, for example directly under rod 124 or at a certain distance from the rod. Optionally, this is also performed with the help of the said tool, that facilitates ring elevation while exerting reasonable loads. The locking ring 108 radially (inward) presses the construct to secure its components, for example by the pressed walls of the collar applying pressure on the rod and/or screw head to prevent the rod and/or screw head for moving, e.g., axially sliding and/or rotating. It is noted, that although the ring does not come in contact with the rod, said final locking prevents rod movement, for example by exerting sufficient radial force on the collar components to press their internal faces, at cavity 126, against the rod 124 to reduce or prevent rod movement.

9. Additionally or alternatively, the rod may be secured, or further secured, by an additional locking component (not shown in the figure). The latter may be a ring, placed over the collar above the rod, or a threaded component (screw/cap) that is screwed to lock the rod in place. The locking threaded component may engage with either internal or external thread at the collar upper end.

10. In some embodiments, the same steps are performed at the contra-lateral side of the spine, and the surgical site is closed using conventional methods.

Alternatively to the above described steps for pedicle screw insertion, the pedicle screw may be inserted into the vertebra while the collar and/or the ring or part of the ring surround it. Prior to screw introduction, the screw, collar and/or locking ring are held together so that the ring slightly encloses the collar and screw head, in a reversible manner that is also sufficient for components grip. Optionally, the ring binds the collar and screw together. Optionally, the binding is loose enough to provide for axial and/or rotational movement of the screw within the collar, until fastening of the ring. In some embodiments, optionally using a dedicated tool, the screw thread is introduced into the vertebra (while the collar and/or the ring or a part of it surround it). If required, the ring may be slightly pushed downward, optionally manually. Additional steps are similar to those described above.

Figure 14:
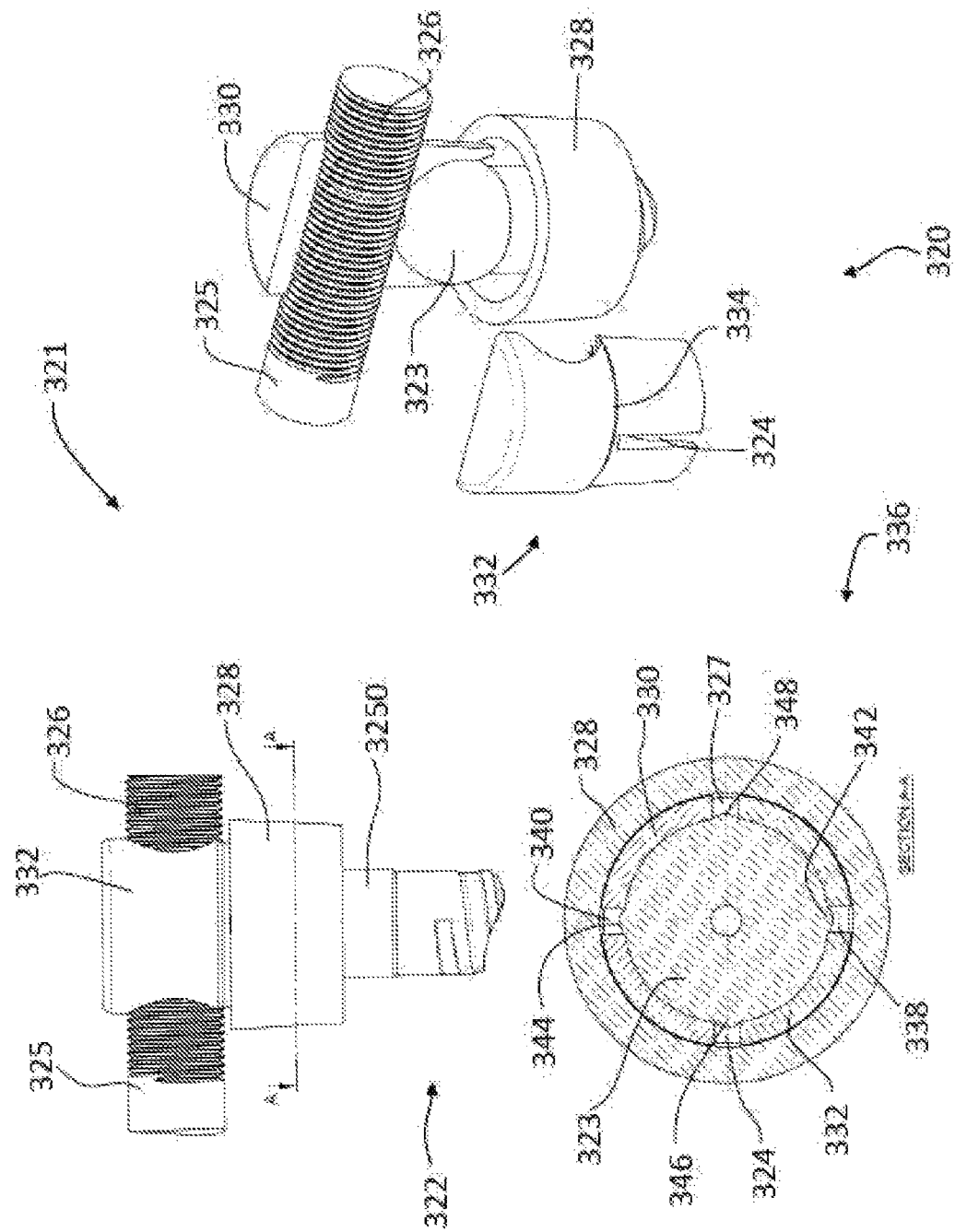
FIGS. 14 and 15 schematically illustrate several views of polyaxial pedicle screw-rod construct, in accordance with some embodiments of the present invention.
Figure 15:
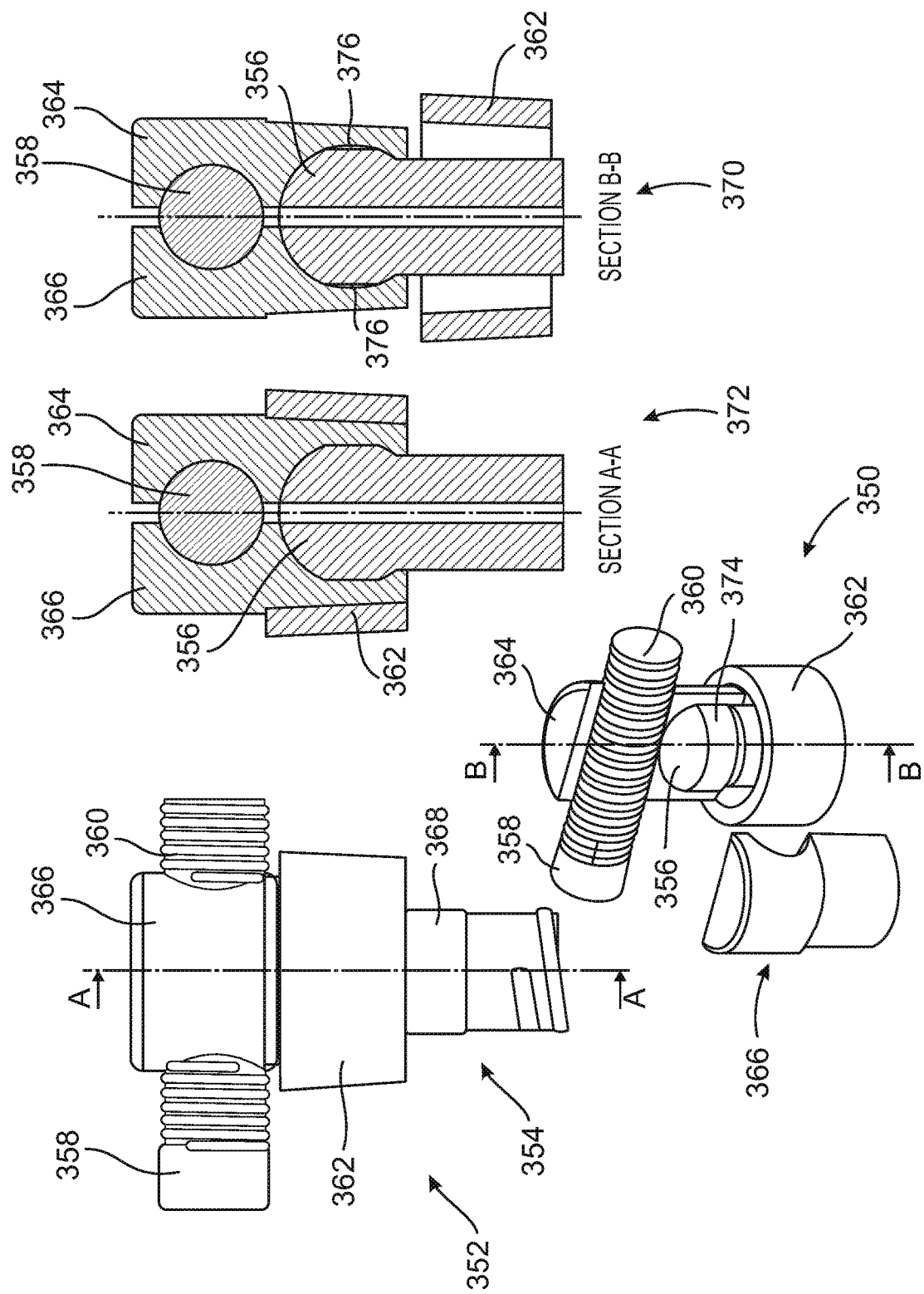

FIGS. 14 and 15 schematically illustrate exemplary pedicle screw-rod constructs including features that enable additional locking between the construct components, for example upon deployment of the ring, according to some embodiment of the invention. According to embodiments of the invention, the locking ring surrounds (at its final location) the lower portion of the collar and screw spherical head, and radially presses said collar and screw head to restrain their movement and lock the construct at a desired position. According to embodiments related to FIGS. 14 and 15, further locking of construct components is enabled due to minor deformation that the composite material components may experience upon ring radial pressing. Optionally, the deformation is such that material of the screw and/or collar and/or rod enters spaces between the components being coupled by the collar (e.g., rod and screw) and the collar, potentially allowing for a closer fit of the collar (e.g., of the walls of the cavities) to the rod and screw head.

FIG. 14 demonstrates two views 320, 321 of the connection area of a pedicle screw 322 with spherical head 323 (only a part of the screw is shown in the figure) and a rod 325 with threaded end 326 (only part of the rod is shown in the figure), using a locking ring 328 and a collar made of two halves 330, 332. View 320 shows the construct prior to components locking: the ring 328 surrounds the pedicle screw neck 3250. View 321 shows the construct following components locking—the ring 328 is elevated and surrounds the collar 330, 332 and screw head 323. As indicated in the figure, a transverse cross section 336 of view 321 is also presented, demonstrating the locking ring 328, collar 330, 332, and screw head 323, in a "locked position".

In some embodiments, each of the collar' halves 330, 332 comprises a slot 324, perpendicular to the common plane of the rod and the pedicle screw, at the lower portion of the collar that embraces the screw head 323. Optionally, slot 324 extends across a wall of the collar half. Optionally, slot 324 comprises a different shape and/or dimensions than those shown in the figure. For example, the slot may comprise a "zigzag" line configuration, defining collar portions that can interlock to each other to increase stability. Optionally, collar halves 330, 332 comprise more than one slot and/or different slot location. Optionally, collar halves 330, 332 comprise an internal recess that does not continue through the entire collar wall, for example a dent which extends radially outward from an internal face of the collar wall towards an external face of the wall, but does not cross the wall.

In some embodiments, following elevation of the locking ring 328 to its final location (for example up to the step 334 at the collar circumference), the collar halves 330, 332 form a collar (e.g., by being approximated to at least partially contact each other), optionally with a small space 338, 340 remaining between its halves. In some embodiments, as the collar and screw spherical head are pressed, the spherical head 323 may slightly undergo deformation, and its material may slightly protrude for example as shown in 342, 344, 346, 348 into the collar slots/recess 324, 327 and/or into the small spaces 338, 340 between collar' halves 330, 332. Optionally, the protrusions 342, 344, 346, 348 of screw head material into and/or between collar halves provide for further geometric locking (optionally in addition to friction), thus increasing the resistance to movement between the components.

FIG. 15 schematically illustrates an additional or alternative method to accomplish increased restriction of components movement, for example movement of the screw head relative to the collar. The figure demonstrates two views 350, 352 of the connection area of a pedicle screw 354 with a relatively spherical head 356 (only a portion of the screw shown in the figure) and a rod 358 with threaded end 360

(only part of the rod is shown in the figure), using a locking ring 362 and a collar made of two halves 364, 366. View 350 shows the construct prior to components locking: the ring 362 surrounds the pedicle screw neck 368. View 352 shows the construct following components locking—the ring 362 is elevated and surrounds the collar 364, 366 and screw head 356. As indicated in the figure, two longitudinal cross sections 370, 372 of views 350 and 352, respectively, are also presented, demonstrating the locking ring 362, collar 364, 366, and screw head 356, before locking (cross section 370) and in a locked position (cross section 372) (note that 370 is actually a cross section of view 350 with collar half 366 in designated place, and not as shown in view 350, for clarity). In some embodiments, screw head 356 is spherical. Alternatively, screw head 356 is non-spherical, or partially spherical. In some embodiments, pedicle screw head 356 has a relatively spherical shape, with a reduced diameter along screw head circumference 374 that is relatively parallel to the ring 362. In some embodiments, the screw head may be described as having a substantially rectangular cross section profile at a middle portion of the head, and a circular cross section profile at the proximal and distal portions of the head above and below the rectangular portion. Optionally, as a result of said reduced diameter 374, prior to elevating the ring 362 a small space 376 exists along part of screw head circumference 374 and collar' internal wall (as shown in 370). Optionally, due to the radial force exerted by the locking ring 362 after it is elevated to its final position, the collar halves 364, 366 may slightly undergo deformation, so that material is slightly pushed into said space 376 (as shown in 372), to provide for further geometric locking (optionally in addition to friction), and thus to increase the resistance to movement between the components, for example by closely fitting over the screw head.

In an exemplary embodiment of the invention, screw head 356 is held substantially only in a band around its equator. For example, such a band can be 15, 30, 45, 60 or 80 degrees or intermediate number of a degrees above and/or below the screw head equator (e.g., a plane perpendicular to the screw body). Optionally, such holding is provided by screw head 356 including a radially raised band, a cylindrical section and/or one or more protrusions thereat. Optionally, screw head 356 has the geometry of a sphere, except for such a raised band. Optionally or alternatively, such a band is provided as one or more protrusions on an inside of collar 364, 366. In an exemplary embodiment of the invention, within such a band there is a contact of between 70 and 90% between the screw head and the collar. In an exemplary embodiment of the invention, the band is between 0.1 and 1.5 mm raised relative to a surface of said screw head at said dome.

In an exemplary embodiment of the invention, a dome section of the screw head has no direct contact with the collar. Optionally, the color cap corresponding to the dome section comprises a cylindrical cut-out or a different, non-dome shape, thereby avoiding contact with the screw head. Optionally or alternatively, the base of the screw head has no contact, for example, because there is no corresponding collar section, to allow articulation of the rod relative to the screw.

In an exemplary embodiment of the invention, the recess has a larger diameter than the screw head so that contact is substantially only in an equatorial band around the recess.

In an exemplary embodiment of the invention, contact with the dome of the screw head is avoided as it may not contribute to the stability of the structure but may reduce contact quality between other parts of the screw head and the structure (e.g., by reducing a pressure thereat).

Figure 8A:
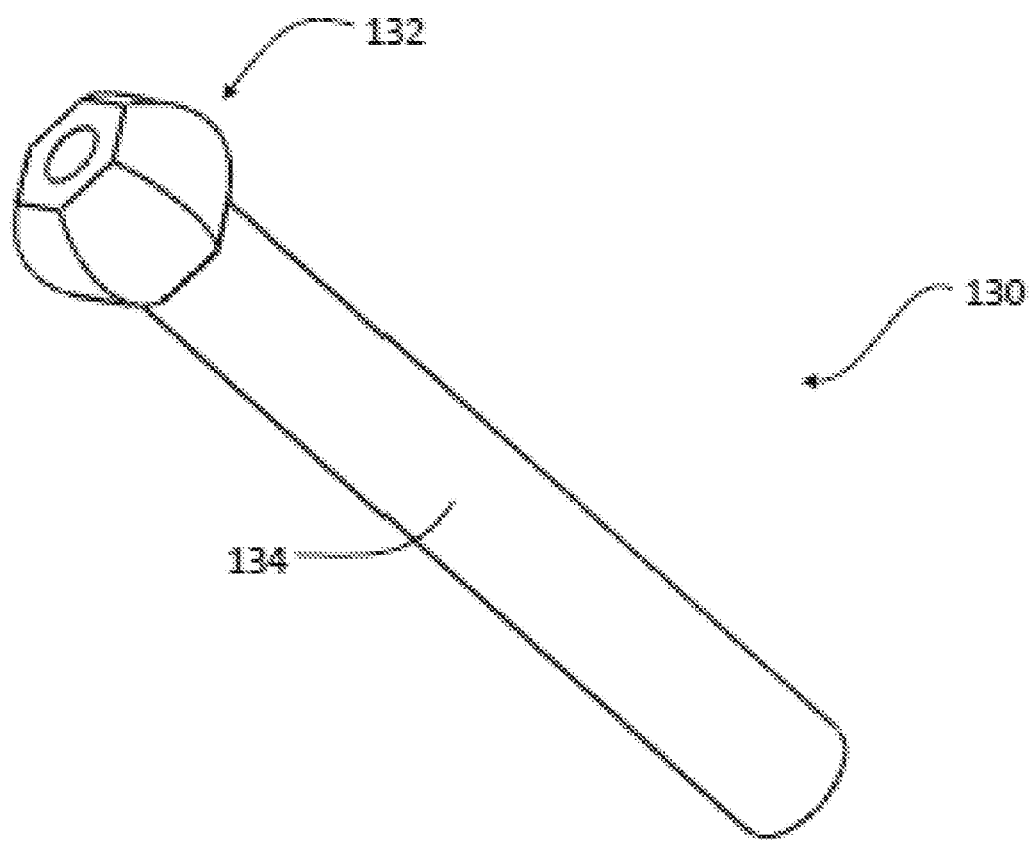
FIGS. 8A-8B schematically illustrate a pedicle screw and a collar components, in accordance with some embodiments of the present invention.
Figure 8B:
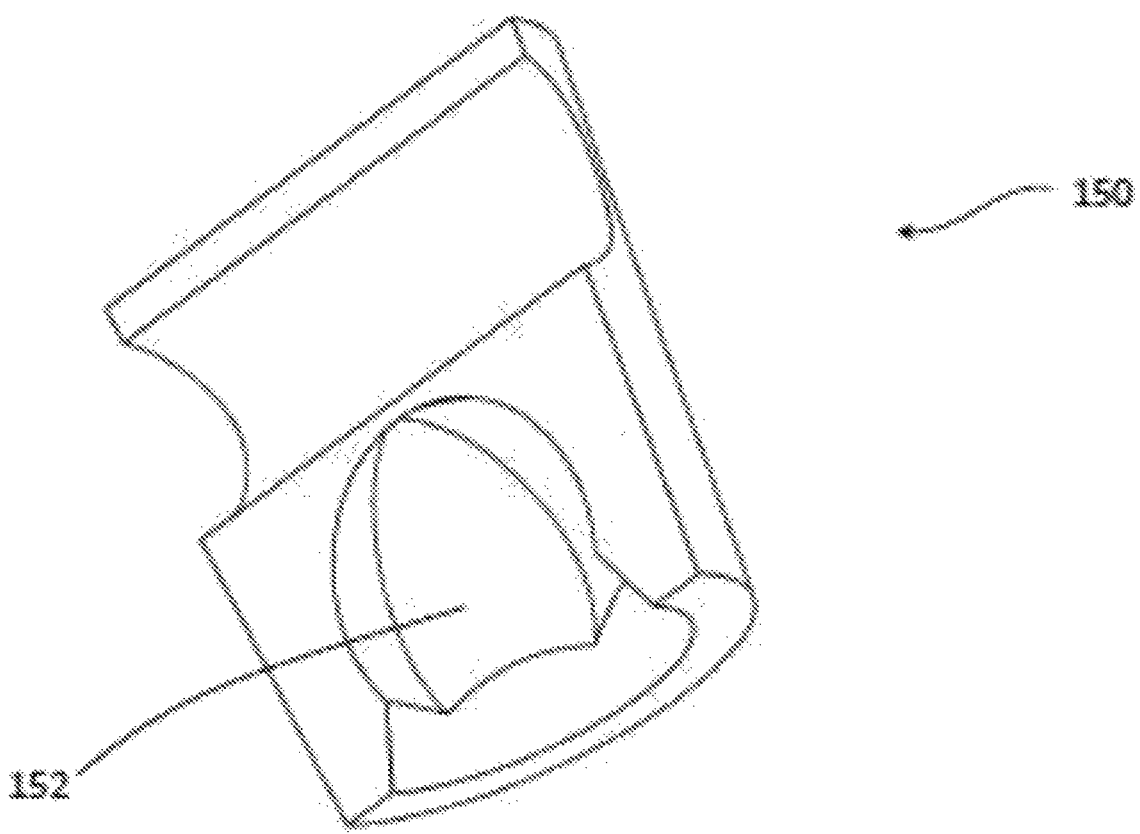

FIGS. 8A and 8B illustrate a different design for a pedicle screw and collar, respectively. In FIG. 8A, pedicle screw 130 comprises a head component 132 with a configuration of ball Allen key. In some embodiments, the screw shank 134 comprises a neck portion, close to the screw head 132, a threaded portion, and a distal tip (the neck, threaded portion and distal tip are not shown in the figure). In some embodiments, shank 134 tapers, or a part of it tapers, toward the distal tip. Other than the screw head design and related features, other embodiments detailed for the spherical head screw may apply here as well (e.g., materials, dimension, coating, design of other part of the screw, etc.).

FIG. 8B displays a collar half component 150, compatible with the screw head of FIG. 8A. In some embodiments, collar half component 150 comprises a socket 152 complementary with the shape of the ball Allen key of the screw head. Other components of the pedicle screw construct (i.e., locking ring and rod) may be similar to those previously described in this document.

A potential advantage of the design of the screw head and collar for example as presented in FIGS. 8A-8B may include providing improved torque transfer upon pedicle screw insertion into the bone, for example in cases in which screw insertion is performed while collar and ring are gripped (e.g., bound) together with the screw.

Figure 9:
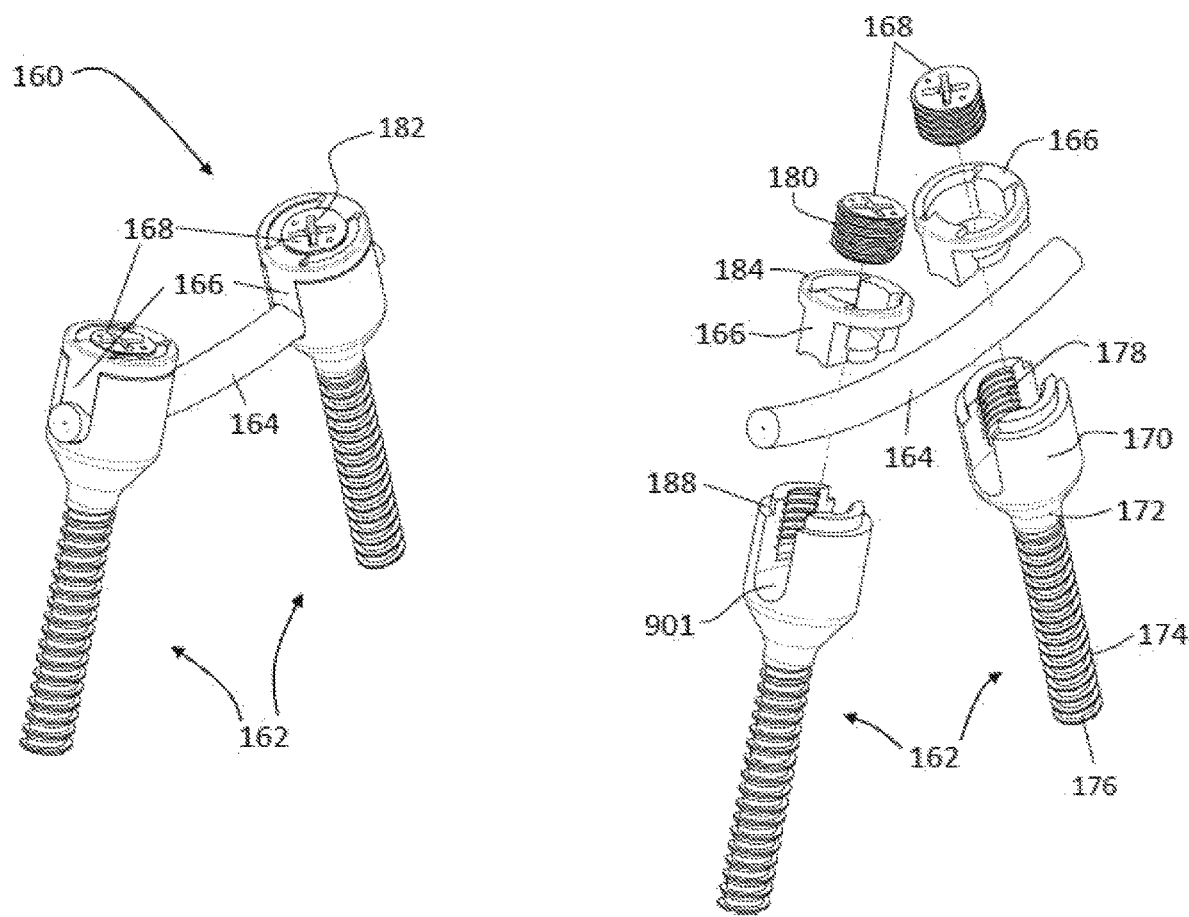
FIG. 9 schematically illustrates components of pedicle screw construct, in accordance with some embodiments of the present invention.

FIG. 9 illustrates a monoaxial pedicle screw construct 160, according to some embodiments of the invention. Materials and/or dimensions may be similar to those described above for other pedicle screw constructs. In the example shown herein, the construct comprises two monoaxial screws 162, a rod 164, and two locking means that secure the rod to the screw. In some embodiments, the locking means are composed of an adaptor 166 and a locking cap 168. In some embodiments, the monoaxial screw 162 is a single-unit component, composed of a head 170, neck 172, a thread portion 174, and a distal tip 176. In some embodiments, the screw head 170 has a tulip-like shape which opens posteriorly for the placement of the rod 164. Optionally, rod 164 is received within recess 901 of the tulip-like head. In some embodiments, the head 170 comprises an internal thread 178, for example configured along the walls of recess 901, compatible with the locking cap thread 180.

In some embodiments, the shank of the screw tapers towards its distal tip.

In some embodiments, screw 162 is cannulated, for example to enable its delivery over a guide wire.

In some embodiments, for example as discussed earlier in this document, the rod 164 may be provided curved or straight (not shown in the figure). Also, the rod may be provided, with means to bend it intra-operatively, as previously described.

In some embodiments, the locking cap 168 and its adapter 166 provide for a two-component locking mechanism that secures the rod to the screw. In some embodiments, the locking cap 168 includes a thread 180, matching the screw head internal thread 178. Optionally, at its upper (posterior) end), the locking cap comprises a socket 182 configured to receive a screwdriver. In some embodiments, the inferior (anterior) portion of the locking cap adapter 166, which is placed over the rod 164, is curved, to match the rod configuration. Posteriorly, the cap adapter 166 optionally comprises a ring 184, which is optionally situated in a designated perimeter groove (e.g., a circumferential recess) which may be provided at the end of the pedicle screw head 188.

FIGS. 16A-16C schematically illustrate an apparatus 400 for bending an implant intra-operatively, for example in order to meet the anatomic needs of a specific patient, according to some embodiments of the invention. Optionally, the implant is made of composite material, such as CFR-PEEK. Optionally, the implant is a rod component of pedicle screw construct, a bone plate, and/or other implant. In some embodiments, apparatus 400 comprises a lower, stationary component 402, and an upper, movable component 404. In some embodiments, bending of the implant is achieved by heating—each of said components 402, 404 includes a dedicated place (e.g., a lumen or recess) 406, 408 for a heating element (heating elements are not shown in the figure). In some embodiments, the upper surface 410 of the fixed component 402 is convex; and the lower portion 412 of the movable component 404 comprises a complementary concave surface. The concave/convex surfaces are configured at a desired radius and/or angle, for example an angle relative to each other. Optionally, said surfaces may be replaced, to provide the most appropriate configuration for every case. Optionally, said surfaces are composed of a few segments, each with a desired radius in a desired plane. This would be beneficial, for example, in patients treated with pedicle screws and long rods, for example to treat scoliosis.

In some embodiments, a dedicated handle (not shown in the figure) is attached to a screw 413, that is connected to the movable component 404. Optionally, operation of said handle pushes the movable component down, towards the lower components. In some embodiments, the apparatus 400 is operated using, for example, a mechanical mechanism, a hydraulic mechanism, and/or an electronic mechanism.

In some embodiments, the apparatus 400 is used in conjunction with two leading elements 414, one of which is shown in FIG. 16C. In some embodiments, each leading element 414 is a metal component (e.g., made for example of stainless steel or nickel-titanium (nitinol)), that comprises a recess 416 to accommodate the implant. In an example, leading element 414 comprises a longitudinal configuration, having an internal recess that matches the shape and size of a straight rod implant. In some embodiments, during the bending process under high temperature (e.g., a temperature within a range that is still lower than the melting temperature of the implant polymer material, for example in the range of 200° C.-400° C., preferably 250° C.-320° C.), said leading elements protect the implant from damage.

In some embodiments, upon usage, the rod implant is introduced into the recess 416 of the two leading elements 414, so that the rod is completely covered, for example covered by the surrounding leading elements. Alternatively, the rod is partially covered by the leading elements. Then, in some embodiments, the leading elements 414, with the rod, are placed in-between the apparatus' fixed and movable components 402, 404, respectively. Optionally, when desired temperature is reached, the handle is operated to press and/or push the movable component 404 downwards. In some embodiments, during the bending process, the leading elements 414 are also slightly modified under heating, for example slightly deformed.

Optionally, a desired implant configuration is verified using a flexible dummy/template of the implant that may be bent and configured (e.g., shaped and/or deformed) at/over the patient location (e.g., a flexible rod, configured (e.g., reshaped and/or otherwise adjusted) to the desired form over the patient involved vertebrae). Then, in some embodiments, the configured (e.g., reshaped and/or otherwise adjusted) template is placed in the apparatus 400, at a dedicate location (e.g., a compartment of the apparatus) that "reads" the desired configuration, for example by optic means. Then, in some embodiments, during the bending process of the implant, apparatus automatically changes implant configuration to the desired one, according to the flexible template measurement, for example according to parameters such as length, width, radius of curvature and/or other dimensions of the adjusted template. In some embodiments, the apparatus comprises a controller. Optionally, the controller is configured to receive parameters of the adjusted template, and operate the apparatus, for example position the movable component relative to the stationary component.

In some embodiments, the apparatus is configured for use in a sterile environment, for example to enable use during surgery. Optionally, the entire bending apparatus 400 and leading elements 414 are provided sterile and may be introduced into the sterile zone in the operation room. Alternatively, only part of the apparatus (e.g., the leading elements 414) is provided sterile, for example provided within dedicated pouch/s that are compatible with the bending temperature. Such pouches may be made, for example, of silicone, PTFE and/or metal foil. Optionally, in this example in which only part of the apparatus is provided sterile, the apparatus 400 is placed outside the sterile zone in the operation room. In an exemplary method of use, the surgeon, in the sterile zone, introduces the sterile implant into the sterile leading elements, and then inserts said components into said sterile pouch(es). The sterile packed implant (within the leading elements) is now given to a "non-sterile" nurse, which places it in the bending apparatus. Optionally, following bending (e.g., bending of a rod of the pedicle screw construct obtained by the bending apparatus), the pouch/s is/are opened to return the sterile components into the sterile zone, and to continue the surgery.

Figure 17A:
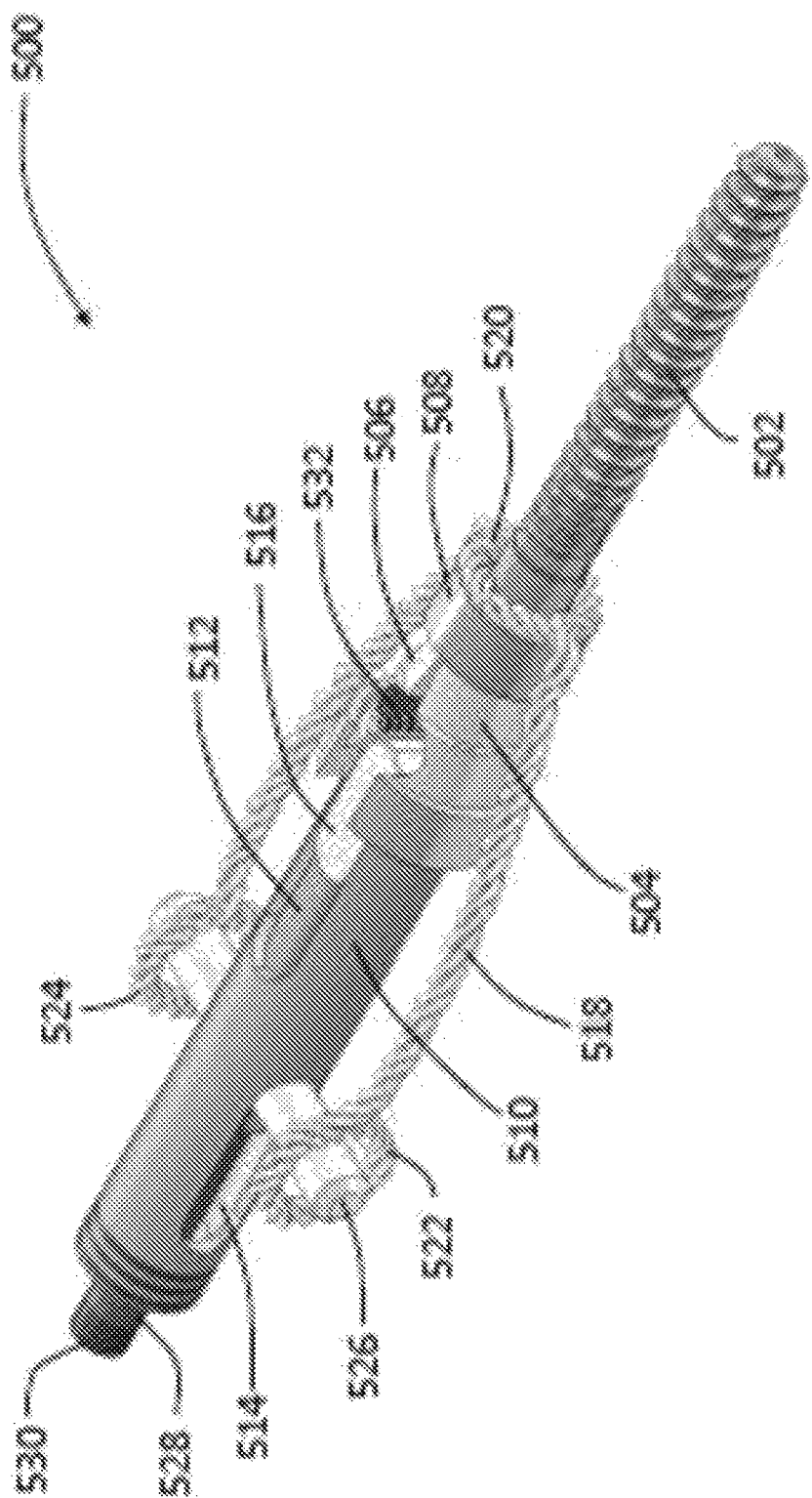
FIGS. 17A-17B schematically illustrate a delivery system intended for pedicle screw assembly insertion as well as for implant components locking, in accordance with some embodiments of the present invention.
Figure 17B:
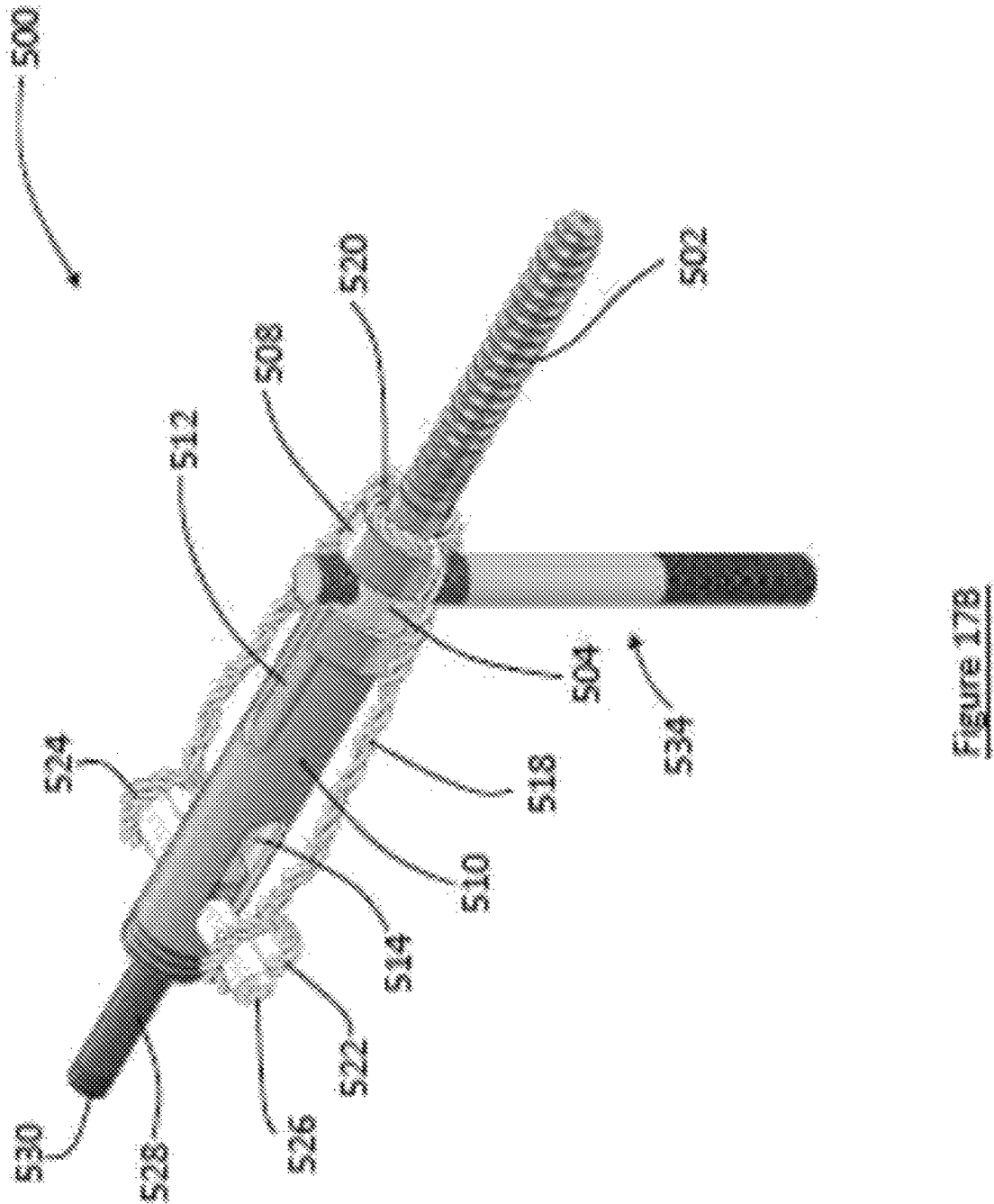

Referring now to FIGS. 17A-17B, illustrating, according to some embodiments, a surgical tool (delivery system) 500 that may be used for insertion of a polyaxial pedicle screw 502 together with its "tulip" (e.g., collar 504, 506 and/or restraining means such as a locking ring 508), as well as for elevating said ring 508 to its final position following rod implant placement, in order to firmly secure the rod to the screw. FIGS. 17A and 17B, illustrate the delivery system 500 prior to—and following elevating the ring 508, respectively.

In FIGS. 17A-17B, the delivery system 500 is shown connected to a pedicle screw assembly. In some embodiments, the delivery system is removably coupled to the screw assembly. In some embodiments, the pedicle screw assembly comprises a polyaxial pedicle screw 502; a collar, formed of two halves 504, 506; and a locking ring 508. It should be appreciated that other configurations of pedicle screw assemblies, that may include different collars/adapters and/or locking rings (for example more than one locking ring; a locking ring located at a different position than the one shown in FIGS. 17A-17B; a tulip-like component with a locking ring; a single component collar; etc.) may also be similarly used, mutatis mutandis, with the device described in FIG. 17A-17B. In some embodiments, at least part of the pedicle screw assembly is made of one or more composite materials such as CFR-PEEK, with additional materials/components for example as described throughout this document, for example, radiopaque markers and/or radiopaque powder/particles and/or coating/shell, etc. In some embodiments, part of the components (e.g., some of the components of the assembly and/or portions of components thereof) may be made of metal such as titanium/titanium alloy. In some embodiments, dimensions of implant components are also similar to those described earlier in this document for similar components.

In some embodiments, the delivery system 500 is composed of several components:

(a) a body 510, which embraces the upper (dorsal) end of the collar' halves 504, 506. In the example shown in this figure, the body has a hollow cylindrical shape, that includes, in some embodiments, a recess 512 at its distal section, and a slot 514 at its proximal part. In some embodiments, the body 510 comprises one or more of various biocompatible materials, preferably metal such as stainless steel;

(b) a spacer 516, which is positioned within the said recess 512 and protrudes between the collar halves 504, 506, (e.g., extends into the gap between the collar halves) to maintain a defined space between said halves into which, or through which, the rod implant will be positioned and/or delivered. In some embodiments, the spacer 516 comprises one or more of various biocompatible materials, including polymers and/or metals;

(c) a rope 518, located beneath the locking ring 508 (e.g., distally to the locking ring) and intended to elevate the ring 508 over the collar 504, 506 and screw spherical head, for example as detailed below. The rope 518 may include several loops. In this figure, for example, the rope 518 includes three loops—a loop 520 at the center of the rope 518, beneath the ring 508 and surrounding the shank of the pedicle screw 502; and two loops 522, 524 at rope ends, threaded over the ends of an horizontal rod 526, which is located within the slot 514 of device body 510. Optionally, loop 520 is positioned substantially in parallel to a plane defined by locking ring 508, and loops 522 and 524 extend is substantially transverse direction to the plane defined by the ring. In some embodiments, the rope 518 comprises one or more biocompatible fiber materials with sufficient tensile strength, such as UHMWPE (e.g., Dyneema®). Optionally, the biocompatible materials are woven or knitted in various manners;

(d) a mechanism for pulling the rope ends and thus elevating the ring 508. In some embodiments, the mechanism may use mechanical means, hydraulic means, electronic means, etc. In the example shown in this figure, the loops 522, 524 at the ends of the rope 518 are placed over the ends of horizontal rod 526, which passes within the device slot 514. In some embodiments, said rod 526 is connected to another, internal, rod 528, which is located within the device body 510, vertically to the horizontal rod 526. In some embodiments, the internal rod 528 is connected to a handle (not shown in the figure), for example using a thread 530. Optionally, the handle component is provided separately, and is connected during operation to the delivery system 500.

FIG. 17A shows the delivery system 500 connected to a pedicle screw assembly, as may be provided to the user, such as the physician. Optionally, said construct is provided sterile. In the exemplary configuration described in FIG. 17A, the locking ring 508 is located at a primary, non-final locking, position, and the rope 518 is slightly loose. Optionally, each collar half 504, 506 comprises a groove (not shown in the figure), and the ring 508 is located up to said groove (e.g., distally to). Optionally, the rope 518 is provided pre-loaded at low force, to prevent the ring 508 from slipping down, which may result in disassembly of the collar 504, 506. Optionally, in order to maintain the rope 518 slightly tense, the device body 510 comprises a spring (not shown in the figure). Optionally, the spring is coupled to the rope and is configured to pull on at least a portion of the rope to maintain a certain tension in the rope.

The following paragraphs describe an example of a surgical procedure including one or more components in accordance with some embodiments of FIGS. 17A-17B. In some embodiments, following preparation of the bone for example as commonly performed in pedicle screw implantation surgeries, pedicle screws are introduced into the pedicles of neighboring vertebrae—for example, four pedicle screws are introduced into the pedicles of two vertebrae.

In some embodiments, each pedicle screw 502 is provided assembled with two collar halves 504, 506 and a locking ring 508, mounted on a delivery system 500. Optionally, the delivery system 500 is a single use, disposable device. During operation, the delivery system 500 is connected to a dedicated handle (optionally a multi-use handle), for example via a thread 530. In some embodiments, the delivery system 500, optionally connected to a handle, may be used for threading the pedicle screw 502 (with the collar 504, 506 and ring 508) into the bone. Optionally, in this position, the ring 508 holds the two collar' halves 504, 506 sufficiently open, e.g., at a position in which there is a large enough gap between the collar halves, to enable subsequent introduction of the rod implant into the designated recess 532 of the collar 504, 506 ((i.e. the recess defined by approximating the collar halves towards each other), as further described in FIG. 17B); as well as provides for sufficient friction between the screw head and the collar halves 504, 406 so that the screw 502 may be threaded into the bone while the device spacer 516 maintains a proper distance between the two collar halves 504, 506 (e.g., a distance sufficient for introducing the rod). It is noted, that the friction force (such as the friction force applied by the ring on the external surfaces of the collar halves) is still low enough to enable the polyaxial movement of the screw's "tulip".

In some embodiments, in order to insert (screw) the pedicle screw 502 into the bone, the entire construct (delivery system connected to a handle), is rotated. Optionally, the handle is then disconnected, leaving the delivery system 500 connected to the pedicle screw assembly. It is noted, that the delivery system 500 may be cannulated (not shown in the figure) and thus may be used over a guide wire. Optionally, delivery system 500 comprises a torque limiter and/or a depth gauge (not shown in the figure), that may be used upon pedicle screw introduction.

In some embodiments, additional pedicle screw assemblies, for example three additional screw assemblies, are introduced, optionally using the same procedure or some of the steps thereof, (so that a total of four pedicle screws 502 are implanted (with their collars 504, 506 and locking rings 508), each connected to a delivery system 500, as depicted in FIG. 17A). Then, the spacer 516 is removed (e.g., by being pulled away) from two of the said constructs, and the rod implant (indicated as 534 in FIG. 17B) is deployed, to longitudinally connect two pedicle screws 502. As indicated before, the design of the implant components enables polyaxial movement of the screw "tulip", to facilitate placement of the rod. In some embodiments the rod is inserted into its designated recess 532 between the collar halves 504, 506, via the recess 512 in device body 510.

It is noted, that the pedicle screw assembly may be inserted using other dedicated screwdrivers, such as Allen key, to thread the screw into the bone.

In some embodiments, at this stage, verification of proper implant and spinal positioning is performed. In case the handle was previously disconnected, it is optionally re-connected to the delivery system 500, to enable locking of the rod to the screw, as shown in FIG. 17B.

Referring now to FIG. 17B, which demonstrates the delivery system 500 and implant following final locking of the rod 534 to the screw 502. As can be seen, the locking ring 508 was elevated to its final locking position, surrounding the screw spherical head and the lower part of the collar 504, 506, just beneath (e.g., distally to) the rod 534. In some embodiments, the ring 502 is elevated using the delivery system 500—optionally operation of the handle (e.g., clockwise rotation of a T-handle) elevates the vertical rod 528 and horizontal rod 526 (for example due to a coupling between vertical rod 528 and horizontal rod 526), which in turn pulls the rope 518 to elevate the ring 508. As shown in the figure, the rope 518 is tense in this configuration. As indicated before, the delivery system 500 may also be used, with the necessary changes, for other pedicle screw assembly designs. For example, a locking ring that is mounted on the delivery system 500, remains located on the delivery system (e.g., coupled to the delivery system) during pedicle screw insertion into the bone; then, using the delivery system, said ring is located over the upper portion of the pedicle screw assembly, above the rod, to secure the rod to the screw. Optionally, two restraining rings are used to firmly secure implant components, one placed above the rod implant- and the other below the rod implant.

In some embodiments, the same stages or some of the stages are performed in order to connect and lock the rod to the screws at the contra-lateral side. Optionally, after final fluoroscopy confirmation, the four delivery systems 500 are disconnected from the implants. The ropes 518 may be removed using, for example, a scalpel.

Figure 18A:
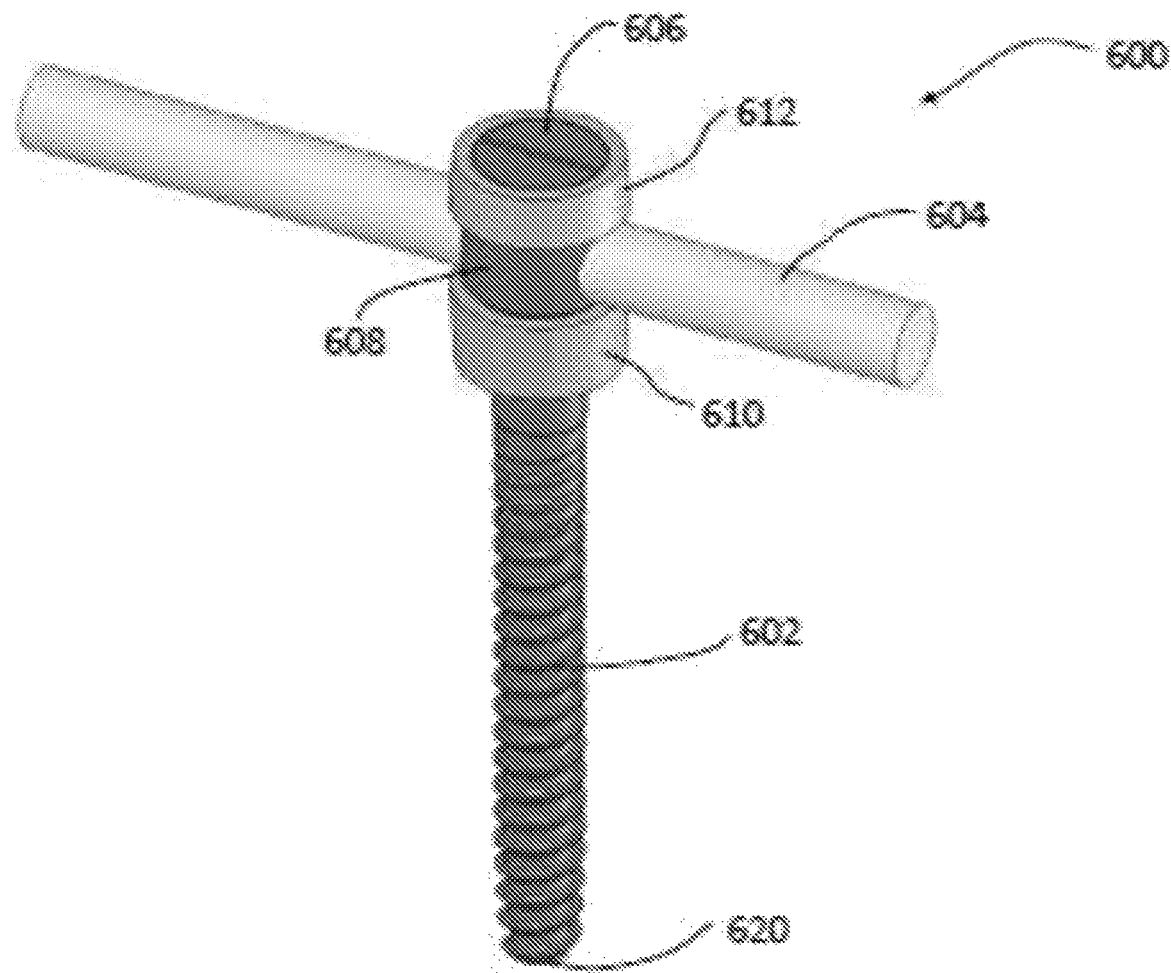
FIGS. 18A-18B schematically illustrate a pedicle screw construct, in accordance with some embodiments of the present invention.
Figure 18B:
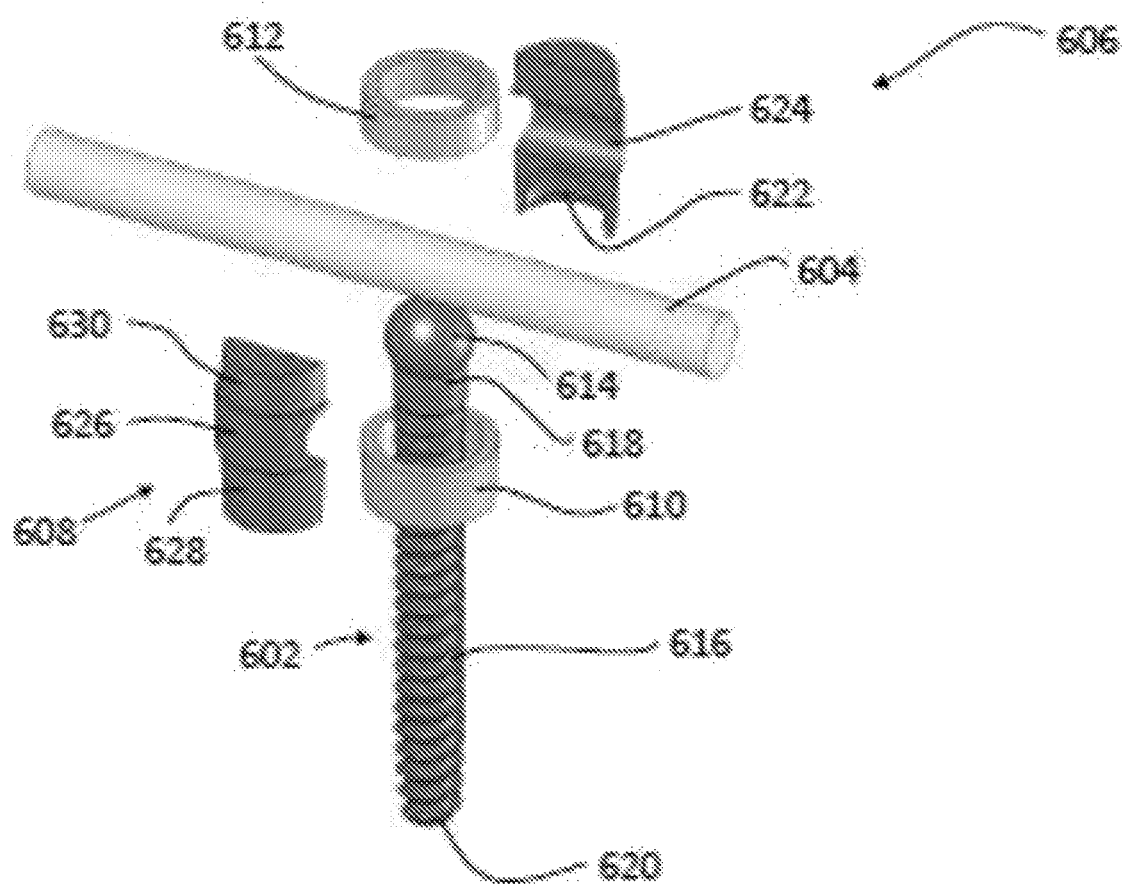

FIGS. 18A-18B illustrate another design for a polyaxial pedicle screw construct 600, comprising a pedicle screw 602; a rod 604; and restraining means including a collar comprising two halves 606, 608; a lower locking ring 610; and an upper locking ring 612, according to some embodiments. FIG. 18A shows the assembled construct 600 with components being locked together, while FIG. 18B displays the un-assembled (exploded view) of the components of the construct, for clarity.

In some embodiments, in practice, two screws 602 are introduced into two pedicles of adjacent vertebrae (e.g., lumbar or thoracic vertebrae), on the same side. In some embodiments, a rod 604 is connected and locked to said screws 602, using a collar 606, 608 and/or locking rings 610, 612. Optionally, a similar construct is implanted on the contra-lateral side.

In some embodiments, one or more components of the construct 600 may be made of composite material (such as CFR-PEEK), metals (such as titanium), other polymeric material, and/or any combination thereof. Additional materials/components as described throughout this document, for example, radiopaque markers and/or radiopaque powder/particles and/or coating/shell, etc., may be incorporated into implant components. In some embodiments, dimensions of implant components are also similar to those described earlier in this document for similar components.

In some embodiments, the pedicle screw 602 component comprises a spherical (or partially spherical) head 614; a threaded stem 616; an unthreaded neck 618, connecting the head 614 to the threaded stem 616; and a distal tip 620. In some embodiments, screw 602 is cannulated, for example to allow screw insertion over a guide wire. In some embodiments, a diameter of the screw shank (e.g., a total diameter of the shank with the thread, or a diameter of the shank without a thread) along various portions of the shank varies. Optionally, the screw shank tapers, or part of it tapers, towards the distal tip 620.

In some embodiments, the rod component 604 is straight, for example as shown in the figure, and may be provided to the user as such. Alternatively, the rod may be provided already bent and/or be bent to a desired curvature during surgery, optionally using a dedicated apparatus for rod bending, for example as described above (FIGS. 16A-16C).

In some embodiments, during implantation of pedicle screw construct 600, the rod 604 should be secured to the pedicle screws 602. According to some embodiments of the invention, a locking element, optionally non-threaded, is composed of a collar that is formed of two halves 606, 608, and two external locking rings 610, 612. In some embodiments, the rings 610, 612, at their final locking position, are designed to restrain the construct motion, for example by exerting radial inward force and/or by binding the components together.

In some embodiments, the assembled collar, comprising halves 606, 608 embraces the spherical head 614 of the screw 602 at its lower portion; the rod 604 is situated at the collar upper portion. According to embodiments related to the figure, two identical halves 606, 608 build a collar. Yet, it is stressed that this invention is not limited to such collar design. For example, a collar of additional components, or non-identical halves, or a single-component collar slotted at its upper or lower portion, may be used as well. In some embodiments, the collar has a relatively tubular external configuration. Each of the collar's half 606, 608 comprises two internal recesses: at the lower portion, a round recess 622 for the screw head 614; and at the upper portion, a tubular cavity 624 for the rod 604. Optionally, when the halves are approximated towards each other, the opposing recesses form a first cavity in which the screw head is received, and a second cavity in which the rod is received. Optionally, one or both recesses comprise a non-smooth internal surface, to provide for further locking of the components. In some embodiments, in case a curved rod 604 is implanted, the rod 604 is forced into the tubular cavity of collar halves. Alternatively, the internal tubular cavity of collar halves is curved, to facilitate the placement of a curved rod (not shown in the figure). In another embodiment, if a curved rod is used, an insert is placed within the tubular cavity of the collar; said insert has an external tubular configuration that matches the collar tubular cavity, and internal curved lumen (for example having a banana-like shape) to match the curved configuration of the rod.

In some embodiments, an external surface of the collar 606, 608 includes two steps, so that the external diameter of the collar at its center 626, is larger than the external diameter of the collar at its lower portion 228 and at its upper portion 630. Optionally, a cylindrical portion of the collar is formed with a larger diameter. Additionally or alternatively, the collar comprises one or more protrusions which extend radially outwards with respect to other collar portions. A potential advantage of the steps and/or larger diameter portion and/or protrusion may include facilitating the placement of the two locking rings 610, 612: the lower ring 610 is located (at its final, locking position) around the spherical head 614 and lower portion of the collar 628, beneath the rod 604; and the upper ring 612 is located (at its final, locking position) around the upper portion of the collar 630, above the rod 604. Another potential advantage may include preventing axial sliding of the rings. Optionally, one or both locking rings 610, 612 comprise internal and/or external conical shape. It is noted, that a similar design with only one locking ring, located beyond (e.g., below, or distally to) the rod implant or alternatively above the rod component, are also within the scope of this invention.

In an embodiment, the pedicle screw 602 may be provided to the user assembled with the collar halves 606, 608 and with the lower locking ring 610, so that said ring 610 is located at a lower position relative to its final locking position, similar to embodiments described in FIGS. 17A and 17B. The pedicle screw assembly may be provided mounted on a designated delivery system (for example similar to the one described in FIGS. 17A-17B and/or 20A-20D), which may be used for both inserting e.g., by threading of the pedicle screw 602 into the vertebral bone, as well as for elevating the lower ring 610 into its final locking position. In some embodiments, said delivery system may also contain the upper locking ring 612, which—following the placement of the rod 604 and elevation of the lower locking ring 610—is deployed to its locking position above the rod 604, where it surrounds the upper portion of the collar 630.

FIGS. 19A-19B illustrate another design of a polyaxial pedicle screw construct 700, in accordance with some embodiments of the present invention. FIG. 19A illustrates a longitudinal cross section of the construct 700. FIG. 19B illustrates the unassembled components of the construct 700. In some embodiments, the polyaxial pedicle screw construct 700 comprises a pedicle screw 702; a rod 704; and restraining means including adapters 706, 708; a collar 710; and a locking ring 712.

In some embodiments, components of the construct 700 comprise one or more of composite material (such CFR-PEEK), metals (such as titanium), other polymeric material, and/or any combination thereof. Additional materials/components as described throughout this documents, for example, radiopaque markers and/or radiopaque powder/particles and/or coating/shell, etc., may be incorporated into implant components. In some embodiments, dimensions of implant components are also similar to those described earlier in this document for similar components.

In some embodiments, pedicle screw 702 comprises a spherical (or partially spherical) head 714; a threaded stem 718; an unthreaded neck 716, connecting the head 714 to the threaded stem 718; and a distal tip 720. In some embodiments, screw 702 is cannulated, for example to allow screw insertion over a guide wire. In some embodiments, a diameter of the screw shank (e.g., a total diameter of the shank with the thread, or a diameter of the shank without a thread) along various portions of the shank varies. Optionally, the screw shank tapers, or part of it tapers, towards the distal tip 720.

In some embodiments, rod component 704 is straight, for example as shown in the figure and may be provided to the user as such. Alternatively, the rod may be provided to the user already bent and/or provided to the user with a dedicated apparatus suitable for bending the rod during surgery to a desired curvature, for example as described above (FIGS. 16A-16C).

In some embodiments, during implantation of pedicle screw construct 700, the rod 704 is secured to the pedicle screws 702. A non-threaded locking element according to some embodiments of the invention is composed of a collar 710, that surrounds at least a part of the circumference of a an axial segment of the rod 704; an adapter, composed of two halves 706, 708, that surrounds at least a part of the screw spherical head 714; and of an external locking ring 712. In some embodiments, the external ring 712 is designed to restrain the construct motion by exerting radial inward force. In some embodiments, the adapters 706, 708 embrace the spherical head 714 of the screw. According to embodiments related to the figure, the adapters 706, 708 are identical, each comprising an internal spherical recess 722 for the screw head 714. In some embodiments, when assembled (e.g., positioned in proximity to each other and/or at least partially contacting each other), the adapters 706, 708 have a relatively conical external configuration. Optionally, when primarily assembled (e.g., prior to locking), the adapters' upper surfaces 724, 726 do not touch each other, leaving a space between the two adapters 706, 708. This space may be used for insertion of the pedicle screw 702 into the bone, for example by providing for engagement with a screw driver, for example in cases in which the adapters 706, 708 are assembled to the screw 702 during said insertion. One or more protrusions at a screwdriver distal end, optionally complementary with the surface details of screw head 714, may be introduced through space 728 to engage the screw head, for example entering a slot 728 at the surface of the screw head. By increasing the contact area between the screw head and the screwdriver distal end (e.g., by complementary projections and recesses), insertion of the screw into the bone may be facilitated. In addition, in some embodiments, upon locking of the construct 700, the locking ring 712 exerts radial forces to secure the construct components and restrain their movement, and said slot 728 allows a minor, optionally limited approximation of the two adapters 706, 708 towards each other.

In some embodiments, upper surfaces 724 and 726 of the adapters cover only a portion of the surface of the head of the screw, for example leaving a top central portion of the screw head exposed.

In some embodiments, the collar 710 has a relatively tubular external configuration, with a step 730 (and/or one or more protrusions, a circumferential protrusion, and/or any other structures suitable to define a position of the locking ring and/or to restrict axial movement of the ring) to enable collar 710 introduction into the locking ring 712 up to a defined location. In some embodiments, the collar 710 comprises an internal tubular cavity 732, to accommodate the rod 704. Optionally, said cavity 732 has, at least in part, a non-smooth internal surface, to provide for further locking of the components, for example by increasing friction between the rod and the internal walls of the cavity. Optionally, said non-smooth internal surface of collar cavity 732 matches a complementary non-smooth area at rod's external surface, for example the rod and the internal surface comprising matching protrusions and indentations.

In the embodiment shown in FIGS. 19A-19B, collar 710 is a single unit, with a slot 736 extending from its lower end and up to and/or beyond the round cavity 732. Yet, other designs are also within the scope of this invention, such as a slot extending from the upper end of the collar, or a collar composed of two or more components, optionally two identical halves. As explained above for the slot 728 between the adapters 706, 708, having a slotted or partial slotted collar 710 allows fastening of the collar parts during locking of the construct components using the locking ring 712.

In some embodiments, the external locking ring 712 surrounds, at its lower portion, the spherical head 714 and adapters 706, 708; at its upper portion, ring 712 surrounds the lower portion of the collar 710. In some embodiments, the ring 712 comprises a step at its external surface so that ring outer diameter at its lower portion 734 is reduced relative to an upper portion of the ring. Optionally, this recess/depression 734 allows the connection to surgical tools such as screwdriver and locking driver, for example as described below in FIGS. 20A-20D. Optionally, locking ring 712 has an internal conical shape.

According to some embodiments of the invention, a portion of the reinforcing fibers of implant material, for example longitudinal carbon fibers, are configured and/or oriented in a specific direction to form device or component with desired and preferred mechanical properties, for instance to enhance implant resistance to exerted loads. For example, the collar 710 and/or locking ring 712 may be constructed from (a) a tape of PEEK with long, parallel carbon fibers, that is wrapped to form a relatively tubular configuration such as the ring 712 or collar 710, where the fibers extend in the circular direction (horizontally); as well as (b) PEEK tapes having long carbon fibers oriented vertically to the direction of the fibers described in (a); and (c) PEEK tapes having long carbon fibers oriented at any angle to the direction of fibers described in (a) (for example, at +/−20 degrees to the horizon). Other orientation and arrangements of fibers, such as fibers oriented in U-shape following the shape of the collar 710, are also within the scope of this invention. In some embodiments, the pedicle screw comprises one or more tapes of PEEK, each tape including elongated carbon fibers substantially parallel to the longitudinal axis of the screw.

In an embodiment, the pedicle screw 702 may be provided to the user assembled with the adapters 706, 708 and locking ring 712, so that the pedicle screw 702 is threaded into the vertebra while assembled with said adapters 706, 708 and locking ring 712. At this stage, the locking ring 712 is not tightly connected to the other components, and is located somewhat lower than illustrated in FIG. 19A, i.e., at its non-final locking position.

Figure 20A:
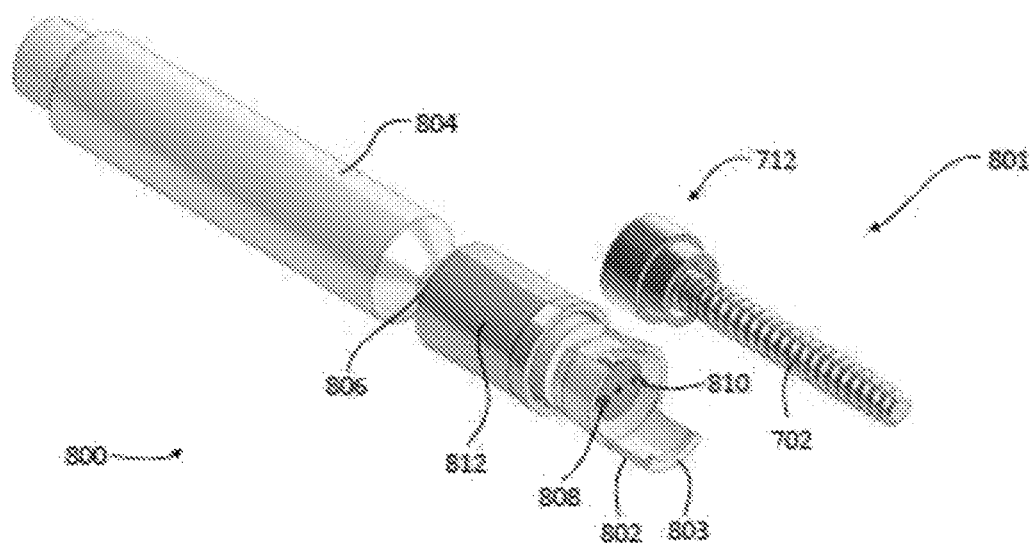
Figure 208:
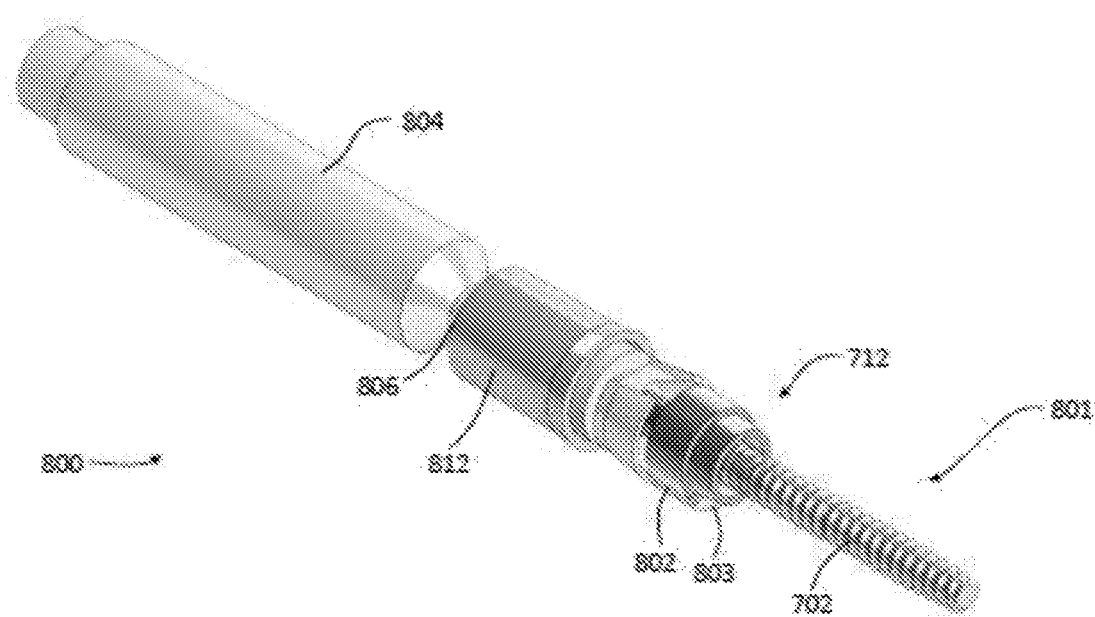

In some embodiments, for example as described in FIGS. 20A-20D, the pedicle screw assembly 801 (comprising a pedicle screw 702; adapters 706, 708 (not shown in this figure); and locking ring 712) is connected to a designated screwdriver 800. FIG. 20A illustrates the pedicle screw assembly 801 and screwdriver 800 unassembled, for clarity. In some embodiments, screwdriver 800 comprises a distal curved section 802 with means 803, such as a protrusion extending in a radial direction, to hold the locking ring 712 from beneath, e.g., from a distal end of the ring; a shaft 804 including an internal rod 806 that ends with two protrusions 808, 810; a tubular, movable component 812, used to lock the screwdriver components to the pedicle screw assembly 801; and a handle at proximal section (not shown in the figure), connected to screwdriver shaft 804.

Figure 20C:
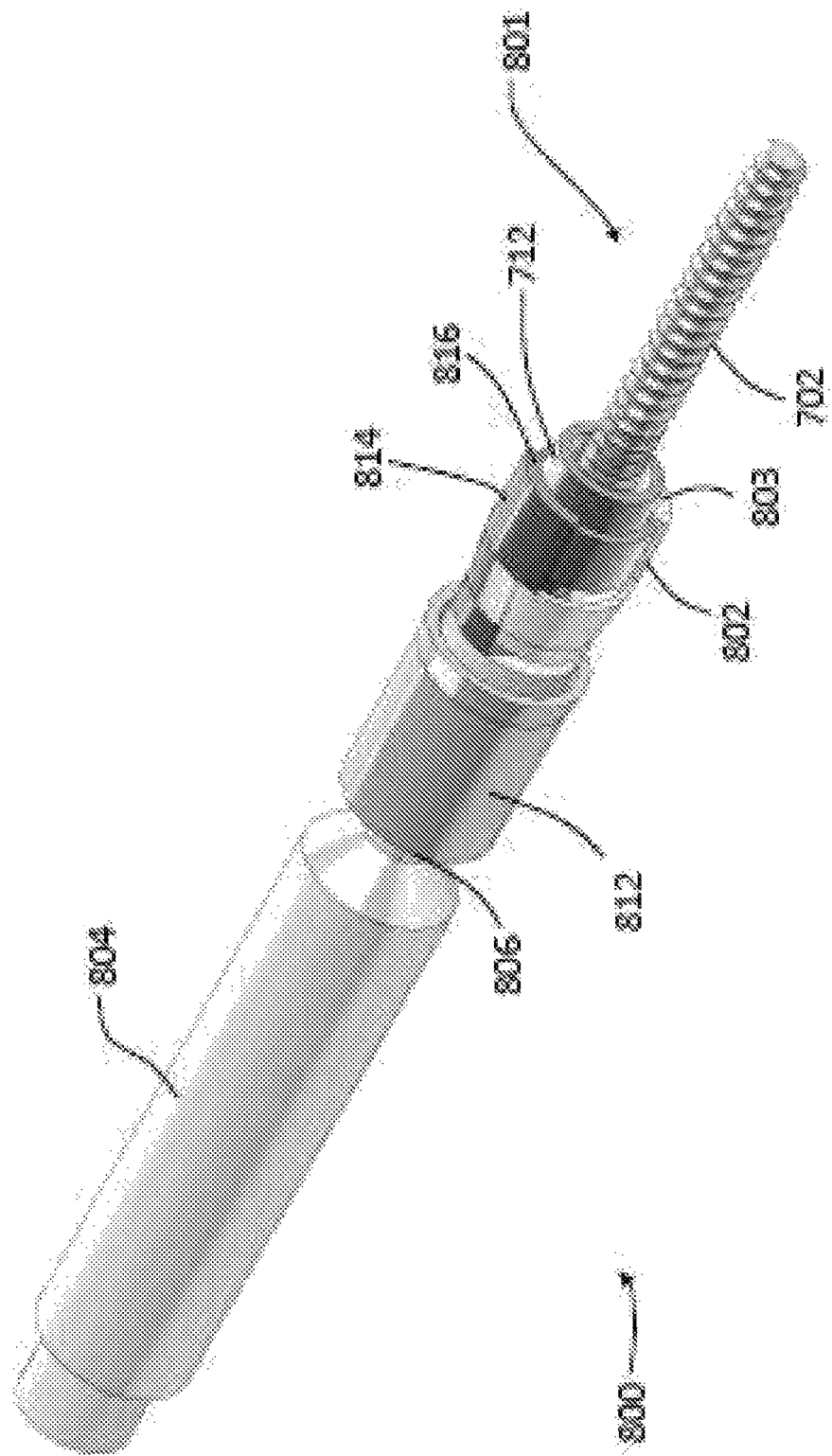
Figure 20D:
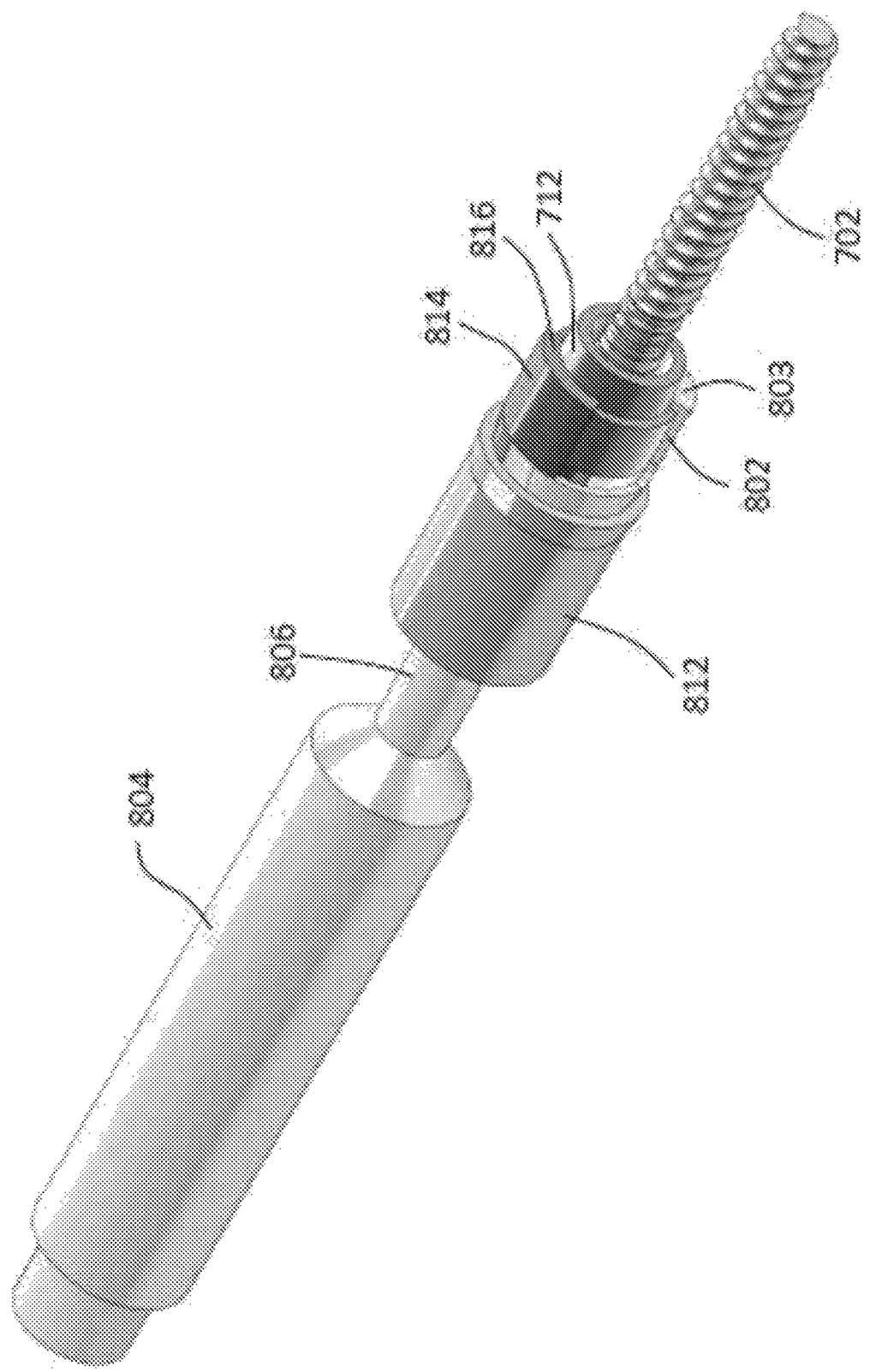

FIG. 20B illustrates the pedicle screw assembly 801 connected (but not locked) to the screwdriver 800. In some embodiments, in order to firmly hold the pedicle screw assembly 801, an additional curved component 814 (for example as shown in FIG. 20C) is attached to the distal section of the screwdriver, for example positioned 180° (e.g., diametrically opposing) to the previous curved component 802, with a portion 816 that grips the locking ring 712 from beneath (see FIG. 20C). Optionally, at this stage (FIG. 20D), the movable component 812 is moved (optionally by threading (e.g., to be screwed on) and/or sliding) over the distal section of the screwdriver 800, to firmly secure the screwdriver 800 to the pedicle screw assembly 801. In some embodiments, the handle (not shown in this figure), for example a T-handle, is rotated to push the protrusions 808, 810 at screwdriver internal rod 806 in between a slot 728 between the two adapters 706, 708 (see FIG. 19B). Optionally, while internal rod 806 slightly moves forward and pushed against the upper surfaces 724, 726 of the adapters 706, 708, (shown in FIG. 19B) the locking ring 712 is slightly elevated (yet, not to its final, locking position). Now, the entire screwdriver 800 is clockwise rotated to thread the pedicle screw 702 into the bone.

Optionally, the screw 702 and screwdriver 800 are cannulated (not shown in the figure) and thus may be used over a guide wire. Optionally, screwdriver 800 comprises a torque limiter and/or a depth gauge (not shown in the figure), that may be used upon pedicle screw introduction.

Alternatively, screwdriver 800 is provided with two straight portions, such as elongated arms, at its distal end (e.g., extending from a distal end of the screwdriver) that grab the locking ring (not shown in the figure). Optionally, in such a case, said two portions are part of the screwdriver and none of them is required to be connected at a later stage. Also, each of said portion is straight (does not comprise a radius) and is narrower than the one 802 described in FIG. 20A, thus enabling easy connection of the pedicle screw assembly. In such a case, the movable component 812 shown in FIGS. 20A-20D may be redundant.

Optionally, screwdriver 800 handle comprise a locking pin (not shown in the figure), used to lock the handle following final connection of screwdriver 800 to pedicle screw assembly 801.

Optionally, other means that provide rotation may be used to thread the pedicle screw or the pedicle screw assembly into the vertebral bone, such as two or more recesses at the upper portion of the locking ring, complementary with protrusions at the distal end of the screwdriver; or a recess at the screw head, complementary with the distal tip of the screwdriver. The recess at the screw head may be of various shapes, for example shaped as an elongated slot, cross, and/or other configurations.

In some embodiments, after the pedicle screws 702 were inserted into the vertebral pedicles, for example—four pedicle screws were inserted into two neighboring vertebrae, two rods 704 are deployed, to longitudinally connect each pair of screws 702. In some embodiments, each rod 704 (straight or bent) is deployed assembled with two collars 710, each at rod end, or proximally to one of the ends of the rod. A potential advantage of the design of the implant components may include enabling polyaxial movement of the screw "tulip", such as to facilitate placement of the rod, e.g., insertion of the rod through cavities of "tulips" of two or more screws. Following verification of proper implant and spinal positioning, locking of implant components may be performed using a locking driver. The concept of the locking driver is, in some embodiments, similar to that of the device illustrated in FIGS. 20A-20D, however the locking driver is designed to withstand higher forces, for example even of 1,000 kg. In addition, the locking driver does not include the protrusions that exist at screwdriver internal rod, so that the space between adapters may be closed, or partially closed, upon final locking of the implant components. Upon operation of locking diver, for example by rotating its handle, the device internal rod moves forward and is pushed against the upper surfaces of the adapters, to further elevate the locking ring, to its final, locking position (see for example FIG. 19A).

Referring now to FIG. 21, illustrating another design of a polyaxial pedicle screw construct 900, in accordance with some embodiments of the present invention. FIG. 21A is a longitudinal cross section of the construct 900. FIG. 21B illustrates the unassembled, exploded view of the components of the construct 900. In some embodiments, the polyaxial pedicle screw construct 900 comprises a pedicle screw 902; a rod 904; and restraining means including collar 906, 908; and two locking rings 910, 912.

In some embodiments, one or more components of the construct 900 are made of or comprise one or more of composite material (such CFR-PEEK), metals (such as titanium), other polymeric material, or any combination thereof. Additional materials/components as described throughout this documents, for example, radiopaque markers and/or radiopaque powder/particles and/or coating/shell, etc., may be incorporated into implant components. In some embodiments, dimensions of implant components are also similar to those described earlier in this document for similar components.

In some embodiments, pedicle screw 902 comprises a spherical (or partially spherical) head 914; a stem 916, in some embodiments threaded; a neck 918, in some embodiments unthreaded, connecting the head 914 to the threaded stem 916; and a distal tip 920. Screw 902 may be cannulated, to allow screw insertion over a guide wire. In some embodiments, the diameter along the screw shank may vary, so that it tapers, or part of it tapers, towards the distal tip 920.

In some embodiments, the rod component 904 is straight, and may be provided to the user as such, for example as shown in the figure. Alternatively, the rod may be provided already bent or be bent to a desired curvature during surgery, optionally using a dedicated apparatus for rod bending, for example as described above (FIGS. 16A-16C).

In some embodiments, during implantation of pedicle screw construct 900, the rod 904 is secured to the pedicle screws 902. A non-threaded locking element according to some embodiments of the invention is composed of a collar, comprising two halves 906, 908, structured to surround the rod 904 and the spherical head 914 of the pedicle screw 902; and of two locking rings 910, 912, placed at the ends of the collar 906, 908. In some embodiments, each of collar halves 906, 908 includes a tubular cavity 922 at the upper portion of its internal surface, to accommodate the rod 904; and a round recess 924 at the lower portion of its internal surface, for the screw head 914. Optionally, tubular cavity 922 is elongated, for example sized to extend along at least a part of the rod received within it. In some embodiments, the two locking rings 910, 912 are placed over the collar ends 926, 928.

FIGS. 22A-22C illustrate another design of a polyaxial screw construct 1000, in accordance with some embodiments of the present invention. FIG. 22A illustrates the unassembled components of construct 1000. FIG. 22B illustrates the assembled construct 1000. FIG. 22C illustrates a cross section of construct 1000 along line A-A depicted in FIG. 22B. In some embodiments, the polyaxial pedicle screw construct 1000 comprises a pedicle screw 1040; a rod 1020; and restraining means including a collar 1010 and a locking ring 1030.

In some embodiments, the components of the construct 1000 comprise one or more of composite material (such CFR-PEEK), metals (such as titanium), other polymeric material, or any combination thereof. Additional materials/components as described throughout this documents, for example, radiopaque markers and/or radiopaque powder/particles and/or coating/shell, etc., may be incorporated into implant components. In some embodiments, dimensions of implant components are also similar to those described earlier in this document for similar components.

In some embodiments, pedicle screw 1040 comprises a spherical (or partially spherical) head 1044; a stem 1046, in some embodiments threaded; optionally, a neck 1048, in some embodiments unthreaded, connecting the head 1044 to the threaded stem 1046; and a distal tip 1049. In some embodiments, screw 1040 is cannulated, with cannula 1042 (i.e. an internal lumen), to allow screw insertion over a guide wire. In some embodiments, the diameter along the screw shank varies, so that the screw shank tapers, or part of it tapers, towards the distal tip 1049. In some embodiments, pedicle screw head 1044 comprises a connection detail 1045, such as a recess or protrusion to accommodate and/or fit into a respective connection detail of an insertion tool. Connection detail 1045 may be of any shape to comply with the connection detail of an insertion tool (for example, a slot).

In some embodiments, the rod component 1020 is straight, and may be provided to the user as such, for example as shown in the figure. Alternatively, the rod may be provided already bent or be bent to a desired curvature during surgery, optionally using a dedicated apparatus for rod bending, as described above (FIGS. 16A-16C).

In some embodiments, during implantation of pedicle screw construct 1000, the rod 1020 is secured to the pedicle screws 1040. A non-threaded locking element, according to some embodiments of the invention, is composed of a collar 1010, that surrounds rod 1020 and of an external locking ring 1030. In some embodiments, the external ring 1030 is designed to restrain the construct motion by exerting radial inward force.

In some embodiments, collar 1010, for example as illustrated also in FIGS. 23A-23D, incorporates an internal tubular cavity 1012, to accommodate a rod 1020, and a cavity 1013 to accommodate the head portion 1044 of a pedicle screw 1040.

Optionally, cavity 1012, and/or cavity 1013 have a non-smooth, optionally textured, internal surface to provide for further locking of the components, for example by increasing friction between the surfaces of the rod and/or screw head and the collar. Optionally, said non-smooth surfaces match non-smooth areas at the rod and/or screw head external surfaces. In some embodiments, collar 1010 comprises slot 1014, as well as a slot 1016, located at an angle to slot 1014. Such angle may be, for example, 90 degrees, 75 degrees, 45 degrees or intermediate, larger or smaller angles. The double-slotted design of the collar 1010 allows connection to the screw head 1044 by pressing the collar against the screw head. Optionally, the slots provide for compressively fitting the collar over the screw head. Collar 1010 may have additional slots such as slot 1016, optionally located at different angles with respect to each other and/or to slot 1014.

In some embodiments, ring 1030 surrounds collar 1010 which encloses the screw spherical head 1044 and the rod 1012. Optionally, ring 1030 comprises, a step 1032 at its external surface so that ring outer diameter below step 1032 is reduced, for example relative to the upper portion of the ring. This allows the connection to surgical tools, such as locking driver, as described, for example, in FIGS. 35A-35C below. Optionally, locking ring 1030 has an internal conical shape, as already described above.

FIGS. 23A-23D further illustrate collar 1010, according to some embodiments of the invention. FIG. 23A illustrates a perspective view of collar 1010 in non-locked position. FIG. 23B provides a bottom view of said collar 1010 in non-locked position. In some embodiments, the design of the double-slotted portion 1018 of the collar 1010 is such that, when in non-locked mode the contour of portion 1018 is somewhat elliptic (so that, at bottom view, areas 1017a and 1017b look thinner (e.g., narrower) than areas 1019a and 1019b). As the internal contour of ring 1030 (FIGS. 22A-C) is circular, once ring 1030 is pulled over section 1018 of collar 1010, to lock the construct, it places higher pressure value along sections 1011a and 1011b of portion 1018 of collar 1010, as compared to the pressure experienced by sections 1015a and 1015b of portion 1018 of collar 1010. This provides for the reduction of slot 1014 (both 1014a and 1014b portions of the slot), without affecting the width of slot 1016 (both 1016a and 1016b portions of the slot). FIGS. 23C and 23D illustrate collar 1010 when in a locked mode. The width of slot 1014 (both 1014a and 1014b portions of the slot) is reduced, without affecting the width of slot 1016 (both 1016a and 1016b portions of the slot). Optionally, once fully locked, the outer contour of portion 1018 is circular, complying with the inner contour of ring 1030 (so that, at bottom view, areas 1017a and 1017b look of the same width as areas 1019a and 1019b).

Figure 24A:
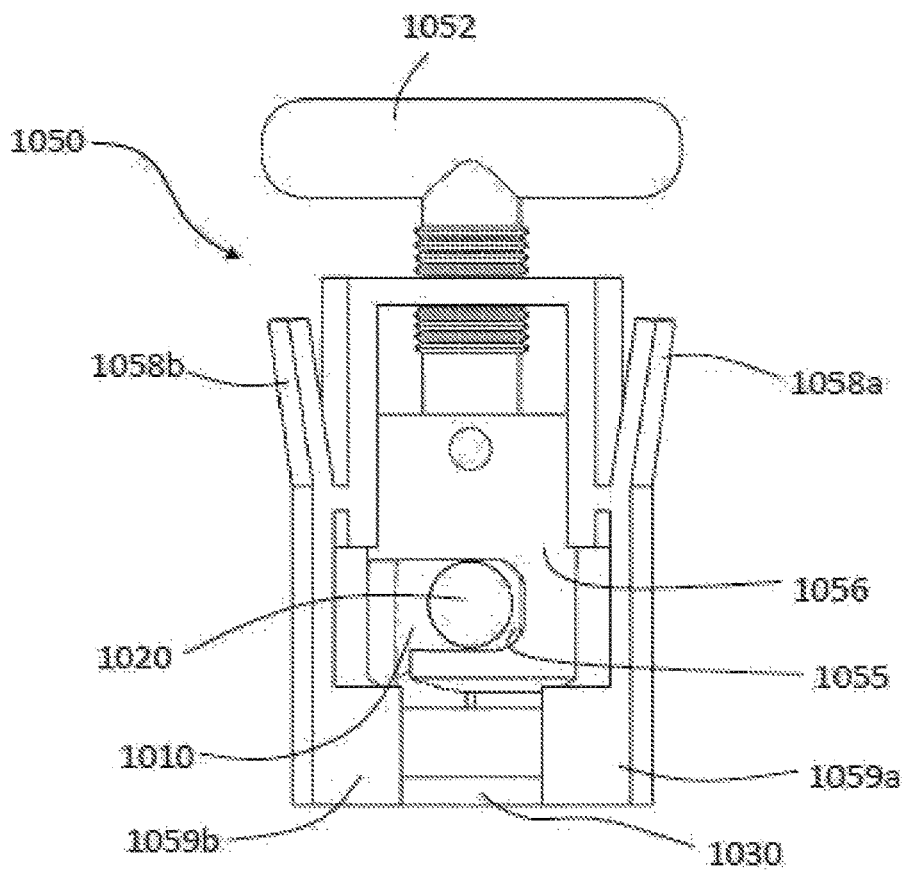
Figure 24B:
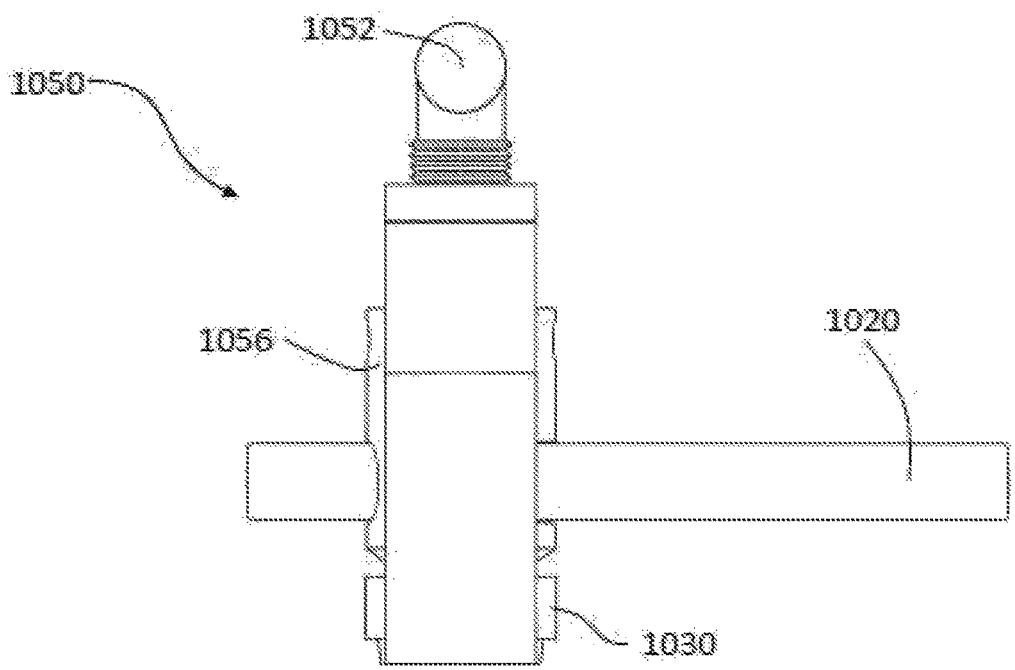

In an embodiment, collar 1010 may be provided to the user preassembled with rod 1020 and/or ring 1030. FIGS. 24A-24B and 25A-25D illustrate a device 1050 for connecting the collar 1010, rod 1020, and ring 1030 in order to facilitate placement of said combination over a pedicle screw already located within a vertebra (for example as shown in FIG. 7B). FIGS. 24A and 24B illustrate different views of insertion device 1050 as provided to the user (optionally preassembled with one or more of collar 1010, rod 1020, and/or ring 1030, for example as detailed hereinafter); FIGS. 25A-25D illustrate different views of said insertion device 1050 in an exemplary configuration in which it is provided to the user, such as along with screw 1040.

In some embodiments, rod 1020 is placed through cavity 1012 of collar 1010. The assembly of collar 1010 and rod 1020, with ring 1030 placed over the distal section of collar 1010, in non-locked position, is located within body 1056 of insertion device 1050, such that arms 1059a, 1059b of insertion device 1050 hold ring 1030, for example clamp the ring laterally. In some embodiments, device body 1056 is optionally provided with openings 1055 on both sides, facing opposite directions, to enable placement and removal of the insertion device 1050 over the assembly of collar 1010 and rod 1020. In an exemplary embodiment, rod 1020 is provided to the user with a number of insertion devices 1050 (along with collars 1010 and rings 1030) placed over it, for example distributed along the long axis of the rod at locations in which pedicle screws will be coupled to the rod (e.g., by the collar). Optionally, the number of insertion devices positioned over the rod complies with the number of pedicle screws 1040 to be connected by said rod 1020.

In an embodiment, the user presses insertion device 1050, preassembled with collar 1010, rod 1020, and ring 1030, over screw 1040, for example by pushing the device distally over the screw such that screw head 1044 engages within cavity 1013 of collar 1010. In case several assemblies are provided on a single rod, all assemblies are pressed onto the screws, e.g., are advanced distally to fit over the screw heads. Optionally, at this stage, handle 1052 (for example T-handle) is operated so that component 1057, located within body 1056 moves downwards (optionally by converting rotational into linear motion). In some embodiments, component 1057 presses collar 1010 against ring 1030 held by arms 1059a, 1059b, to provide for initial locking, or coupling, of rod 1020 to screw 1040, (e.g., by the collar connecting between the rod and screw) such that relative movement of ring 1030 over collar 1010 is enabled. If desired, handle 1052 can be operated in the opposite direction to push ring 1030 from collar 1010, after initial locking is performed, for example returning the ring to a looser position (e.g., over the screw) to allow repositioning of the components such as the collar and screw relative to each other. Optionally, following completion of initial locking process, the user presses arms 1058a, 1058b so that arms 1059a, 1059b move outwards and release ring 1030. Insertion device 1050 can then be removed.

FIGS. 26A-26C illustrate a non-threaded locking ring component 1060 of a pedicle screw system, in accordance with some embodiments of the present invention. Locking ring 1060 is similar to locking rings of non-threaded design described above, for example, for use with polyaxial screw (e.g., locking ring 1030 of FIG. 22A and locking ring 712 of FIG. 19B), and, in some embodiments, may be similar in material, general design and/or dimensions to the locking rings described herein. In some embodiments, for example as shown in locking ring 1060, a body 1064 of the locking ring is structured such that a "shoulder" (protruding part, or step) 1062 is located close to the proximal part of collar 1070, for example at the level of rod 1020. A potential advantage of this design may include easier connection of insertion/extraction tools (for example, screwdriver 800 in FIGS. 20A-20D) that engage with "shoulder" 1062 of ring 1060, as the connection area is farther from the screw, and hence may be farther away from the patient's body, providing easier access to a physician. Collar 1070 may be of any design as described above throughout this document (for example, collar 1010 of FIGS. 23A-23D, collar 710 with adapter 706, 708 of FIGS. 19A-19B, or any other collar design in accordance with the present invention which may be used with such non-threaded ring).

Figure 27C:
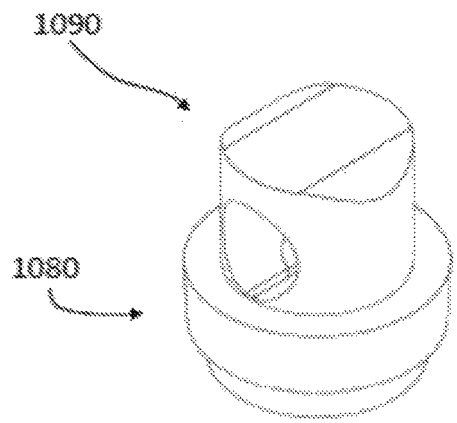
FIGS. 27A-27D schematically illustrate locking ring and collar components, in accordance with some embodiments of the present invention.
Figure 27A:
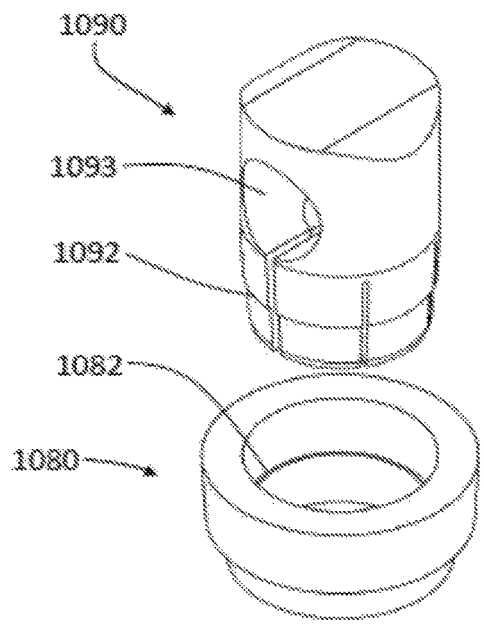
Figure 27D:
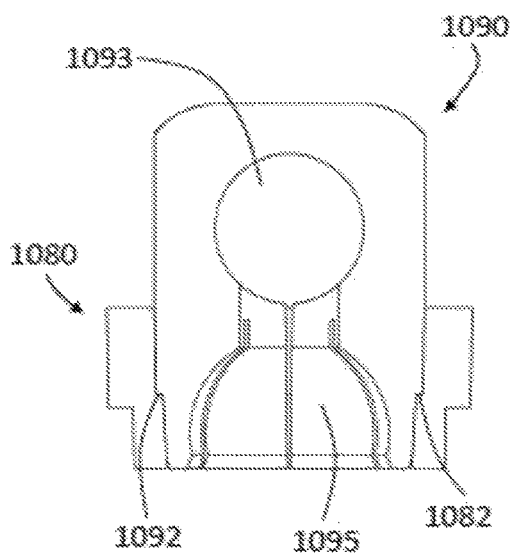
Figure 27B:
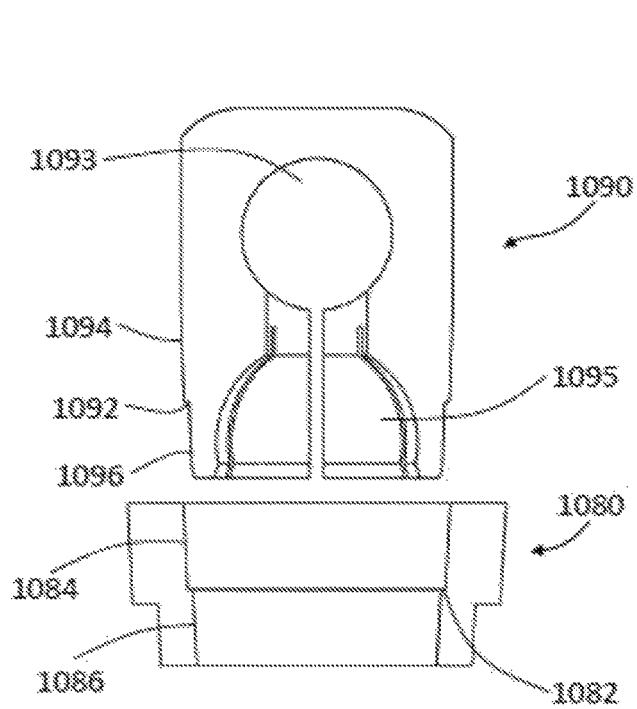

FIGS. 27A-27D illustrate another design of a non-threaded ring 1080, and a collar 1090, in accordance with some embodiments of the present invention. Locking ring 1080 and collar 1090 may, in some embodiments, be similar to locking rings of non-threaded design and collars for example as described above, for example, for use with polyaxial screw (e.g., locking ring 1030 of FIG. 22A and locking ring 712 of FIG. 19B; collar 1010 of FIGS. 23A-23D), and, in some embodiments, may be similar in material, general design and/or dimensions to the locking rings described herein. In some embodiments, ring 1080 comprises an internal step 1082 (e.g., a circumferential protrusion) and collar 1090 comprises a step 1092 (e.g., a circumferential depression, optionally compatible with step 1082 of the ring). FIGS. 27A and 27B illustrate a perspective view and a cross section view, respectively, of collar 1090 and ring 1080 in unassembled mode; FIGS. 27C and 27D illustrate a perspective view and a cross section view, respectively, of collar 1090 and ring 1080 in locked mode. In some embodiments, collar 1090 incorporates an internal tubular cavity 1093, to accommodate a rod, and a cavity 1095 to accommodate the head portion of a pedicle screw (for example screw 1040 of FIG. 22A).

In some embodiments, slope 1086 (e.g., the slanted internal wall of the ring) at the ring portion beneath step 1082 is different (e.g., comprises a different angle than) slope 1084 (e.g., the slanted internal wall of the ring) at the ring portion above step 1082. The different slopes of ring 1080 comply with the shape of collar 1090, which comprises step 1092. Optionally, slope 1096 of the collar portion beneath step 1092 complies with slope 1086 of ring 1080. Optionally, slope 1094 of the collar portion above step 1092 complies with slope 1084 of ring 1080. The different slopes 1084, 1094 and 1086, 1096 provide the ability to exert different radial force (e.g., a varying radial force) on the collar at those different areas, thus providing different locking force on the portion in which the screw head is received and a different locking force on the portion in which the rod is received. This in turn may affect the locking force that has to be exerted in order to locate the ring in the locked position over the collar.

FIGS. 28A-28C and 29A-29C illustrate collar 1110 and locking ring 1120, forming assembly 1100, in accordance with some embodiments of the present invention. FIGS. 28A-28C illustrate the collar and ring in a non-locked position; FIGS. 29A-29C illustrate the collar and ring in a locked position. FIGS. 28A and 29A provide a perspective view of the assembly; FIGS. 28B and 29B provide a side view of the assembly; FIGS. 28C and 29C provide a cross section of the assembly (along line A-A of FIGS. 28B and 29B respectively).

The components of the assembly 1100 may be made of or comprise composite material (such CFR-PEEK), metals (such as titanium), and/or any combination thereof. In some embodiments, additional materials/components for example as described throughout this documents, for example, radiopaque markers and/or radiopaque powder/particles, etc., may be incorporated into implant components. In some embodiments, dimensions of implant components are similar to those described earlier in this document for similar components.

In some embodiments, collar 1110 incorporates an internal tubular cavity 1116, to accommodate a rod, and a cavity 1118 to accommodate the head portion of a pedicle screw (for example screw 1040 of FIG. 22A). Collar 1110 may be of any design for example as described above throughout this document (for example, collar 1010 of FIGS. 23A-23D, collar 710 with adapter 706, 708 of FIGS. 19A-19B, or any other collar design in accordance with the present invention which may be used with such non-threaded ring).

In some embodiments, slope 1112 of collar 1110 (e.g., the slanting of the collar wall) is directed such that the radius (or diameter) of collar 1110 is smaller in the collar portion comprising cavity 1116 as compared to the radius (or diameter) at the collar portion comprising cavity 1118, forming a sharp angle 1115 (e.g., a cone with its larger diameter located at the bottom 1111 of collar 1110, tapering in a proximal direction).

In some embodiments, ring 1120 comprises an internal slope 1114 (e.g., a slanted inner wall) complying with the external slope 1112 of collar 1110, once in locked position. In general, and as noted above, locking ring 1120 is, in some embodiments, similar to those described earlier in this document (e.g., locking ring 72 of FIG. 5, locking ring 1030 of FIG. 22A, locking ring 712 of FIG. 19B, etc.), only its internal slope 1114 is tapering upwards.

As an example, in order to lock the components of assembly 1100, after positioning of a rod in cavity 1116 and a screw (screw head) in cavity 1118, ring 1120 is pulled/pushed down, for example relative to the collar. Optionally, slot 1117 of collar 1110 is narrowed due to the radial pressure exerted by ring 1120. Optionally, at this stage, slope 1114 of ring 1120 is placed against slope 1112 of collar 1110.

In some embodiments, ring 1120 is provided pre-assembled over collar 1110. Optionally, assembly 1100 may be provided to the user preassembled with a rod. Alternatively, ring 1120 may be placed over collar 1100 during operation, prior to inserting a rod through cavity 1116.

FIGS. 30A-30C, 31A-31C, 32A-32C illustrate a few collar designs (1130, 1140, 1150) in accordance with some embodiments of the present invention. FIGS. 30A, 31A and 32A provide a perspective view of the collars; FIGS. 30B, 31B and 32B provide a side view of the collars; FIGS. 30C, 31C and 32C provide a cross section of the collars (along line A-A of FIGS. 30B, 31B and 32B respectively).

In some embodiments, collars 1130, 1140, 1150, and/or any components thereof, are made of or comprise of composite material (such CFR-PEEK), metals (such as titanium), and/or any combination thereof. Additional materials/components for example as described throughout this documents, for example, radiopaque markers and/or radiopaque powder/particles, etc., may be incorporated into implant components. In some embodiments, dimensions of implant components are similar to those described earlier in this document for similar components.

In some embodiments, in general, collars 1130, 1140, 1150 incorporate an internal tubular cavity, to accommodate a rod, and a cavity to accommodate the head portion of a pedicle screw (for example screw 1040 of FIG. 22A). Optionally, collar 1110 may be of any design as described above throughout this document (for example, collar 1010 of FIGS. 23A-23D, collar 710 (which is used with adapter 706, 708) of FIGS. 19A-19B, or any other collar design in accordance with the present invention which provides for a single unit collar). In some embodiments, the cavity for rod insertion (1132, 1142, 1152, respectively) may comply with a straight or with a bent rod, as detailed hereinafter, for example in a similar manner to the described earlier in this document for a two-part collar (for example, collar 606, 608 of FIG. 18A).

FIGS. 30A-30C illustrate a collar 1130, designed for use with a straight rod. Cavity 1132, for rod insertion, is straight (e.g., extends directly transversely across the collar), complying with the diameter and/or curvature of the rod. In some embodiments, an internal wall of cavity 1132 is formed with a geometry that complies with a curvature of the rod. In some embodiments, relative motion between the collar and the rod around the rod long axis is possible prior to final locking of the pedicle screw construct.

FIGS. 31A-31C illustrate a collar 1140, designed for use with a bent and/or curved rod. Cavity 1142, for rod insertion, is bent and/or curved, complying with the diameter and configuration (e.g., a curvature) of the rod. In some embodiments, collar 1140 is configured for setting a position of the rod within the collar, for example not enabling rotation of the rod within the collar cavity 1142 prior to final locking of the pedicle screw construct.

FIGS. 32A-32C illustrate a collar 1150, designed for use with a bent rod. Cavity 1152 is straight (e.g., extends directly transversely across the collar). In some embodiments, cavity 1152 comprises a diameter that is larger than the diameter of the rod. In some embodiments, an insert 1154 is provided to be placed within cavity 1152. In some embodiments, insert 1154 has an external tubular configuration and dimensions that match the collar tubular cavity, and an internal curved lumen to match the curved configuration, and dimensions, of the rod. Insert 1154 may be provided with slot 1156 along its entire length, to facilitate locking of the construct (for example, with a non-threaded type locking ring). A potential advantage of the insert comprising at least one slot may include increasing compliance of the collar—rod assembly, as the slot allows for circumferential portions of the insert to overlap, thereby potentially obtaining a firmer, closer grip on the rod that is positioned within the insert. Another potential advantage of an insert positioned between the collar cavity and the rod may include providing for relative motion between the collar and the rod, for example movement around the rod long axis such as rotational movement, for example prior to final locking of the pedicle screw construct. In some embodiments, the tubular cavity comprises one or more teeth or projections for aligning the insert relative to the collar cavity and/or for limiting movement such as rotational and/or axial movement of the insert in the cavity. In some embodiments, a tooth 1158 (e.g., a radial projection) is configured at one end of tubular cavity 1152, to function as a stopper during the insertion of insert 1154 into the tubular cavity, and/or for stopping of the rod when threaded into insert 1154.

Figure 33A:
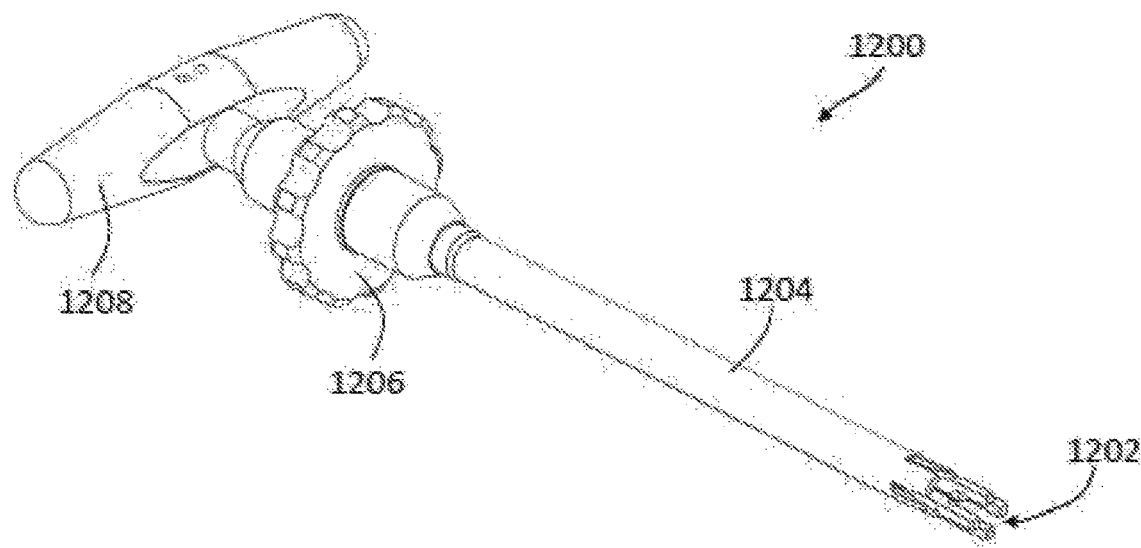
FIGS. 33A-33B schematically illustrate an insertion tool for a pedicle screw, in accordance with some embodiments of the present invention.
Figure 33B:
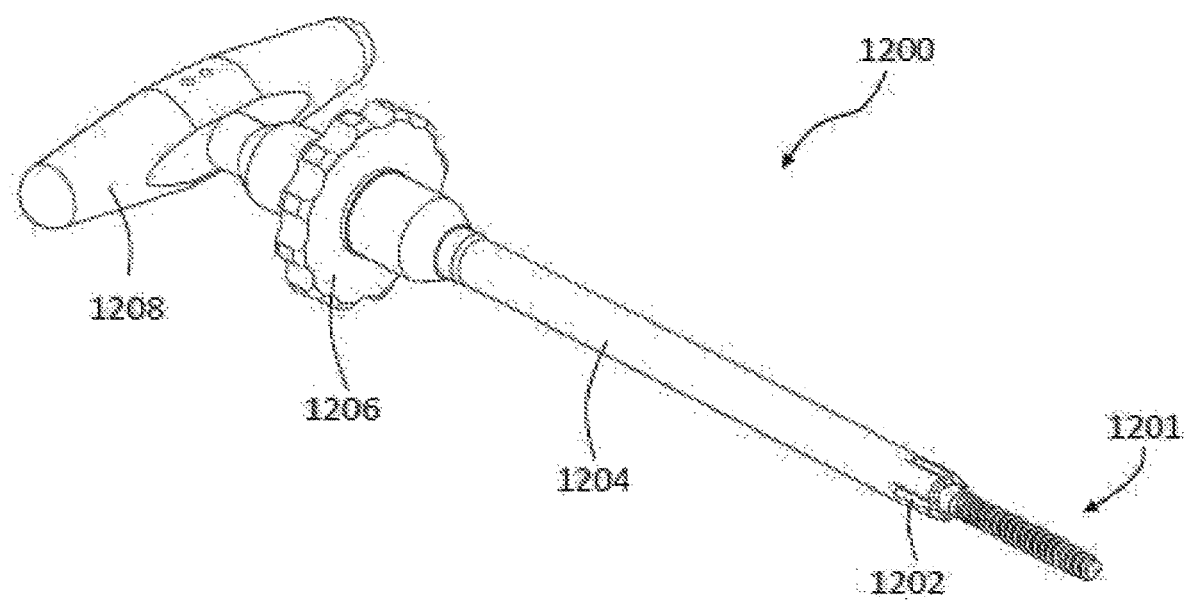

FIGS. 33A-33B illustrate another insertion tool for a pedicle screw, in accordance with some embodiments of the present invention. In some embodiments, insertion tool 1200 may be cannulated (not shown in the figure), for example to used over a guide wire. In some embodiments, at its distal end, tool 1200 comprises teeth 1202, forming an internal rounded socket (such as socket in between the circularly arranged teeth), designed to surround the head of a polyaxial screw. In some embodiments, teeth 1202 are enclosed within a sleeve 1204. FIG. 33A illustrates insertion tool 1200 in "open" position. During operation, the head of screw 1201 is placed within the socket created by teeth 1202. In some embodiments, knob 1206 is rotated, moving sleeve 1204 forward to lock teeth 1202 over the screw head, securing tool 1200 to screw 1201. In some embodiments, handle 1208 (optionally a T-handle) facilitates use of tool 1200 for screw insertion into the pedicle, for example by being rotated by a user such as a physician to insert the screw into the pedicle.

Figure 34A:
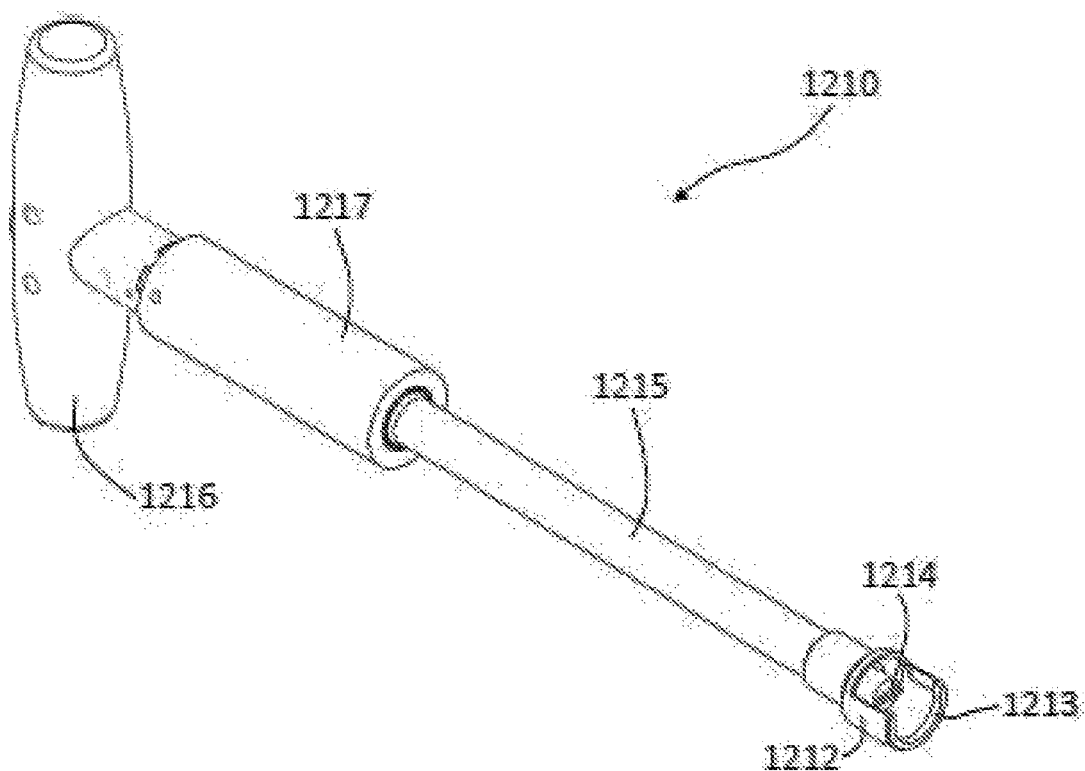
FIGS. 34A-34C schematically illustrate an insertion tool for a pedicle screw, in accordance with some embodiments of the present invention.
Figure 34B:
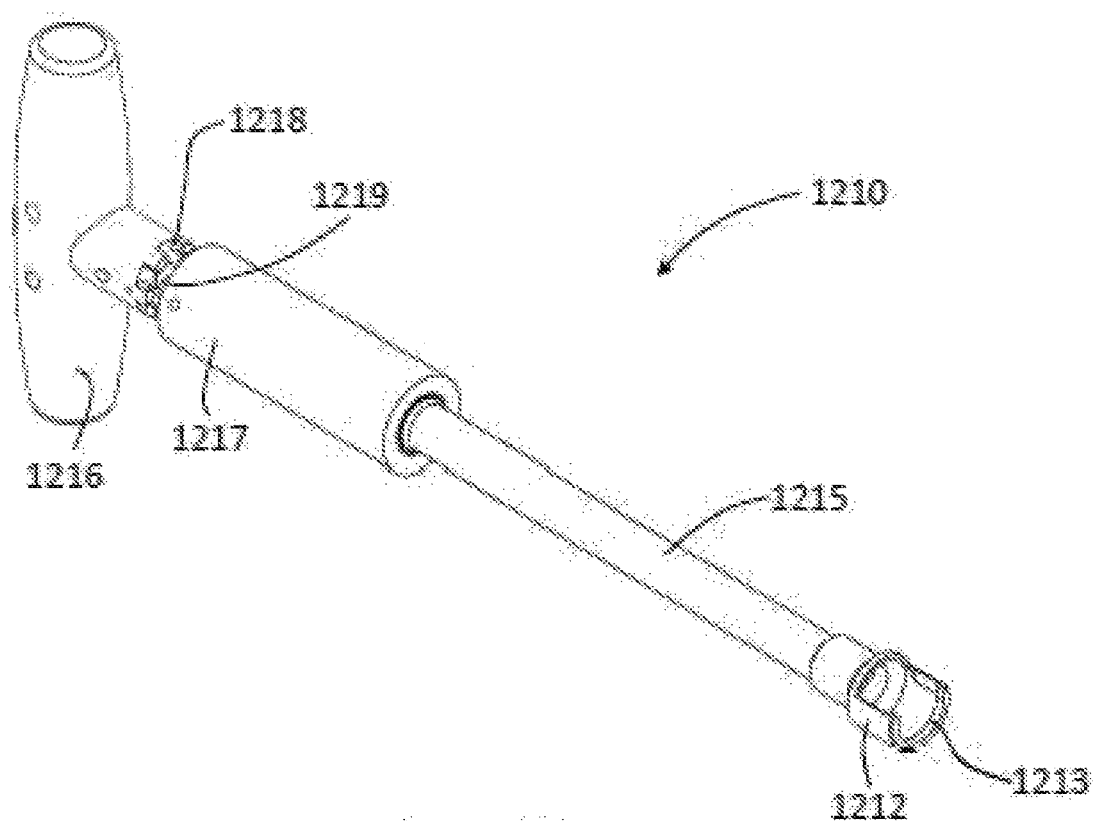
Figure 34C:
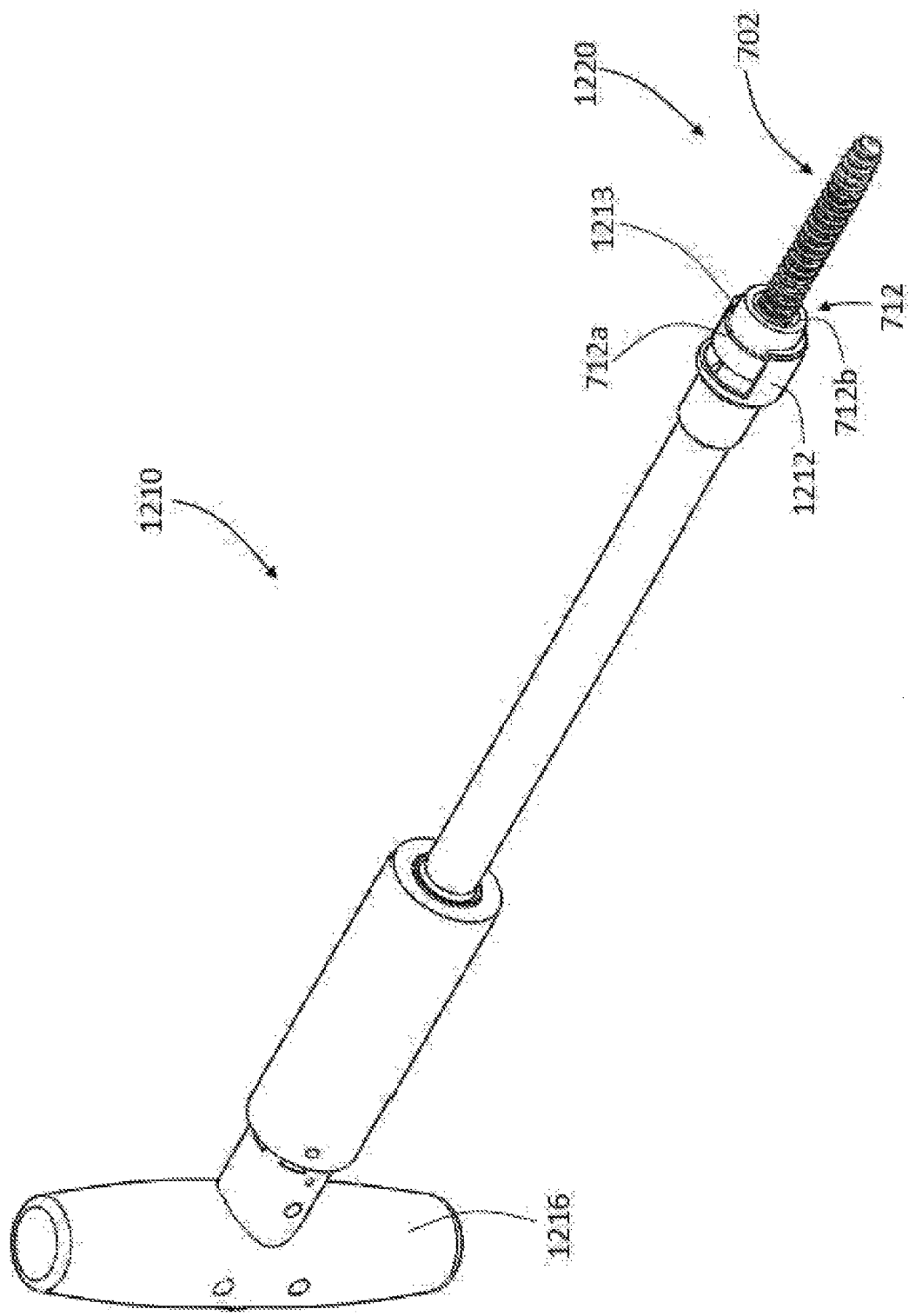

FIGS. 34A-34C illustrate yet another insertion tool 1210 for a pedicle screw assembly 1220 comprising, for example, a pedicle screw 702 (for example as shown in FIG. 22A) and a locking ring 712, optionally comprising adapters 706, 708 (for example as shown in FIGS. 19A-19B). Alternatively, the pedicle screw assembly includes any screw with a connection detail at its head (such as detail 1045 of screw 1040 in FIG. 22A), and any ring-type locking element, optionally with an outer step, surrounding said screw head.

In some embodiments, insertion tool 1210 comprises a distal, curved, section 1212, with its internal surface contour following that of a locking ring, with means 1213 (such as a radial projection, clamp, and/or other means) suitable to hold the locking ring, for example to engage the ring from beneath, and/or at an external step of the ring. In addition, in some embodiments, tool 1210 comprises an internal shaft 1215 and an external shaft 1217. In some embodiments internal shaft 1215 ends with connection detail 1214, complying with the connection detail at the head of the screw. In some embodiments, shaft 1217 is equipped with teeth 1219, which engage teeth 1218 of handle 1216 (for example T-handle), for example to provide a detachable interface between shaft 1217 and handle 1216. FIG. 34A illustrates tool 1210 in a "locked" mode, with connection detail 1214 protruding within part 1212, and with teeth 1218 engaged with teeth 1219. FIG. 34B illustrates tool 1210 in a non-locked mode, prior to placement of screw assembly 1220 into tool 1210. In some embodiments, handle 1216 is pulled back to disengage teeth 1218 from teeth 1219, and thus connection detail 1214 is pulled back as well, for example pulled into a lumen of shaft 1215. FIG. 34C illustrates screw assembly 1220 locked to insertion tool 1210. In an exemplary embodiment, screw assembly 1220 is placed within tool 1210 such that ring 712 is placed within distal part 1212, with detail 1213 placed against the lower part of step 712*a* of ring 712. Alternatively, detail 1213 may be placed against surface 712*b* of ring 712 (for example, in a ring with no external step). Optionally, once the screw assembly is in place, handle 1216 is pulled backwards to release teeth 1218 from teeth 1219, and handle 1216 is rotated until connection detail 1214 engages with the connection detail at the screw head (e.g., detail 1045 of screw 1040, FIG. 22A). Optionally, handle 1216 may be further rotated to somewhat press screw 702 and adapter 706, 708 against ring 712, such that they provide for stable-enough connection to allow screwing of the screw into the bone, but still providing for screw tilting against the ring (e.g., pivoting of the screw relative to the ring). In some embodiments, handle 1216 is returned forward, optionally by manually pressing it, to re-engage teeth 1218 with teeth 1219. In some embodiments, once teeth 1218, 1219 engage, handle 1216 can be used to facilitate use of tool 1210 for screw insertion into the pedicle, such as by rotating the handle to rotate the screw during insertion.

Figure 35A:
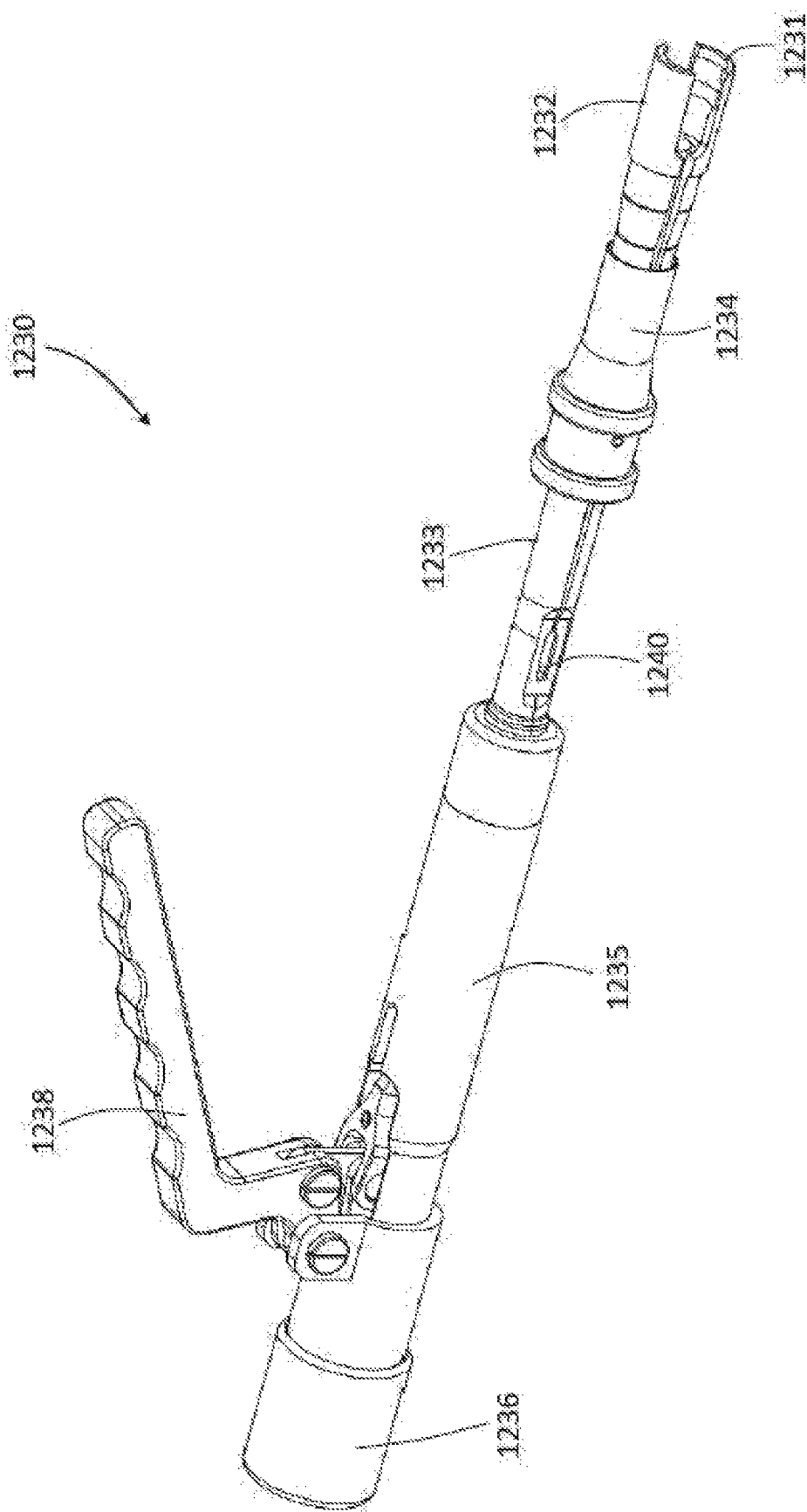
FIGS. 35A-35D schematically illustrate a locking tool, in accordance with some embodiments of the present invention.
Figure 35B:
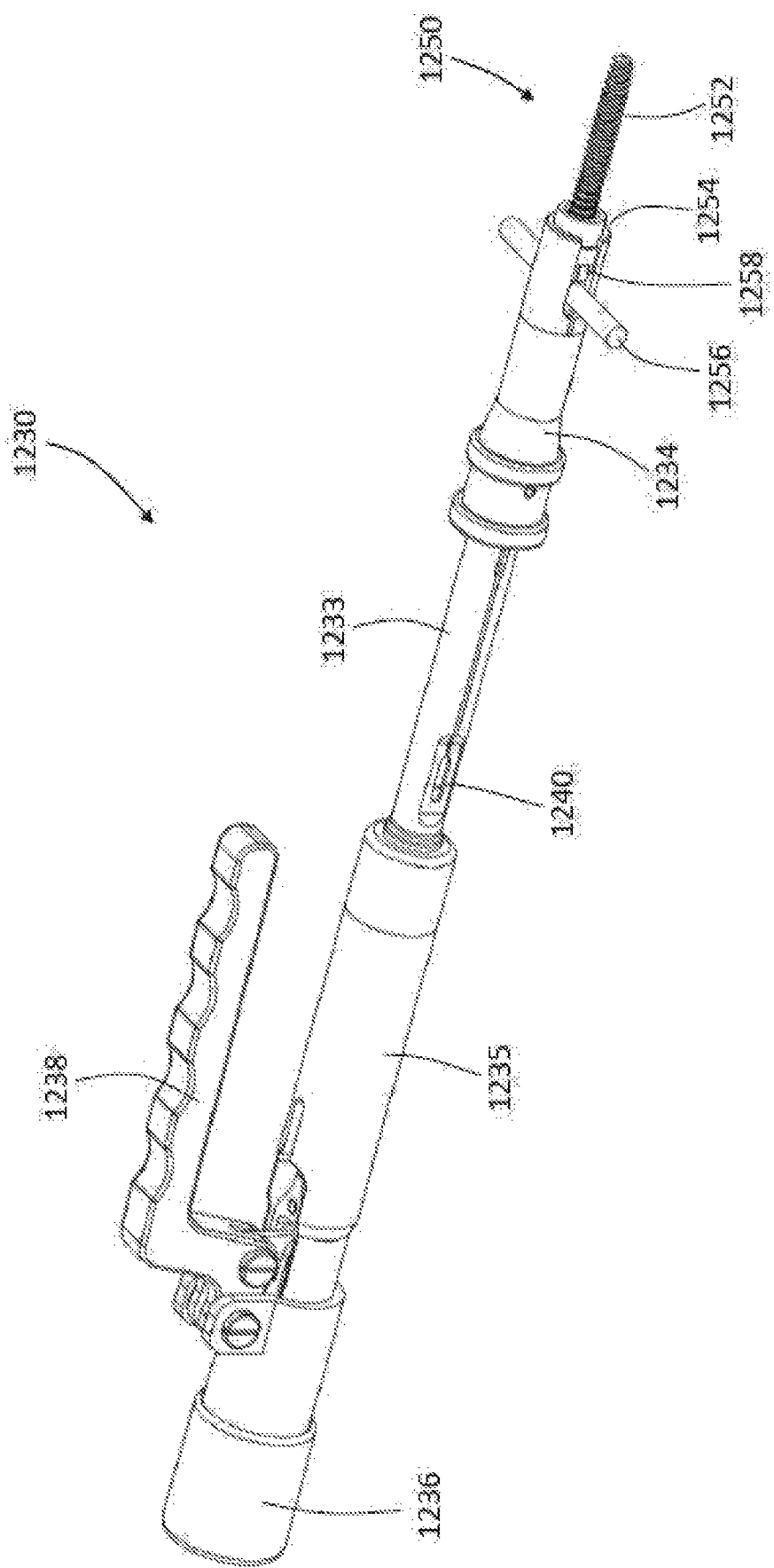
Figure 35C:
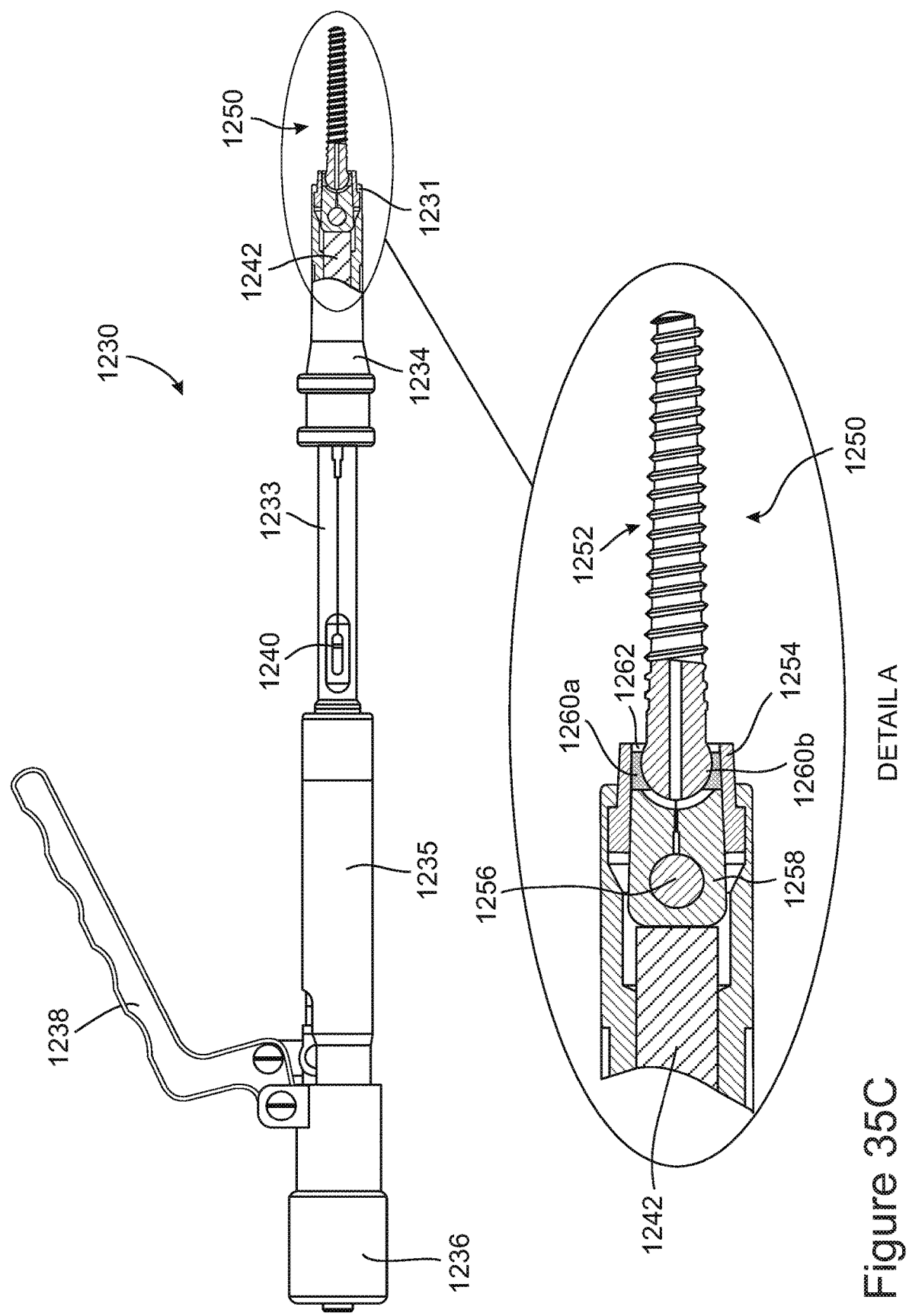
Figure 35D:
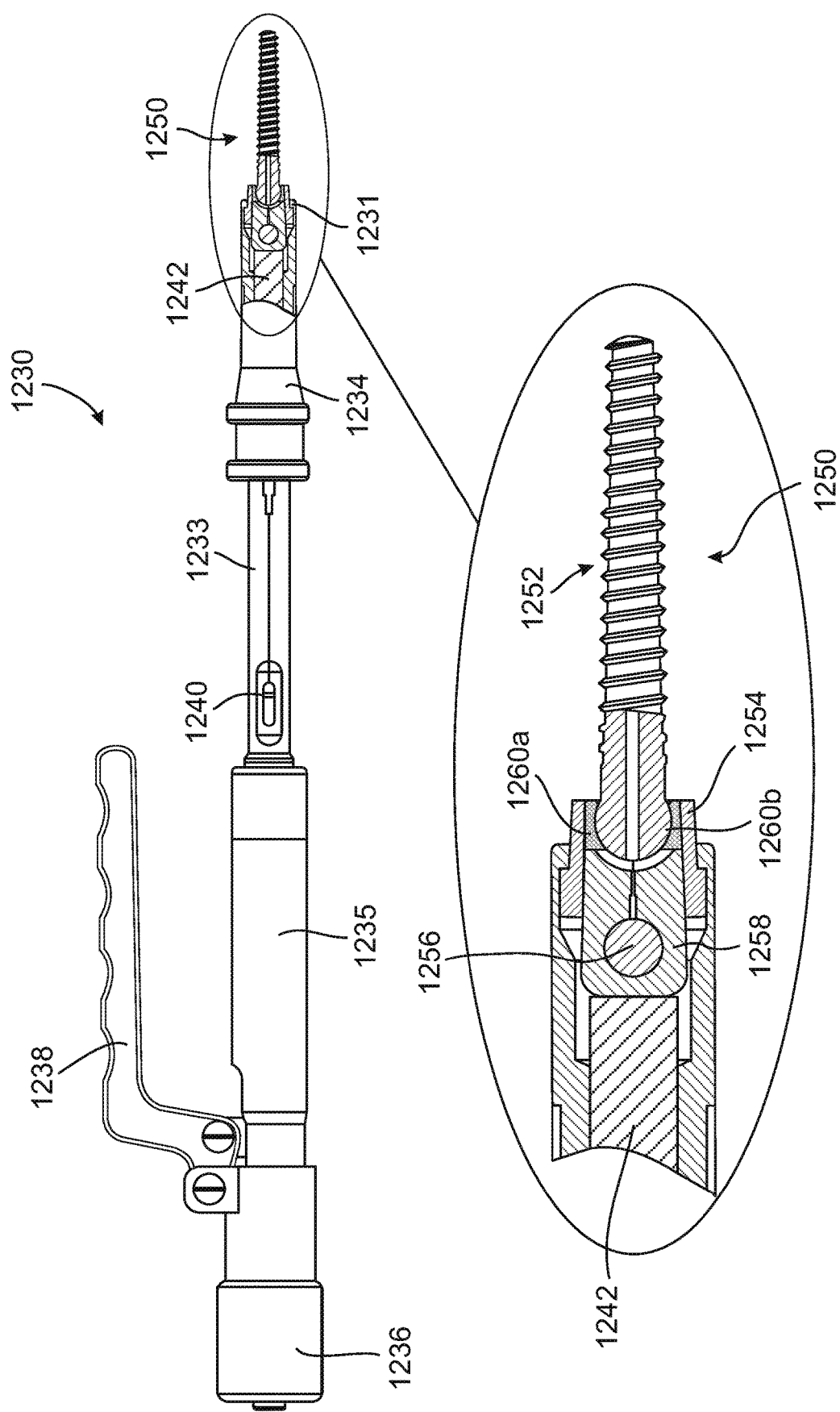

FIGS. 35A-35D illustrate a locking tool, in accordance with some embodiments of the present invention. In some embodiments, locking tool 1230 is used for final locking of a polyaxial pedicle screw construct, for example following initial placement of the locking element (e.g., locking ring) over the collar. FIG. 35A illustrates locking tool 1230 in an exemplary configuration in which it may be provided to the user, not connected to the pedicle screw construct. In FIGS. 35B-35D locking tool 1230 is shown connected to a pedicle screw construct 1250. In some embodiments, locking tool 1230 is configured to exert a relatively high force over the implant without the user such as a physician having to directly apply such high force. In some embodiments, locking tool 1230 is designed such that it enables exertion of high force over the implant, sufficient to lock the pedicle screw construct (for example, 500 Kg), with device operation made possible using manual hand power (for example, 10 Kg). In some embodiments, locking tool 1230 provides for force amplification, preferably in the range of 10 to 100 times.

In these exemplary illustrations construct 1250 is composed of a screw 1252, a collar 1258, a rod 1256 and a locking element 1254. The construct may include also adapters 1260*a*, 1260*b*. Collar 1258 may be a single unit or may be composed of 2 halves for example as described above. It should be appreciated that other configurations of pedicle screw construct as per the present invention may also be similarly used, mutatis mutandis, with the tool described in FIGS. 35A-35D. In some embodiments, materials and/or dimensions of implant components may be similar to those described earlier in this document for similar components.

In some embodiments, locking tool 1230 is composed of several components:

(a) A distal end 1232, composed of a few arms (for example, two (2)), defining an internal shape complying with that of the pedicle screw construct 1250, for example a substantially tubular shape. In some embodiments, distal end 1232 comprises with a protrusion 1231 to engage a step along the perimeter of the locking element 1254 and/or to engage the bottom end of said locking element.

(b) A tube 1233, connecting distal end 1232 to body 1235 (see below), and enclosing (e.g., containing) a rod 1242.

(c) A sleeve 1234, which is manually pushed over distal end 1232, for example after the pedicle screw construct is properly located within distal end 1232, to firmly attach the locking tool to the construct. Optionally, once locking of the construct is completed, sleeve 1234 is pulled back to space the arms of distal end 1232 and allow removal of locking tool 1230 from construct 1250.

(d) A body 1235, enclosing the locking tool mechanism. The mechanism enclosed in body 1235 may include a spring (not shown) to return arm 1238 (see below for details) to its position (e.g., to an initial position relative to body 1235) following each activation.

(e) A handle 1236 (for example, a knob type handle), used for advancing the internal mechanism of locking tool 1230, resulting in advancing rod 1242 so that it contacts construct 1250.

(f) A lever arm 1238, used for pushing rod 1242 (see below) against construct 1250, resulting in movement of collar 1258 against ring 1254, so that they engage towards locking the construct.

(g) A rod 1242 (FIGS. 35C-35D), connected to lever arm 1238 via the mechanism enclosed in body 1235. In some embodiments, each activation of arm 1238 (e.g., by pressing down the arm towards body 1235) advances rod 1242 a set (e.g., predetermined) distance (for example, 1 mm).

(h) An indicator 1240, providing indication as to the stage of locking process.

The following paragraphs describe an exemplary procedure for using tool 1230, in accordance with some embodiments of the present invention. In some embodiments, tool 1230 is connected to construct 1250 after the screws are implanted within the vertebrae, the rod was connected to the screws (with the help of the collar and locking element), initial locking was carried out (manually or using another tool), and final alignment of the construct components is obtained (for example a desired angle of the screws relative to the rods is set).

In some embodiments, distal end 1232 of tool 1230 is located over one construct 1250 such that protrusions 1231 are placed beneath the step along the perimeter of ring 1254. Optionally, sleeve 1234 is pushed down, to press the arms of distal end 1232, so that they firmly hold construct 1250. At this stage arm 1238 is in its non-pressed position, and indicator 1240 is at the most proximal position.

In some embodiments, handle 1236 is rotated until rod 1242 contacts construct 1250 (optionally, contact is made between a distal end of rod 1242 and a proximal end of collar 1258). Optionally, at this stage, arm 1238 is pressed down; this advances rod 1242 a set distance, thus pushing collar 1258 against ring 1254. Optionally, indicator 1240 is advanced distally. Optionally, at this stage, arm 1238 is released and returns to its non-pressed position (e.g., with the help of a spring; not shown). This procedure of turning handle 1236 and pressing arm 1238 may be repeated, for example until indicator 1240 reaches its final location. Optionally, at this stage, construct 1250 is locked, for example by the ring being positioned over the collar at a location suitable to exert sufficient radial force to reduce or prevent movement of the components of the construct relative to each other and/or relative to the spine.

FIG. 35B provides an illustration of construct 1250 connected to tool 1230 during initial press of arm 1238 (e.g., approximation of the arm towards body 1235). Optionally, indicator 1240 is in its proximal position. FIG. 35C illustrates construct 1250 in the process of locking, with indicator 1240 at a point along its scale, such as a middle point; Detail A of FIG. 35C shows space 1262 between the bottom end of ring 1254 and the bottom end of adapters 1260a, 1260b, indicating that ring 1254 is not yet in its final position over collar 1258. FIG. 35D illustrates construct 1250 connected to tool 1230 following final locking step, with indicator 1240 at its most distal location; Detail A of FIG. 35D illustrates construct 1250 following the last activation of arm 1238, with locking ring 1254 fully locked to collar 1258.

In some embodiments, once construct 1250 is fully locked, sleeve 1234 is pulled backwards to release the connection between distal end 1232 of tool 1230 and construct 1250. Optionally, the process of final locking is repeated for every such construct 1250, to lock the rod to all screws used in the operative procedure.

In some cases, while retracting the ring, the collar may be advanced, for example, between 0.1 and 1 mm. Optionally, advancing is avoided by having the collar rest against a dome of the screw head. Alternatively, such movement is allowed by providing a gap between the dome of the screw head and the collar.

Optionally, operation of tool 1230 is manual. Alternatively, the operation of tool 1230 is carried by electronic means, either in full or in part.

Figure 36A:
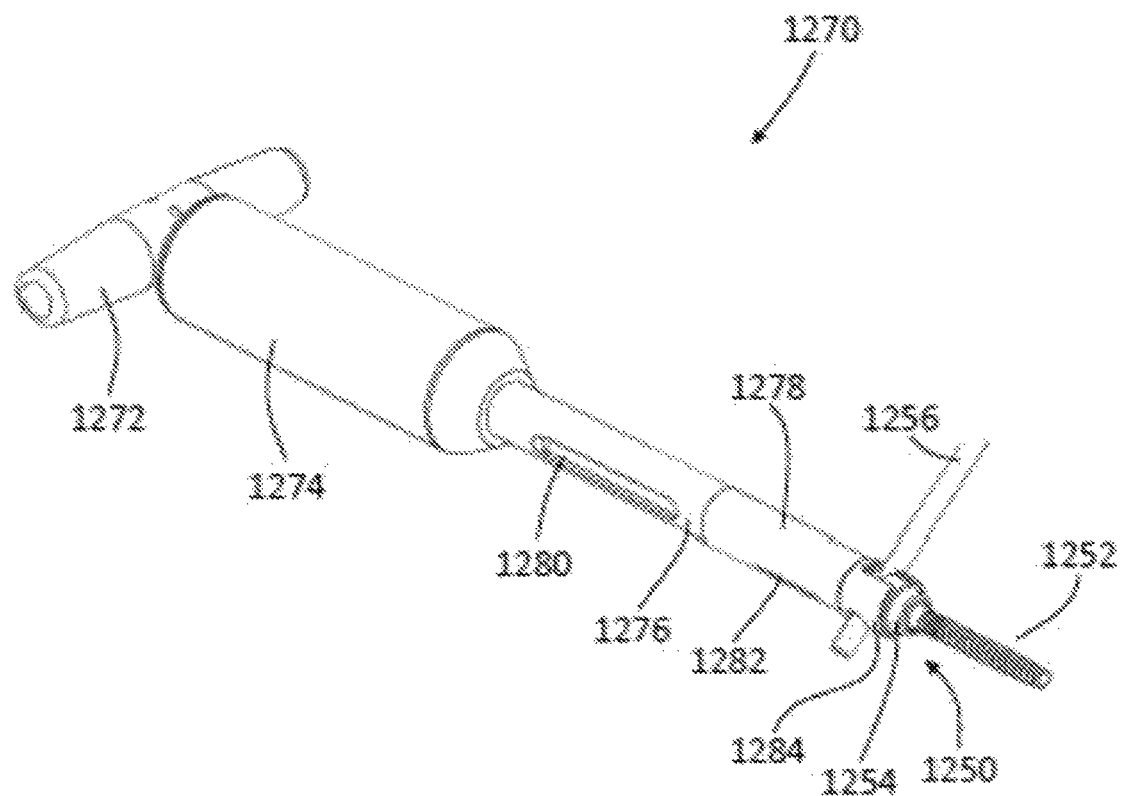
FIGS. 36A-36F schematically illustrate an extraction tool for rod and collar detachment from a screw, in accordance with some embodiments of the present invention.
Figure 36B:
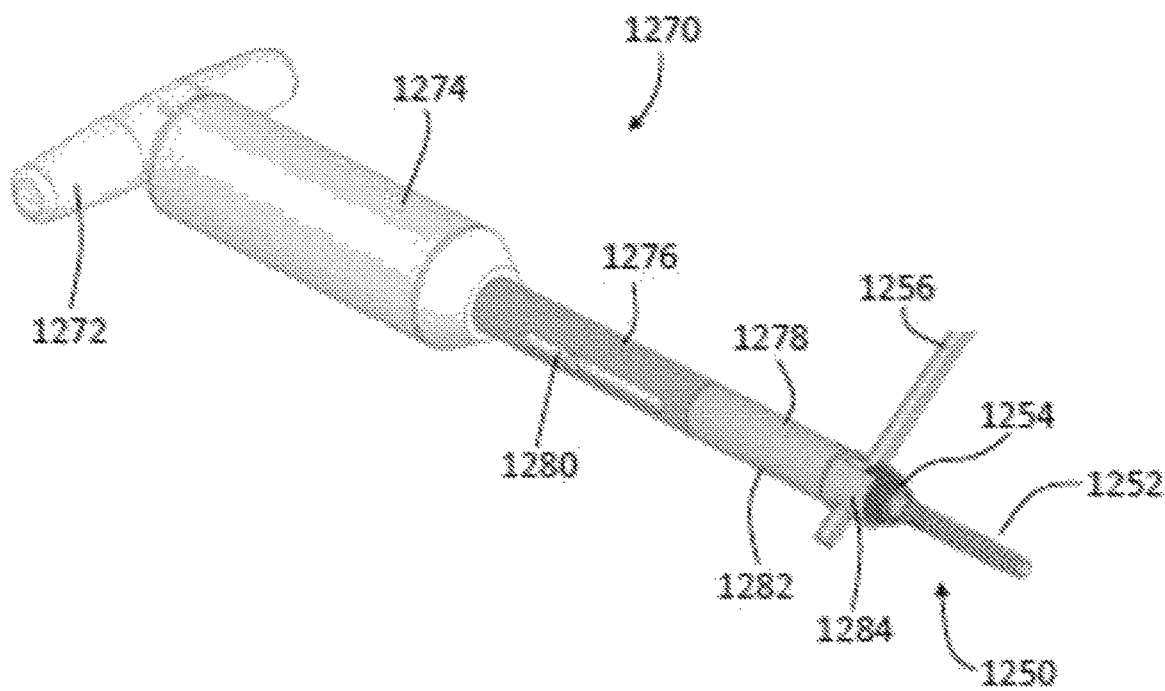
Figure 36C:
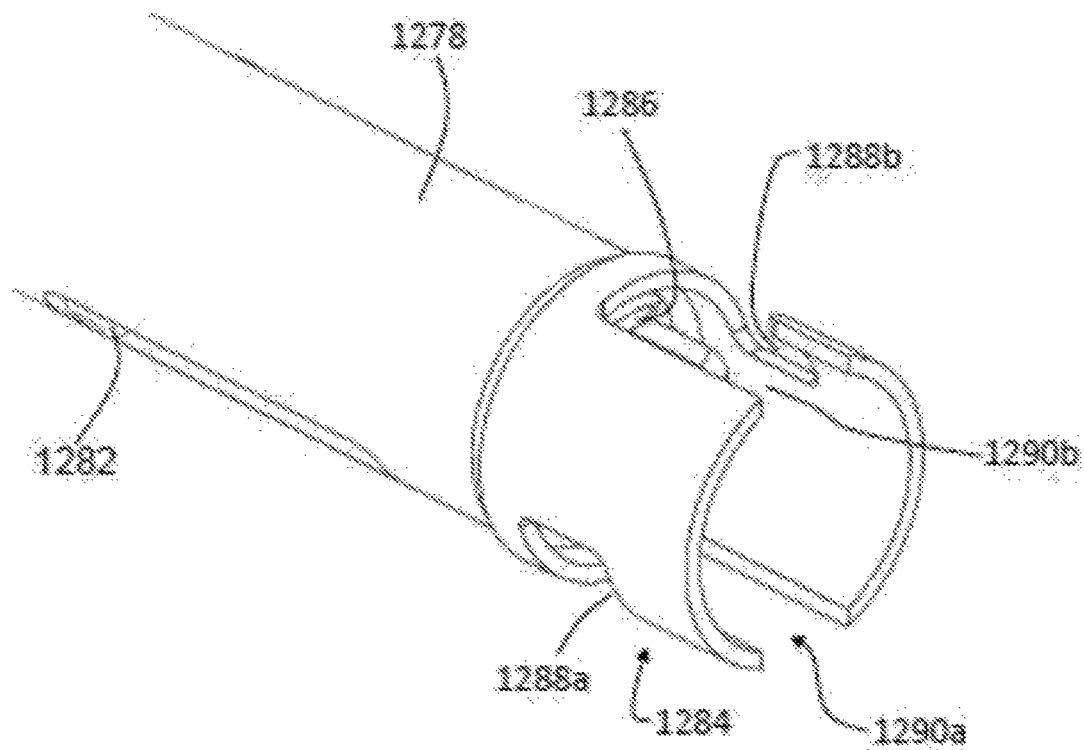
Figure 36D:
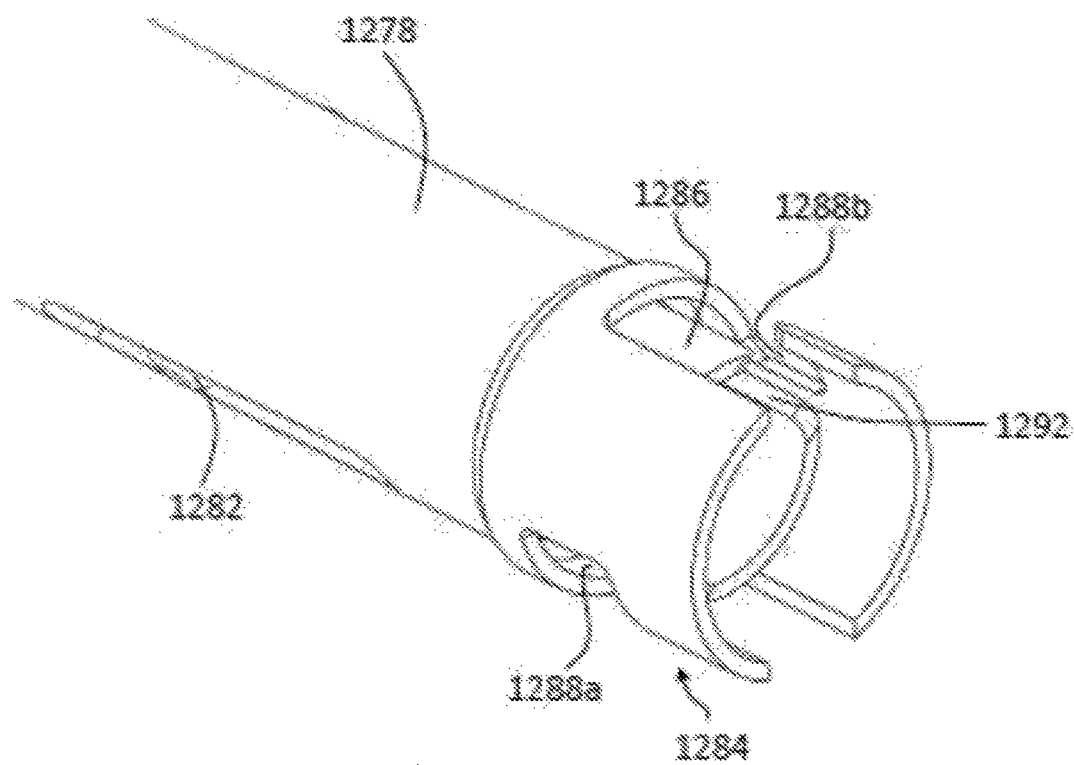
Figure 36E:
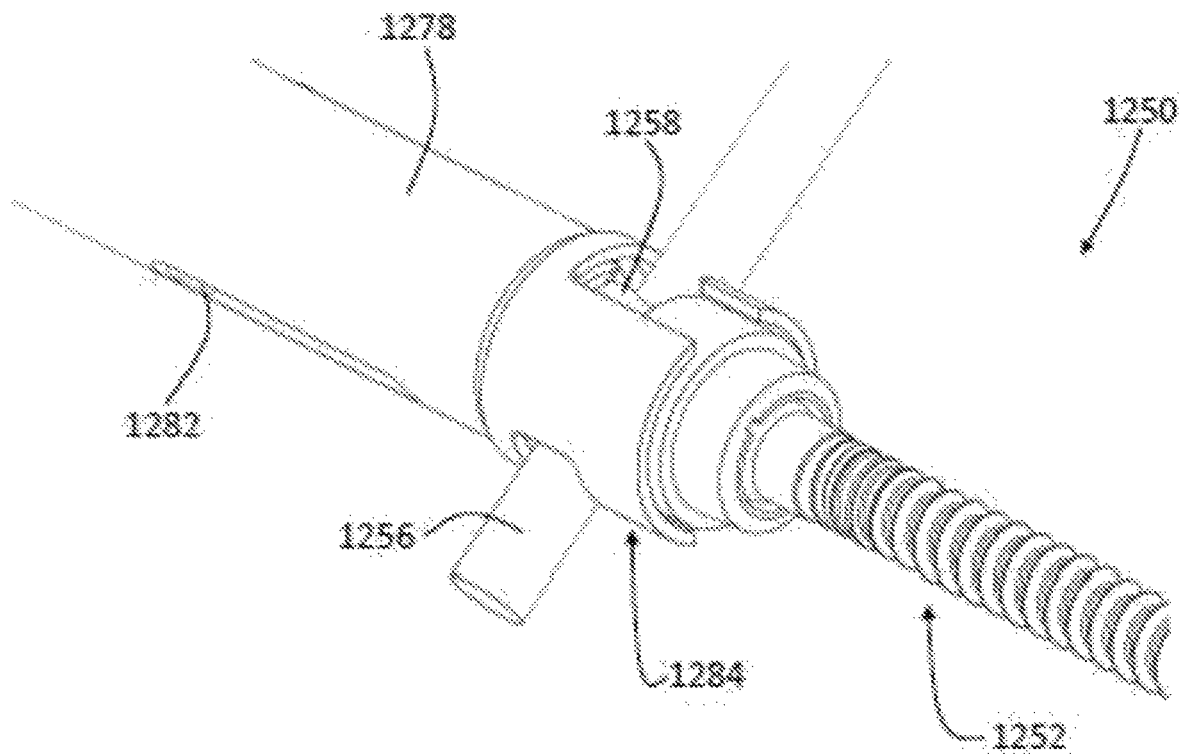
Figure 36F:
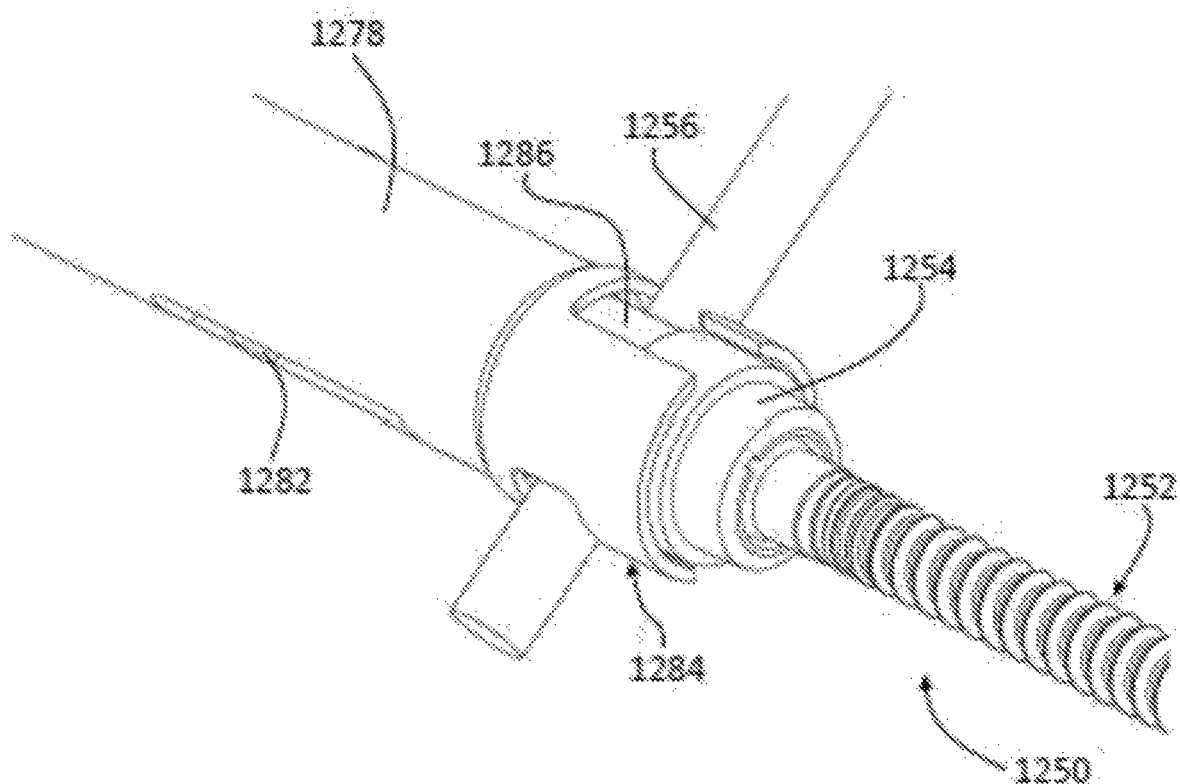

FIGS. 36A-36F illustrate an extraction tool for detachment of a rod from a screw, in accordance with some embodiments of the present invention. FIGS. 36A-36B illustrate extraction tool 1270 connected to pedicle screw construct 1250 (construct 1250 for example as described above). FIGS. 36C-36D illustrate the distal portion of tool 1270, without construct 1250, and FIGS. 36E-36F illustrate the distal portion of tool 1270 connected to construct 1250.

In some embodiments, tool 1270 is composed of body 1274, connected, optionally on its proximal end, to a handle 1272 (for example, T-handle), optionally on its distal end, to a tube 1276. In some embodiments, tube 1276 connects to tube 1278 which is connected to distal end 1284. In some embodiments, tubes 1276 and/or 1278 enclose rod(s) ending with distal end 1286. In some embodiments, indicators 1280, 1282 are incorporated in tubes 1276, 1278. In some embodiments distal end 1284 has 2 openings 1288a, 1288b to enable engagement of tool 1270 with construct 1250.

The following paragraphs describe an exemplary procedure for using tool 1270, in accordance with some embodiments of the present invention. In some embodiments, tool 1270 is connected to construct 1250—optionally, distal end 1284 of the tool is placed over collar 1258 and ring 1254 with rod 1256 inserted via slots 1290a, 1290b (FIG. 36C). Optionally, tool 1270 is then rotated such that implant rod 1256 engages with openings 1288a, 1288b. At this stage, indicators 1280, 1282 are located at their most proximal position, and the distal end of rod 1286 is fully retracted.

In some embodiments, in order to release the locking of construct 1250, handle 1272 of tool 1270 is rotated. Rotation of handle 1272 results in advancement of rod 1286, with indicators 1280, 1282 moving distally. In some embodiments, the distal end of rod 1286 ends with a slot 1292, for example extending transversely through rod 1286 in proximity to a distal end of the rod. Optionally, once distal end of rod 1286 is advanced, implant rod 1256 is positioned within slot 1292, and distal end or rod 1286 is placed against the upper surface of ring 1254. Optionally, further rotation of handle 1272 presses distal end of rod 1286 against ring 1254, such that ring 1254 is pushed away from collar 1258. Once ring 1254 is removed from collar 1258 tool 1270 is rotated so that implant rod 1256 is located against slots 1290a, 1290b (e.g., in a configuration which prevents rod 1256 from disengaging the tool, whereby the walls of slots 1290a, 1290b support the rod) and tool 1270 is pulled backwards to remove rod 1256 from the implants, such as from one or more screw implants.

The procedure for using tool 1270 may be repeated for all screw constructs involved. Optionally, following removal of ring 1254 from collar 1258, collar 1258 with rod 1256 can be detached from screw 1252. It is noted that tool 1270 can be used either for implants removal, or for partially unlocking a construct during operation to improve and/or otherwise adjust a relative location of screw 1252 and/or of rod 1256 prior to re-locking construct 1250.

FIGS. 37A-B are schematic illustrations of forces acting on a single component collar (37A) and a double component collar (37B).

FIG. 37A illustrates a single component collar 3701 (shown in an isometric view, side view, and cross section view), and a ring 3703 configured to be positioned over at least a portion of the collar.

In some embodiments, collar 3701 comprises an upper portion 3707 formed with a cavity 3711, in which a rod is received. In some embodiments, lower portion 3705 comprises a cavity 3708 in which a screw head is at least partially received. In some embodiments, a transversely extending slot 3717 extends between cavity 3709 and cavity 3711, separating lower portion 3705 into sub portions 3719 and 3721. In some embodiments, an external profile of lower portion 3705 comprises a conical configuration, tapering in a distal direction, for example as described hereinabove.

In some embodiments, a top portion 3709 of upper portion 3707, configured substantially above cavity 3711, is formed without any recesses, slots and/or dents. Optionally, portion 3709 acts as a bridging element between the sub portions 3719 and 3721 of the lower portion 3705 of the collar which are at least partially separated from each other by slot 3717. In some embodiments, closed top portion 3709 increases a size of the circumference of the rod which comes in contact with the walls of cavity 3711. Optionally, area 3729 in which slot 3717 connects with cavity 3711 is the only area in which the rod received within the collar does not contact the walls of the collar. In some embodiments, the walls of cavity 3711 encompass at least 85%, 90%, 95% or intermediate, larger or smaller percentages of the circumference of the rod. A potential advantage of increasing a contact area between the rod and the collar, such by having a closed top portion 3709, may include providing a firmer hold of the rod by the collar. Closed top portion 3709 may further protect the rod from compression forces acting on the collar in a distal direction.

In some embodiments, portion 3709 comprises an arched cross section profile. Alternatively, portion 3709 may comprise a squared cross section profile, trapezoidal cross section profile, and/or any other configuration.

In some embodiments, such as during and/or following elevation of ring 3703 over the lower portion 3705 of the collar, a radial force F2 is exerted on the lower portion 3705. Force F2 is schematically illustrated to act at a distance L2 from a center point 3725 of top portion 3709. The moment of force F2, relative to center point 3725, can be calculated as M2=F2*L2. In some embodiments, application of force F2 on lower portion 3705, which potentially approximates sub portions 3719 and 3721 towards each other, induces a second force F1 on upper portion 3707, schematically illustrated to act at a distance L1 between center point 3725 of top portion 3709 to a center 3729 of cavity 3711. The moment of force F1 can be calculated as M1=F1*L1. Since the applied moments are equal to each other, it is presumed that force F1 is substantially equal to force F2, multiplied by the ratio between distance L2 and L1, namely F1=(L2/L1)*F2. Potentially, the amplification of F1 relative to F2 is enabled by the ability to approximate sub portions 3719 and 3721 towards each other, such as when radially inward force is applied to the external surfaces of the sub portions by ring 3703. A potential advantage of this force distribution may include exerting increased pressure on a rod positioned within cavity 3711, for example relative to a collar which does not comprise partially separated, conically profiled sub portions that can be approximated towards each other when force such as radial force is applied. Optionally, the increased pressure applied onto the rod by collar 3701 strengthens the engagement with the rod, thereby potentially enhancing the coupling which is provided by collar 3701 between the rod and the screw that is received within cavity 3708.

FIG. 37B illustrates a two component collar 3731. In some embodiments, collar 3731 is formed of two components 3733 and 3735. In some embodiments, components 3733 and 3735 complete each other to form two cavities, a first cavity 3737 for receiving the rod, and second cavity 3739 for receiving the screw head. In some embodiments, a locking ring 3743 is inserted over at least a lower portion 3741 of collar 3731, potentially approximating components 3733 and 3735 towards each other. Optionally, during and/or following positioning of ring 3743 over the collar, a force F3, such as radial force, is exerted on lower portion 3741. Optionally, application of force F3 on the conical lower portion of the collar induces a similar force F4 on upper portion 3745 in which the rod is received. Components 3733 and 3735 are squeezed towards each other in a pliers-like manner, grasping the rod that is received within cavity 3737 in between the components and thereby coupling the rod to screw received within cavity 3739.

In some embodiments, a length 3761 of the collar ranges between, for example, 12-17 mm, or intermediate, longer or shorter lengths. In some embodiments, a length 3763 from a distal end of cavity 3711 to a distal end of the collar ranges between, for example, 5-9 mm, or intermediate, longer or shorter lengths. Optionally, length 3763 is selected to be large enough so that radial compression applied to a distal portion of the collar, such as by the locking ring, is increased by a factor of the distance, for example as described hereinabove. In some embodiments, a diameter 3765 of the collar ranges between, for example, 8-12 mm, or intermediate, larger or smaller ranges. Optionally, diameter 3765 varies along the length of the collar.

Figure 38:
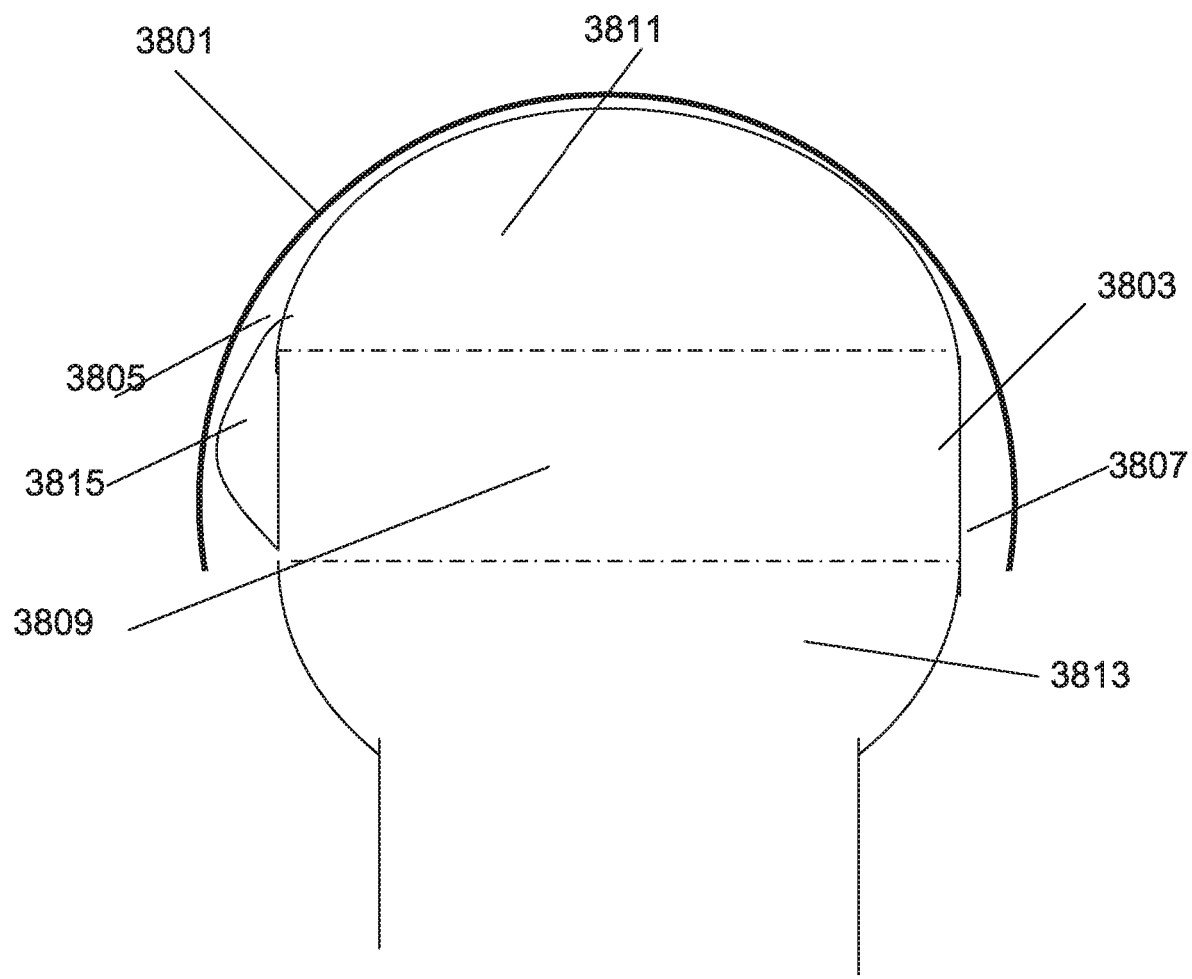
FIG. 38 is a schematic illustration of a screw head and receiving cavity shaped to have one or more gaps between the screw head and the cavity that are at least partially filled with deformed screw and/or collar material during locking, according to some embodiments of the invention.

FIG. 38 illustrates an exemplary non-spherical pedicle screw head 3803 received within a spherical cavity 3801, such as a cavity of a collar for coupling the screw to a rod.

In some embodiments, head 3803 is shaped to form one or more gaps such as 3805 and 3807 when received within the spherical walls of cavity 3801. In some embodiments, during fastening of the collar onto the screw head, such as by positioning a locking ring over the collar, the walls of cavity 3801 are squeezed towards head 3803. Optionally, the applied force causes a slight deformation of the head material and/or the cavity walls material, such that some material 3815 enters gaps 3805 and/or 3807. In some embodiments, the material fills up at least a portion of gaps 3805 and 3807. A potential advantage of the material entering gaps between the cavity and the screw head may include obtaining a tighter fit of the cavity walls to the screw head, which may strengthen the gripping of the screw by the collar and provide a better hold by snugly fitting the screw head. In some embodiments, the material is composite material from which the head and/or cavity walls are comprised of.

An exemplary geometry of head 3803 that is suitable to obtain the above described gaps is shown in this figure. In some embodiments, head 3803 comprises a substantially cylindrical central portion 3809, and two dome-shaped portions 3811 and 3813 configured above and below the central cylindrical portion. Optionally, gaps 3805 and 3807 are formed in between the walls of cylindrical portion 3809 and the spherical walls of cavity 3801.

Figure 39A:
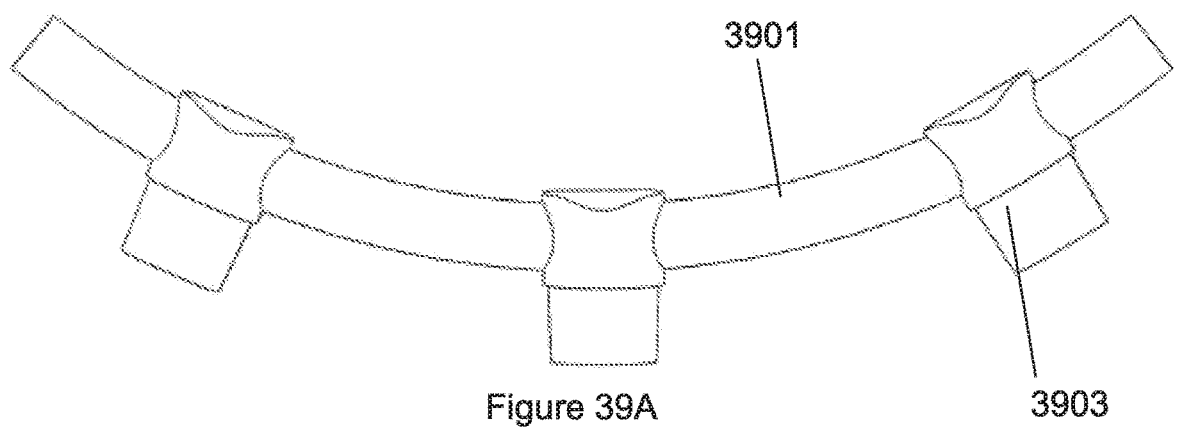
FIGS. 39A-39B illustrate two exemplary curved configurations of a rod comprising a plurality of collars positioned over the rod, according to some embodiments of the invention.
Figure 39B:
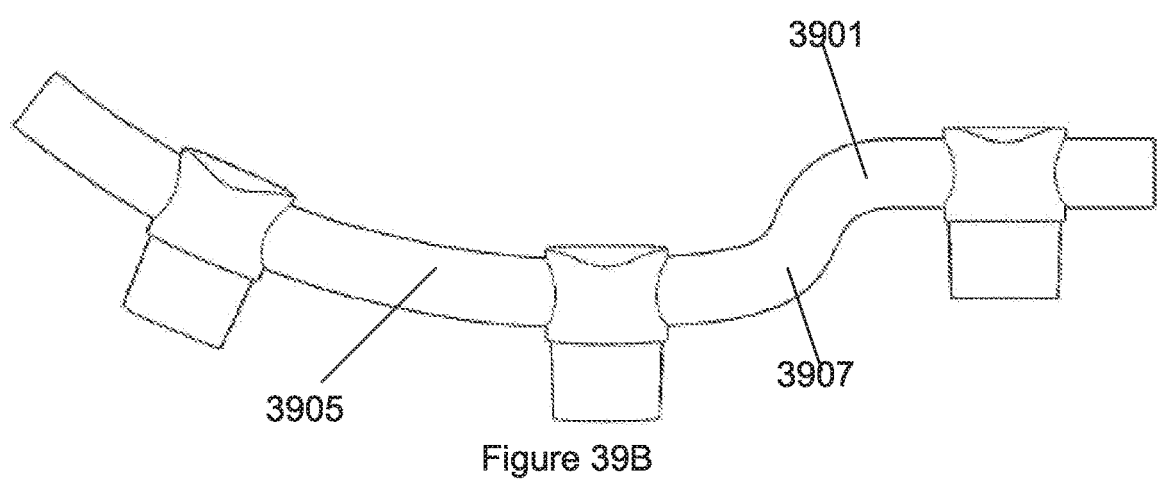

FIGS. 39A-B illustrate two exemplary curved configurations of a rod 3901 comprising a plurality of collars 3903 positioned over the rod, according to some embodiments of the invention. In some embodiments, for example as shown in FIG. 39A, rod 3901 is formed with a constant curvature. Alternatively, for example as shown in FIG. 39B, rod 3901 is formed with a varying curvature. In some embodiments, the collars 3903 are equally spaced on the rod. Alternatively, the collars are distributed at various distances from one another. In some embodiments, bending of the rod is performed prior to positioning of the collars over the rod. Additionally or alternatively, the collars are positioned on the rod and the rod is bent to the desired curvature. In some embodiments, bending of a rod sections such as 3905 and/or 3907, for example a rod section extending between neighboring collars, is performed separately.

Figure 40:
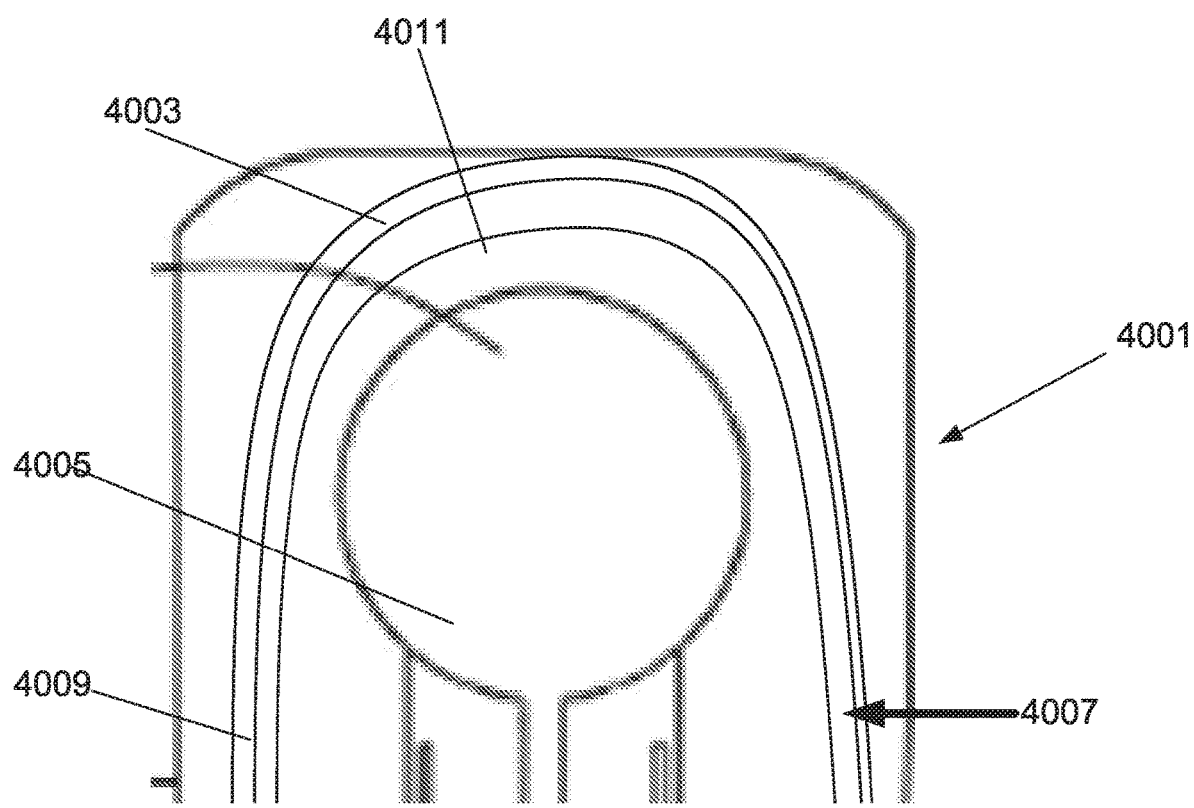
FIG. 40 illustrates an upper portion of a collar, comprising a fiber arrangement that complies with a contour of the collar, according to some embodiments of the invention.

FIG. 40 illustrates an upper portion of a collar 4001, comprising a fiber arrangement that complies with a contour of the collar, according to some embodiments of the invention. In the example shown herein, a plurality of reinforcing fibers 4003, such as carbon fibers, comprise an upside down U-shaped curvature which complies with the shape of the collar. In some embodiments, the fibers extend to surround at least a portion of rod cavity 4005. In some embodiments, when force such as radially inward force 4007 is applied to a lower, substantially linear portion 4009 of the fibers (e.g., by the locking ring), the force is transferred to the upper, bridge-like portion 4011 of the fibers. A potential advantage of the upside down U-shaped fibers may include distributing load between the upper and lower portions of the collar and/or between the transverse portions of the collar (e.g., portions on opposite sides of the longitudinal axis of the collar). Another potential advantage may include transferring force to the bridging portion (uppermost portion) of the collar to restrain the rod in the cavity.

Figure 41:
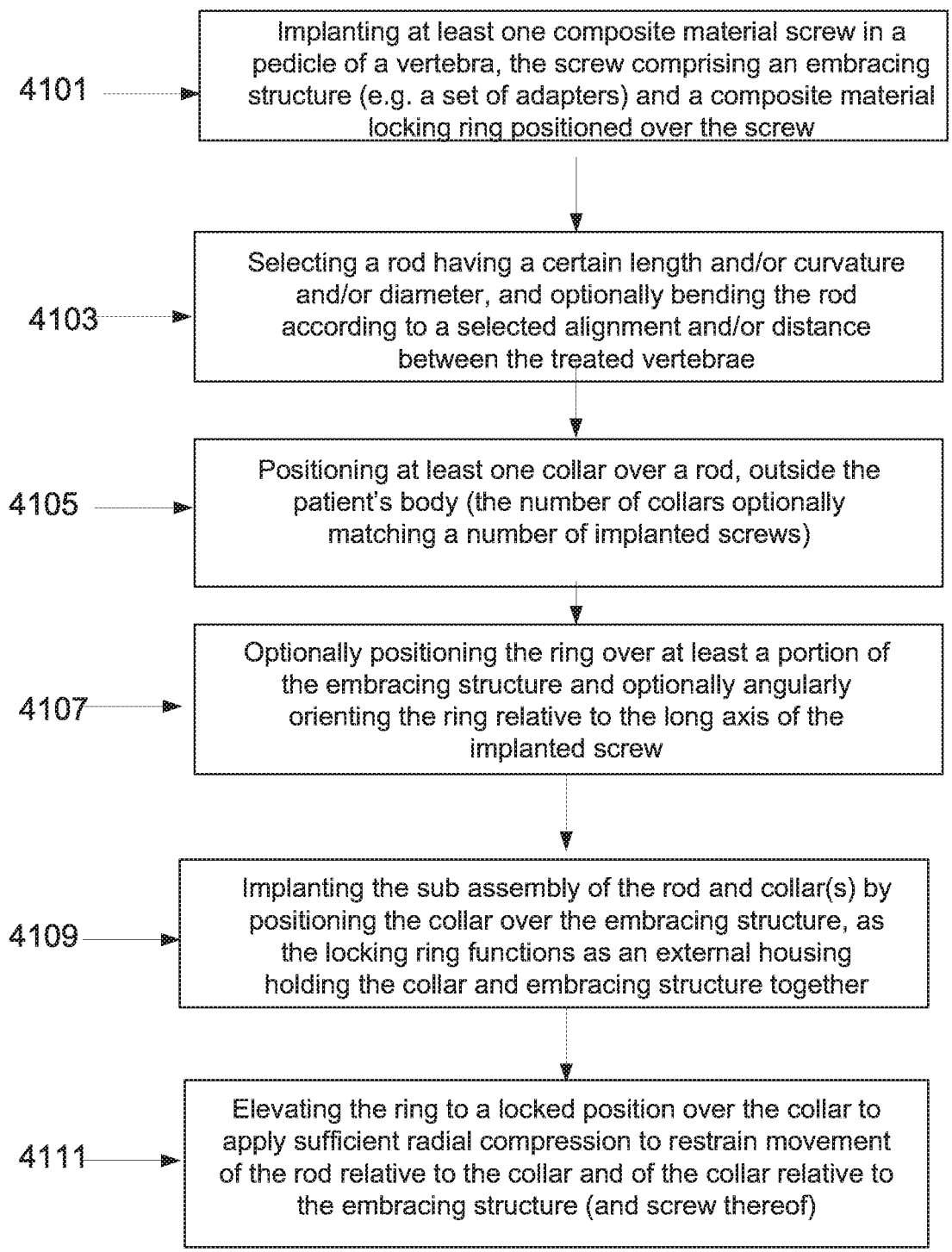
FIG. 41 is a flowchart of a method for constructing a pedicle screw construct, according to some embodiments of the invention.

FIG. 41 is a flowchart of an exemplary method for constructing a pedicle screw construct, for example a construct in which the collar does not comprise a cavity for receiving the head of the screw, according to some embodiments of the invention.

In some embodiments, at least one composite material (e.g., carbon reinforced PEEK) screw is implanted in a pedicle of a vertebra (4101). In some embodiments, a screw of certain properties such as length, diameter, axial extent of thread, and/or parameters is selected according to the patient's anatomy and needs. Optionally, the screw is implanted through an incision made in the tissue. In some embodiments, a channel in the pedicle is reamed prior to insertion of the screw. In some embodiments, the screw comprises an embracing structure, for example formed of one or more adapters which receive at least a portion of the head of the screw. In some embodiments, the screw comprises a composite material (e.g., carbon reinforced PEEK) locking ring positioned over the screw. In some embodiments, the locking ring is pre-assembled, for example during manufacturing, over at least a portion of the adapters such that a proximal end of the ring extends beyond the adapters, forming a recess above the adapters in which at least a portion of the collar can be received.

In some embodiments, a rod is selected (4103). Optionally, a rod having a certain length and/or diameter and/or curvature is selected, to obtain a selected alignment and/or distance between the treated vertebrae. In some embodiments, a physician inserts one or more rod templates into the treated area to decide which rod parameters would be used. Optionally, a physician bends the rod to a selected curvature, for example by using the deforming device such as described in figure FIGS. 16A-C.

In some embodiments, outside the body, one or more collars are positioned over the selected rod (4105). Optionally, the number of collars corresponds to the number of implanted screws. In some embodiments, the rod is passed through the cavities of the collars.

In some embodiments, the ring is axially and/or angularly positioned relative to the implanted screw (4107), for example by axially sliding the ring over the screw (and/or adaptors) and/or tilting the ring. Tilting the ring may facilitate coupling the sub assembly of the rod and collar to the screw.

In some embodiments, the externally assembled rod-collars assembly is implanted, and at least a portion of the collar is positioned within the recess defined by the ring, over the adaptors, such that the ring acts as an external housing holding the adaptors and collar together (4109). Optionally, the collar is pressed in a distal direction against the ring, optionally manually. This may provide a partial locking, which restrains at least some movement of the rod and screw relative to the collar.

In some embodiments, the ring is elevated over the adaptors and/or collar to a locked configuration, in which it applies sufficient radial compression to restrain movement of the rod and/or adapters (and screw thereof) relative to the collar (4111). In some embodiments, movement of the collar relative to the adapters (and embraced screw head thereof) is restrained possibly even before locking, for example, by friction and/or radial force applied by the ring. Optionally, the ring is elevated by a tool for example as described herein. Additionally or alternatively, the ring is elevated directly by the physician. Additionally or alternatively, the embracing element (adapters) are pushed distally relative to the ring, such that the ring is positioned over a portion of larger diameter of the collar and/or adapters in which it is effective to apply radial compression.

Figure 42:
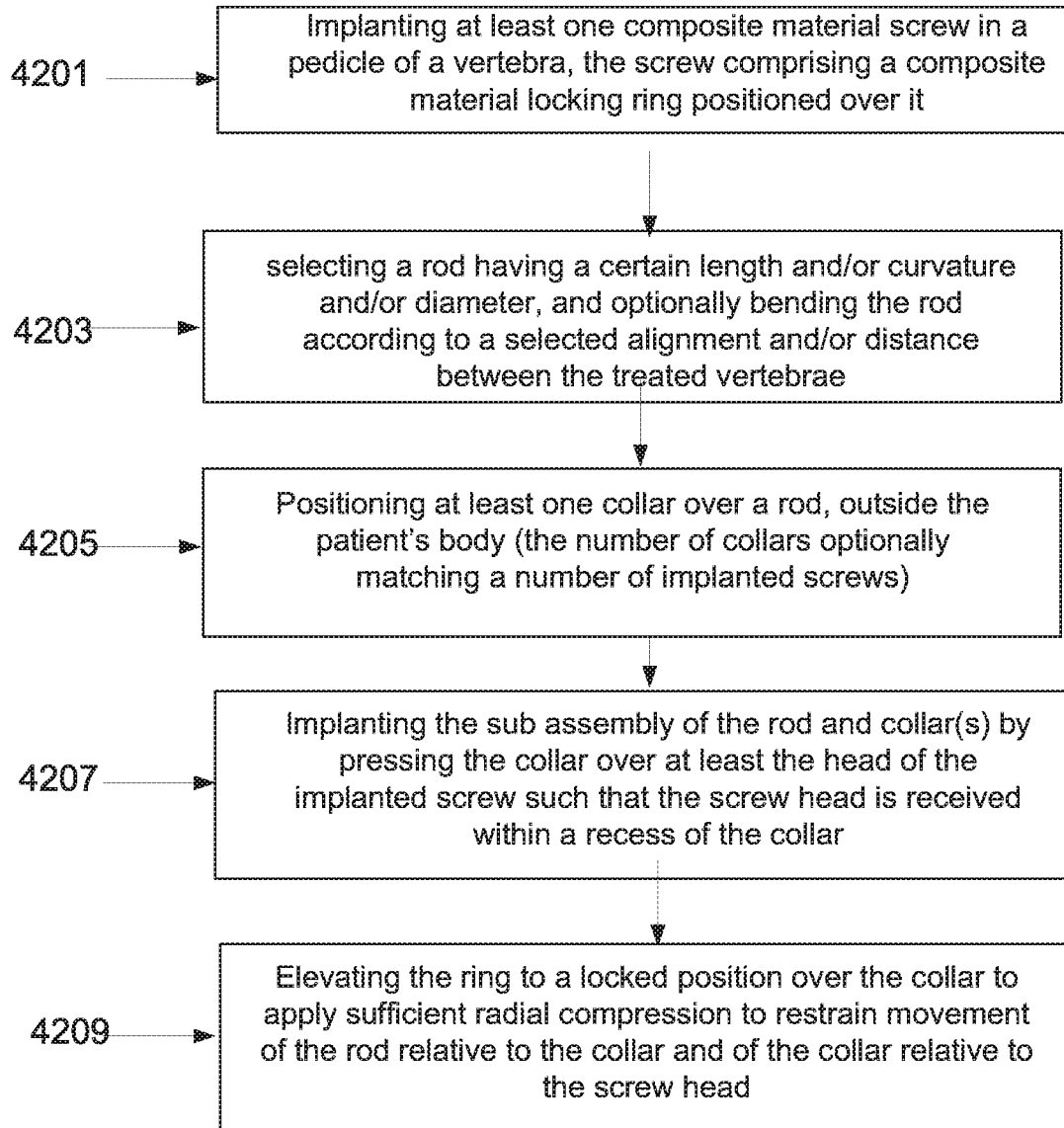
FIG. 42 is a flowchart of a method for constructing a pedicle screw construct, according to some embodiments of the invention.

FIG. 42 is a flowchart of an exemplary method for constructing a pedicle screw construct, for example a construct in which the collar comprises a cavity for receiving the head of the screw, for example as described in Figures-22A-C, according to some embodiments of the invention.

In some embodiments, a composite material (e.g., carbon reinforced PEEK) pedicle screw is implanted (4201), for example as described hereinabove. Optionally, the pedicle screw comprises a composite material (e.g., carbon reinforced PEEK) locking ring positioned over it. In some embodiments, the steps of selecting a rod, optionally bending the rod, (4203) and positioning one or more collars over the rod (4205) are performed for example as described hereinabove in FIG. 41.

In some embodiments, the sub assembly of the rod and collars is implanted. (4209). Optionally, the collar is compressively fitted over the screw head, such that at least a portion of the screw head is received within a recess of the collar.

Optionally, at this point, the ring is elevated from a direction of the screw onto the collar to a locking position in which the ring applies sufficient radial compression to restrain movement of the rod and/or screw head relative to the collar (4209). In some embodiments, movement of the collar relative to the screw head is restrained, for example, as noted above with reference to FIG. 41.

Figure 43:
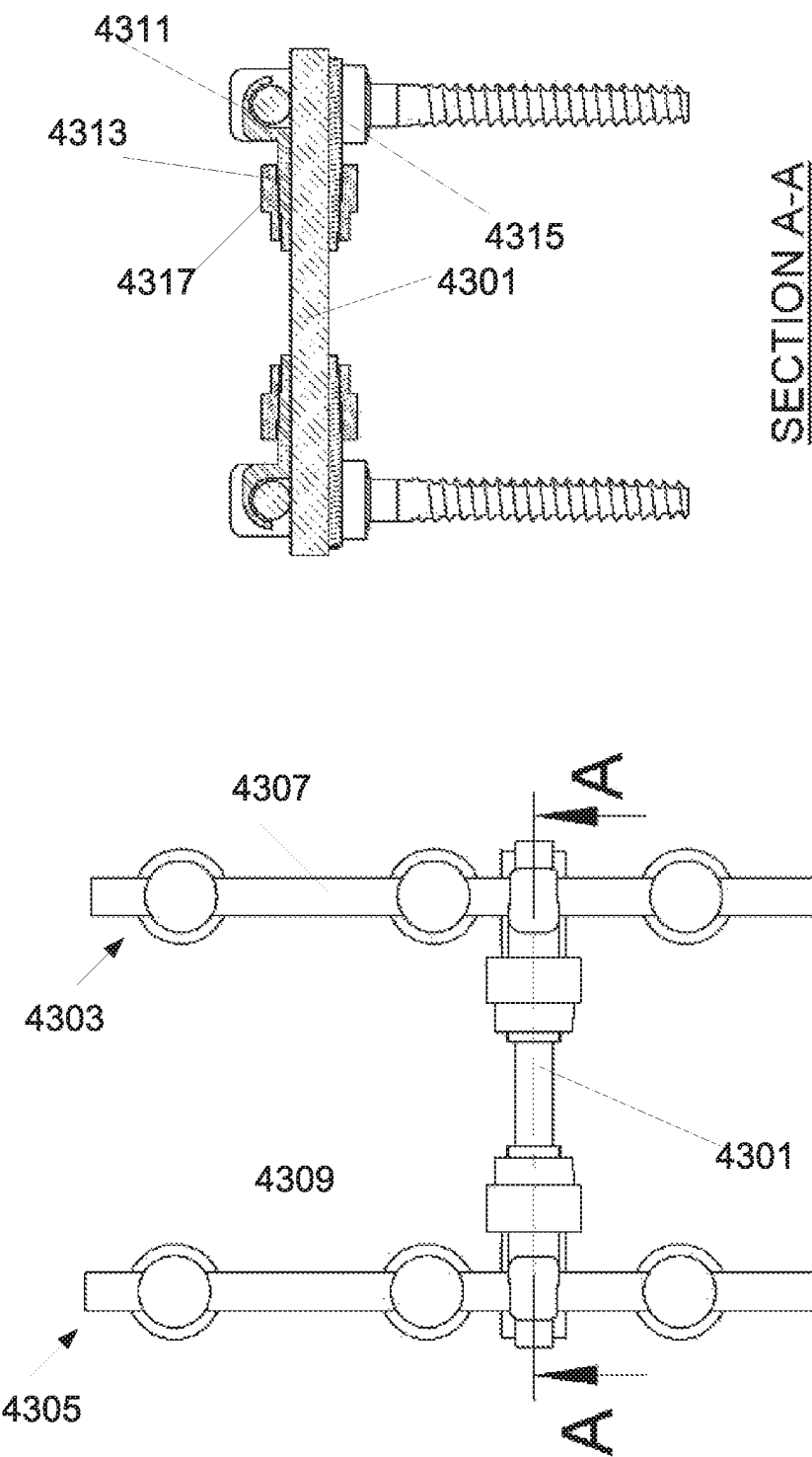
FIG. 43 is an exemplary transverse connection between two constructs, according to some embodiments of the invention.

FIG. 43 is an exemplary transverse connection between two constructs, according to some embodiments of the invention and which may be used, for example, with any of the above rod-screw attachments and is not limited to the specific coupling design shown.

In some embodiments, one or more connections are made between two or more constructs, positioned for example on opposing sides of the spine, such as to fixate opposing spinal sections transversely. In this exemplary configuration, a transverse rod 4301 extends between two constructs 4303 and 4305.

In an exemplary embodiment of the invention, the rods are engaged using a collar design (e.g., one or two parts) which is held closed in compression against the rod by an encircling ring. Designs for ring locking and/or advancing and/or collar tapering and or slots may be used, for example as described above for a screw-rod coupling. It is noted, however, that as two rods are interconnected, in some embodiments, the coupling creates tension forces between the rods to assist in engaging thereof.

In some embodiments, transverse rod 4301 is coupled, at its ends, to rod 4307 and rod 4309 of constructs 4303 and 4305 respectively. In some embodiments, the coupling comprises a hook shape element 4311, (for example as shown in the cross section A-A), which is designed to grasp at least a portion of rod 4307 and/or 4309, and, once engaged, does not release the rod. In some embodiments, the rod is engaged between the hook and element 4315 (described below. In some embodiments, the hook encircles a sufficient part of the rod to prevent disengagement therefrom when also a rod at an opposite side of rod 4301 is engaged (e.g., above 270 degrees, for example). Optionally, hook element 4311 comprises a linearly extending portion 4313 which extends from the hook and is configured in parallel to rod 4301. In some embodiments, the coupling comprises a second linearly extending element 4315, configured to be positioned in parallel to rod 4301 from an opposing side of element 4311. In some embodiments, the space defined between element 4315 and 4311 is reduced by engaging thereof by a ring, such as described below. Optionally, elements 4315 and 4311 are integrally connected and/or provided as a single molded piece which, optionally, can be opened to allow the fitting of rod 4307 or 4309 therein and then closed by compression by a ring (e.g., 4317).

In some embodiments, elements 4311 and 4315 define a tapering profile, for example decreasing in the direction of rod 4301 away from the area of coupling.

In some embodiments, the coupling comprises a ring 4317, positionable over at least the linearly extending portions of hook element 4311 and element 4315, to lock the coupling, for example by advancing the ring to lay over the tapering portion of the elements, in a direction opposite the tapering direction.

In some embodiments, an inner wall of the ring tapers, for example as described herein for a screw-rod coupling. Optionally, the inner wall defines a conical profile, for example defining a channel which decreases in diameter in a direction similar to the tapering direction of elements 4311 and 4315.

In the example shown herein, ring 4317 comprise an external profile comprising a "step", in which a portion away from the coupling comprises a diameter smaller than a portion closer to the coupling. Alternatively, the ring may comprise other external profiles, such as cylindrical or conical or otherwise tapered and/or including one or more tabs or recesses for engagement thereof by a complementary tool.

FIG. 43 shows an example where rings 4317 lie between rods 4307 and 4309. In some embodiments of the invention, one or both of rings 4317 (or an equivalent component) does not lay between rods 4307 and 4309. In an exemplary embodiment of the invention, transverse rod 4301 extents transversely past one or both of rods 4307 and 4309. The same mechanism described in FIG. 43 can be used when applied from the free end(s) of rod 4301 towards rods 4307 and 4309 and ring 4317 fastened by lateral movement towards a rod 4307 or 4309, from outside the construct. A potential advantage of such a mirror arrangement is that rings 4317 can be more easily mounted after the construct and rods 4307, 4309 and 4301 are in place. Optionally or alternatively, it may be more convenient to apply force to ring 4317 if one end of rod 4301 is free. A potential disadvantage of some implementations is that the transverse dimension of the construct may be increased. However, this may assist in mounting additional items on the construct.

Exemplary Use of Curved Rods

Figure 44A:
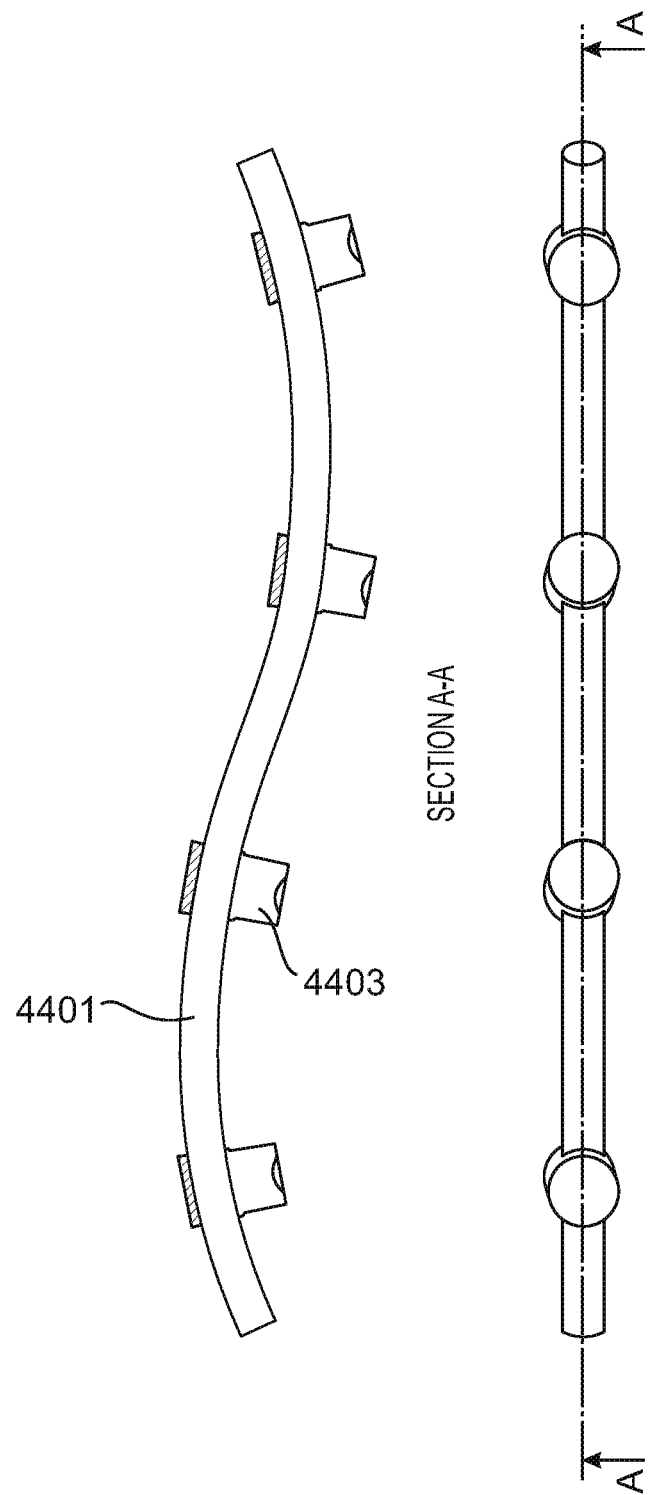
FIG. 44A shows an exemplary curvature of a rod configured to comply with a natural curvature of the spine, according to some embodiments of the invention

FIG. 44A shows an exemplary curvature of a rod 4401 configured to comply with a natural curvature of the spine, according to some embodiments of the invention.

In some embodiments, rod 4401 comprises an S-shaped curvature, for example as shown herein. Optionally, the S-shaped curvature complies with an anatomic curvature of the spine. In some embodiments, the curved rod is configured to couple between a plurality of pedicle screws, for example 4 screws. As shown in this example. 4 collars 4403 are positioned over rod 4401. In some embodiments, the rod can be shortened, optionally during operation, to connect between a smaller number of screws, for example by cutting the distal and/or proximal ends of the rod.

In some embodiments, a recess of one or more of collars 4403 comprises a geometry suitable for receiving a curved portion of the rod, for example determined according to an axial location of the collar relative to the rod. For example, a recess may be formed with a concavity and/or a convexity at the inner surface of the recess, such as to fit a curved portion of the rod more closely.

Exact fitting of rod curvature and collar rod channel curvature may interfere with mounting of the collars over an arbitrarily bent rod. In an exemplary embodiment of the invention, curved collars are inserted from a suitable direction so that their channel curvature matches the rod curvature. For example, collars with a U-shaped (e.g., concave) inner channel (e.g., the two right collars) may be inserted from the right side of the depicted rod 4401 and the channels with an inverted U (e.g., convex) channel (the two left ones, inserted form the left). Optionally or alternatively, the channels are rotated around the rod axis, after insertion, to match the rod curvature and/or assist in navigating past rod curvature direction changes. Optionally or alternatively, the collars have enough flexibility and/or channel size (e.g., when in non-restrained configuration) so that they can be advanced over the curved rod, also over parts with mismatching rod-channel curvature directions. In some embodiments, two part collars or collars with a wide enough slot are used so they can be mounted transversely over a rod, rather than need to travel along the rod longitudinal axis.

Figure 44B:
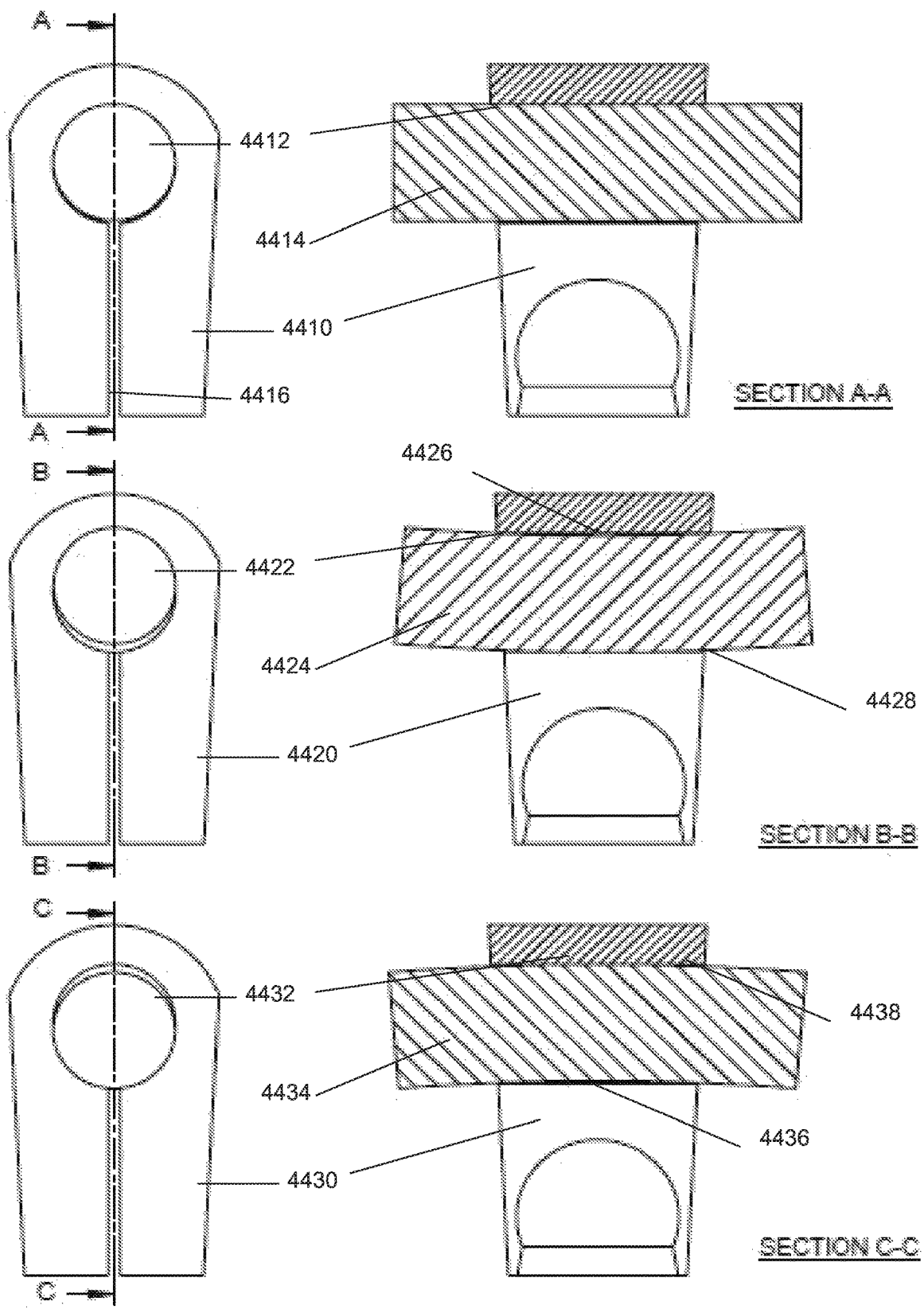
FIGS. 44B and 44C show various designs of collars with curved and/or otherwise asymmetric lumens, in accordance with exemplary embodiments of the invention.
Figure 44C:
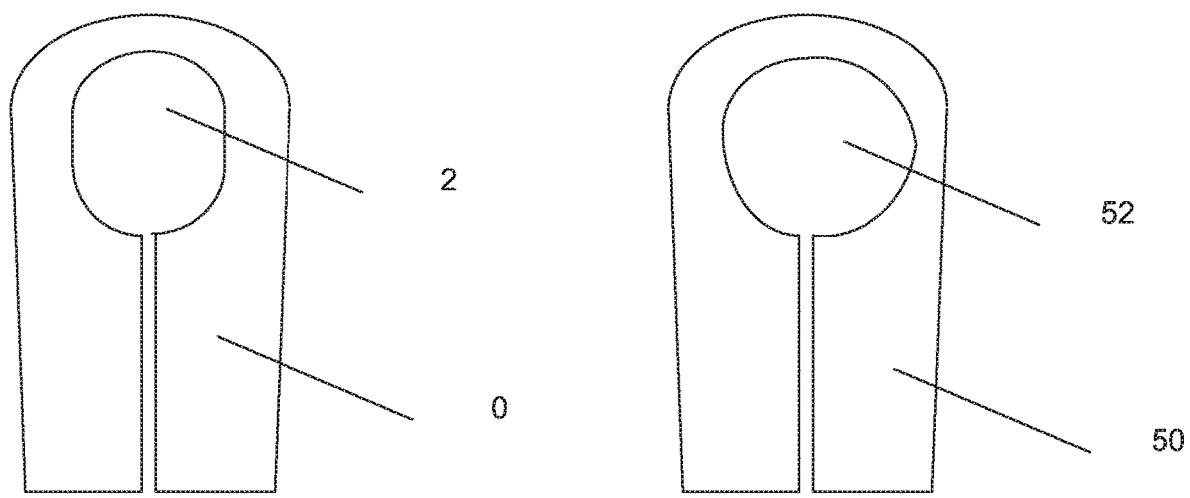

FIGS. 44B and 44C shows various designs of collars with lumens which are asymmetric and/or adapted for fitting multiple rod geometries, in accordance with exemplary embodiments of the invention. For example, the lumens may be curved, flared and/or with other geometries, for example as described below, including both rotationally symmetric and asymmetric lumens and/or lumens which are not aligned with one or more collar axes.

In particular, it is a feature of some embodiments of the invention, that a same collar be suitable to engage rods having different bending radiuses, for example, over a range of 30-240 mm of bending radius for a 5-6 mm diameter rod.

FIG. 44B shows a symmetrical lumen 4412 in a collar 4410, in accordance with some embodiments of the invention. A rod 4414, unbent, fits in lumen 4412. Optionally, (not shown) lumen 4412 may be offset laterally from its location. Optionally or alternatively, (also not shown) lumen 4412 may not be perpendicular to the vertical axis of collar 4410, for example, angling up or down.

Also shown in the figure is a slot 4416. As shown, the slot is vertical and symmetrically arranged, however, in some alternative embodiments (e.g., for this and/or other collars as described herein), the slot can have a different geometry. For example, the slot may be angled, for example, between 2 and 25 degrees to the vertical. Optionally or alternatively, the slot may be laterally displaced, for example, between 5% and 30% of the collar maximum diameter, from the centerline. Optionally or alternatively, the slot may be curved and/or formed of sections with different shapes and/or orientations (e.g., zig-zag and/or include an elbow).

FIG. 44B also shows a collar 4420, in which a lumen 4422 is wider at either end than a rod diameter. So, for example, if a bent rod 4424 (bent upwards) is inserted therein, spaces may be formed at an edge 4428. Optionally, lumen 4422 (as show) is not made wider (or is less wider) at a middle than at an end, so no space is formed at a location 4426 thereof. Optionally, this allows a same lumen (and collar) to engage bent and unbent rods (e.g., at ends and/or middle) thereof. In some embodiments, the lumen has a same general shape at the ends and the middle, so a space is also formed at a location 4426 thereof.

FIG. 44B also shows an opposite geometry in which a collar 4430 with a lumen that is designed for downwards bending rods is used. As shown, when a rod 4434 is inserted, a space may be formed at a location 4438 at the edge of a passageway 4432, between the collar and the rod, while no space is provided in a middle, bottom location 4436 between the rod and the collar.

The term "wide" can refer to any direction radially away from the lumen 4412, 4422, 4432, for example, the width may be increased in a vertical direction, horizontal direction or in an intermediate direction. Also widening (relative to middle of the lumen and/or general shape of the rod) may be in two directions, for example, both in an upwards direction and a downwards direction (on same side of the collar).

Also, it is noted that a collar may be designed for more complex curves, for example, being wide enough and/or being shaped to support a rod which is bent up at one side and bent down at another side of the collar.

In some exemplary embodiments of the invention, the widening is over between 10% and 100% of the length of the lumen, for example, between 20 and 60% of a length thereof. Optionally, the widening is between 1% and 10% of the diameter, for example, between 2% and 8%. For example, a 6 mm diameter collar lumen may be widened at its ends to 6.2 mm.

FIG. 44C shows a collar 4440, in which a lumen 4442 has a cross-section of two half circles attached by straight lines (e.g., the widening is in the middle), over its entire length. This means that a same collar may be used for various shaped rods, for example, straight and bent. Optionally, an inner surface of lumen 4442 is roughened and/or includes one or more projection, to engage the rod after locking of collar 4440 thereto.

FIG. 44C also shows a collar 4450 in which a lumen 4452 is asymmetric to a lateral side. Optionally or alternatively, lumen 4452 may be curved laterally (e.g., rather than vertically as shown in FIG. 44B).

It is noted that in the figures, the locking ring is generally rotationally symmetric. Optionally, it is asymmetric. Optionally, the slot in the collar is made wide enough so that a radially inward protrusion of the ring is provided and can fit into the slot. Optionally, this allows the ring to apply direct force on, for example, the screw and/or serve as a wall of the cavity.

Figure 44D:
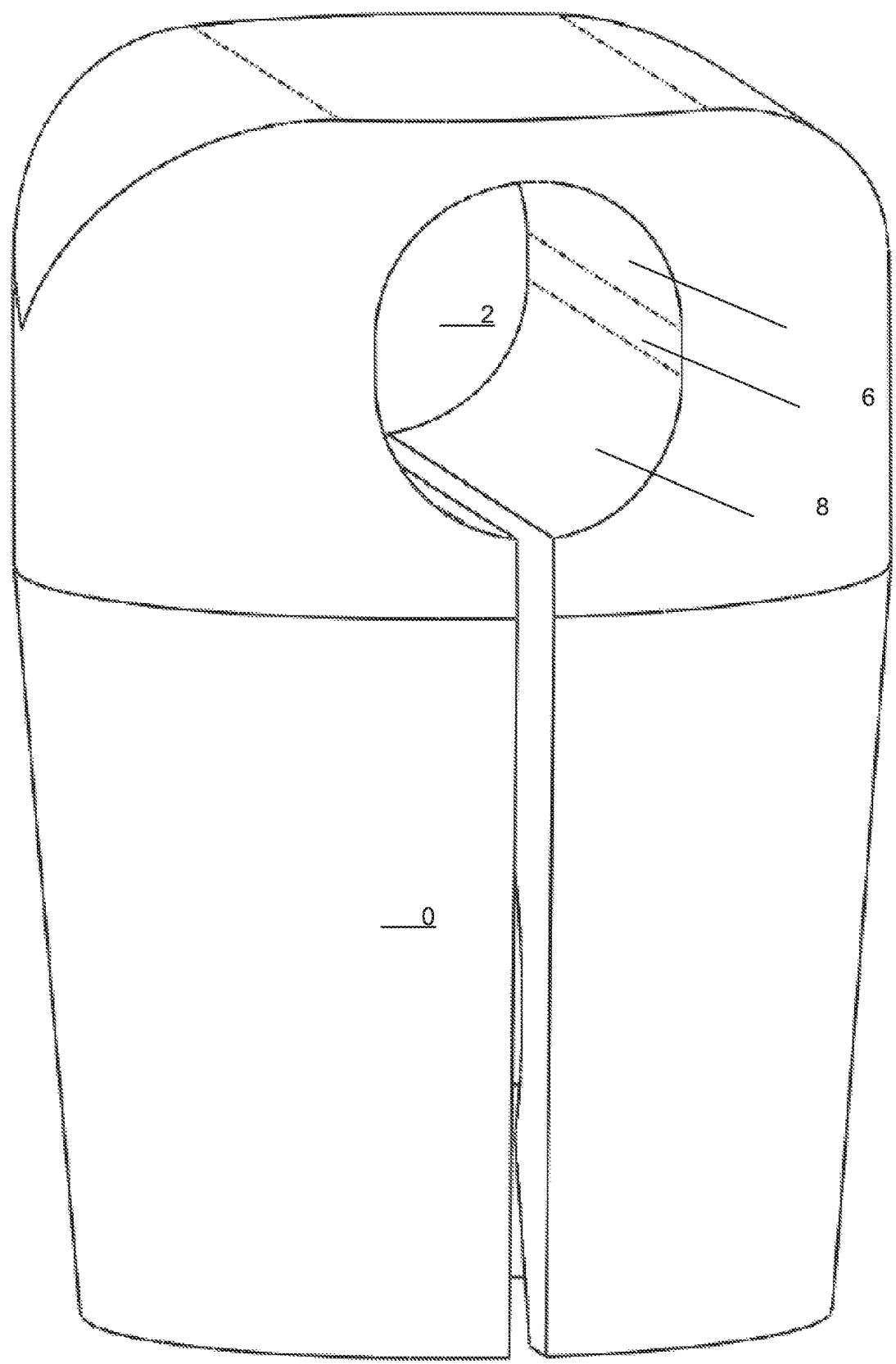
FIG. 44D is a perspective view showing a collar with a vertically elongated passageway, suitable for vertically bent rods and straight rods, in accordance with some embodiments of the invention.
Figure 44E:
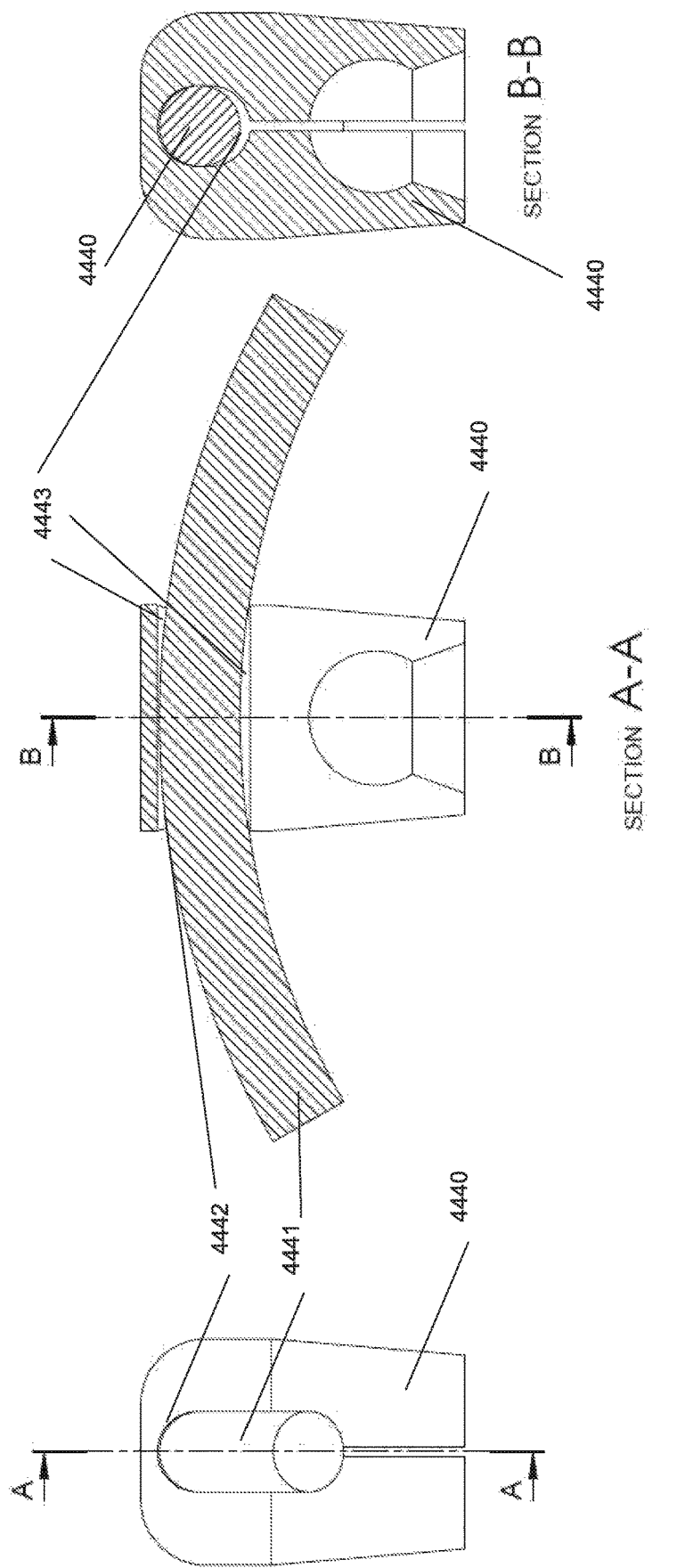
FIG. 44E shows multiple views of the collar of FIG. 44D, with a bent rod therein, in accordance with some embodiments of the invention.

FIG. 44D is a perspective view showing a collar with a vertically elongated passageway, for example, collar 4440 as in FIG. 44C, suitable for vertically bent rods and straight rods, in accordance with some embodiments of the invention; and FIG. 44E shows multiple views of the collar of FIG. 44D, with a bent rod therein, in accordance with some embodiments of the invention.

As can be seen in FIG. 44D, in some embodiments, passageway 4442 is in a general shape of two half cylinders 4444 and 4448, separated by rectangular sections 4446 (only one visible in this perspective).

FIG. 44E shows a rod 4441 inserted in passageway 4442. Section A-A shows exposed portions of passageway 4442, not covered by rod 4441, indicated as spaces 4443. Rod 4441 is at a minimum supported bending radius and contacts the walls of passageway 4442 both at a middle of the passageway and at either end thereof.

While passageway 4442 is shown symmetric, it need not be, for example, the vertical position and/or extent at one side of the color may be different from another side thereof. Also, passageway 4442 may be twisted (e.g., the two apertures thereof being rotated one relative to the other).

Exemplary collar locking mechanisms FIGS. 45A-H show, in pairs, various collar based locking mechanisms, in accordance with some exemplary embodiments of the invention which use a closed top and/or other single-piece collar. FIGS. 45A, 45C, 45E, 45G show the collar 4501 (and 4511; 4521 and 4531 respectively) and rings 4503, 4505 (and 4513,4515; 4523,4525 and 4533,4535 respectively) assembly prior to fastening the rings; FIGS. 45B, 45D, 45F, 45H show the assembly after fastening the rings.

In some embodiments, for example as shown herein, the collar (e.g., 4501, 4511, 4521, 4531) is a single-component (one piece) collar, comprising a slot (e.g., 4509, 4519, 4529, 4539) at its distal portion for fitting over the screw head. Alternatively, the collar may be formed of two or more components, for example as described hereinabove.

In some embodiments, for example as shown herein, both the lower, distal, ring (e.g., 4503, 4513, 4523, 4533) and the upper, proximal ring (e.g., 4505, 4515, 4525, 4535) are positioned over the collar (e.g., 4501, 4511, 4521, 4531) such that even when moved to a fastened position, the rings are located distally to a recess (e.g., 4507, 4517, 4527, 4537) in which a rod is received. One difference between the various embodiments relates to the type of relative motion of the rings, which may affect the design of the ring mover and/or forces applied to implant. Another difference is the location of the ring relative to the pivot (the top of the collar) and the cavities for the rod and screw head, between the different embodiments. The differences in design may be important with respect to the type and direction of force application and/or what object the force is applied to. For example, in FIG. 45A/B the force applied (by the ring mover) is between the top of the collar (or the rod) to the bottom of the rings. In FIGS. 45C/D and 45G/H, the ring mover applies the force between the two rings, relative to each other, possibly without any contact with the top of the collar, or at least without applying substantial force thereto.

In the Example, of FIG. 45E/F, the force is optionally applied between the rod and the rings, for example, between the bottom of the rod and the rings.

In some exemplary embodiments of the invention, the ring (e.g., for any of the locking ring embodiments described herein) is formed of a composite material, for example, fibers in a polymer matrix. In some exemplary embodiments of the invention, at least 50%, 70%, 90% or intermediate percentages or more of the fibers (by weight) are aligned in a general circumferential direction (e.g., to resist bursting of the locking ring by forces applied by the collar).

In some exemplary embodiments of the invention, a locking ring has a radial thickness of between 0.5 or 1 and 4 mm, for example, between 2.5 and 3 mm. Optionally or alternatively, a locking ring has a vertical height of between 0.5 and 5 mm, for example, between 2 and 4 mm. Optionally or alternatively, a locking ring has internal diameter of between 5 and 15 mm, for example, between 8 and 12 mm. Optionally or alternatively, a locking ring is smooth. Alternatively, the ring includes one or more grooves, notches and/or perturbations, for example, a circumferential ridge, which may be used for engaging and moving the locking ring. In some embodiments of the invention, the ring includes one or more radio-opaque markers, for example, a circumferential (optionally embedded) fiber, and/or a plurality of dots or cylinders.

In some exemplary embodiments of the invention, one or both rings are premounted on the collar. Optionally or alternatively, the distal ring (e.g., 4503) is located so it does not extend below the collar (e.g., 4501). Or at least does not extend more than for example, 3 mm, 2 mm or 1 mm, optionally with no extension before locking and/or after locking.

FIGS. 45A and 45B show an exemplary configuration in which both lower ring 4503 and upper ring 4505 are elevated to a fastened position, approximating collar portions on opposing sides of slot 4509 that fit over the screw head to each other. As can be seen in the call-out, ring 4505 lies against an optional radially extending step in collar 4501, to prevent undesired movement and can be made to slide up a gradual widening towards a proximal end of collar 4501, thereby tightening the collar. In some embodiments, friction holds the locking ring in place before and/or after tightening thereof. In some embodiments, the contact surface between the ring and the collar includes one or more protrusions, optionally direction protrusions, to improve engagement and/or prevent slippage.

In some exemplary embodiments of the invention, the gradual widening defines a general partial-cone-shaped section in the collar.

Distal ring 4503 may use a similar mechanism. Optionally, first ring 4503 is tightened and then ring 4505. Alternatively they are tightened in an opposite order. Alternatively they are tightened together, alternatively, one ring is tightened, then the other ring and then the first ring tightened again.

Figure 47A:
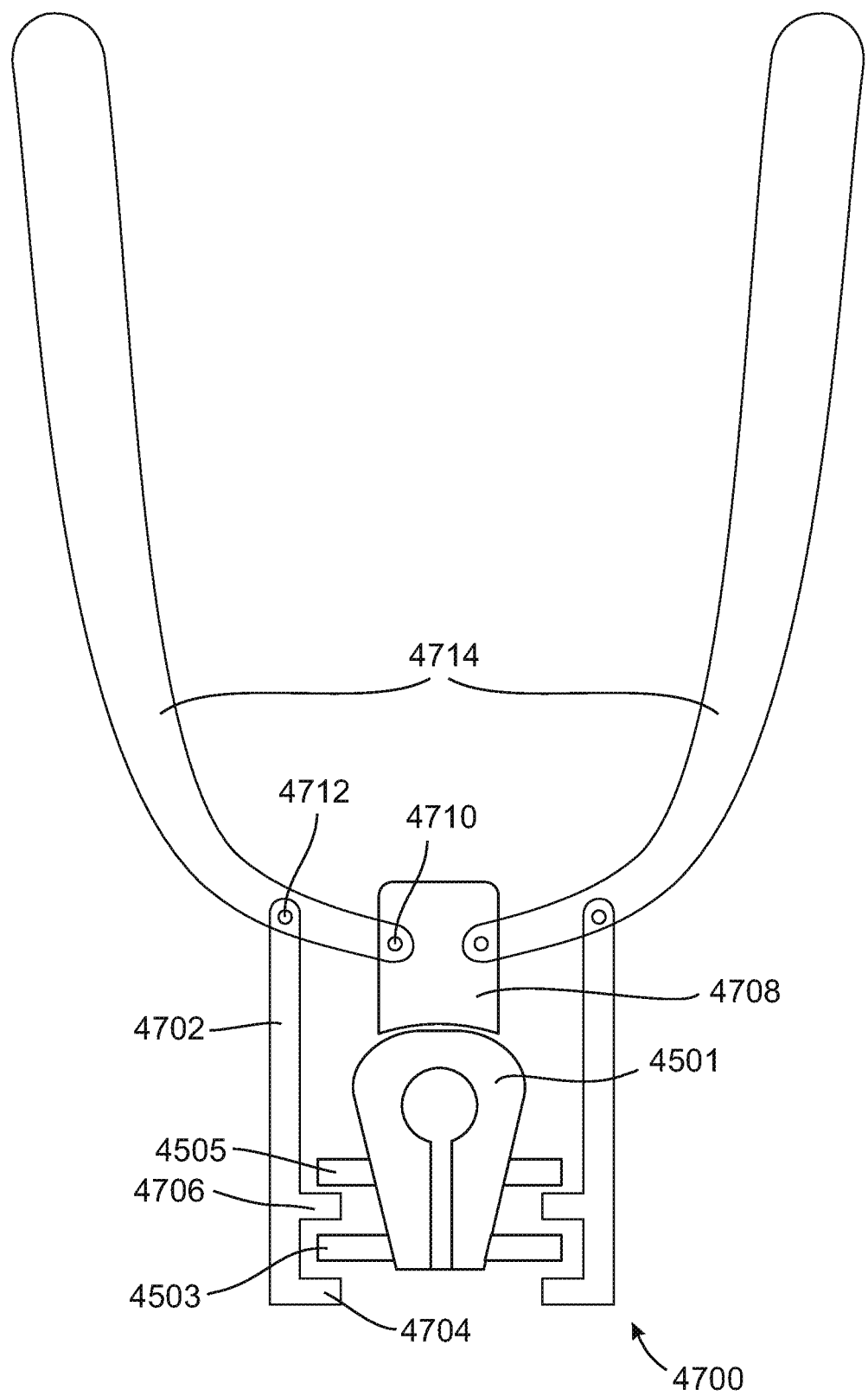
FIGS. 47A and 47B schematically show mechanism for tightening two locking rings on a single collar, in accordance with some embodiments of the invention.
Figure 47B:
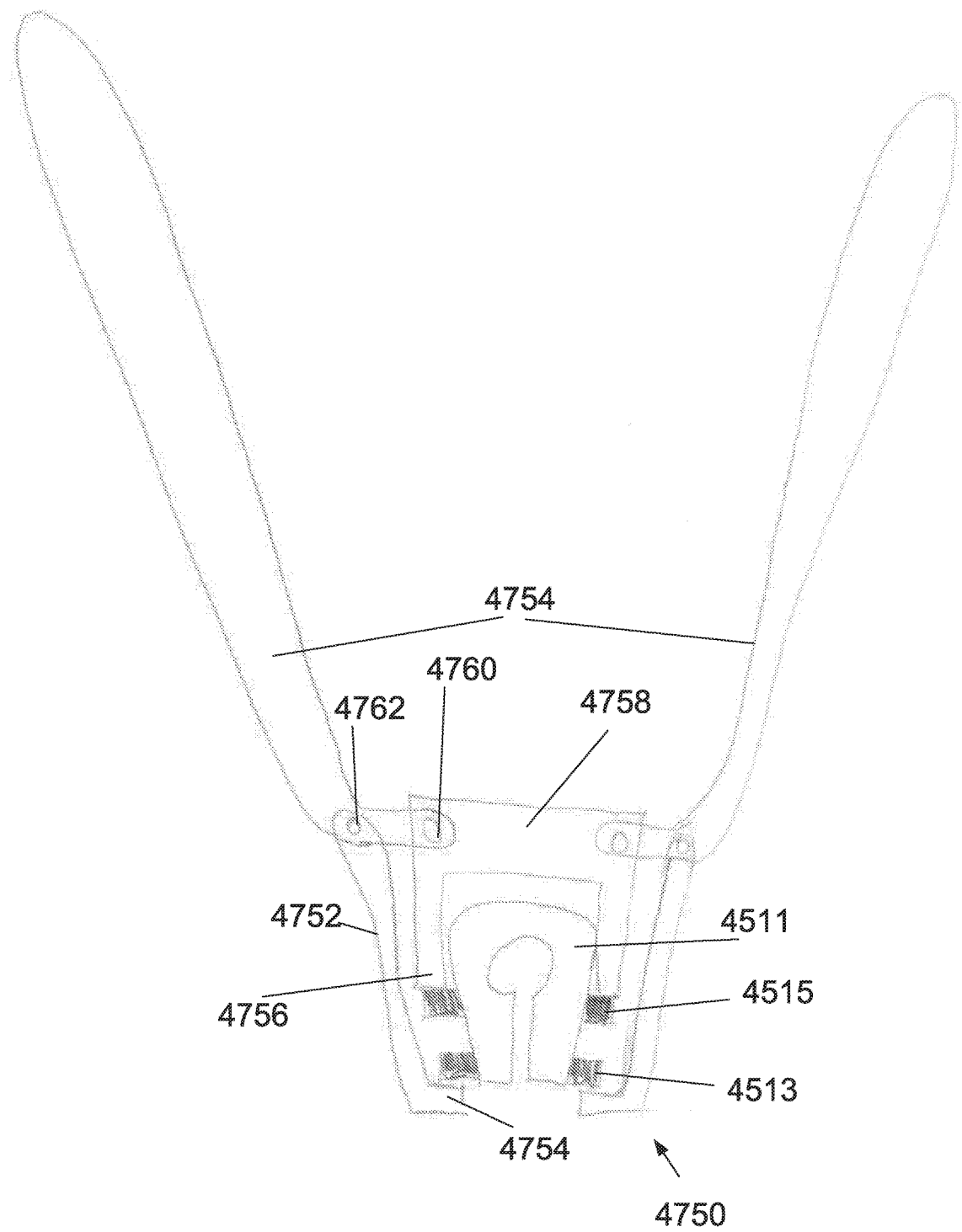

In some exemplary embodiments of the invention, for example using the ring locking devices of FIGS. 47A and 47B, the rings are optionally locked together. Optionally, these devices ensure a relative final position of the two rings. In some embodiments, the absolute position of the rings is set as well.

In some exemplary embodiments of the invention, tightening is as follows. Proximal ring 4505 is used to connect the rod to the collar, and distal ring 4503 is used to connect the screw to the collar. Optionally, distal ring 4503 can be used to fix the angle between the screw and the collar, while allowing the collar to be slid over the rod, for example, to adjust the correct distance between adjacent collars, before closing proximal ring 4505. In some embodiments, proximal ring 4505 is closed first, and the angle between the screw and the collar can be adjusted, before closing distal ring 4503.

In some exemplary embodiments of the invention, the distal and proximal rings of this and/or other embodiments are the same (e.g., to reduce inventory). Optionally or alternatively, different ring designs are used, for example, different height, diameter and/or thickness.

FIGS. 45C and 45D show an exemplary configuration in which lower ring 4513 is elevated and upper ring 4515 is lowered to a fastened position, approximating collar portions on opposing sides of slot 4519 that fit over the screw head to each other. The same type of gradual collar widening mechanism, with an optional step, is shown. In some exemplary embodiments of the invention, the widening is at an angle of between 0.1 and 10 degrees, for example, between 1 and 5 degrees, for example, between 2 and 3 degrees. The angle may be fixed, monotonic and/or varying, optionally including a negative angle (e.g., to define a resting location). Optionally, the angle is circumferentially uniform for a vertical position.

In some exemplary embodiments of the invention, a ring is designed to move between 1 and 5 mm, for example, between 1.5 and 2.5 mm (e.g., and the widening increases at that point and/or terminates in a step). Optionally, the radial size of a step which prevents ring movement is between 0.2 and 4 mm, for example, between 1 and 3 mm.

A potential advantage of this design is that the rings can be moved one relative to the other without applying vertical forces on the implant. As shown, collar 4513 may extend distally past collar 4511 before tightening thereof.

FIGS. 45E and 45F show an exemplary configuration in which both lower ring 4523 and upper ring 4525 are lowered to a fastened position, approximating collar portions on opposing sides of slot 4529 that fit over the screw head to each other.

FIGS. 45G and 45H show an exemplary configuration in which lower ring 4533 is lowered and upper ring 4535 is elevated to a fastened position, approximating collar portions on opposing sides of slot 4539 that fit over the screw head to each other. FIGS. 45G and 45H also show a design variant for the rings (e.g., for this and/or other embodiments), in which a ring includes a notch, optionally a circumferentially extending notch, which may assist in engagement by the ring moving tool. Optionally or alternatively, the notch is used to allow the ring moving tool to fit between the rings if the rings are close together or even touching.

A potential advantage of an assembly that comprises a plurality of locking rings, such as two locking rings, for example as compared to a single locking ring, may include increasing the angle range for positioning of the screw relative to the collar. In some embodiments, the plurality of rings impose fewer limitations when orientating the screw relative to the collar and/or may reduce the vertical profile of the system.

A potential advantage of lowering a locking ring such as lower locking ring 4503 to fasten it over the collar, as opposed to elevating the ring, may include reducing an axial distance between the screw head and the surface of the bone, as the pre-fastened ring is positioned proximally to a distal portion of the screw head that faces the bone surface, and does not interfere with approximating the screw head to the bone surface during insertion to the bone. Such configuration may reduce the length of a screw shaft section extending between the bottom of the screw head and the bone surface, which was pre-occupied by the ring (prior to fastening) and remained exposed to forces such as bending loads acting on the implanted assembly.

Optionally, the rings are fastened one after the other and not simultaneously, allowing gradual locking of the assembly.

FIGS. 46A-H show, in pairs, various collar based locking mechanisms, in accordance with some exemplary embodiments of the invention which use an open top collar, for example, a single component collar that is slotted at proximal and distal portions of the collar. The arrangements generally correspond to those of FIGS. 45A-H, with the difference that a proximal locking ring (e.g., 4605, 4615, 4625, 4635) may optionally be on an opposite side of the rod than a distal locking ring (e.g., 4603, 4613, 4623, 4633). This may allow more independent locking of the screw head and the rod and/or provide less coupling between failure of one mechanism and failure of the other. This may be traded off with the designs of FIGS. 45A-H, in which two rings share the locking forces. In some embodiments (not shown) the collar is split over its entire length. Preloading of such a collar with a locking ring may assist in its maintaining its shape and make it easier to manipulate even before tightening. Optionally, while the proximal and distal slots are shown as being in a same plane, the two slots are not in a same plane, for example, being perpendicular to each other. The slot designs described herein with reference to FIGS. 46A-H may be used with other locking mechanisms, for example, as described herein.

In some exemplary embodiments of the invention, a potential advantage of having separate distal and proximal slots is that each may be locked separately (completely or partially) allowing adjustment of the implant to proceed in steps (e.g., locking to screw while allowing manipulation of the rod, or vice versa. This is, in general a potential advantage of using two locking rings, but it may be more pronounced when each ring corresponds to a slot.

In some embodiments, for example as shown herein, the collar (e.g., 4601, 4611, 4621, 4631) is a single-component (one piece) collar, comprising a slot (e.g., 4609, 4619, 4629, 4639) at its distal portion for fitting over the screw head, and a slot (e.g., 4608, 4618, 4628, 4638) at its proximal portion through which the rod can be passed to be positioned within recess 4607

In some embodiments, for example as shown herein, the rings are positioned over collar 4601 such that upper ring 4605 is positioned proximally to recess 4607, and lower ring 4603 is positioned distally to recess 4607, even when the rings are moved to a fastened position.

FIGS. 46A and 46B show an exemplary configuration in which both lower ring 4603 and upper ring 4605 are elevated to a fastened position; ring 4605 approximates collar portions on opposing sides of slot 4608, and ring 4603 approximates collar portions on opposing sides of slot 4609 to each other.

FIGS. 46C and 46D show an exemplary configuration in which lower ring 4613 is elevated and upper ring 4615 is lowered to a fastened position; ring 4615 approximates collar portions on opposing sides of slot 4618, and ring 4613 approximates collar portions on opposing sides of slot 4619 to each other.

FIGS. 46E and 46F show an exemplary configuration in which both lower ring 4623 and upper ring 4625 are lowered to a fastened position; ring 4625 approximates collar portions on opposing sides of slot 4628, and ring 4623 approximates collar portions on opposing sides of slot 4629 to each other.

FIGS. 46G and 46H show an exemplary configuration in which lower ring 4633 is lowered and upper ring 4635 is elevated to a fastened position; ring 4635 approximates collar portions on opposing sides of slot 4638, and ring 4633 approximates collar portions on opposing sides of slot 4639 to each other.

As may be appreciated, a collar (e.g., based on ring designs of FIGS. 45A-H, 46A-H) may include, for example, a split at a distal and/or a proximal side and a locking ring overlaying such a split, and/or distanced from such a split, depending on the implementation. In particular, identifying as a pivot point a location where two sides of the collar are connected (e.g., permanently or by a ring), a ring may be on the same side of an element to be engaged (e.g., rod or screwhead) as the pivot or at an opposite side thereof.

Exemplary Two-Ring Locking Mechanism

FIGS. 47A and 47B schematically show mechanisms for tightening two locking rings on a single collar, in accordance with some embodiments of the invention.

FIG. 47A shows a mechanism 4700 which may be used for collar 4501 of FIG. 45A. One or more arms 4702 engages rings 4503 and 4505. Optionally, the engaging is via protrusions 4704 and 4706, respectively. While two arms 4702 are shown, a larger or smaller number of arms may be used. Each of the protrusions 4704 and 4706 may extend circumferentially, for example, between 5 and 350 degrees, for example, between 10 and 40 degrees and/or may extend circumferentially more than arm 4702.

In some exemplary embodiments of the invention, force is applied manually. A block 4708 is shaped to rest against a top of collar 4501 and is connected by a hinge 4710 to a handle 4714. Optionally, hinge 4710 acts as the fulcrum of a lever. Arm 4702 is attached at a second hinge 4712 to handle 4714 (e.g., to allow it to move parallel to the collar). Optionally, two handles 4714 are provided, so that when squeezed, retract rings 4503 and 4505 relative to collar 4501. Other designs may be used and/or the design changed for, for example, downward movement of the rings (e.g., block 4708 is shaped to engage the inserted rod from underneath).

FIG. 47B shows (also in cross-section) a similar lever based mechanism 4750 which may be used for collar 4511 of FIG. 45C, to move rings 4513 and 4515 towards each other (e.g., by pushing against the upper ring, rather than the collar). Ring 4513 is engaged underneath by a protrusion 4754 of an arm 4752. Ring 4515 is engaged from above, by an extension 4756 of a block 4758. Two handles 4764 are optionally used (e.g., squeezed together) to provide relative movement between protrusion 4754 and extension 4756. Optionally, arm 4752 is attached by a hinge 4762 to handle 4764, which handle is attached by a hinge 4760 (acting as a fulcrum) to block 4758.

While manually achieved mechanical advantage using two levers is shown, other designs can be used, for example, other manners of providing mechanical advantage, such as screws or hydraulics. Optionally or alternatively, a ratchet mechanism is used so that each "squeeze" of the handles advances the rings and locks the arm mechanism in place using a ratchet, so as to allow additional squeezes to be applied. Optionally, hinge 4712 (and 4762) are replaced and/or enhanced by a ratchet mechanism to this effect. Optionally or alternatively to manual force application, power is provided by other means, for example, using an electric motor in the device, using pneumatics and/or using hydraulics (e.g., from outside the device, for example, via a standard hospital outlet.

Exemplary Usage

In some exemplary embodiments of the invention, the kit for spinal fixation is provided with no metal and/or heavy elements (e.g., less than 0.5% by weight of metal or heavy elements and as low as 0% ("metal free"). Optionally, elements with an atomic weight of over 40, 30, 25, 20, 15 13 are avoided. A potential advantage of such a kit is that this avoids metal or other material which might otherwise interfere with radiation treatment of a patient. Another potential advantage is minimizing artifacts in MRI and/or CT and/or NM images. It is noted, however, that in imaging methods, artifacts not adjacent an area of interest may be acceptable. For radiation treatment, any material along the path of the beam may be an issue.

A particular feature of some embodiments of the invention is that the connection between the locking ring and the collar is unthreaded and uses friction. It is noted that, in general, non-metallic threading is difficult to achieve, while friction locking in composite materials may be better than in metal due to, for example, the dynamic and/or static coefficients of friction of the composite materials. Elasticity of the composite materials may allow more range of movement and/or force application than possible with some metals.

Surgical care for patients suffering from primary spinal neoplasms and vertebral metastasis frequently necessitates the use of permanent stabilization with spinal instrumentation (posterior rod and pedicular screw). Radiation therapy is commonly recommended postoperatively. Treatment success is dependent on delivery of adequate radio-biological dose delivered to the tumor and avoidance of radiation induced permanent damage to the spinal cord which is often adjacent to the tumor. Cord tolerance (45 Gy in 23-25 fractions) dictates a narrow therapeutic window for this treatment. This is particularly challenging in cases of low grade malignancies (e.g. Chordoma, chondrosarcoma) in which local disease control can cure the patient. These tumors, are not particularly sensitive to radiation treatment, requiring radiation doses>70 Gy.

Conventional metallic implants can be obstacle to the delivery of safe and effective adjuvant therapy. Titanium (as well as other metal alloys) are poorly compatible with modern imaging techniques (CT or MRI) can obscure accurate postoperative assessment. Adjuvant radiotherapy treatment planning mandates clear imaging as accurate dose calculations are based on CT values (Hounsfield Units, HU) which are then calibrated to relative radiation stopping power for dosimetry calculations and is compromised by hardware artifact. Treatment under conditions where CT data would be corrupted by metal artifacts may induce a 5% to 10% dose reduction to tissues in regions adjacent to metal implants, for example, due to incorrect diagnosis and/or by the part of the implant which caused the artifact also interfering with the radiation itself. Further radiation perturbation which may stem from backscattering and attenuation of the radiation beam can further interfere with calculations and/or delivery.

Several clinical and experimental studies have investigated this problem. The presence of titanium implants in patients treated for chordoma and chondrosarcoma was reported to be a significant risk factor for local treatment failure. Also reported has been severe under-dosing due to perturbation of dose distribution produced in a patient with a bilateral hip prosthesis for a proton plan as well as for photon and electron plans. Tantalum markers, used for the localization of the eye in uveal melanoma treatments, were found to produce significant perturbations in the absorbed dose distribution and may cause significant dose shadows beyond the clips.

In some exemplary embodiments of the invention, no metal markers are used. Optionally the surgery is open surgery, without any radio-opaque markers on any component of the system.

Optionally or alternatively, the kit includes cannulated portions, for example, screws, and inserts, such as a k-wire, are used, which fit in the cannulation and include radio-opaque markers. Optionally or alternatively, the kit includes one or more mounted radio-opaque components for use during implantation. However, such components are removable after implantation. In one example, the components are coupled to a pull-wire or thread and can be pulled out of the body (e.g., being temporarily attached, for example, using adhesive and/or fitting in a socket or slot in the kit component). Optionally or alternatively, dissolvable radio-opaque markers, for example, as described in U.S. Pat. No. 6,626,936, the disclosure of which is incorporated by reference, are used. In some exemplary embodiments of the invention, a non-metallic stabilization system is used in such patients. Optionally or alternatively, an existing stabilization system is removed and replaced by a non-metallic system, for example, as described herein.

In some exemplary embodiments of the invention, a kit as described herein has the following dimensions: Screw thread outside diameter range 3 to 8 mm, for example 4, 5, 5.5, 6, 6.5, 7, 7.5 mm; and/or screw thread length 30 to 70 mm, for example 35, 40, 45, 50, 55 mm; and/or screw head diameter 5 to 9 mm, for example 8, 8.3 mm; and/or rod diameter range 4 to 7 mm, for example 6 mm. The collar and/or locking rings are optionally sized to fit the screw and rod and have a minimal additional size, for example, a minimal size which is strong enough to resist breakage in the body.

General

As various features of devices and methods have been described it will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

It should also be appreciated that some of the embodiments are described only as methods or only as apparatus, however the scope of the invention includes both methods for using apparatus and apparatus for applying methods. The scope of the invention also covers machines for creating the apparatus described herein. In addition, the scope of the invention also includes methods of using, constructing, calibrating and/or maintaining the apparatus described herein. When used in the following claims or in the text above, the terms "comprises", "comprising", "includes", "including", "having" and their conjugates mean "including but not limited to". The term "consisting of" generally means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pedicle screw implant construct kit, comprising:
at least one pedicle screw including a head, said screw comprising composite material including reinforcing filaments embedded in a polymer matrix;
a rod;
at least one collar, said collar comprising composite material including reinforcing filaments embedded in a polymer matrix, said collar including at least one recess defining a cavity for receiving said rod, said cavity defining a lumen including an end having a first cross-sectional profile and including a middle having a second cross-sectional profile, said first cross-sectional profile larger than said second cross-sectional profile, said first cross-sectional profile being between 1% to 10% larger than said second cross-sectional profile;
said collar sized, shaped and configured to be coupled to said head of said pedicle screw;
said rod being an elongated rod sized and shaped for connecting said collar to one or more additional collars, thereby coupling between said at least one pedicle screw and one or more additional screws, said rod comprising composite material including reinforcing filaments embedded in a polymer matrix; and
at least one restraint, said restraint comprising composite material including reinforcing filaments embedded in a polymer matrix, said restraint sized and shaped to be positioned over at least portion of said collar and restrict relative movement of one or both of the screw head and the rod relative to said collar, by exerting radial compression force onto said collar.

2. A kit according to claim 1, wherein said kit is less than 1% by weight atoms with an atomic number over 25.

3. A kit according to claim 1, wherein said lumen in which said rod is received is rotationally asymmetric.

4. A kit according to claim 3, wherein said first cross-sectional profile includes an elongation in a direction radial to a longitudinal axis of said lumen.

5. A kit according to claim 4, wherein said elongation is different at said ends of said lumen from any elongation at a center of said lumen.

6. A kit according to claim 4, wherein said elongation support the engagement by said cavity of both straight rods and rods bent with a radius of curvature of at least 30 mm.

7. A kit according to claim 4, wherein said elongation is vertical with respect to a long axis of said collar.

8. A kit according to claim 1, wherein said restraint is mounted in a narrowing in an outer profile of said collar, vertically adjacent to a gradual widening in said outer profile and is configured to lock to said widening by friction.

9. A kit according to claim 1, comprising two restraints for said collar and wherein said collar includes two regions for locking of said restraints to said collar.

10. A kit according to claim 9, wherein said collar includes at least one radial extension which prevents sliding off of at least one restraint from said collar.

11. A kit according to claim 9, wherein said collar is shaped so that locking one restraint only restricts the movement of one of said rod and said head of said screw.

12. A kit according to claim 9, wherein said collar is shaped so that locking of the two restraints requires movement of the two restraints in a same direction or instead in opposite directions.

13. A kit according to claim 9, wherein said two restraints are mounted below said rod.

14. A kit according to claim 1, wherein said collar is shaped so that a restraint can be mounted thereon without said restricting and then locked without extending during a mounting state nor during a locking state more than 1 mm below said collar.

15. A kit according to claim 14, wherein said collar is shaped so that said restraint locks by a distal movement away from said cavity in which said rod is received and from a cavity in which said screw head is received.

16. A kit according to claim 1, wherein said rod is curved, having a bending radius of between 30-240 mm.

17. A kit according to claim 1, wherein said first cross-sectional profile defines a widening extending between 10-90% of a length of said lumen.

18. A kit according to claim 1, wherein when said rod is received within said lumen it contacts the walls of said lumen at an approximate center of said lumen.

19. A kit according to claim 1, wherein said lumen flares towards said ends of said lumen.

20. A kit according to claim 1, wherein said collar is comprised of a unitary, single piece body.

21. A kit according to claim 1, wherein said end includes a widening radially away from said lumen, said widening being 1% to 10% wider than said rod.

22. A kit according to claim 1, wherein said lumen includes a widening at either end relative to a center of said lumen, each said widening being between 1% to 10% wider than a cross-sectional profile of a rod received within said lumen.

23. A kit according to claim 1, wherein said restraint comprises a locking ring.

* * * * *